(12) United States Patent
Tu et al.

(10) Patent No.: US 10,676,467 B2
(45) Date of Patent: Jun. 9, 2020

(54) COMPOSITIONS FOR BINDING SPHINGOSINE-1-PHOSPHATE RECEPTOR 1 (S1P1), IMAGING OF S1P1, AND METHODS OF USE THEREOF

(71) Applicants: Zhude Tu, Frontenac, MO (US); Adam Rosenberg, Nashville, MO (US); Hui Liu, Creve Coeur, MO (US); Junbin Han, Shanghai (CN)

(72) Inventors: Zhude Tu, Frontenac, MO (US); Adam Rosenberg, Nashville, MO (US); Hui Liu, Creve Coeur, MO (US); Junbin Han, Shanghai (CN)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/025,324

(22) Filed: Jul. 2, 2018

(65) Prior Publication Data

US 2019/0002450 A1 Jan. 3, 2019

Related U.S. Application Data

(60) Provisional application No. 62/527,259, filed on Jun. 30, 2017.

(51) Int. Cl.
| | |
|---|---|
| *C07D 413/04* | (2006.01) |
| *C07D 419/04* | (2006.01) |
| *C07D 413/10* | (2006.01) |
| *C07D 271/06* | (2006.01) |
| *C07B 59/00* | (2006.01) |
| *C07D 413/12* | (2006.01) |

(52) U.S. Cl.
CPC .......... *C07D 413/04* (2013.01); *C07B 59/002* (2013.01); *C07D 271/06* (2013.01); *C07D 413/10* (2013.01); *C07D 413/12* (2013.01); *C07B 2200/05* (2013.01)

(58) Field of Classification Search
CPC ............................ C07D 413/04; C07D 419/04
See application file for complete search history.

(56) References Cited

U.S. PATENT DOCUMENTS

| 3,192,103 | A | 6/1965 | Sousa et al. |
|---|---|---|---|
| 6,277,872 | B1 | 8/2001 | Brenner et al. |
| 7,041,685 | B2 | 5/2006 | Cai et al. |
| 2002/0013327 | A1 | 1/2002 | Tiebes et al. |
| 2003/0045546 | A1 | 3/2003 | Cai et al. |

FOREIGN PATENT DOCUMENTS

| CN | 103251950 | * | 8/2013 |
|---|---|---|---|
| WO | 87/06429 | A1 | 11/1987 |
| WO | 2006/114400 | A1 | 11/2006 |
| WO | WO 2006131336 | * | 12/2006 |
| WO | W 2008037476 | * | 4/2008 |
| WO | 2010/112461 | A1 | 10/2010 |
| WO | WO 2014/063199 | * | 5/2014 |

OTHER PUBLICATIONS

Basham et al. (Bioorganic & Medicinal Chemistry Letters (2014), 24(11), 2473-2476).*
Blaho, V.A., et al., "An Update on the Biology of Sphingosine 1-Phosphate Receptors," 2014, J Lipid Res, 55/8:1596-1608, 13 pages.
Bolli, M H., et al., "Novel S1P1 Receptor Agonists—Part 2: From Bicyclo[3.1.0]hexane-Fused Thiophenes to Isobutyl Substituted Thiophenes," 2014, J Med Chem, 57:78-97, 20 pages.
Daum G. et al., "Sphingosine 1-phosphate: a regulator of Arterial Lesions," 2009, Arterioscler Thromb Vasc Biol, 29:1439-1443, 5 pages.
Demont, E H., et al., "Discovery of a Brain-Penetrant S1P3-Sparing Direct Agonist of the S1P1 and S1P5 Receptors Efficacious at Low Oral Dose," 2011, J Med Chem, 54/19:6724-6733, 10 pages.
Dev, K.K., et al., "Brain Sphingosine-1-Phosphate Receptors: Implication for FTY720 in the Treatment of Multiple Sclerosis," 2008, Pharmacol Ther, 117/1:77-93, 17 pages.
Elhai, J., et al., "Conjugal Transfer of DNA to Cyanobacteria," 1988, Methods in Enzymology, 167:747-754, 8 pages.
Fishburn, C.S., "The Pharmacology of PEGylation: Balancing PD and PK to Generate Novel Therapeutics," 2008, J Pharma Sci, 97:4167-4183.
Ghose, A.K., et al., Knowledge-Based, Central Nervous System (CNS) Lead Selection and Lead Optimization for CNS Drug Discovery, 2012, ACS Chem. Neurosci. 3:50-68, 19 pages.
Gilmore, J.L., et al., "Discovery and Structure-Activity Relationship (SAR) of a Series of Ethanolamine-Based Direct-Acting Agonists of Sphingosine-1-phosphate (S1P1)," 2016, Journal of Medicinal Chemistry, 59:6248-6264, 17 pages.
Guerrero, M., et al., "Sphingosine 1-Phosphate Receptor 1 Agonists: a Patent Review (2013-2015)," 2016, Expert Opin Ther Pat, 26/4:455-470. Abstract Only.
Harris, J.M., et al., "Effect of PEGylation on Pharmaceuticals," 2003, Nature Reviews Drug Discovery, 2:214, 8 pages.
Hennessy, E.J., et al., "Discovery of Heterocyclic Sulfonamides as Sphingosine 1-Phosphate Receptor 1 (S1P1) Antagonists," 2015, Bioorg Med Chem Lett, 25:2041-2045, 5 pages.
Hughes, J.E., et al., "Sphingosine-1-Phosphate Induces an Antiinflammatory Phenotype in Macrophages," 2008, Circ Res, 102/8:950-958, 9 pages.

(Continued)

*Primary Examiner* — Bruck Kifle
(74) *Attorney, Agent, or Firm* — Stinson LLP

(57) ABSTRACT

Among the various aspects of the present disclosure is the provision of a compositions for binding sphingosine-1-phosphate receptor 1 (S1P1), imaging of S1P1, and methods of use thereof. Provided are imaging agents for imaging S1P1 and S1P1 associated diseases, disorders, and conditions. Also provided are therapeutic compositions and methods for the treatment of S1P1 associated diseases, disorders, and conditions.

20 Claims, 18 Drawing Sheets

(9 of 18 Drawing Sheet(s) Filed in Color)

(56) References Cited

OTHER PUBLICATIONS

Jin, H., et al., "A Promising Carbon-11-Labeled Sphingosine-1-Phosphate Receptor 1-Specific PET Tracer for Imaging Vascular Injury," 2016, J Nucl Cardiol, 24/2:558-570, 13 pages.

Karuppuchamy, T., et al., "Sphingosine-1-Phosphate Receptor-1 (S1P1) is Expressed by Lymphocytes, Dendritic Cells, and Endothelium and Modulated During Inflammatory Bowel Disease," 2017, Mucosal Immunol, 10/1:162-171, 20 pages.

Kono, M., et al., Bioluminescence Imaging of G Protein-Coupled Receptor Activation in Living Mice, 2017, Nat Commun, 8:1163, 11 pages.

Kunkel, G.T., et al., "Targeting the Sphingosine-1-Phosphate Axis in Cancer, Inflammation and Beyond," 2013, Nat Rev Drug Discov, 12/9:688-702, 30 pages.

Lee, H., et al. "STAT3-Induced S1PR1 Expression is Crucial for Persistent STAT3 Activation in Tumors," 2010, Nat. Med., 16/12:1421-1428, 26 pages.

Liang, J., et al., "Sphingosine-1-Phosphate Links Persistent STAT3 Activation, Chronic Intestinal Inflammation, and Development of Colitis-Associated Cancer," 2013, Cancer cell, 23/1:107-120, 14 pages.

Liu, H., et al. "PET Study of Sphingosine-1-Phosphate Receptor 1 Expression in Response to Vascular Inflammation in a Rat Model of Carotid Injury," 2017, Mol Imaging, 16:153 6012116689770, 7 pages.

Liu, H., et al. "Optimization of S1P1-specific PET Radioligands for Imaging Neuroinflammation," May 1, 2017, J Nucl Cardiol, 58/Supp 1 10, 2 pages.

Liu, H., et al., "Optimization of S1P1-Specific PET Radioligands for Imaging Neuroinflammation," Brain Imaging Council Young Investigator Award Symposium, 2017 SNMMI Meeting Presentation, 14 pages.

Liu, H., et al., "Optimization of S1P1-Specific PET Radioligands for Imaging Neuroinflammation," 2017, J. Nucl. Med., vol. 58 No. Supplement 1 10 (SNMMI Meeting Abstract), 2 pages.

Liu, H., et al., "PET Imaging Study of S1PR1 Expression in a Rat Model of Multiple Sclerosis," 2016, Mol Imaging Biol, 18/5:724-732, 18 pages.

Liu H., et al., "Comparison of [11C]TZ1964B and [18F]MNI659 for PET Imaging Brain PDE10A in Nonhuman Primates," 2016, Pharmacol Res Perspect, 4/5:e00253, 12 pages.

Luo, Z., et al., "Syntheses and in vitro Evaluation of New S1PR1 Compounds and Initial Evaluation of a Lead F-18 Radiotracer in Rodents," 2018, European J Med Chem, 150:796-808, 13 pages.

Nishimura, H., et al., "Cellular Localization of Sphingosine-1-Phosphate Receptor 1 Expression in the Human Central Nervous System," 2010, J Histochem Cytochem, 58/9:847-856, 10 pages.

Ohuchi, H., et al., "Expression Patterns of the Lysophospholipid Receptor Genes During Mouse Early Development," Dev. Dyn. 237 (2008) 3280-3294, 15 pages.

Pike, V.W., "Considerations in the Development of Reversibly Binding PET Radioligands for Brain Imaging," 2016, Curr Med Chem, 23/18:1818-1869, 105 pages.

Ponnusamy, S., et al., "Communication Between Host Organism and Cancer Cells is Transduced By Systemic Sphingosine Kinase 1/Sphingosine 1-Phosphate Signalling to Regulate Tumour Metastasis," 2012, EMBO Mol Med, 4/8:761-775, 15 pages.

Pyne, N.J., et al., "Sphingosine 1-Phosphate and Cancer," 2010, Nat Rev Cancer, 10/7:489-503.

Poti, F., et al., "KRP-203, Sphingosine 1-Phosphate Receptor Type 1 Agonist, Ameliorates Atherosclerosis in LDL-R-/-Mice," 2013, Arterioscl Throm Vas, 33:1505-1512, 8 pages.

Quattropani, A., et al., "Pharmacophore-Based Design of Novel Oxadiazoles as Selective Sphingosine-1-Phosphate (S1P) Receptor Agonists with in vivo Efficacy" 0000, Chem. Med. Chem. 10:688-714, 27 pages.

Rankovic, Z., "CNS Drug Design: Balancing Physicochemical Properties for Optimal Brain Exposure," 2015, J Med Chem, 58/6:2584-2608, 25 pages.

Rankovic, Z., "CNS Physicochemical Property Space Shaped by a Diverse Set of Molecules with Experimentally Determined Exposure in the Mouse Brain," 2017, J Med Chem, 60/14:5943-5954, 12 pages.

Roberts, E., et al., "Sphingosine 1-Phosphate Receptor Agonists: a Patent Review (2010-2012)," 2013, Expert Opin Ther Pat, 23/7:817-841. Abstract Only.

Rosenberg, et al., "Design, Synthesis and in vitro and in vivo Evaluation of an 18F-Labeled Sphingosine 1-Phosphate Receptor 1 (S1P1) PET tracer," Jul. 14, 2016, J Med Chem, 59/13:6201-6220, 49 pages.

Rosenberg, et al., "Development and in vivo Evaluation of Three F-18 Labeled S1P1 Ligands as PET Tracers for MS," May 1, 2016, J Nucl Med, 57/Supp 2, Abstract Only.

Rosenberg, et al., "A practical process for the preparation of [(32)P]S1P and binding assay for S1P receptor ligands," 2015, Applied Radiation and Isotopes: Including Data, Instrumentation and Methods for use in Agriculture, Industry and Medicine, 102:5-9, 12 pages.

Shaikh, R.S., et al., "Synthesis and Evaluation of Fluorinated Fingolimod (FTY720) Analogues for Sphingosine-1-Phosphate Receptor Molecular Imaging by Positron Emission Tomography," 2015, J Med Chem, 58:3471-3484, 14 pages.

Soliven, B., et al., "The Neurobiology of Sphingosine 1-Phosphate Signaling and Sphingosine 1-Phosphate Receptor Modulators," 2011, Neurology, 76/8 Suppl 3:S9-14, 7 pages.

Studier, FW. "Protein Production by Auto-Induction in High-Density Shaking Cultures," 2005, Protein Expr Purif, 41/1:207-234, 28 pages.

Sucksdorff, M., et al., "Evaluation of the Effect of Fingolimod Treatment on Microglial Activation Using Serial PET Imaging in Multiple Sclerosis," 2017, J Nucl Med, 58/10:1646-1651, 7 pages.

Toman, R.E., et al., "Lysophospholipid Receptors in the Nervous System," 2002 Neurochem. Res. 27:619-627, 9 pages.

Van Der Giet, M., et al., "Relevance and Potential of Sphingosine-1-Phosphate in Vascular Inflammatory Disease," 2008, Biol Chem, 389/11:1381-1390, 10 pages.

Wager, T.T., et al., "Central Nervous System Multiparameter Optimization Desirability: Application in Drug Discovery," 2016, ACS Chem. Neurosci. 7:767-775, 9 pages.

Wager, T.T., et al., "Moving Beyond Rules: the Development of a Central Nervous System Multiparameter Optimization (CNS MPO) Approach to Enable Alignment of Druglike Properties," 2010, ACS Chem. Neurosci. 1:435-449, 15 pages.

Watson, C., et al., "High Expression of Sphingosine 1-Phosphate Receptors, S1P1 and S1P3, Sphingosine Kinase 1, and Extracellular Signal-Regulated Kinase-1/2 is Associated with Development of Tamoxifen Resistance in Estrogen Receptor-Positive Breast Cancer Patients," 2010, Am J Pathol, 177/5:2205-2215, 11 pages.

Yogi, A., et al., "Sphingosine-1-Phosphate-Induced Inflammation Involves Receptor Tyrosine Kinase Transactivation in Vascular Cells Upregulation in Hypertension," 2011, Hypertension, 57:809-818, 23 pages.

* cited by examiner

A

B

C

A

B

COMPOSITIONS FOR BINDING SPHINGOSINE-1-PHOSPHATE RECEPTOR 1 (S1P1), IMAGING OF S1P1, AND METHODS OF USE THEREOF

CROSS-REFERENCE TO RELATED APPLICATIONS

This application claims benefit of U.S. provisional application Ser. No. 62/527,259, filed Jun. 30, 2017, the entire disclosure of which is incorporated herein by reference.

STATEMENT REGARDING FEDERALLY SPONSORED RESEARCH OR DEVELOPMENT

This invention was made with government support under grant number DESC0008432 awarded by the U.S. Department of Energy. The government has certain rights in the invention.

FIELD OF THE INVENTION

The present disclosure generally relates to compounds and compositions for use in imaging agents, and to methods of use for monitoring and/or treating conditions or diseases related to sphingosine-1-phosphate (S1P) signaling.

BACKGROUND

Sphingosine-1-phosphate (S1P) is a natural metabolite of sphingolipids, which comprise cell plasma membranes. Aside from its role in intracellular signaling, S1P is also released and acts in an autocrine or paracrine fashion on a family of G-protein coupled receptors (GPCRs): Sphingosine-1 Receptors 1-5 (S1P1-S1P5). S1P signaling has been linked to a variety of cellular processes including cell motility, invasion, angiogenesis, vascular maturation and lymphocyte trafficking. Recently, a modulator of S1P1 and S1P3-S1P5, fingolimod (also known as FTY-720 or Gilenya), has been found to be an effective treatment for relapsing-remitting multiple sclerosis (RRMS). Fingolimod promotes the internalization of S1P1, reducing the aberrant lymphocyte trafficking common in MS. The surface expression level of S1P1 can be used as a marker of several diseases, including multiple sclerosis (MS), cancer, cardiovascular disease and rheumatoid arthritis. S1P1 levels can be assessed using imaging techniques such as positron emitting tomography (PET), which uses radioisotope labeled ligands that bind to a target and release gamma rays that can be detected for localization and quantification.

Given the association between S1P1 expression and signaling in various disease states, there is a need for new compounds having high affinity and selectivity for the S1P1.

SUMMARY OF THE INVENTION

Among the various aspects of the present disclosure is the provision of a compositions for binding sphingosine-1-phosphate receptor 1 (S1P1), imaging of S1P1, and methods of use thereof.

Generally, the present invention relates to various compounds, compositions and methods that are useful for binding to, modulating or monitoring expression of sphingosine-1-phosphate (S1P) receptors in tissue. In various aspects, the present invention is directed to a compound having a structure of Formula (I) or (II), a pharmaceutically acceptable salt or a prodrug thereof:

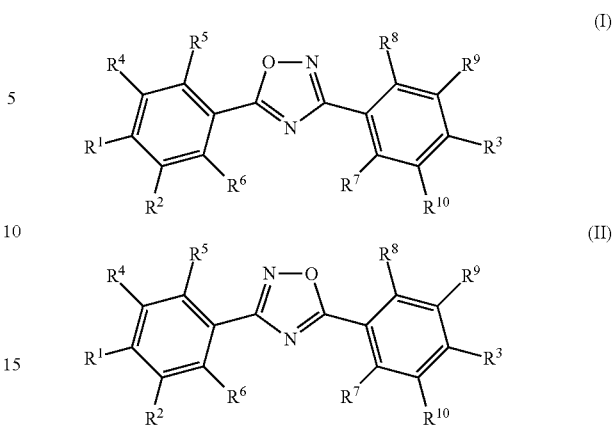

wherein: $R^1$ and $R^4$ are each independently hydrogen, substituted or unsubstituted $C_1$-$C_6$ alkyl, or substituted or unsubstituted $C_1$-$C_6$ alkoxy, wherein at least one of $R^1$ and $R^4$ is not hydrogen;

$R^2$ is $C_1$-$C_4$ haloalkyl, cyano or hydrogen;

$R^3$, $R^9$ and $R^{19}$ are each independently hydrogen, halo, hydroxy, substituted or unsubstituted amino, substituted or unsubstituted sulfonyl, substituted or unsubstituted hydrocarbyl, wherein at least one of $R^3$, $R^9$ and $R^{19}$ is not hydrogen; and $R^5$, $R^6$, $R^7$ and $R^8$ are each independently hydrogen, halo, hydroxy, substituted or unsubstituted $C_1$-$C_6$ alkyl, or substituted or unsubstituted $C_1$-$C_6$ alkoxy, and wherein $R^3$ is not —$CH_2OH$ when $R^1$ is —$OCH_2CH_2F$ and $R^2$ is —$CF_3$.

In other aspects, the present invention is directed to compounds having a structure of Formula I or II that are radiolabeled with a radioactive isotope.

In further aspects, the present invention is directed to pharmaceutical compositions comprising a radiolabeled compound of Formula I or II, wherein the compound of Formula I or II comprises at least one synthetic radioactive isotope.

Additional aspects of the present invention include methods of diagnosing or monitoring an S1P1 associated disease, disorder or condition in a mammal comprising administering a composition comprising a radiolabeled compound of Formula I or II to the mammal and detecting the compound in the mammal.

In some aspects, the present invention is also directed to methods of quantifying S1P1 expression in a mammal comprising administering a composition comprising a radiolabeled compound of Formula I or II to the mammal and detecting the compound in the mammal.

In still further aspects, the present invention is directed to methods of treating an S1P1 associated disease, disorder, or condition in a subject in need thereof, comprising: administering to the subject a pharmaceutical composition comprising a therapeutically effective amount of an S1P1 modulating agent comprising any compound described herein, and inhibiting, slowing the progress of, or limiting the development of the S1P1 associated disease, disorder, or condition Other objects and features will be in part apparent and in part pointed out hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 Representative in vitro autoradiographic images of brain sections from control or blocking condition using [$^{18}$F]12a.

Corresponding reference characters indicate corresponding parts throughout the drawings.

Figure 1:
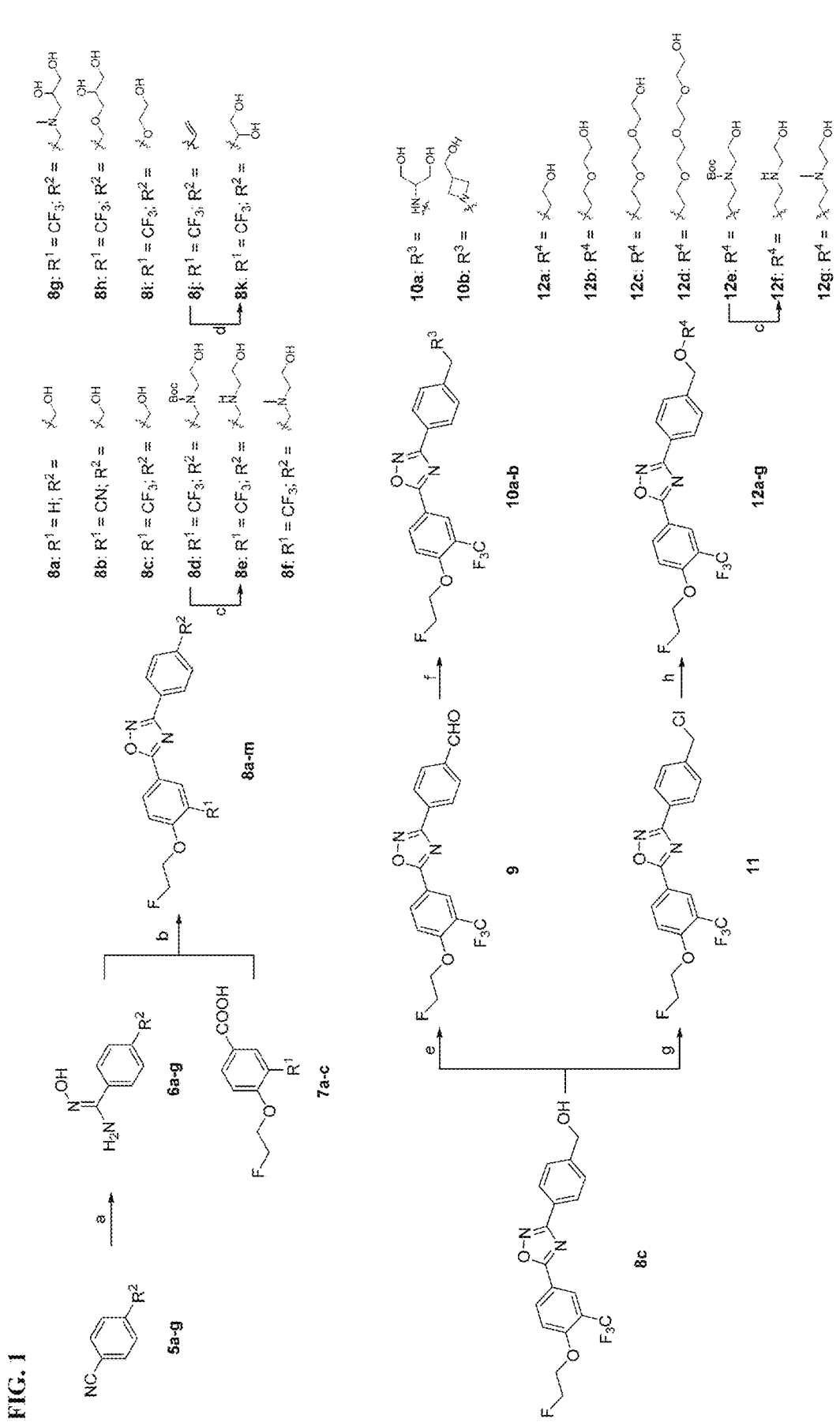
FIG. 1. General synthesis of compounds 6a-g, 8a-m, 9, 11, 10a-b, and 12a-g. Reagents and conditions: (a) hydroxylammonium chloride, NaHCO$_3$, methanol, reflux; (b) TBTU, HOBt, DIPEA, DMF, RT-120° C.; (c) 4.0 M HCl in dioxane, RT; (d) 4-methylmorpholine N-oxide, OsO$_4$, THF, H$_2$O, overnight; (e) oxalyl chloride, DMSO, CH$_2$Cl$_2$, triethylamine, −78° C.-RT; (f) NaBH$_3$CN, amines, acetic acid, methanol, RT; (g) cyanuric chloride, DMF, CH$_2$Cl$_2$, RT; (h) NaH, alcohols, THF, reflux.

Those of skill in the art will understand that the drawings, described below, are for illustrative purposes only. The drawings are not intended to limit the scope of the present teachings in any way

DETAILED DESCRIPTION OF THE INVENTION

The present invention relates to various compounds, compositions and methods that are useful for monitoring expression of sphingosine-1-phosphate (S1P) receptors in tissue. To this end, various compounds having a high affinity for S1P receptors are provided herein. These compounds can be, in some embodiments, labeled with a radiolabel (e.g., a radioisotope) and be used alongside molecular imaging techniques to visualize S1P expression in tissue (e.g., in a subject). Also provided are methods of monitoring S1P1 associated diseases, disorders, or conditions by monitoring S1P expression in a subject. The present invention further includes methods of tracking and/or monitoring the effectiveness of a certain therapy or treatment for an S1P1 associated disease, disorder, or condition. Still further, the present invention provides for methods of treating S1P1 associated diseases, disorders, or conditions by administering a compound having a high affinity for S1P1.

The present invention is based, at least in part, on the discovery that newly synthesized compounds have high affinity and selectivity for sphingosine-1-phosphate receptors (S1P), particularly S1P1. Compounds were radiolabeled with F-18 for in vivo evaluation as Positron Emission Tomography (PET) radiotracers. In vivo microPET, ex-vivo biodistribution, ex-vivo autoradiography studies were performed in different disease animal models: Experimental autoimmune encephalomyelitis (EAE) rat model of multiple sclerosis, and Lipopolysaccharides (LPS) acute induced inflammation mice model and compared to shame control animal. MicroPET studies were performed for the brains of nonhuman primates to show the capability of these radiolabeled compounds in penetrating the blood brain barrier. Additional immunochemistry studies on the corresponding tissues confirmed the pathological changes.

Based the results of these studies, quantification of the expression of S1P was accomplished. The new radiolabeled compounds (e.g., $^{18}$F-labeled PET tracers) can be used as radiopharmaceuticals for quantifying S1P1 in vivo for using in diagnosis, monitoring the progress of disease and response to therapeutic for MS and other inflammation diseases via S1P inhibition strategies. The compounds can be used as therapeutic drugs for treating different inflammatory diseases including neurological diseases, psychological disorders, cardiovascular diseases atherosclerosis, cancer and other inflammatory relative diseases. Using microPET, ex-vivo biodistribution, autoradiography, and immunohistochemistry methods, it was found that these radiolabeled compounds were able to diagnose and monitor the progress of liver injury and MS.

Experiments described herein also demonstrate quantifying the changes of S1P receptors by using an S1P receptor specific radioligand with PET. This also provides a methodology for assessing the therapeutic efficacy of treating MS and other inflammation diseases using S1P inhibition strategy.

S1P receptor plays a key role for inflammatory disease. Since the radiotracer is able to quantify the change of the S1P receptor, it provides a noninvasive methodology to quantify the expression of S1P receptor in vivo response to the progression of inflammatory diseases.

Thus, the radiotracers described herein can be used as a unique tool to assess the therapeutic response for treating inflammatory diseases using S1P inhibition. The compounds as described herein also can be therapeutic drugs for treating inflammation diseases. In both cases, the compounds and radiotracers can be used to monitor, diagnose and/or treat various neuroinflammatory diseases, pulmonary infection diseases, and vascular injury relative diseases that are associated with changes of S1P receptor levels.

Current methods and compositions for use in radiotracers require in vivo phosphorylation and have specific metabolic properties (e.g., need to retain radiolabeled isotope, rapid de-fluorination), and are not specific for S1P1. The compounds and compositions as described herein exhibit certain advantages over current compositions and methods. For example, various compounds have high specificity for S1P1 over other S1P receptors, have low metabolism, are not as subject to metabolic loss of the radionuclide, do not require in vivo phosphorylation, and have been validated in animal models of inflammation and MS.

Compounds

Various compounds described herein include an S1P1 modulating agent. As defined herein, an S1P1 modulating agent is a compound that binds to and/or modulates S1P1 surface expression on a cell.

The S1P1 modulating agent can comprise a compound having the structure of Formula (I) or (II), as defined herein. In addition, the modulating agent can comprise a benzoxazole or an oxadiazole core.

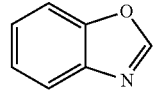
benzoxazole

oxadiazole

Various compounds useful for targeting/modulating the S1P receptor, particularly S1P1, include compounds of Formula (I) or Formula (II), or a pharmaceutically acceptable salt or a prodrug thereof:

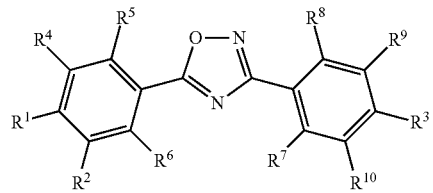

(I)

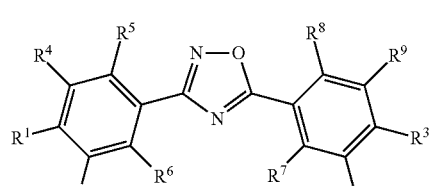

(II)

wherein $R^1$ and $R^4$ are each independently hydrogen, substituted or unsubstituted $C_1$-$C_6$ alkyl, or substituted or unsubstituted $C_1$-$C_6$ alkoxy, wherein at least one of $R^1$ and $R^4$ is not hydrogen;

$R^2$ is $C_1$-$C_4$ haloalkyl, cyano or hydrogen (particularly, $C_1$-$C_4$ haloalkyl or cyano);

$R^3$, $R^9$ and $R^{10}$ are each independently hydrogen, halo, hydroxy, substituted or unsubstituted amino, substituted or unsubstituted sulfonyl, substituted or unsubstituted hydrocarbyl, wherein at least one of $R^3$, $R^9$ and $R^{10}$ is not hydrogen;

$R^5$, $R^6$, $R^7$ and $R^8$ are each independently hydrogen, halo, hydroxy, substituted or unsubstituted $C_1$-$C_6$ alkyl, or substituted or unsubstituted $C_1$-$C_6$ alkoxy, and, and wherein $R^3$ is not —$CH_2OH$ when $R^1$ is —$OCH_2CH_2F$ and $R^2$ is —$CF_3$.

In various embodiments, $R^1$ or $R^4$ is substituted or unsubstituted $C_1$-$C_6$ alkoxy. In additional embodiments, $R^1$ or $R^4$ is a halo-substituted $C_1$-$C_6$ alkoxy. For example, $R^1$ or $R^4$ can be a $C_1$-$C_6$ fluoroalkoxy (e.g., —$OCH_2CH_2F$).

In some embodiments, $R^4$ is hydrogen or a $C_1$-$C_6$ alkyl. In certain embodiments, $R^4$ is hydrogen.

In various embodiments, $R^2$ is —$CF_3$.

In various embodiments, at least one of $R^3$, $R^9$ or $R^{10}$ is a substituted or unsubstituted $C_1$-$C_6$ alkyl or a substituted or unsubstituted $C_1$-$C_6$ alkoxy. For example, in various embodiments, at least one of $R^3$, $R^9$, or $R^{10}$ is —$CH_2$ ($OCH_2CH_2)_n$OH or —($OCH_2CH_2)_n$OH, where n is from 0 to 10, from 0 to 8, from 0 to 6, from 0 to 4, or from 0 to 2. In certain embodiments, n is from 1 to 10, from 1 to 8, from 1 to 6, from 1 to 4. For example, n can be from 1 to 3 or from 1 to 2.

In various embodiments, at least one of $R^3$, $R^9$ or $R^{10}$ is —$CH_2R^{11}$ where $R^{11}$ is substituted alkoxy, substituted or unsubstituted amino, a substituted or unsubstituted amido, an azide, a substituted or unsubstituted sulfonyl, a substituted sulfur-containing ring, or a substituted or unsubstituted nitrogen-containing ring In various embodiments, at least one of $R^3$, $R^9$ or $R^{10}$ is

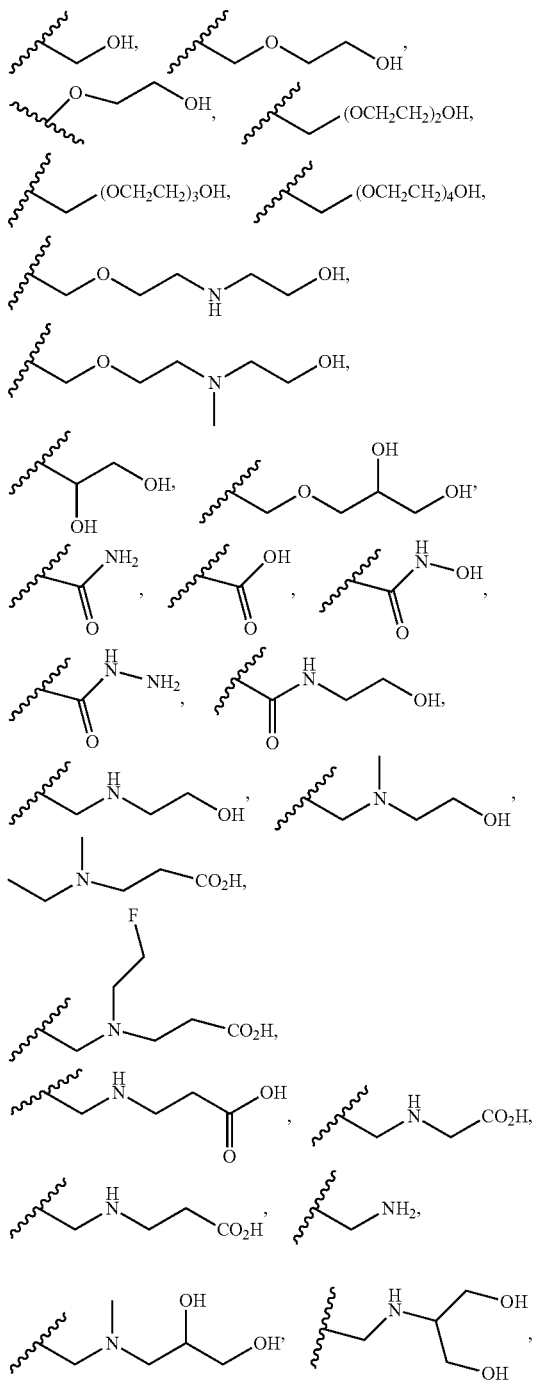

In some embodiments, at least one of $R^3$, $R^9$ or $R^{10}$ is —CH(OH)$CH_2$OH.

In certain embodiments, $R^3$ is one of the aforementioned moieties. In these and other embodiments, $R^9$, and $R^{10}$ are each independently hydrogen.

In various embodiments, $R^5$, $R^6$, $R^7$, $R^8$, $R^9$, and $R^{10}$ are each independently hydrogen, halo, hydroxy, $C_1$-$C_6$ alkyl, or $C_1$-$C_6$ alkoxy. In some embodiments, $R^5$, $R^6$, $R^7$, $R^8$, $R^9$, and $R^{10}$ are each independently hydrogen or a $C_1$-$C_6$ alkyl. For example, $R^5$, $R^6$, $R^7$, $R^8$, $R^9$, and $R^{10}$ can each independently be hydrogen.

As mentioned, the compounds of the present invention can have the structure of Formula I or Formula II. In some embodiments, the compound has the structure of Formula I or a pharmaceutically acceptable salt or a prodrug thereof. In other embodiments, the compound has the structure of Formula II or a pharmaceutically acceptable salt or a prodrug thereof.

When the compound has the structure of Formula I, it can have a structure selected from the group consisting of:

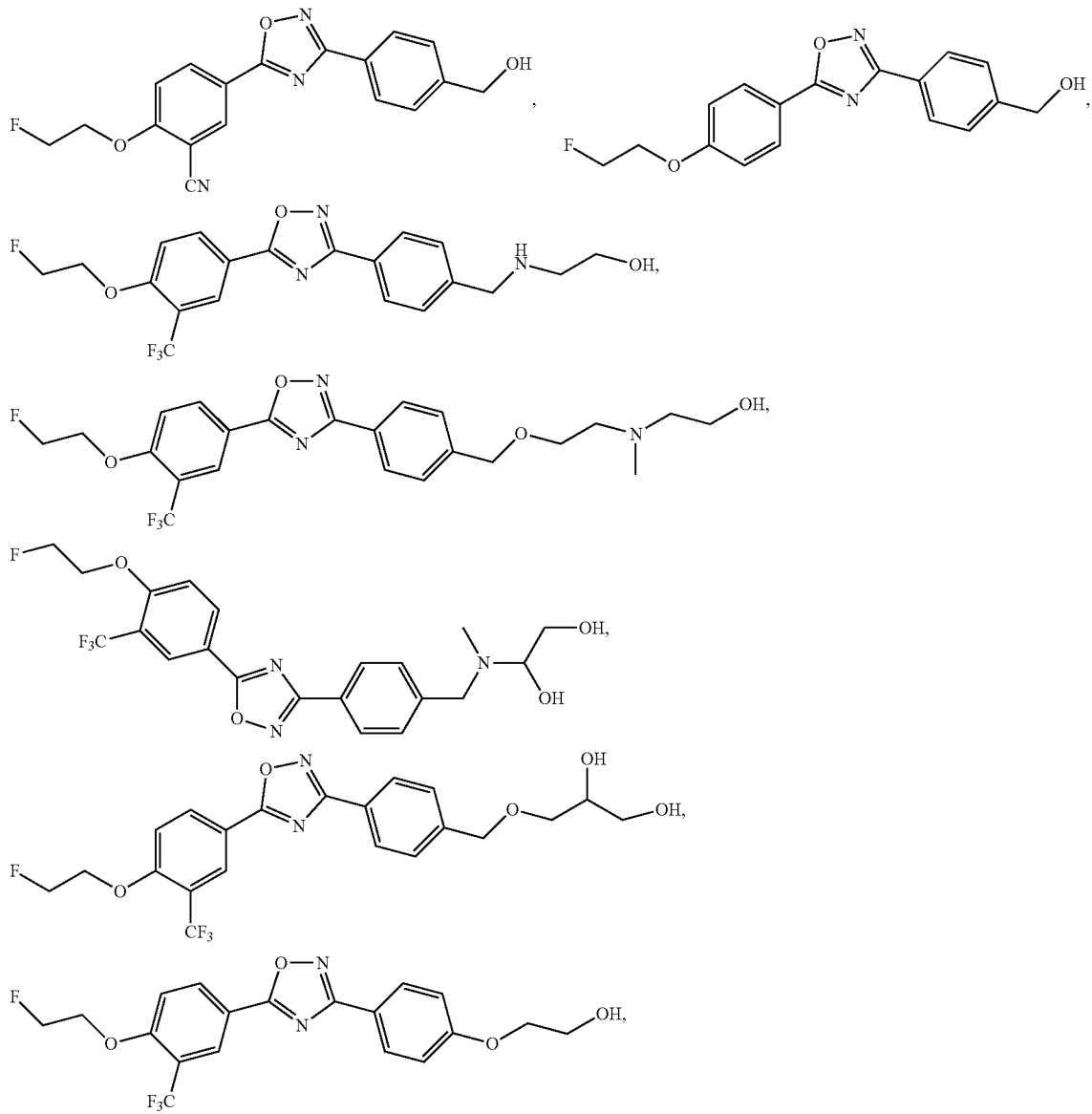
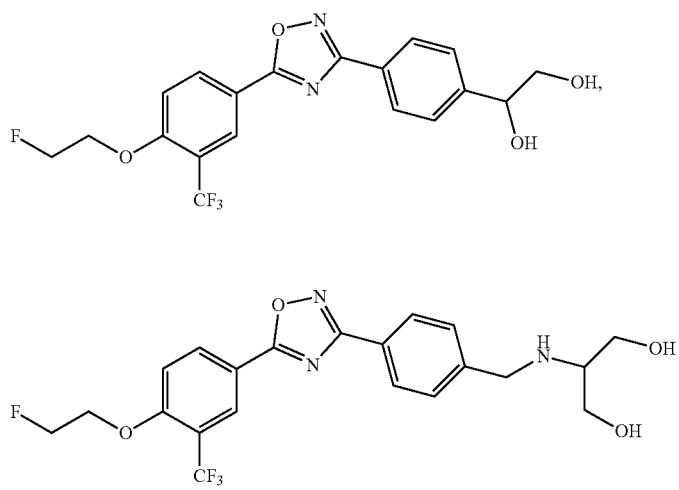

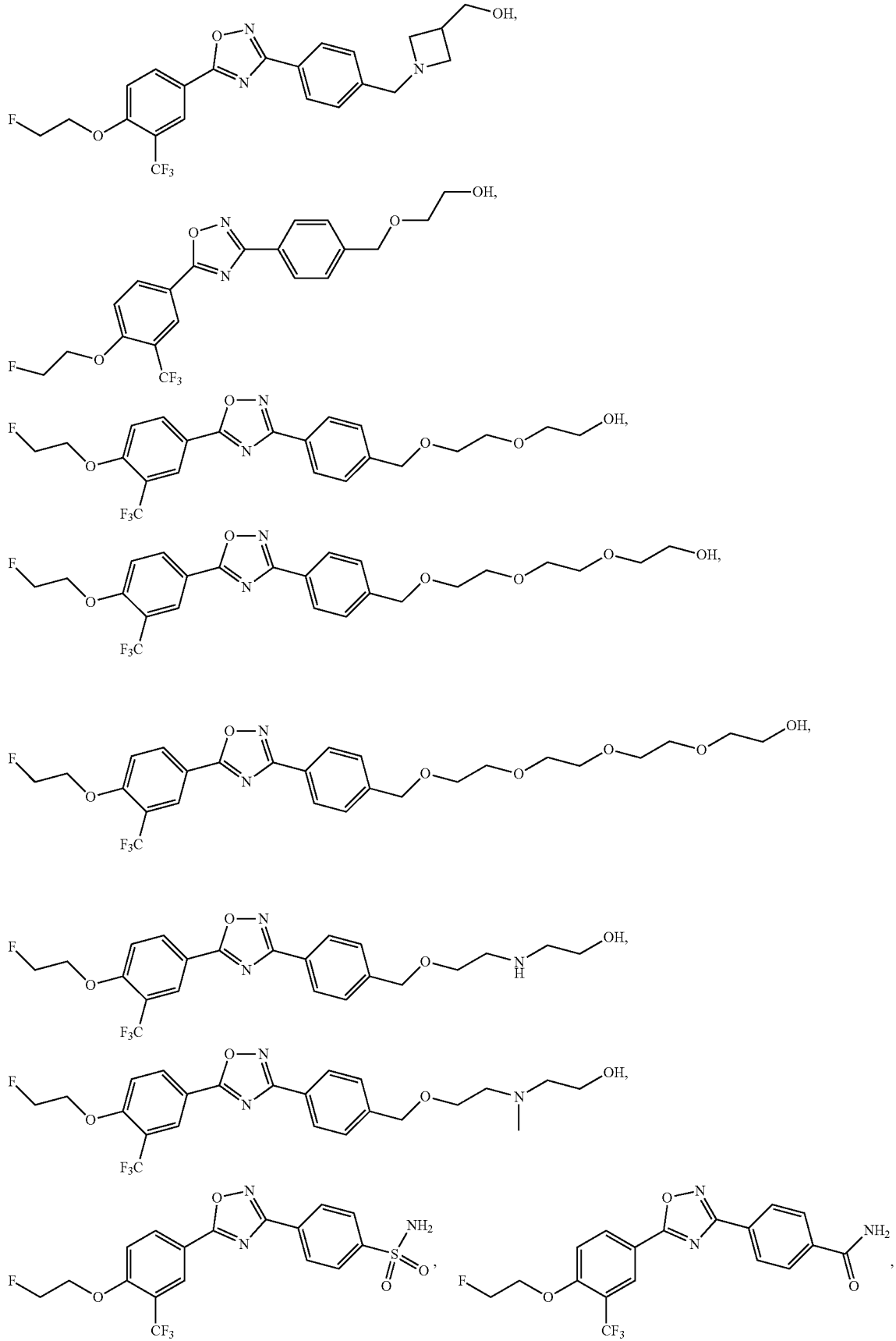

-continued
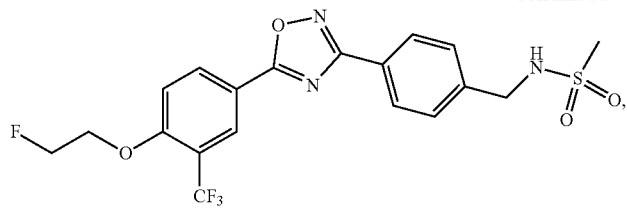
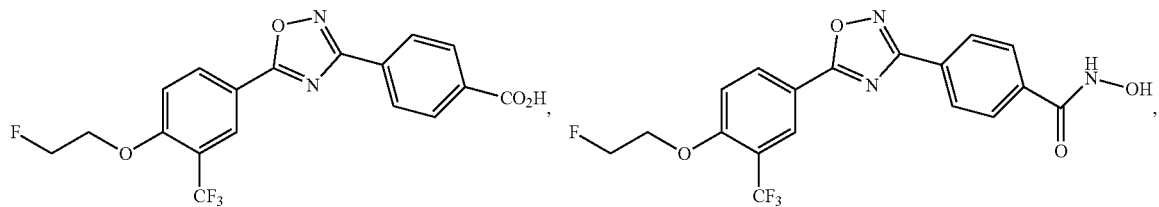
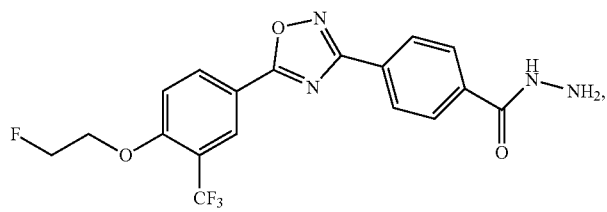
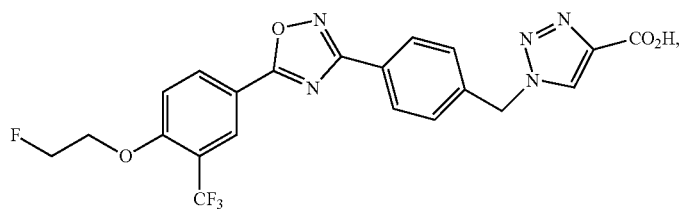
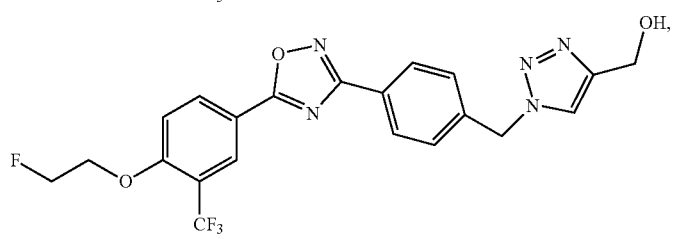
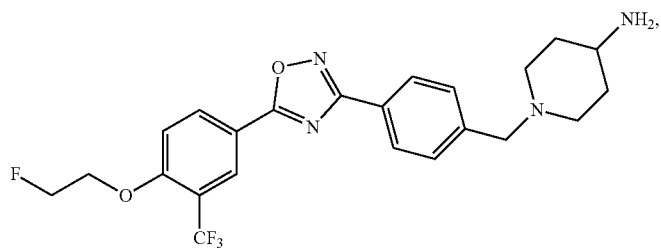
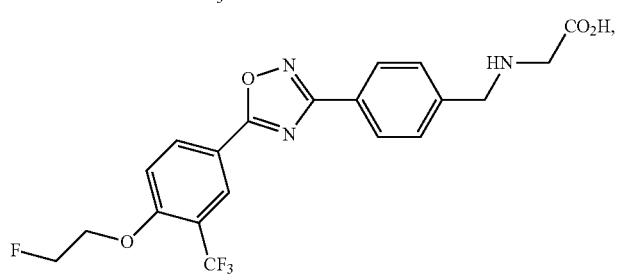

-continued
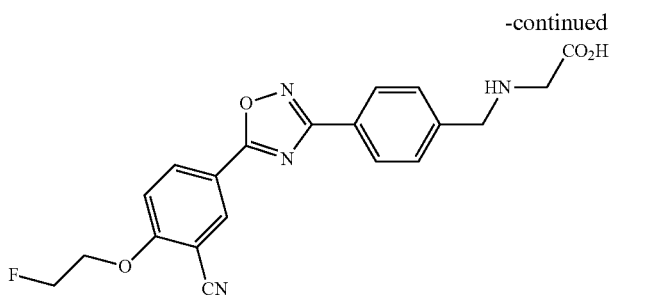
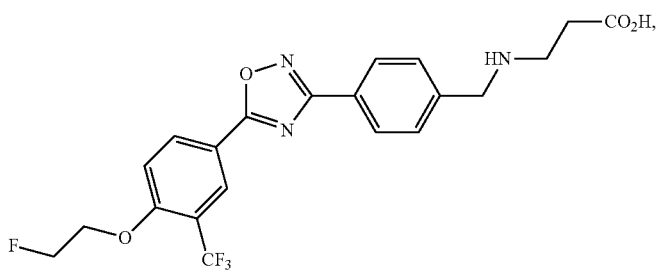
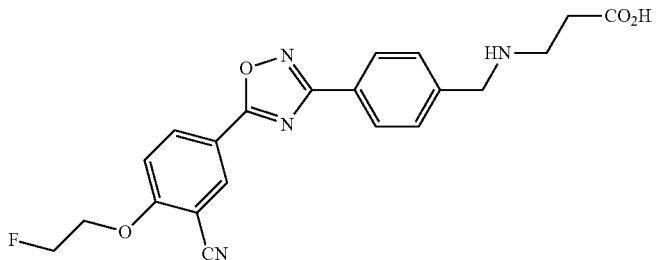
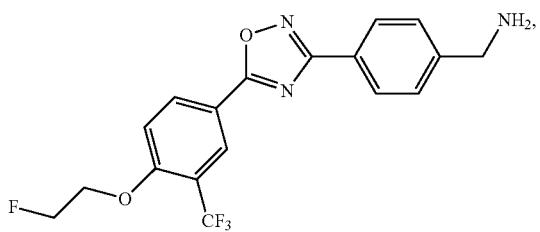
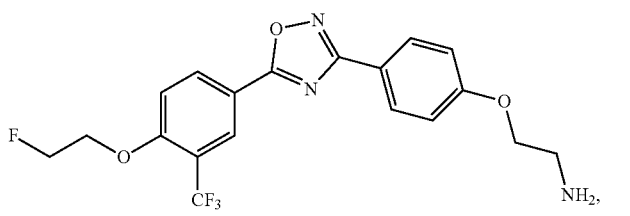
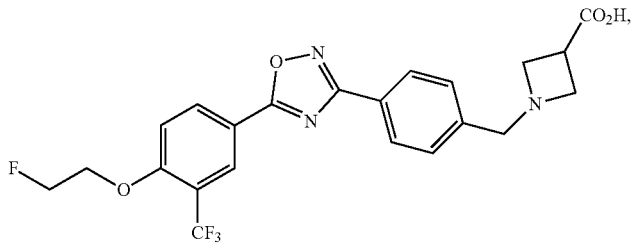
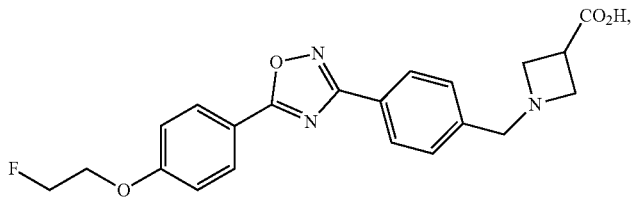

-continued
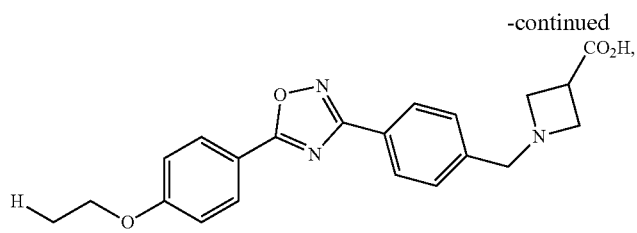
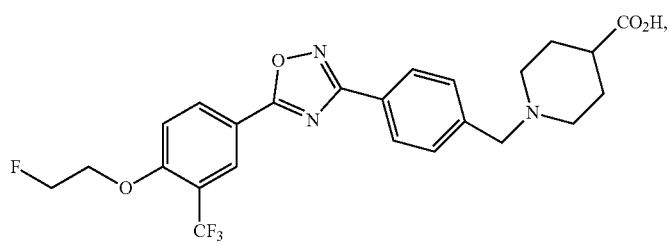
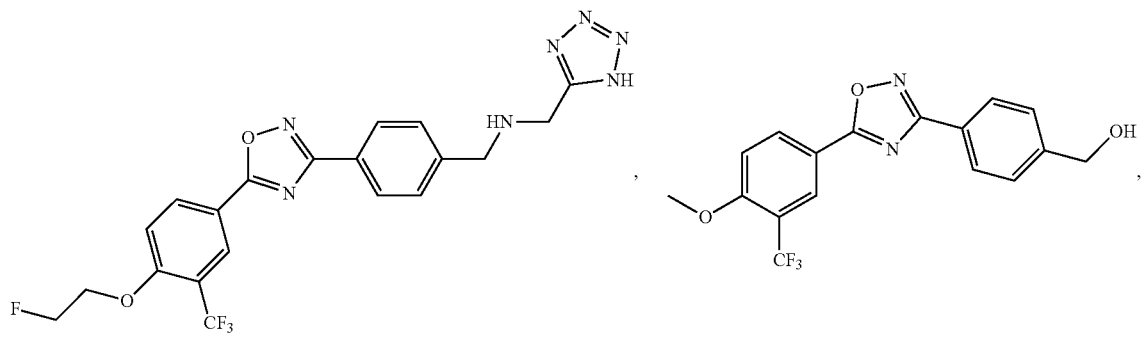
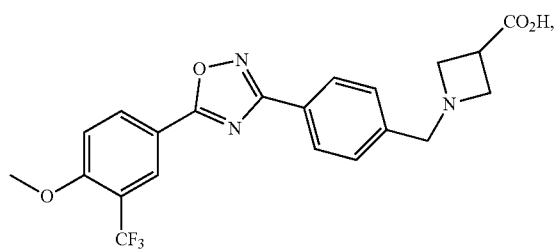
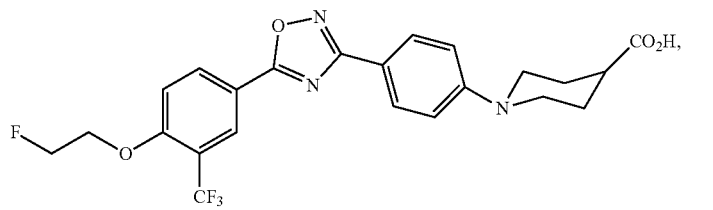
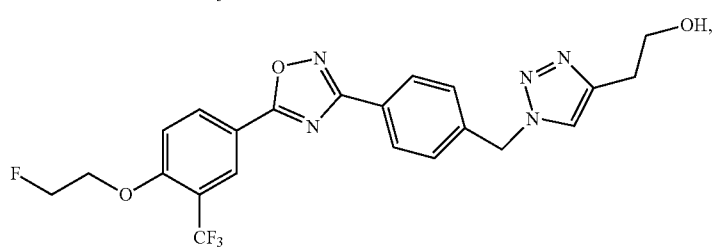

-continued
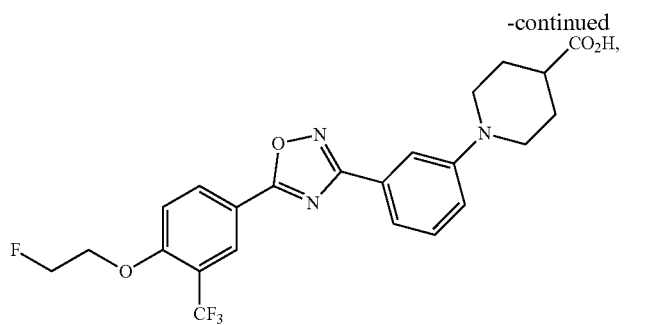
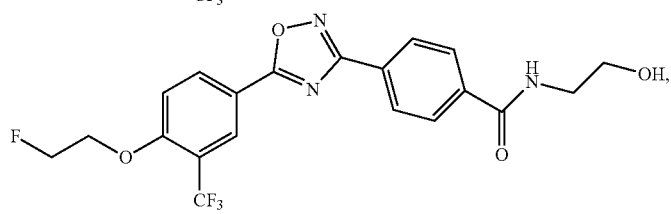
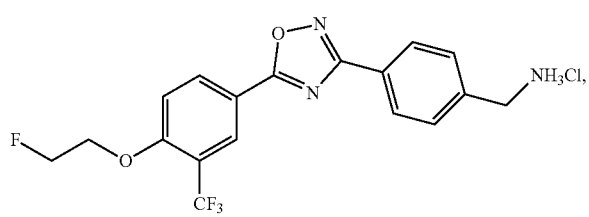
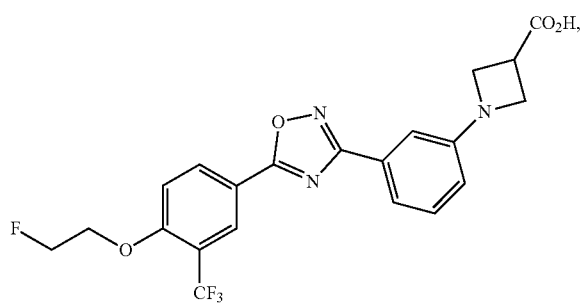
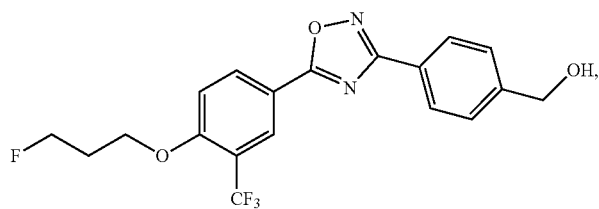
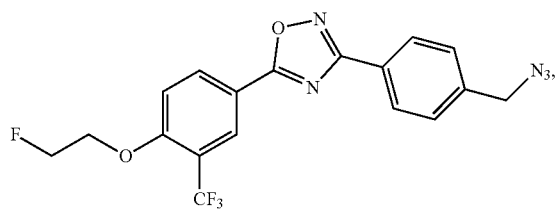 [SMILES: [N-]=[N+]=NCc1ccc(-c2noc(-c3ccc(OCCF)c(C(F)(F)F)c3)n2)cc1]
pharmaceutically acceptable salts thereof, prodrugs thereof, and mixtures thereof.

As another example, the compound (e.g., S1P1 modulating agent) can comprise:

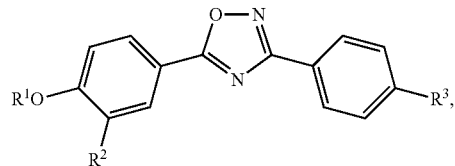

wherein

| R¹ | R² | R³ |
|---|---|---|
| FCH₂CH₂ | CF₃ | ⌇⌇⌇∕∖OH |
| FCH₂CH₂ | CN | ⌇⌇⌇∕∖OH |
| FCH₂CH₂ | H | ⌇⌇⌇∕∖OH |
| FCH₂CH₂ | CF₃ | ⌇⌇⌇∕∖O∕∖OH |
| FCH₂CH₂ | CF₃ | ⌇⌇⌇∕O∕∖OH |
| FCH₂CH₂ | CF₃ | ⌇⌇⌇∕∖(OCH₂CH₂)₂OH |
| FCH₂CH₂ | CF₃ | ⌇⌇⌇∕∖(OCH₂CH₂)₃OH |
| FCH₂CH₂ | CF₃ | ⌇⌇⌇∕∖(OCH₂CH₂)₄OH |
| F∕∖O∕∖∕⌇⌇⌇ | CF₃ | ⌇⌇⌇∕∖OH |
| FCH₂CH₂ | CF₃ | ⌇⌇⌇∕∖NH∕∖OH |
| FCH₂CH₂ | CF₃ | ⌇⌇⌇∕∖N(CH₃)∕∖OH |
| FCH₂CH₂ | CF₃ | ⌇⌇⌇∕∖O∕∖NH∕∖OH |

-continued
| R¹ | R² | R³ |
|---|---|---|
| FCH₂CH₂ | CF₃ | 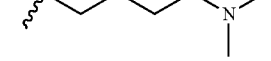 |
| FCH₂CH₂ | CF₃ |  |
| FCH₂CH₂ | CF₃ | 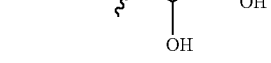 |
| FCH₂CH₂ | CF₃ | 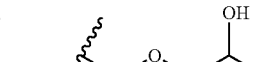 |
| FCH₂CH₂ | CF₃ | 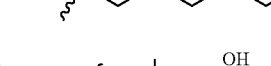 |
| FCH₂CH₂ | CF₃ | 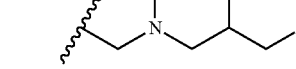 |
| FCH₂CH₂ | CF₃ | 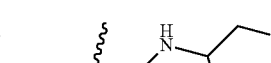 |
| FCH₂CH₂ | CF₃ |  |
pharmaceutically acceptable salts thereof, prodrugs thereof, and combinations thereof.
As another example, the compound (e.g., S1P1 modulating agent) can comprise:
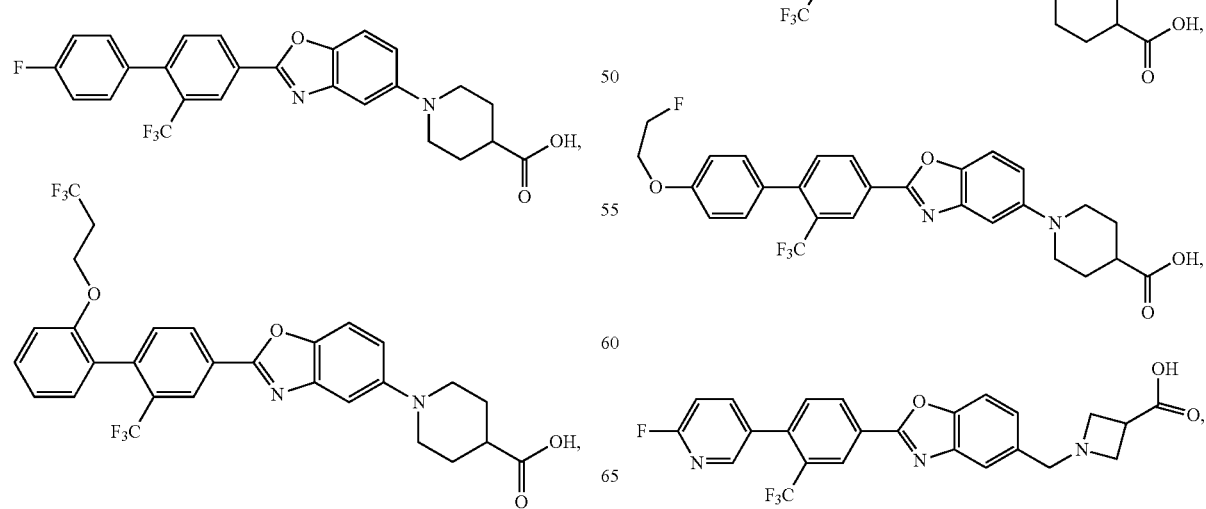

25
-continued
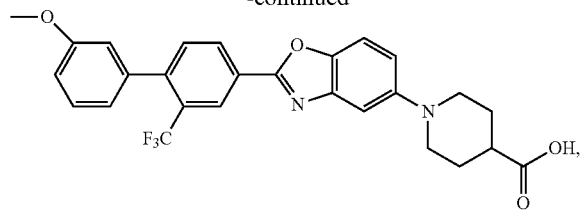
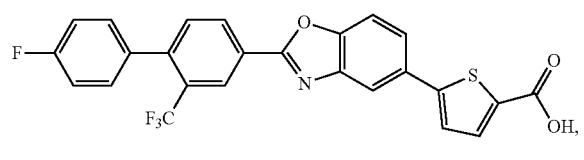
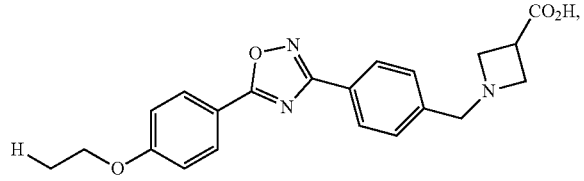
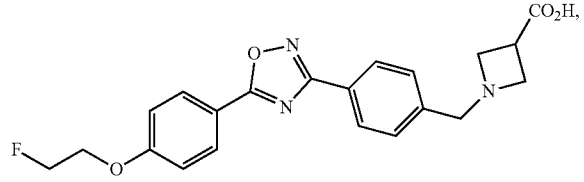
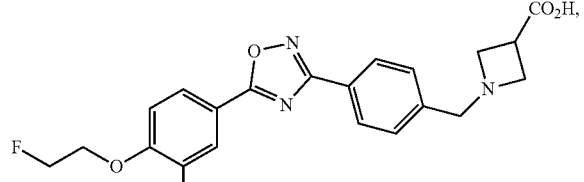
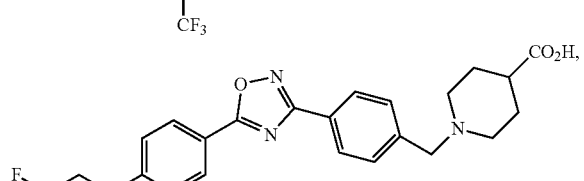
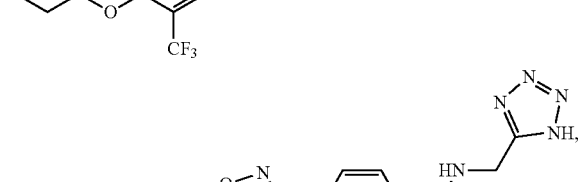
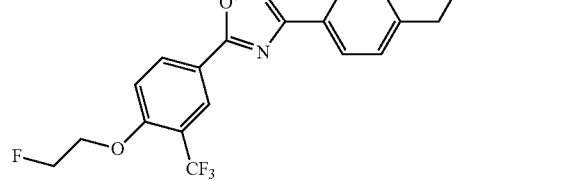
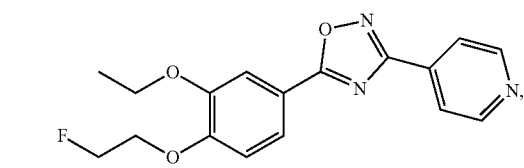
26
-continued
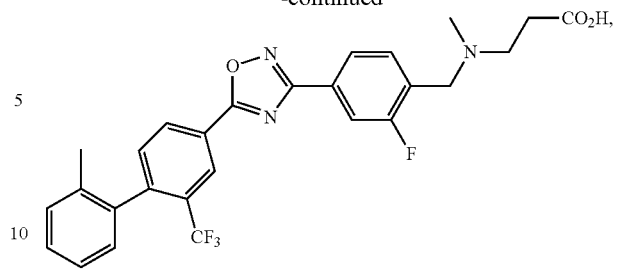
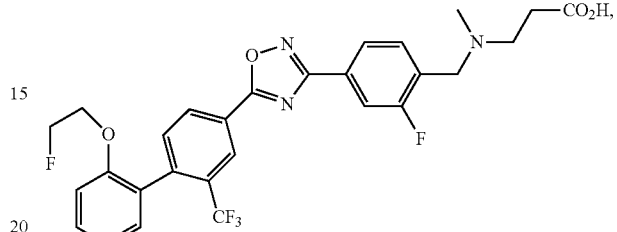
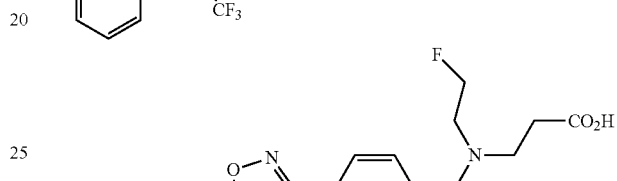
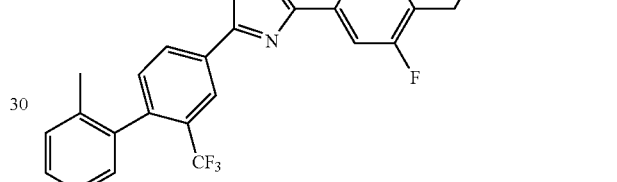
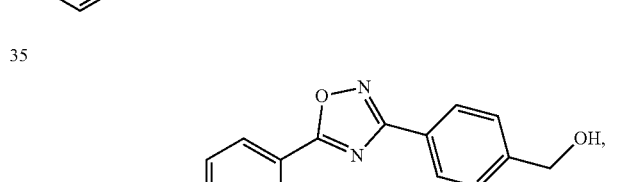
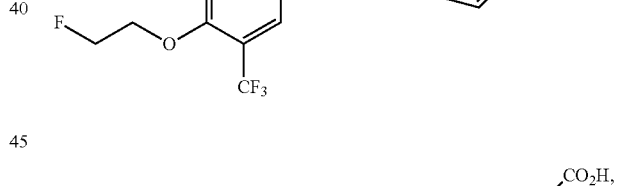
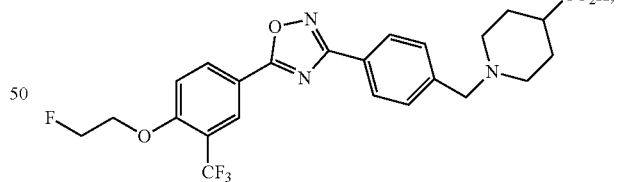
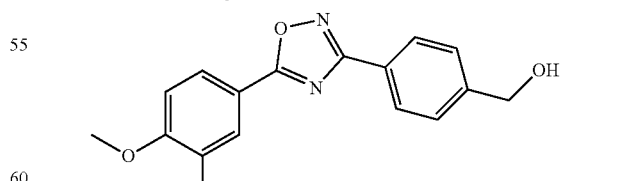
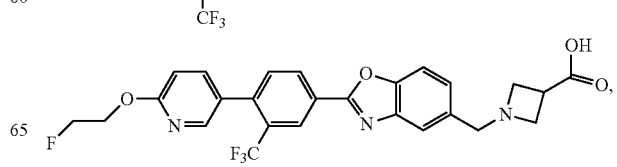

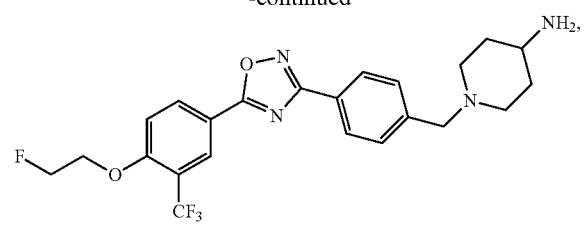

-continued
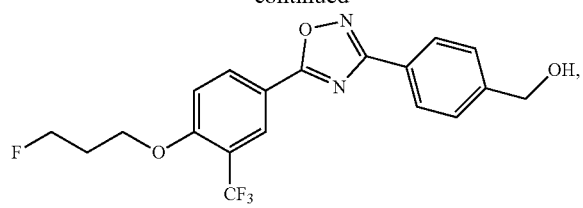
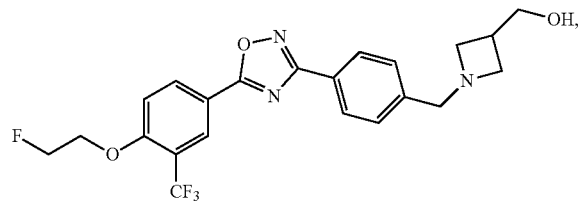
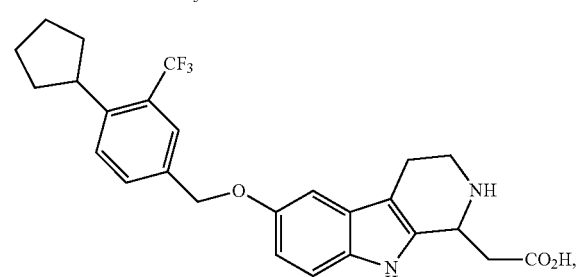
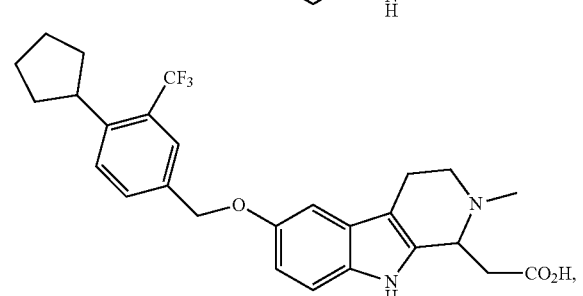
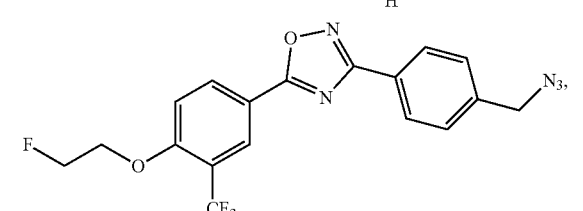
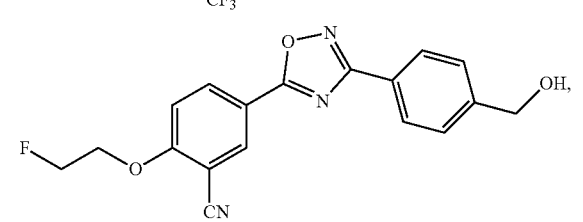
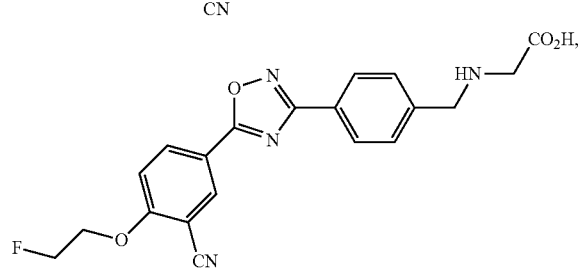
-continued
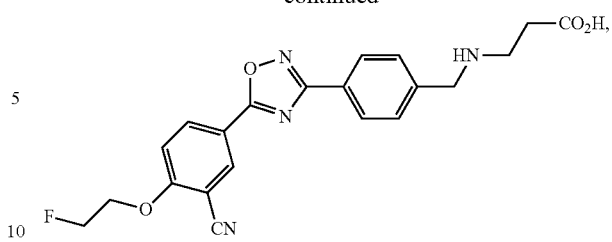
pharmaceutically acceptable salts thereof, prodrugs thereof, and combinations thereof.
In some embodiments, the compound (e.g., S1P1 modulating agent) can comprise:
pharmaceutically acceptable salts thereof, prodrugs thereof, and combinations thereof.
In some embodiments, the compound (e.g., S1P1 modulating agent) can comprise:

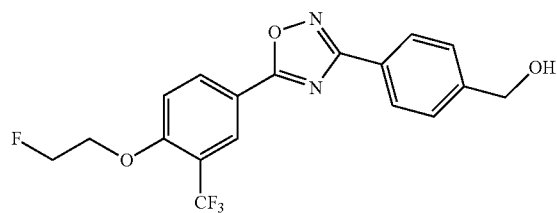
,
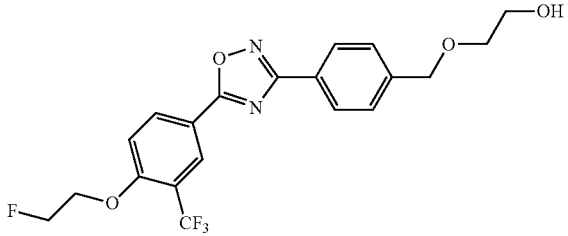
,
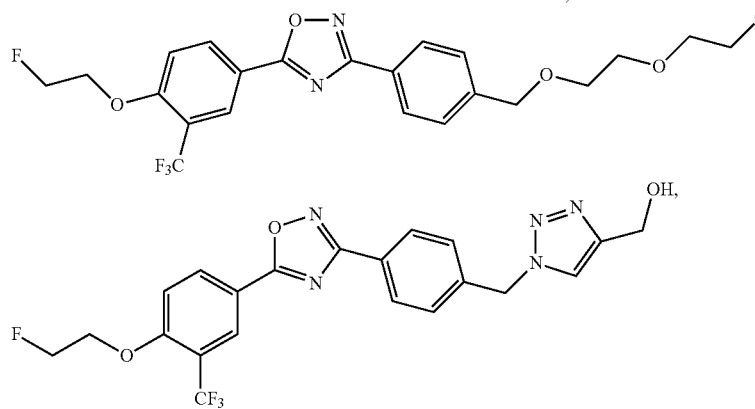

pharmaceutically acceptable salts thereof, prodrugs thereof, and combinations thereof. In various cases the compound (e.g., S1P1 modulating agent) has a high binding affinity and selectivity for the S1P1 over other S1P receptors (e.g., S1P2-S1P5). In some cases, the compound (e.g., S1P1 modulating agent) binds to the receptor with high affinity and triggers internalization of the receptor into a cell, thereby reducing S1P1 surface expression on the cell. As will be described herein, this reduction in S1P1 surface expression can be useful in the treatment of various S1P1 associated diseases, disorders, or conditions.

Methods of determining the affinity of a compound for its receptor are generally known in the art. One way to measure affinity is use of a general competition binding assay. Descriptions of these binding assays, including methods of measuring the affinity of a compound for a S1P receptor are available in the art, for example in Rosenberg et al., (2015) "A practical process for the preparation of [(32)P]S1P and binding assay for S1P receptor ligands" *Applied Radiation and Isotopes: Including Data, Instrumentation and Methods for use in Agriculture, Industry and Medicine.* 102:5-9, which is incorporated herein by reference.

In some embodiments, the compounds (e.g., modulating agents) of the present invention compete with S1P binding to a S1P receptor with an $IC_{50}$ of less than 100 nM, less than 75 nM, less than 50 nM, less than 25 nM, or less than 15 nM. For example, the compounds can have an $IC_{50}$ of from about 1 nM to about 15 nM, from about 1 nM to about 10 nM, from about 1 nM to about 5 nM or from about 5 nM to about 10 nM. One advantage of this invention is the higher affinity some of the compounds have for the S1P1 receptor over the other four subtypes. In some embodiments, the compounds (e.g., modulating agents) of the present invention have a high affinity (e.g., less than 100 nM, less than 75 nM, less than 50 nM, less than 15 nM) for the S1P1 receptor while having a lower affinity (e.g., >1000 nM) at the other S1P receptors (S1P2-S1P5).

Radiolabel

One embodiment of the present disclosure provides for a radiolabeled compound or composition, or a compound or composition with a radionuclide.

The radiolabeled compound or composition can comprise any compound (e.g., modulating agent) described herein (e.g., a compound of Formula I or II) radiolabeled with a radioactive isotope. References herein to "radiolabeled" include a compound where one or more atoms are replaced or substituted by an atom having an atomic mass or mass number different from the atomic mass or mass number typically found in nature (i.e., naturally occurring). One non-limiting exception is $^{18}F$, which allows detection of a molecule which contains this element without enrichment to a higher degree than what is naturally occurring. Compounds carrying the substituent $^{18}F$ may thus also be referred to as "labeled" or the like. The term radiolabeled may be interchangeably used with "isotopically-labeled", "labeled", "isotopic tracer group", "isotopic marker", "isotopic label", "detectable isotope", "radiotracer, and "radioligand".

In one embodiment, the compound comprises a single radiolabeled group.

Examples of suitable, non-limiting radiolabel groups can include: $^{2}H$ (D or deuterium), $^{3}H$ (T or tritium), $^{11}C$, $^{13}C$, $^{14}C$, $^{64}Cu$, $^{67}Cu$, $^{177}Lu$, $^{13}N$, $^{15}N$, $^{15}O$, $^{17}O$, $^{18}O$, $^{18}F$, $^{89}Sr$, $^{35}S$, $^{153}Sm$, $^{36}Cl$, $^{82}Br$, $^{75}Br$, $^{76}Br$, $^{77}Br$, $^{123}I$, $^{124}I$, $^{125}I$, $^{131}I$, $^{111}In$, $^{67}Ga$, $^{68}Ga$, $^{177}Lu$, 186Re, $^{188}Re$, $^{201}Tl$, $^{99m}Tc$, $^{90}Y$, or $^{89}Zr$. It is to be understood that an isotopically labeled compound needs only to be enriched with a detectable isotope to, or above, the degree which allows detection with a technique suitable for the particular application, e.g., in a detectable compound labeled with $^{11}C$, the carbon-atom of the labeled group of the labeled compound may be constituted by $^{12}C$ or other carbon-isotopes in a fraction of the molecules. The radionuclide that is incorporated in the radiolabeled compounds will depend on the specific application of that radiolabeled compound. For example, "heavy" isotope-labeled compounds (e.g., compounds containing deuterons/heavy hydrogen, heavy nitrogen, heavy oxygen, heavy carbon) can be useful for mass spectrometric and NMR based studies. As another example, for in vitro labeling or in competition assays, compounds that incorporate $^3$H, $^{14}$C, or $^{125}$I can be useful. For in vivo imaging applications $^{11}$C, $^{13}$C, $^{18}$F, $^{19}$F, $^{120}$I, $^{123}$I, $^{131}$I, $^{75}$Br, or $^{76}$Br can generally be useful. In one embodiment, the radiolabel is $^{11}$C. In an alternative embodiment, the radiolabel is $^{14}$C. In a yet further alternative embodiment, the radiolabel is $^{13}$C. In still another alternative embodiment, the radiolabel is $^{18}$F.

In some embodiments, the compounds can be radiolabeled with a synthetic radioactive isotope selected from the group consisting of $^{11}$C, $^{13}$N, $^{15}$O, $^{18}$F, $^{76}$Br, $^{123}$I, and $^{125}$I.

In various embodiments, the radiolabeled compound is selected from the group consisting of:

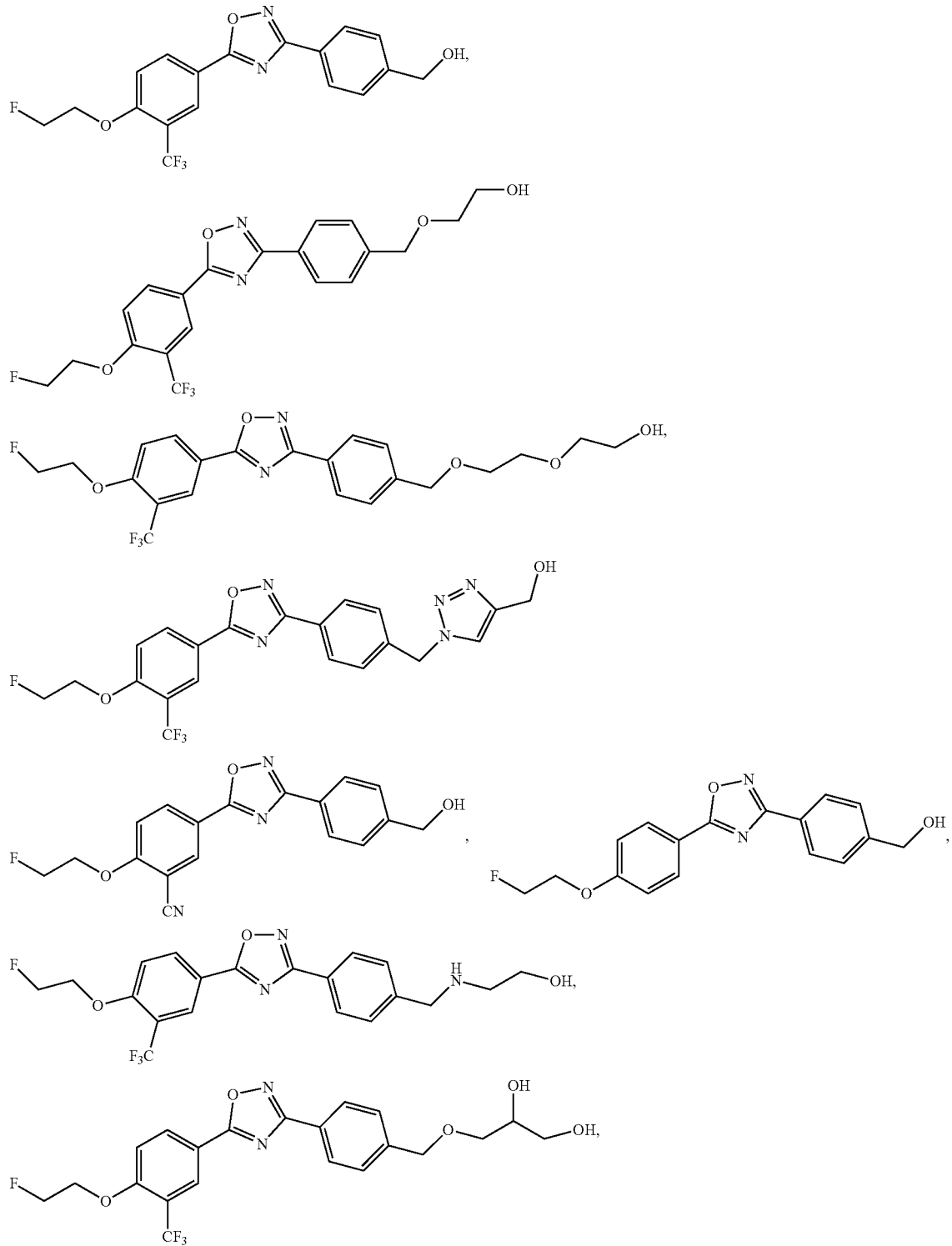

-continued
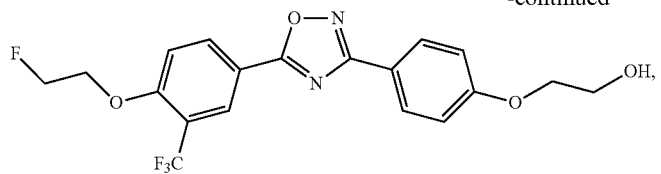
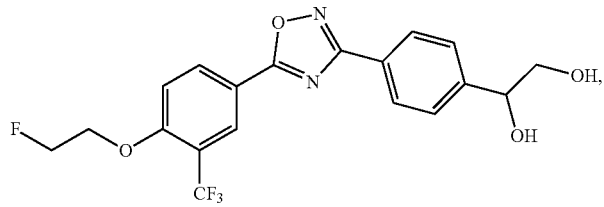
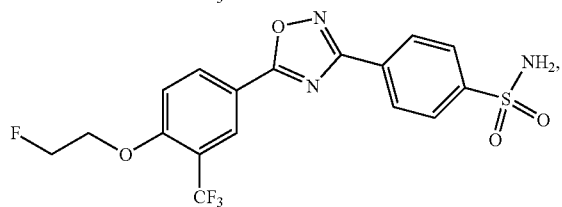
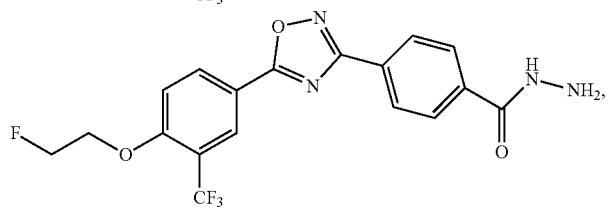
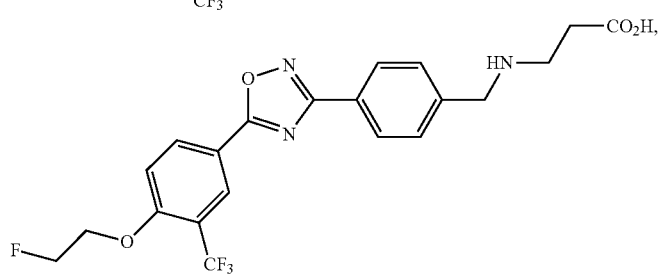
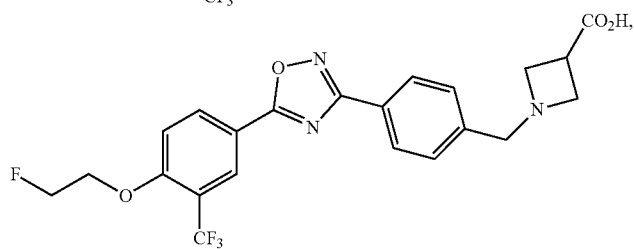
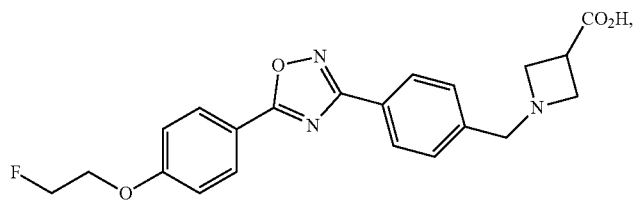
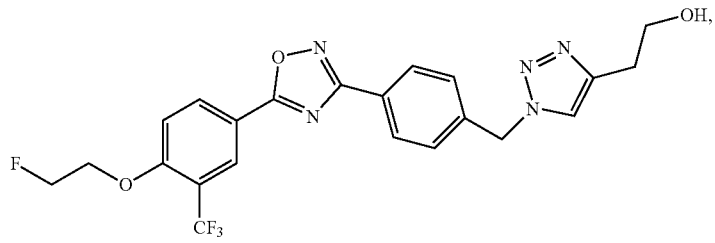

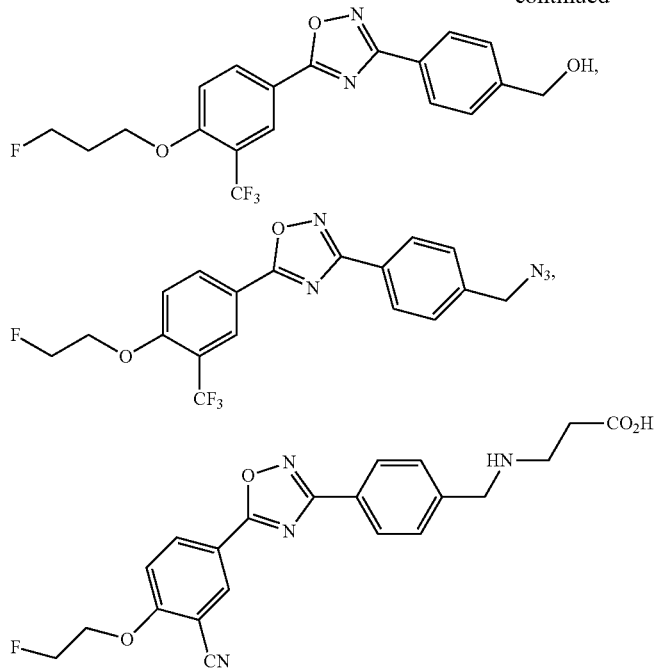
pharmaceutically acceptable salts thereof, prodrugs thereof, mixtures thereof and wherein each compound comprises at least one synthetic radioactive isotope.
In various embodiments, the radiolabeled compound can be selected from the group consisting of:
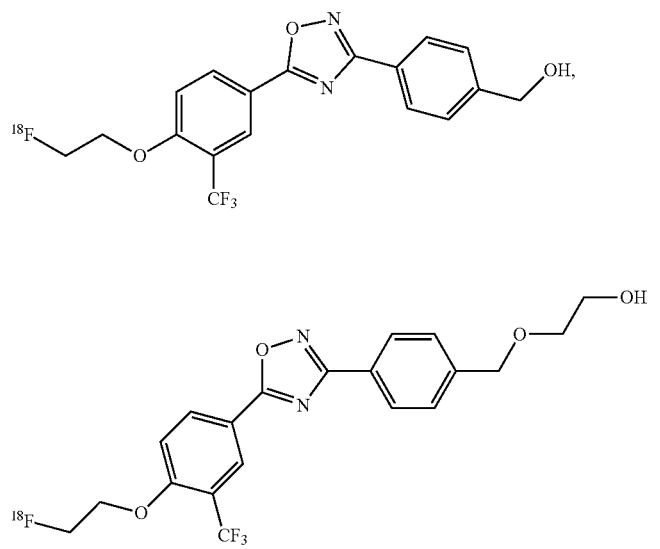
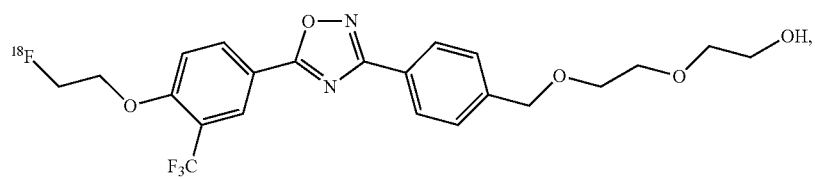

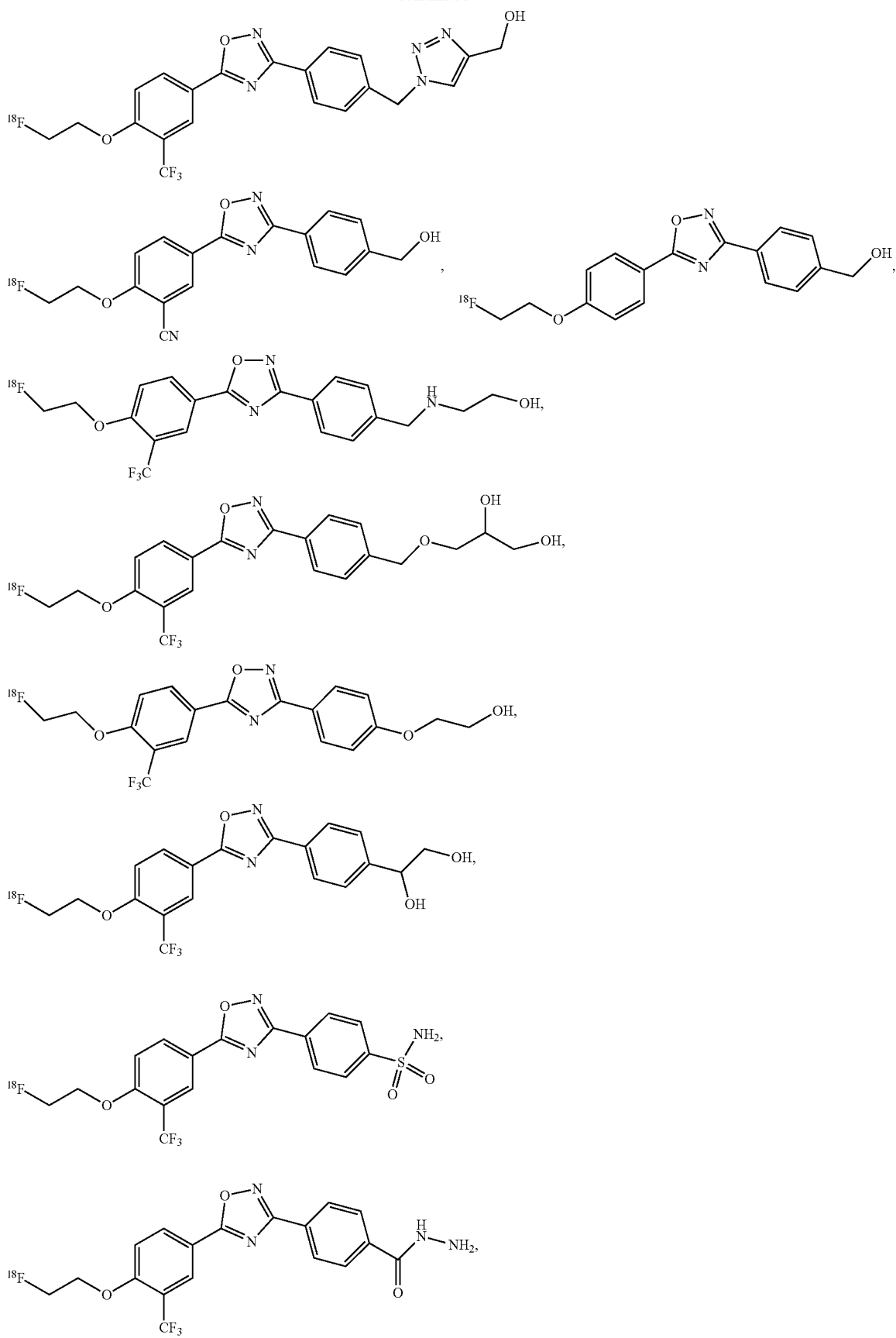

-continued
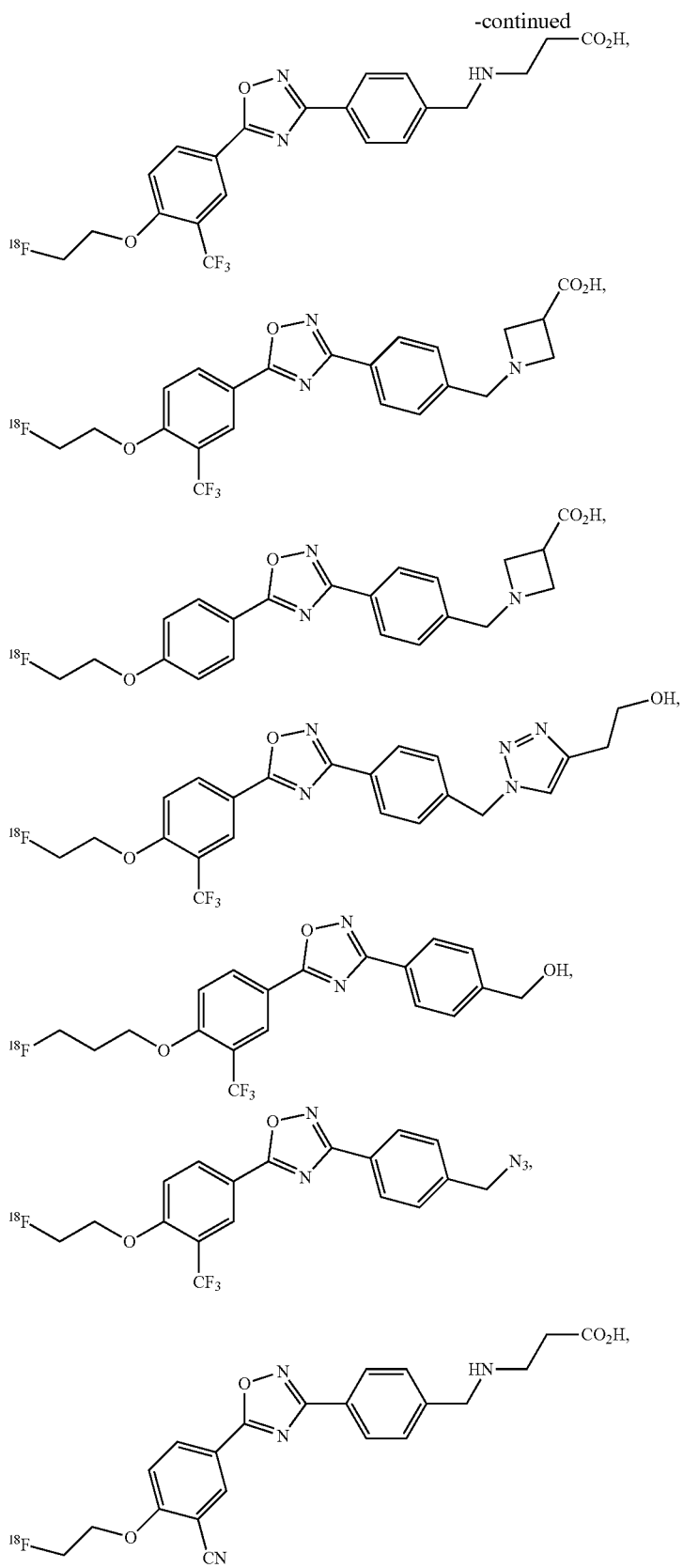
pharmaceutically acceptable salts thereof, prodrugs thereof, and mixtures thereof.
In other embodiments, the radiolabeled compound is selected from the group consisting of:

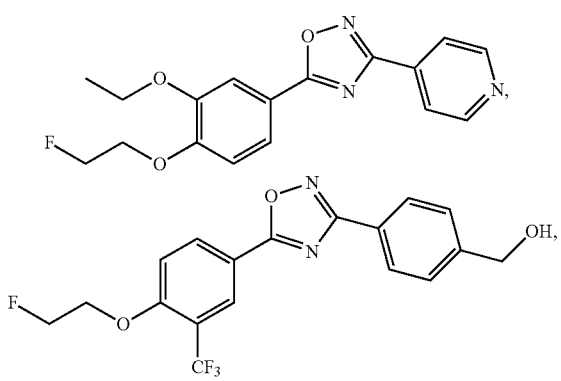

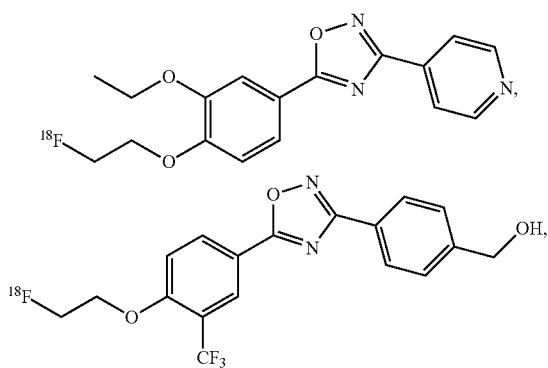

pharmaceutically acceptable salts thereof, prodrugs thereof, and mixtures thereof, wherein the compound contains at least one synthetic radioactive isotope.

For example, the radiolabeled compound can be selected from the group consisting of:

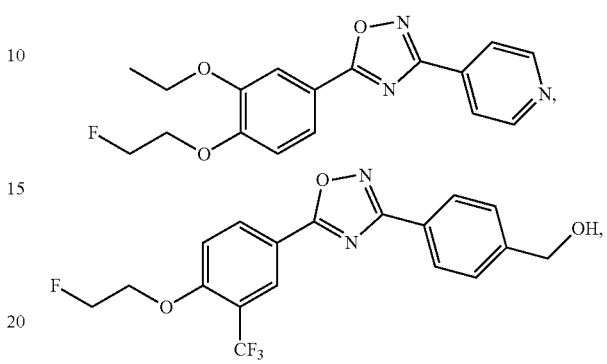

pharmaceutically acceptable salts thereof, prodrugs thereof, or mixtures thereof.

S1P1 modulates lymphocyte trafficking, a hallmark of inflammation. Up-regulated S1P1 levels can be detected in: multiple sclerosis (ms), cancer, cardiovascular disease, or other inflammatory diseases. Tracking S1P1 expression in vivo can assist in assessing therapeutic efficacy or assessing disease progression.

Pharmaceutical Compositions or Formulations

As noted, various embodiments of the present invention relate to pharmaceutical compositions comprising a therapeutically effective amount of at least one of the compounds as described herein (e.g., a compound of Formula (I) or Formula (II) or salt or prodrug thereof). In various embodiments, the pharmaceutical composition comprises at least one radiolabeled compound of Formula (I) or (II) as described herein.

In further embodiments, the composition can comprise a radiolabeled compound selected from the group consisting of:

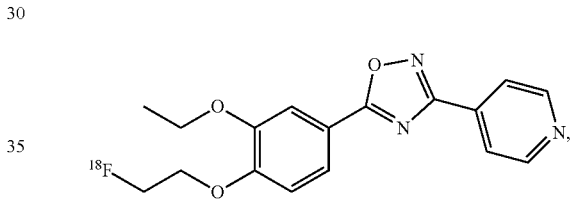

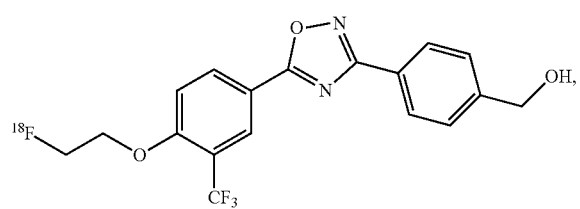

pharmaceutically acceptable salts thereof, prodrugs thereof, and mixtures thereof, wherein the compound contains at least one synthetic radioactive isotope. For example, the radiolabeled compound can comprise:

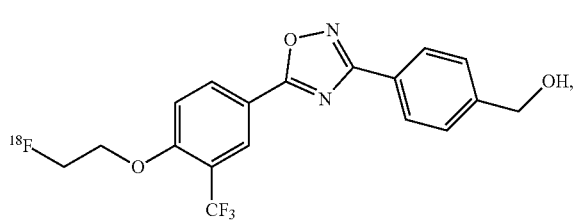

pharmaceutically acceptable salts thereof, prodrugs thereof, or mixtures thereof.

In some embodiments, the composition can comprise a radiolabeled compound selected from the group consisting of:

-continued
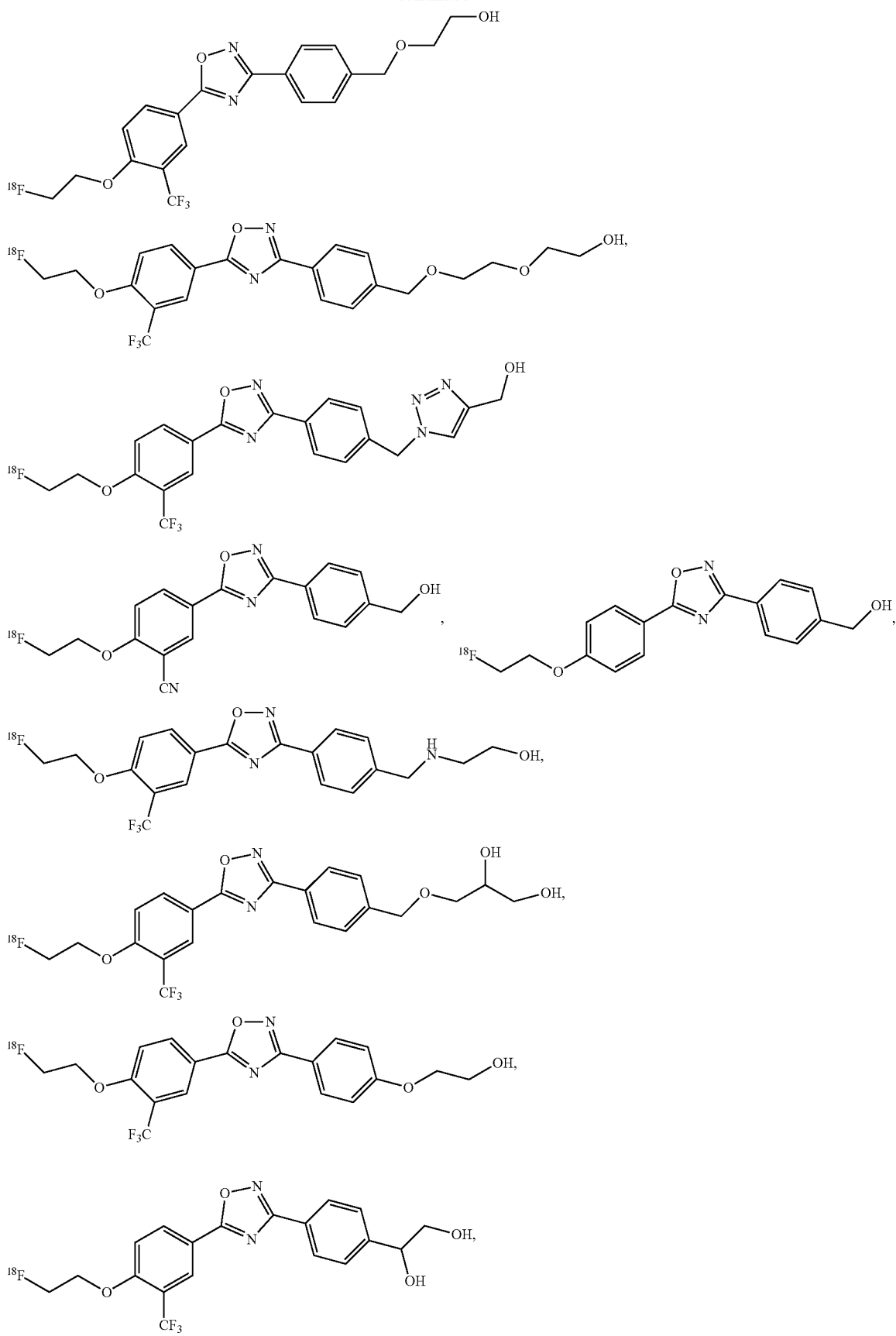

-continued
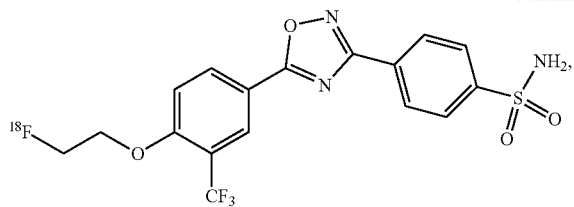
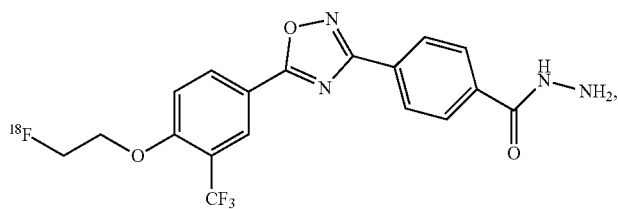
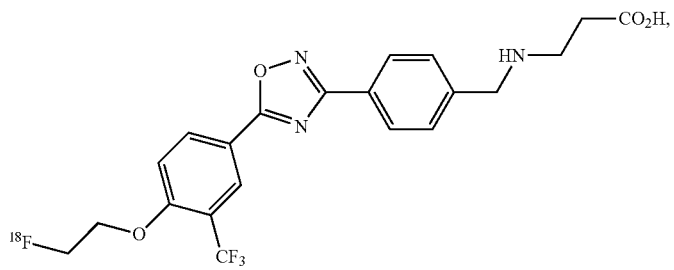
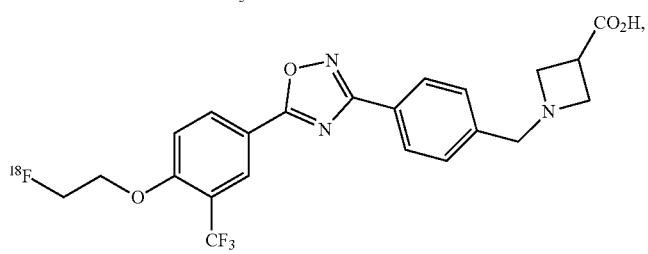
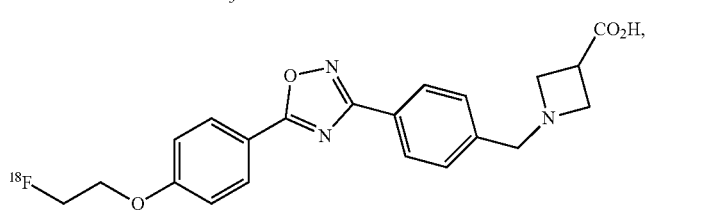
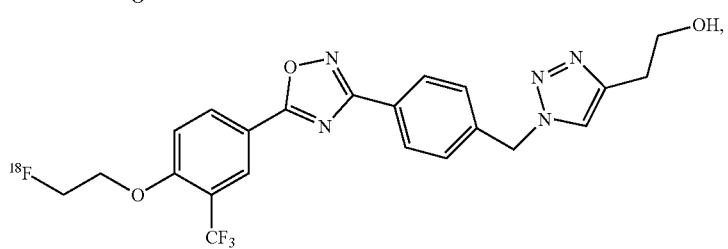
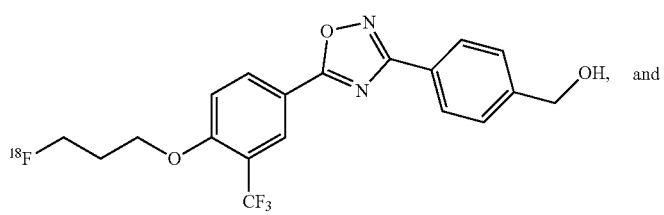

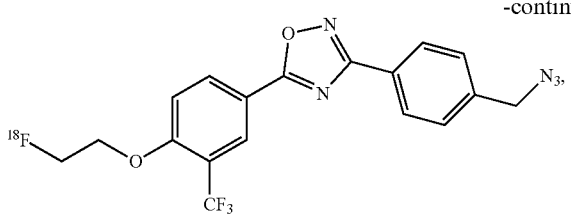

pharmaceutically acceptable salts thereof, prodrugs thereof, and mixtures thereof.

The pharmaceutical composition can comprise from about 0.001 mg to about 10 g of the radiolabeled compound and at least about 10 wt. %, at least about 25 wt. %, at least about 50 wt. %, at least about 75 wt. %, at least about 90 wt. %, or at least about 95 wt. % of the compound in the pharmaceutical composition is radiolabeled.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers. Pharmaceutically acceptable excipients for use in the compositions of the present invention are selected based upon a number of factors including the particular compound used, and its concentration, stability and intended bioavailability; the subject, its age, size and general condition; and the route of administration.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. Routes of administration include, but are not limited to, oral, parenteral (e.g., intravenous, intra-arterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration. For example, the agents of use with the current disclosure can be formulated by known methods for administration to a subject using several routes including: parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

The pharmaceutical compositions can be formulated, for example, for oral administration. The pharmaceutical compositions can be formulated as tablets, dispersible powders, pills, capsules, gel-caps, granules, solutions, suspensions, emulsions, syrups, elixirs, troches, lozenges, or any other dosage form that can be administered orally. Pharmaceutical compositions can include one or more pharmaceutically acceptable excipients. Suitable excipients for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, microcrystalline cellulose, colloidal silicon dioxide, croscarmellose sodium, talc, magnesium stearate, and stearic acid. Further, such solid dosage forms can be uncoated or can be coated to delay disintegration and absorption.

The pharmaceutical compositions can also be formulated for parenteral administration, e.g., formulated for injection via intravenous, intra-arterial, subcutaneous, rectal, subcutaneous, intramuscular, intraorbital, intracapsular, intraspinal, intraperitoneal, or intrasternal routes. Dosage forms suitable for parenteral administration include solutions, suspensions, dispersions, emulsions or any other dosage form that can be administered parenterally.

Pharmaceutically acceptable excipients are identified, for example, in *The Handbook of Pharmaceutical Excipients*, (American Pharmaceutical Association, Washington, D.C., and The Pharmaceutical Society of Great Britain, London, England, 1968). Additional excipients can be included in the pharmaceutical compositions of the invention for a variety of purposes. These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, non-volatile silicones, adhesives, bulking agents, flavorings, sweeteners, adsorbents, binders, disintegrating agents, lubricants, coating agents, and antioxidants.

Compound described herein can be prepared as a salt. "Salt" as used herein refers to pharmaceutically acceptable salts of the compounds described herein which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). Examples of pharmaceutically acceptable salts include, but are not limited to, nontoxic acid addition salts which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

In other embodiments, the compounds may be prepared as "prodrugs" in a pharmaceutically acceptable compositions/formulation. As used herein, the term "prodrug" refers to a derivative of a compound that can hydrolyze, oxidize, or otherwise react under biological conditions (in vitro or in vivo) to provide a compound as described herein. Prodrugs may only become active upon some reaction under biological conditions, but they may have activity in their unreacted forms. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs and their uses are well known in the art (see, e.g., Berge, et al. 1977 J. Pharm. Sci. 66:1-19). Prodrugs can typically be prepared using well-known methods, such as those described in Burger's Medicinal Chemistry and Drug Discovery (1995, Manfred E. Wolff ed., 5thed. 172-178, 931-932).

Agents or compositions described herein can also be used in combination with other therapeutic modalities, as described further below. Thus, in addition to the therapies described herein, one may also provide to the subject other therapies known to be efficacious for treatment of the disease, disorder, or condition.

Methods of Use

Dysregulation in S1P1 signaling is associated with inflammatory diseases in multiple organ systems, including the central nervous system (Soliven B et al., The neurobiology of sphingosine-1-phosphate signaling and sphingosine 1-phosphate receptor modulators. Neurology. February 2011; 76(8):59-514). S1P1 is extensively expressed on lymphocytes and endothelial cells, and it participates in neuroinflammatory process by regulating immune cell trafficking in the brain (Blaho V A et al., An update on the biology of sphingosine-1-phosphate receptors. *Journal of lipid research*. January 2014; 55(8):1596-1608). In the CNS, S1P1 is expressed in neurons and glia, including astrocytes, which modulate inflammatory responses throughout the gray and white matter; microglia, the specialized macrophages of the brain; and oligodendrocytes, which produce the myelin needed for nerve conduction (Soliven B et al., 2011; Nishimura H et al., Cellular Localization of Sphingosine-1-phosphate Receptor 1 Expression in the Human Central Nervous System. J Histochem Cytochem. September 2010; 58(9):847-856). The relevance of S1P1 in clinical disease has become readily apparent with the FDA approval of the S1P1 modulator FTY720 (fingolimod) for treating relapsing-remitting multiple sclerosis (RR-MS), which is a chronic autoimmune, inflammatory, demyelinating neurodegenerative disease (Dev K K et al., Brain sphingosine-1-phosphate receptors: Implication for FTY720 in the treatment of multiple sclerosis. Pharmacol Therapeut. January 2008; 117(1):77-93).

The role of S1P/S1P1 in vascular inflammation has also been studied in stroke-prone spontaneously hypertensive rats (SHRSPs). S1P stimulates inflammatory signaling pathways via transactivation of receptor tyrosin kinase (RTK) through S1P1, leading to increased expression of intercellular adhesion molecular 1 (ICAM-1) and vascular cell adhesion protein 1 (VCAM-1) and promotes monocyte adhesion (Yogi A et al., (2011) Sphingosine-1-Phosphate-Induced Inflammation Involves Receptor Tyrosine Kinase Transactivation in Vascular Cells Upregulation in Hypertension. *Hypertension* 57:809-818). Moreover, high S1P1 expression has been found in endothelial cells, macrophages and proliferated vascular smooth muscle cells (VSMCs), which are major components of atherosclerotic plaques (Daum G. et al., (2009) Sphingosine 1-phosphate: a regulator of arterial lesions. *Arterioscler Thromb Vasc Biol* 29:1439-1443). This is in agreement with a study that demonstrated that a specific S1P1 agonist treatment reduced lesion size in low-density lipoprotein receptor (LDLR)-deficient mice (Poti F et al., (2013) KRP-203, Sphingosine 1-Phosphate Receptor Type 1 Agonist, Ameliorates Atherosclerosis in LDL-R-/- Mice. *Arterioscl Throm Vas* 33:1505-1512). Therefore, S1P1 is a promising target for molecular imaging of atherosclerotic lesions, and may serve as a potential therapeutic target to inhibit atheroprogression and plaque vulnerability.

Methods of Quantifying S1P1 Expression In Vivo

Methods of quantifying S1P1 expression in vivo are provided. These methods comprise administering to a subject a composition comprising a radiolabeled compound as described herein and detecting the compound in the subject. In various embodiments, the radiolabeled compound has a high affinity (e.g., has an $IC_{50}$ less than 100 nM, less than 50 nM, or less than 25 nM) for the S1P1 receptor. In some embodiments, detecting the compound can comprise positron emission tomography (PET) imaging, and single photon emission computed tomography (SPECT) imaging, mass spectrometry, gamma imaging, magnetic resonance imaging (MRI), magnetic resonance spectroscopy, fluorescence spectroscopy, CT, ultrasound, or X-ray. In some embodiments, the molecular imaging technique is PET.

In various embodiments, the method comprises detecting the compound in a specific organ or organ system in the subject, in order to quantify the amount of S1P1 expression in the organ or organ system. In some embodiments, the method comprises quantifying S1P1 expression in a mammalian brain or central nervous system. In these cases, the subject's brain or central nervous system is imaged by, for example, positron emission tomography. Also envisioned are methods of quantifying S1P1 expression in other physiological organ systems (e.g., the cardiovascular system), or pathological organ states (e.g., cancerous tumors). In each case, the radiolabeled compound can be used to visualize S1P1 expression in the organ or organ system of interest using positron emission tomography or other suitable molecular imaging technique.

Methods of Monitoring an S1P1 Associated Disease, Disorder or Condition

Also provided are methods of monitoring an S1P1 associated disease, disorder, or condition. The methods comprise administering a composition comprising a radiolabeled compound described herein to a subject in need thereof, and detecting the compound. The compound can be detected using any suitable molecular imaging technique. For example, the compound can be detected using positron emission tomography (PET) imaging, and single photon emission computed tomography (SPECT) imaging, mass spectrometry, gamma imaging, magnetic resonance imaging (MRI), magnetic resonance spectroscopy, fluorescence spectroscopy, CT, ultrasound, or X-ray. In some embodiments, the molecular imaging technique is PET.

Methods described herein are generally performed on a subject in need thereof. A subject in need of diagnosis described herein can be a subject suspected of having or at risk for developing an S1P1 associated disease, disorder, or condition. The subject in need of monitoring described herein can be a subject having, or diagnosed with the S1P1 associated disease disorder or condition. The subject in need of monitoring can be administered treatment for the S1P1 associated disease disorder or condition, prior to, concurrently with, or after the monitoring. A determination of the need for monitoring or diagnosis will typically be assessed by a history and physical exam consistent with the disease or condition at issue. The subject can be an animal subject, including a mammal, such as horses, cows, dogs, cats, sheep, pigs, mice, rats, monkeys, hamsters, guinea pigs, and chickens, and humans. For example, the subject can be a human subject.

The S1P1 associated disease, disorder or condition can be an inflammatory disease, a neuroinflammatory disease, a pulmonary infection disease, vascular injury disease, an autoimmune disease, a neurological disease, a psychological disorder, a cardiovascular disease, atherosclerosis, multiple sclerosis, rheumatoid arthritis, or cancer.

The radiolabeled compound can be detected in any organ or organ system in the subject as determined by one skilled in the art. For instance, when monitoring or diagnosing a neurological disease, using the methods described herein, the radiolabeled compound can be detected in the brain or nervous system.

Methods of Treating an S1P1 Associated Disease, Disorder or Condition

Also provided is a process of treating an S1P1 associated disease, disorder, or condition in a subject in need administration of a therapeutically effective amount of a compound as described herein (e.g., a S1P1 modulating agent), so as to substantially inhibit an S1P1 associated disease, disorder, or condition, slow the progress of an S1P1 associated disease, disorder, or condition, or limit the development of an S1P1 associated disease, disorder, or condition. The method of treating an S1P1 associated disease disorder, or condition in a subject in need thereof comprises administering a pharmaceutical composition comprising a compound as described herein (e.g., a S1P1 modulating agent) and inhibiting, slowing the progress of, or limiting the development of the S1P1 associated disease, disorder, or condition.

In various embodiments, the compound as described herein (e.g., a S1P1 modulating agent) has a high affinity and selectivity for the S1P1. In some embodiments the compound having a high affinity and selectivity for S1P1 has an $IC_{50}$ for the S1P1 receptor of less than 100 nM, less than 50 nM, or less than 25 nM, and has an $IC_{50}$ for S1P2-S1P5 of greater than 1000 nM.

In some embodiments, the S1P1 associated disease, disorder, or condition is an inflammatory or autoimmune disease. For example, the S1P1 associated disease, disorder, or condition can be multiple sclerosis.

Methods described herein are generally performed on a subject in need thereof. A subject in need of the therapeutic methods described herein can be a subject having, diagnosed with, suspected of having, or at risk for developing an S1P1 associated disease, disorder, or condition. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of the compound (e.g., a S1P1 modulating agent) is, for example, that amount that would cause the desired therapeutic effect in a subject while minimizing undesired side effects. In various embodiments, an effective amount of a compound as described herein (e.g., a S1P1 modulating agent) can substantially inhibit an S1P1 associated disease, disorder, or condition, slow the progress of an S1P1 associated disease, disorder, or condition, or limit the development of an S1P1 associated disease, disorder, or condition.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a compound as described herein (e.g., a S1P1 modulating agent) can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit an S1P1 associated disease, disorder, or condition, slow the progress of an S1P1 associated disease, disorder, or condition, or limit the development of an S1P1 associated disease, disorder, or condition.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Shargel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a compound as described herein (e.g., a S1P1 modulating agent) can occur as a single event or over a time course of treatment. For example, a compound as described herein (e.g., a S1P1 modulating agent) can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for an S1P1 associated disease, disorder, or condition.

A compound as described herein (e.g., a S1P1 modulating agent) can be administered simultaneously or sequentially with another agent, such as an antibiotic, an anti-inflammatory, or another agent. For example, a compound as described herein (e.g., a S1P1 modulating agent) can be administered simultaneously with another agent, such as an antibiotic or an anti-inflammatory. Simultaneous administration can occur through administration of separate compositions, each containing one or more of a compound as described herein (e.g., a S1P1 modulating agent), an antibiotic, an anti-inflammatory, or another agent. Simultaneous administration can occur through administration of one composition containing two or more of a compound as described herein (e.g., a S1P1 modulating agent), an antibiotic, an anti-inflammatory, or another agent. A compound as described herein (e.g., a S1P1 modulating agent) can be administered sequentially with an antibiotic, an anti-inflammatory, or another agent. For example, a compound as described herein (e.g., a S1P1 modulating agent) can be administered before or after administration of an antibiotic, an anti-inflammatory, or another agent.

Methods of Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present invention.

Background to the Examples

The following examples detail the synthesis and characterization of a series of compounds derived from radiolabeled fingolimod analogs previously shown to have good affinity for the S1P Receptor 1 (S1P1), but poor biodistribution or uptake in the rat or monkey brain (labeled [$^{18}$F]3 and [$^{18}$F]4) below. Both precursors have the same 3,5 diphenyl 1,2,4 oxadiazole core but have different para substitutions on the 3-phenyl. [$^{18}$F]3 has a hydrophilic azetidine-3-carboxylic acid moiety, while [$^{18}$F]3 has a hydroxyl containing (1,2,3-triazol-4-yl)methanol moiety. Examples 1-53, relate to the modification of [$^{18}$F]3 to replace the (1,2,3-triazol-4-yl)methanol group with other hydroxyl-containing groups, such like amino alcohols, alkyl alcohols, and ether alcohols. Examples 54-106 relate to the modification of [$^{18}$F]4 to replace the azetidine-3-carboxylic acid moiety with other hydrophilic groups such as aryl sulfonamide, amide, N-hydroxyamide, hydrazide, alcohol, carboxyl acid and amine groups. Characterization and in vitro monitoring of these new compounds are described throughout and in Examples 107-109.

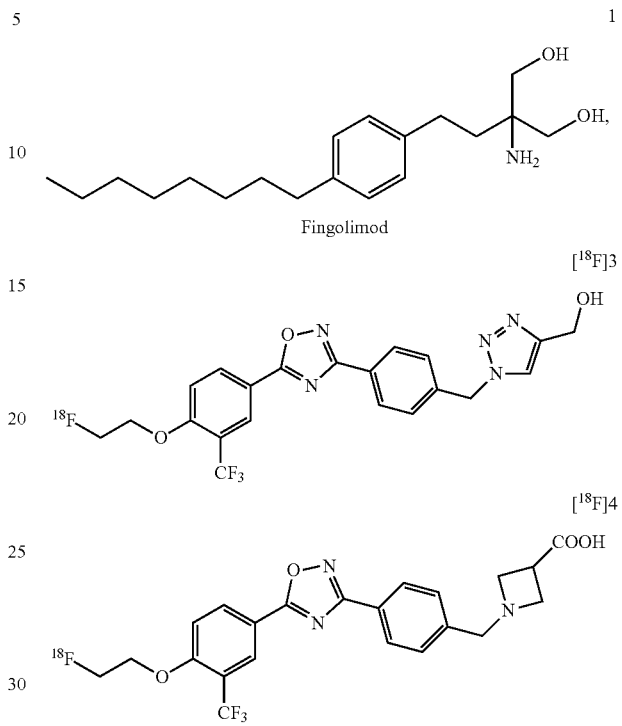

Example 1: Synthesis of Hydroxyl Containing Oxadiazole Compounds

This Example provides an overview of the synthesis of hydroxyl containing oxadiazole compounds derived from [$^{18}$F]3.

The first group of target compounds described in Examples 1 to 38 (8a-c, 8e-1, 8k, 10a-b, 12a-d, and 12f-g) and their synthesis are diagrammed in FIG. 1. Briefly: the coupling of aromatic carboxylic acids 7a-c with N-hydroxybenzamidines 6a-i afforded compounds 8a-d and 8f-j; the reductive amination of aldehydes 9 with corresponding amines gave compounds 10a-b; the nucleophilic substitution of compound 11 with alcohols yielded compounds 12a-e and 12g; the deprotection of tert-butyloxycarbonyl groups of 8d and 12e gave compounds 8e and 12f, respectively; and the oxidation of 8j afforded di-alcohol compound 8k.

Figure 2:
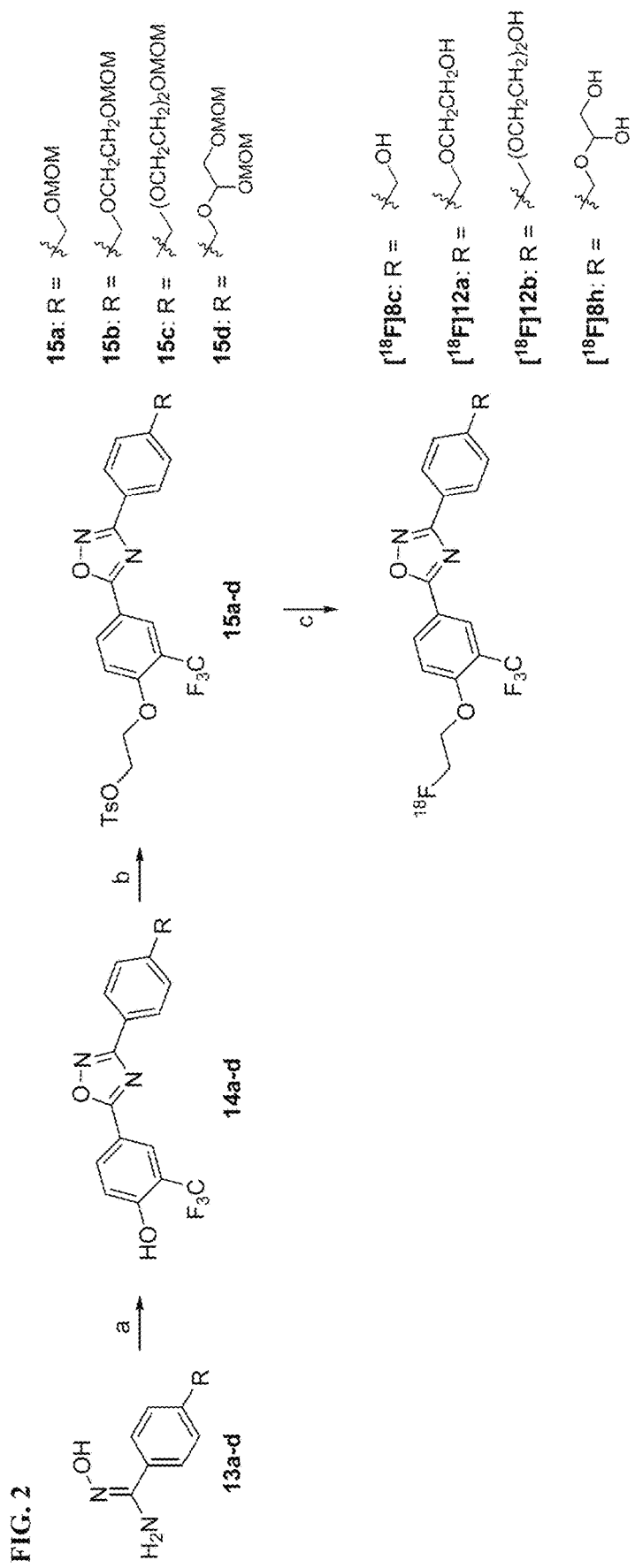
FIG. 2. General syntheses of precursors 15a-d and radiotracers [$^{18}$F]8c, [$^{18}$F]8h, [$^{18}$F]12a, and [$^{18}$F]12b. Reagents and conditions: (a) 4-hydroxy-3-(trifluoromethyl) benzoic acid, TBTU, HOBt, DIPEA, DMF, RT-120° C.; (b) ethylene ditosylate, K$_2$CO$_3$, CH$_3$CN, 90° C.; (c) [$^{18}$F]KF, Kryptofix 222, K$_2$CO$_3$, CH$_3$CN, 110° C., 15 min, 6 N HCl, 5 min.

The first group of target compounds was analyzed to determine their binding affinity for S1P receptors (described in Example 39) and potent candidates 8c, 8h, 12a, and 12b were identified and radiolabeled with F-18 isotope. However, prior to the radiosynthesis of [$^{18}$F]8c, [$^{18}$F]12a, [$^{18}$F]12b, and [$^{18}$F]8h, the precursors 15a-d were prepared by following the scheme diagrammed in FIG. 2. The cyclization of methoxymethyl (MOM) protected hydroxybenzimidamide 13a-d and 4-hydroxy-3-(trifluoromethyl)benzoic acid afforded 14a-d, which were alkylated with ethylene ditosylate to give precursors 15a-d.

Therefore, Examples 2 through 38 detail the synthetic protocol outlined in FIG. 1. Examples 41 to 51 describe the synthesis outlined in FIG. 2. The remaining examples describe in vitro binding affinity studies, in vivo autoradiography and biodistribution studies of each of the target compounds.

All reagents and chemicals were obtained from standard commercial sources and used without further purification unless otherwise stated. Organic reaction was carried out under inert nitrogen and moisture-free with dry solvent. Thin layer chromatography (TLC) was used to monitor the reaction. Final organic product was purified by flash column chromatography using 230-400 mesh silica gel purchased from Silicycle. Melting points were determined on a MEL-TEMP 3.0 apparatus without corrected. All deuterated solvents were purchased from Cambridge Isotope Laboratories. $^1$H and $^{13}$C NMR spectra were recorded on a 400 M Hz Varian instrument. Chemical shifts were reported in parts per million (ppm) and were calibrated using a residual undeuterated solvent as an internal reference (CDCl$_3$: δ 7.26 ppm; CD$_3$OD: δ 3.31 ppm; DMSO-d6: δ 2.50 ppm; Acetone-d6: δ 2.05 ppm). Multiplicities are indicated by s (singlet), d (doublet), t (triplet), q (quartet), p (pentet), h (hextet), m (multiplet) and br (broad). High-resolution positive ion mass was acquired by a Bruker MaXis 4G Q-TOF mass spectrometer with electrospray ionization source.

Examples 2-5: Synthesis of 5a-g

The following examples describe the synthesis of 5a-g, diagrammed below. Note that the synthesis of 4-(Hydroxymethyl)benzonitrile (5a) and 4-vinylbenzonitrile (5g) are not described in the following examples since they are commercially available.

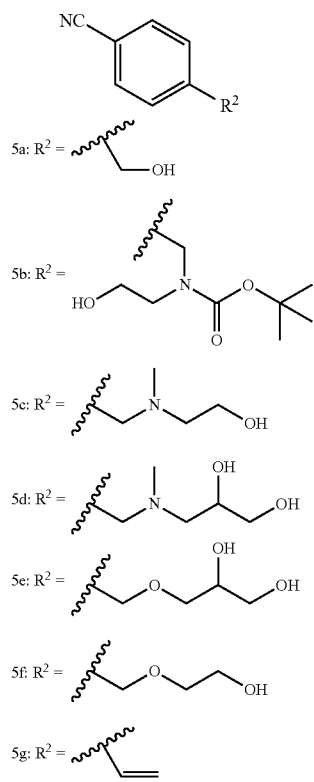

Example 2: Synthesis of Tert-butyl (4-cyanobenzyl)(2-hydroxyethyl)carbamate (5b)

To a round-bottom flask equipped with a stir bar was added 4-formylbenzonitrile (6.0 g, 45.8 mmol), etha-nolamine (2.8 g, 45.8 mmol), and methanol (80 mL). The mixture was stirred in a pre-heated 60° C. oil-bath for 6 h, and then cooled to 0° C. followed by adding sodium borohydride (8.7 g, 229 mmol) portionwise. The reaction was warmed to room temperature (RT) slowly and stirred for additional 5 h. Then, the reaction mixture was concentrated under vacuum, the residue was dissolved in ethyl acetate (200 mL), washed with water (100 mL) and saturated brine (100 mL), and dried over anhydrous MgSO$_4$. After filtering and concentration, the residual solid was re-dissolved in dichloromethane (100 mL). To the above solution was added di-tert-butyl dicarbonate (6.7 g, 30.6 mmol) and 1 N NaOH (17.0 mL). The mixture was stirred at RT overnight, then the mixture was washed with water and saturated brine, dried over anhydrous MgSO$_4$. After filtering and concentration, the crude semi-solid product 5b was obtained. (8.6 g, 68%) $^1$H NMR (400 MHz, CDCl$_3$) δ 7.61 (d, J=8.0 Hz, 2H), 7.33 (d, J=7.9 Hz, 2H), 4.53 (s, 2H), 3.72 (s, 2H), 3.41 (s, 2H), 1.40 (s, 9H).

Example 3: Synthesis of 4-(((2-Hydroxyethyl) (methyl)amino)methyl)benzonitrile (5c)

To a round-bottom flask equipped with a stir bar was added 4-(bromomethyl)benzonitrile (3.0 g, 15.3 mmol), 2-(methylamino)ethan-1-ol (1.0 g, 13.3 mmol), and acetonitrile (20 mL). After cooling to 0° C., triethylamine (2.8 g, 27.7 mmol) was added to the mixture dropwise. The mixture was warmed to RT and stirred overnight. Then, the mixture was concentrated under vacuum, the residue was purified by flash chromatography on silica gel using hexane and ethyl acetate as eluent to afford the semi-solid product. (2.0 g, 79%) $^1$H NMR (400 MHz, CDCl$_3$) δ 7.63-7.58 (m, 2H), 7.42 (d, J=7.9 Hz, 2H), 3.68-3.59 (m, 5H), 2.63-2.57 (m, 2H), 2.23 (s, 3H).

Example 4: Synthesis of 4-(((2,3-Dihydroxypropyl) (methyl)amino)methyl)benzonitrile (5d)

To a round-bottom flask equipped with a stir bar was added 4-(bromomethyl)benzonitrile (3.9 g, 20.0 mmol), 3-(methylamino)propane-1,2-diol (2.5 g, 23.0 mmol), K$_2$CO$_3$ (6.9 g, 50.0 mmol), and acetonitrile (50 mL). The mixture was stirred overnight at RT. Then, the mixture was concentrated under vacuum, the residue was purified by flash chromatography on silica gel using hexane and ethyl acetate as eluent to afford oil product. (3.0 g, 68%) $^1$H NMR (400 MHz, CDCl$_3$) δ 7.63 (d, J=4.6 Hz, 2H), 7.40 (d, J=3.7 Hz, 2H), 3.76-3.68 (m, 4H), 3.51-3.45 (m, 2H), 2.70-2.61 (m, 3H), 2.39-2.36 (m, 1H), 2.24 (s, 3H).

Example 5: Synthesis of 4-((2,3-Dihydroxypropoxy)methyl)benzonitrile (5e)

Commercially available DL-1,2-lsopropylideneglycerol (3.0 g, 22.5 mmol) was added to a suspension of NaH (0.6 g, 25.8 mmol) in THF (30 mL) at 0° C. under nitrogen. The mixture was stirred for 30 mins during which time 4-cyanobenzyl bromide (4.0 g, 20.4 mmol) was added dropwise over 5 mins followed by warming of the reaction mixture to RT. After 2 h, the reaction mixture was partitioned between ammonium chloride solution and ethyl acetate. The aqueous phase was extracted with ethyl acetate and the combined organics dried over anhydrous MgSO$_4$. After filtering and concentration, the residue was purified by flash chromatography on silica gel using hexane and ethyl acetate as eluent to afford off-white solid product. (3.8 g, 90%) MP: 80-83°

C. $^1$H NMR (400 MHz, CDCl$_3$) δ 7.63 (d, J=8.1 Hz, 2H), 7.43 (d, J=7.9 Hz, 2H), 4.61 (s, 2H), 3.97-3.89 (m, 1H), 3.76-3.69 (m, 1H), 3.66-3.56 (m, 3H), 2.75 (s, 1H), 2.29 (s, 1H).

Example 6: Synthesis of 4-((2-Hydroxyethoxy)methyl)benzonitrile (5f)

A solution of ethylene glycol (7.9 g, 127 mmol) in THF (20 mL) was added to a suspension of NaH (1.0 g, 41.7 mmol) in THF (30 mL) at 0° C. under nitrogen dropwise. The resulting mixture was stirred for 30 mins before adding a solution of 4-(bromomethyl)benzonitrile (5.0 g, 25.5 mmol) in THF (20 mL) dropwise. The reaction mixture was then stirred under nitrogen overnight at RT. Then, water was added to quench the reaction and the solvent was removed under vacuum. The residue was dissolved in ethyl acetate (200 mL), washed with water (100 mL) and saturated brine (100 mL), and dried over anhydrous MgSO$_4$. After filtering and concentration, the crude product was purified by flash chromatography on silica gel using hexane and ethyl acetate as eluent to afford semi-solid product. (3.3 g, 72%) MP: 110-115° C. $^1$H NMR (400 MHz, CDCl$_3$) δ 7.65 (d, J=8.2 Hz, 2H), 7.46 (d, J=7.9 Hz, 2H), 4.63 (s, 2H), 3.84-3.78 (m, 2H), 3.67-3.61 (m, 2H), 1.93 (t, J=5.8 Hz, 1H).

Example 7: General Procedure for the Synthesis of 6a-g

Intermediates 6a-g (shown below) were synthesized from 5a-g using the following general procedure (labeled as "a" on FIG. 1). To a round-bottom flask equipped with a stir bar was added 5a-g (1.0 eq), hydroxylamine hydrochloride (2.0 eq), NaHCO$_3$ (4.0 eq), and methanol (5.0 mL/mmol). The reaction was refluxed and stirred in a pre-heated 75° C. oil-bath for 6 h. The reaction mixture was cooled to room temperature, and the precipitate was filtered off and washed with methanol. The filtrate was concentrated in vacuo without further purification.

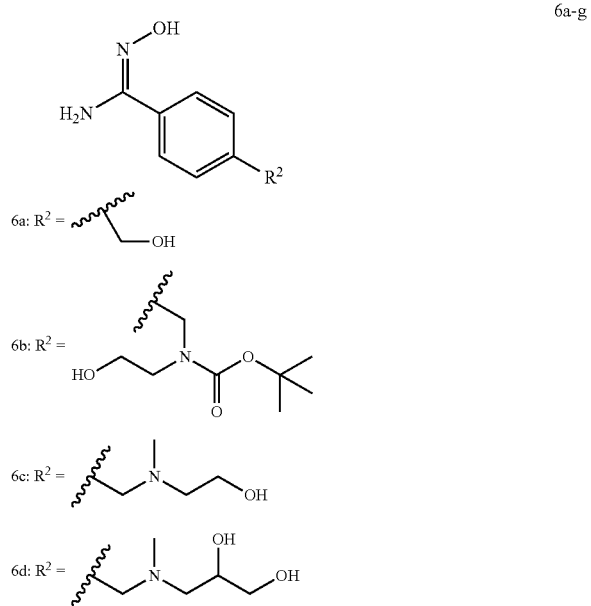

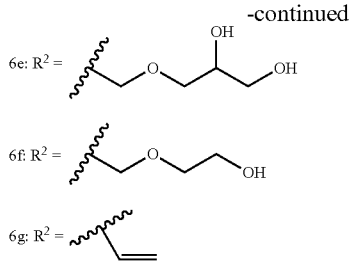

Example 8: Synthesis of (E)-N'-hydroxy-4-(hydroxymethyl)benzimidamide (6a)

The synthesis follows the general procedure described in Example 7. Yield: 70%, MP: 217-219° C. $^1$H NMR (400 MHz, DMSO-d6) δ=7.88-7.78 (m, 4H), 5.93 (s, 2H).

Example 9: Synthesis of Tert-butyl (E)-(4-(N'-hydroxycarbamimidoyl)benzyl)(2-hydroxyethyl)carbamate (6b)

The synthesis follows the general procedure described in Example 7. Yield: 71%, MP: 138-141° C. $^1$H NMR (400 MHz, CDCl$_3$) δ 7.64-7.50 (m, 2H), 7.33-7.17 (m, 4H), 5.28 (s, 2H), 4.92-4.75 (m, 2H), 4.57-4.38 (m, 2H), 3.75-3.60 (m, 2H), 3.49-3.28 (m, 3H), 1.44 (s, 9H).

Example 10: Synthesis of (E)-N'-hydroxy-4-(((2-hydroxyethyl)(methyl)amino)methyl) benzimidamide (6c)

The synthesis follows the general procedure described in Example 7. Yield: 60%, MP: 162-165° C. $^1$H NMR (400 MHz, DMSO-d6) δ 9.62 (s, 1H), 7.66 (d, J=7.1 Hz, 2H), 7.35 (d, J=7.4 Hz, 2H), 5.81 (s, 2H), 4.44 (s, 1H), 3.55 (s, 4H), 2.47 (t, J=6.2 Hz, 2H), 2.20 (s, 3H).

Example 11: Synthesis of (E)-4-(((2,3-dihydroxypropyl)(methyl)amino)methyl)-N'-hydroxybenzimidamide (6d)

The synthesis follows the general procedure described in Example 7. Yield: 51%, MP: 160-164° C. $^1$H NMR (400 MHz, CD$_3$OD-d4) δ 7.50 (d, J=7.8 Hz, 2H), 7.27 (d, J=7.9 Hz, 2H), 3.74-3.70 (m, 1H), 3.48-3.33 (m, 3H), 3.22-3.19 (m, 1H), 2.42-2.37 (m, 2H), 2.15 (s, 3H).

Example 12: Synthesis of (E)-44(2,3-dihydroxypropoxy)methyl)-N'-hydroxybenzimidamide (6e)

The synthesis follows the general procedure described in Example 7. Yield: 45%, MP: 142-144° C. $^1$H NMR (400 MHz, CD$_3$OD-d4) δ 7.60 (d, J=8.0 Hz, 2H), 7.37 (d, J=7.9 Hz, 2H), 4.56 (s, 2H), 3.81-3.74 (m, 1H), 3.61-3.45 (m, 4H).

Example 13: Synthesis of (E)-N'-hydroxy-4((2-hydroxyethoxy)methyl) benzimidamide (6f)

The synthesis follows the general procedure described in Example 7. Yield: 58%, MP: 145-148° C. $^1$H NMR (400 MHz, MeOD-d4) δ=9.62 (br s, 1H), 7.64 (d, J=7.6 Hz, 2H), 7.32 (d, J=8.0 Hz, 2H), 5.80 (br s, 2H), 4.69 (br s, 1H), 4.50 (s, 2H), 3.57-3.50 (m, 2H), 3.48-3.42 m, 2H).

Example 14: Synthesis of (E)-N'-hydroxy-4-vinylbenzimidamide (6g)

The synthesis follows the general procedure described in Example 7. Yield: 95%. The detailed procedure was followed by literature.[25]

Example 15: Synthesis of 4-(2-Fluoroethoxy)benzoic acid (7a), 3-Cyano-4-(2-fluoroethoxy)benzoic acid (7b), and 4-(2-fluoroethoxy)-3-(trifluoromethyl)benzoic acid (7c)

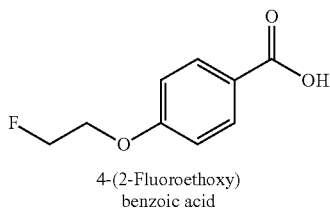

7a 4-(2-Fluoroethoxy) benzoic acid

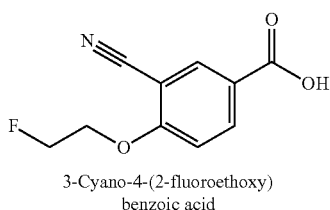

7b

3-Cyano-4-(2-fluoroethoxy) benzoic acid

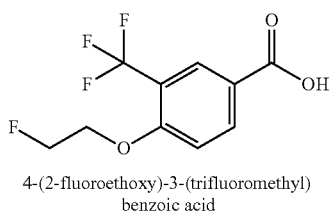

7c 4-(2-fluoroethoxy)-3-(trifluoromethyl) benzoic acid 4-(2-Fluoroethoxy)benzoic acid (7a) and 4-(2-fluoroethoxy)-3-(trifluoromethyl)benzoic acid (7c) were synthesized as described in the literature (A. J. Rosenberg, H. Liu, H. Jin, X. Yue, S. Riley, S. J. Brown, Z. Tu, J. Med. Chem. 2016, 59, 6201-6220.) Note that the synthesis of 7c is also described in Example 56 below (as Compound 16) To synthesize 3-Cyano-4-(2-fluoroethoxy)benzoic acid (7b), the following procedure was followed. To a round-bottom flask equipped with a stir bar was added 4-fluoro-3-(trifluoromethyl)benzoic acid (5.0 g, 30.3 mmol), 2-fluoroethanol (2.9 g, 43.5 mmol), and DMSO (20 mL). The mixture was stirred at 0° C. for 5 mins before adding NaH (1.6 g, 68.2 mmol) portionwise. Then, the reaction was warmed to RT and stirred overnight. After the reaction was completed, the mixture was poured into ice water (500 mL) and acidified with 12 M HCl to pH<1. The precipitate was filtered and washed with water and hexane to afford the off-white solid. (6.0 g, 95%) MP: 197-199° C.

Example 16: General Procedure for the Synthesis of 8a-d and 8f-j

The synthesis of 8a-d and 8f-j is indicated as reaction "b" in FIG. 1. To a round-bottom flask equipped with a stir bar was added acid 7a-c (1.0 eq), HOBt (0.2 eq), TBTU (1.0 eq), DIPEA (3.0 eq), and DMF (5.0 mL/mmol). The reaction mixture was stirred for 0.5 h followed by adding amidoxime 6a-g (1.0 eq). The reaction mixture was stirred for 1 h at room temperature, then refluxed in a pre-heated 120° C. oil-bath for 4 h and monitored by TLC. After cooling, the reaction mixture was diluted with water and extracted with ethyl acetate. The ethyl acetate layer was washed with 1 M HCl, saturated brine, and dried over anhydrous MgSO$_4$. After filtration and concentration, the residue was purified on a silica gel column.

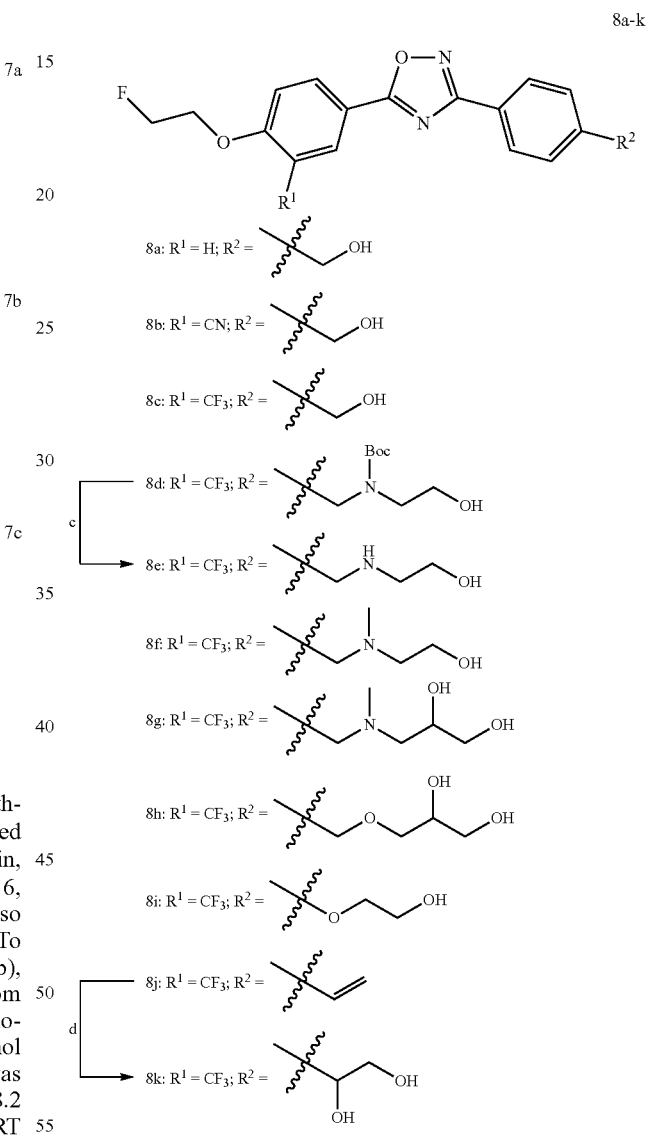

8a-k

Example 17: Synthesis of (4-(5-(4-(2-Fluoroethoxy)phenyl)-1,2,4-oxadiazol-3-yl)phenyl)methanol (8a)

The synthesis follows the general procedure described in Example 16. Yield: 45%, white solid, MP: 140-142° C. $^1$H NMR (400 MHz, CDCl$_3$) δ 8.16-8.08 (m, 4H), 7.45 (d, J=8.0 Hz, 2H), 7.03 (d, J=8.7 Hz, 2H), 4.85-4.80 (m, 1H), 4.73-4.69 (m, 1H), 4.61 (s, 2H), 4.33-4.28 (m, 1H), 4.26-4.21 (m, 1H).

Example 18: Synthesis of 2-(2-fluoroethoxy)-5-(3-(4-(hydroxymethyl)phenyl)-1,2,4-oxadiazol-5-Obenzonitrile (8b)

The synthesis follows the general procedure described in Example 16. Yield: 30%, white solid, MP: 150-151° C. $^1$H NMR (400 MHz, Acetone-d6) δ 8.35-8.45 (m, 2H), 8.01-8.08 (m, 2H), 7.45-7.56 (m, 3H), 4.80-4.96 (m, 2H), 4.73 (s, 2H), 4.54-4.67 (m, 2H). $^{13}$C NMR (101 MHz, Acetone-d6) δ 173.8, 168.6, 163.1, 146.3, 134.2, 133.5, 127.1, 126.8, 125.1, 117.4, 114.6, 113.7, 102.9, 81.5 (d, $J_{C\text{-}F}$=170 Hz), 69.1 (d, $J_{C\text{-}F}$=18.1 Hz), 63.3. HRMS (ESI) calcd for $C_{18}H_{14}F_1N_3O_3$ [M+H$^+$] 340.1092, found 340.1087.

Example 19: Synthesis of (4-(5-(4-(2-Fluoroethoxy)-3-(trifluoromethyl)phenyl)-1,2,4-oxadiazol-3-yl)phenyl)methanol (8c)

The synthesis follows the general procedure described in Example 16. Yield: 55% yield). $^1$H NMR (400 MHz, CDCl$_3$) δ 8.45 (d, J=2.0 Hz, 1H), 8.33 (dd, J=8.8 Hz, 2.0 Hz, 1H), 8.13 (d, J=8.0 Hz, 2H), 7.50 (d, J=8.0 Hz, 2H), 7.16 (d, J=8.4 Hz, 1H), 4.90-4.74 (m, 4H), 4.48-4.35 (m, 2H). $^{13}$C NMR (101 MHz, CDCl$_3$) δ=174.4, 168.9, 159.7, 144.4, 133.4, 127.8, 127.8 (q, $J_{C\text{-}F}$=5.2 Hz), 127.3, 122.9, (q, $J_{C\text{-}F}$=274 Hz), 120.4 (q, $J_{C\text{-}F}$=32.1 Hz), 117.2, 113.5, 81.4 (d, $J_{C\text{-}F}$=173 Hz), 68.5 (d, $J_{C\text{-}F}$=21.1 Hz), 64.9. MP: 146-147° C. HRMS (ESI) calcd for $C_{10}H_{14}F_4N_2O_3$ [M+H$^+$] 383.1013. Found [M+H$^+$] 383.1011.

Example 20: Synthesis of Tert-butyl (4-(5-(4-(2-fluoroethoxy)-3-(trifluoromethyl)phenyl)-1,2,4-oxadiazol-3-yl)benzyl)(2-hydroxyethyl)carbamate (8d)

The synthesis follows the general procedure described in Example 16. Yield: 42%, white solid, MP: 120-122° C. $^1$H NMR (400 MHz, CDCl$_3$) δ 8.45 (s, 1H), 8.33 (d, J=8.8 Hz, 1H), 8.11 (d, J=8.0 Hz, 2H), 7.36 (d, J=7.7 Hz, 2H), 7.16 (d, J=8.8 Hz, 1H), 4.90-4.85 (m, 1H), 4.78-4.73 (m, 1H), 4.61-4.49 (m, 2H), 4.47-4.42 (m, 1H), 4.40-4.35 (m, 1H), 3.78-3.67 (m, 2H), 3.51-3.35 (m, 2H), 2.88 (br, s, 1H), 1.45 (s, 9H).

Example 21: Synthesis of 2-((4-(5-(4-(2-Fluoroethoxy)-3-(trifluoromethyl)phenyl)-1,2,4-oxadiazol-3-yl)benzypamino)ethan-1-ol (8e)

The synthesis of 8e is indicated as the reaction "c" in FIG. 1. To a solution of 8d (250 mg, 0.48 mmol) in methanol (5.0 mL) was added 4 M HCl in dioxane (5.0 mL). The reaction was stirred at RT for 6 h, then the solvent was removed by and the residue was dissolved in ethyl acetate. The solution was washed with saturated NaHCO$_3$, water, and dried over MgSO$_4$. After filtering and concentration, the final product was obtained. (193 mg, 95%) MP: 126-130° C. $^1$H NMR (400 MHz, Acetone-d6) δ 7.58 (d, J=8.8 Hz, 1H), 7.47 (s, 1H), 7.18 (d, J=8.0 Hz, 2H), 6.67-6.75 (m, 3H), 3.87-4.05 (m, 2H), 3.63-3.78 (m, 2H), 2.96 (s, 3H), 2.65 (t, J=5.6 Hz, 2H), 1.76 (t, J=5.6 Hz, 2H). $^{13}$C NMR (101 MHz, Acetone-d6) δ 174.0, 168.2, 159.4, 145.1, 134.1, 128.6, 126.9, 126.6 (q, J=5.3 Hz), 124.2, 122.9 (q, $J_{C\text{-}F}$=274 Hz), 118.1 (q, $J_{C\text{-}F}$=31 Hz), 115.9, 115.0, 81.7 (d, $J_{C\text{-}F}$=168 Hz), 68.8 (d, $J_{C\text{-}F}$=18.9 Hz), 60.4, 52.5, 51.1. HRMS (ESI) calcd for $C_{20}H_{19}F_4N_3O_3$ [M+H$^+$] 426.1435, found 426.1432.

Example 22: Synthesis of 2-((4-(5-(4-(2-Fluoroethoxy)-3-(trifluoromethyl)phenyl)-1,2,4-oxadiazol-3-yl)benzyl)(methyl)amino)ethan-1-ol (8f)

The synthesis follows the general procedure described in Example 16. Yield: 34%, white solid, MP: 108-111° C. $^1$H NMR (400 MHz, CDCl$_3$) δ 8.38 (s, 1H), 8.27 (d, J=8.8, 1H), 8.04 (d, J=8.1 Hz, 2H), 7.38 (d, J=8.4 Hz, 2H), 7.10 (d, J=8.8 Hz, 1H), 4.67-4.84 (m, 2H), 4.29-4.41 (m, 2H), 3.55-3.61 (m, 4H), 2.57 (t, J=5.6 Hz, 2H), 2.19 (s, 3H). $^{13}$C NMR (101 MHz, CDCl$_3$) δ 174.2, 168.8, 159.9, 142.1, 133.3, 129.4, 127.8 (q, $J_{C\text{-}F}$=5.25 Hz), 127.6, 125.6, 122.7 (q, $J_{C\text{-}F}$=274 Hz), 120.2 (q, $J_{C\text{-}F}$=32 Hz), 117.1, 113.4, 81.2 (d, $J_{C\text{-}F}$=172 Hz), 68.4 (d, $J_{C\text{-}F}$=21.2 Hz), 62.0, 58.5, 58.4, 41.6. HRMS (ESI) calcd for $C_{21}H_{21}F_4N_3O_3$ [M+H$^+$] 440.1592, found 440.1588.

Example 23: Synthesis of 3-((4-(5-(4-(2-Fluoroethoxy)-3-(trifluoromethyl)phenyl)-1,2,4-oxadiazol-3-yl)benzyl)(methypamino)propane-1,2-diol (8g)

The synthesis follows the general procedure described in Example 16. Yield: 40%, white solid, MP: 101-103° C. $^1$H NMR (400 MHz, MeOD-d4) δ 8.17-8.24 (m, 2H), 7.92 (d, J=8 Hz, 2H), 7.34 (d, J=8.4 Hz, 2H), 7.27 (d, J=9.6 Hz, 1H), 4.58-4.75 (m, 2H), 4.27-4.39 (m, 2H), 3.71-3.78 (m, 1H), 3.54 (s, 3H), 3.35-3.51 (m, 2H), 2.40-2.45 (m, 2H), 2.18 (s, 3H). $^{13}$C NMR (101 MHz, MeOD-d4) δ 174.3, 168.5, 159.8, 142.1, 133.3, 129.5, 126.9, 126.6 (q, $J_{C\text{-}F}$=5.4 Hz), 125.4, 122.9 (q, $J_{C\text{-}F}$=274 Hz), 119.3 (q, $J_{C\text{-}F}$=31 Hz), 116.4, 113.8, 81.2 (d, $J_{C\text{-}F}$=171 Hz), 68.9, 68.6 (q, $J_{C\text{-}F}$=20 Hz), 64.9, 62.0, 60.1, 41.7. HRMS (ESI) calcd for $C_{22}H_{23}F_4N_3O_4$ [M+H$^+$] 470.1697, found 470.1694.

Example 24: Synthesis of 3-((4-(5-(4-(2-Fluoroethoxy)-3-(trifluoromethyl)phenyl)-1,2,4-oxadiazol-3-yl)benzypoxy)propane-1,2-diol (8h)

The synthesis follows the general procedure described in Example 16. Yield: 38%, white solid, MP: 102-105° C. $^1$H NMR (400 MHz, MeOD-d4) δ 8.18-8.24 (m, 2H), 7.93 (d, J=8.1 Hz, 2H), 7.40 (d, J=8.0 Hz, 2H), 7.25 (d, J=8.5 Hz, 1H), 4.58-4.75 (m, 2H), 4.51 (s, 2H), 4.26-4.38 (m, 2H), 3.70-3.77 (m, 1H), 3.40-3.56 (m, 4H). $^{13}$C NMR (101 MHz, MeOD-d4) δ 174.3, 168.4, 159.8, 142.1, 133.3, 127.6, 126.9, 126.6 (q, $J_{C\text{-}F}$=5.35 Hz), 125.6, 122.9 (q, $J_{C\text{-}F}$=273 Hz), 119.3 (q, $J_{C\text{-}F}$=31 Hz), 116.3, 113.8, 81.2 (d, $J_{C\text{-}F}$=170 Hz), 72.3, 71.6, 70.9, 68.6 (q, $J_{C\text{-}F}$=20.1 Hz), 63.1. HRMS (ESI) calcd for $C_{21}H_{20}F_4N_2O_5$ [M+H$^+$] 457.1381, found 457.1385.

Example 25: Synthesis of 2-((4-(5-(4-(2-Fluoroethoxy)-3-(trifluoromethyl)phenyl)-1,2,4-oxadiazol-3-yl)benzypoxy)ethan-1-ol (8i)

The synthesis follows the general procedure described in Example 16. Yield: 33%, white solid, MP: 159-160° C. $^1$H NMR (400 MHz, CDCl$_3$) δ 8.42 (s, 1H), 8.30 (dd, J=8.6, 1.4 Hz, 1H), 8.11 (d, J=8.1 Hz, 2H), 7.46 (d, J=8.0 Hz, 2H), 7.13 (d, J=8.7 Hz, 1H), 4.71-4.89 (m, 2H), 4.62 (s, 2H), 4.33-4.45 (m, 2H), 3.78 (m, 2H), 3.63 (m, 2H). 3.78 (t, J=4.4 Hz, 2H), 3.63 (t, J=4.4 Hz, 2H). $^{13}$C NMR (101 MHz, CDCl$_3$) δ 174.2, 168.7, 159.6, 141.4, 133.3, 127.9, 127.7 (q, $J_{C\text{-}F}$=5.2 Hz), 127.6, 126.1, 122.7 (q, $J_{C\text{-}F}$=271 Hz), 120.2 (q, $J_{C\text{-}F}$=32

Hz), 117.0, 113.4, 81.3 (d, $J_{C-F}$=172 Hz), 72.7, 71.7, 68.4 (d, $J_{C-F}$=21 Hz), 61.9. HRMS (ESI) calcd for $C_{20}H_{18}F_4N_2O_4$ [M+H$^+$] 427.1245, found 427.1240.

Example 26: Synthesis of 5-(4-(2-Fluoroethoxy)-3-(trifluoromethyl)phenyl)-3-(4-vinylphenyl)-1,2,4-oxadiazole (8j)

The synthesis follows the general procedure described in Example 16. The crude product was used directly for the next step reaction without further purification.

Example 27: Synthesis of 1-(4-(5-(4-(2-Fluoroethoxy)-3-(trifluoromethyl)phenyl)-1,2,4-oxadiazol-3-yl)phenyl)ethane-1,2-diol (8k)

The synthesis of 8k is indicated as reaction "d" in FIG. 1. To a 50 mL of round bottle flask was added 8j (327 mg, 0.86 mmol), 4-methylmorpholine N oxide (122 mg, 1.03 mmol) and THF/H$_2$O (3/1, 12.0 mL). The mixture was stirred for 5 mins before adding OsO$_4$ (2.5 wt. % in tert-butanol, 545 µL). The reaction was kept stirring at RT overnight. Then, the reaction mixture was diluted with ethyl acetate and water. The ethyl acetate layer was separated and concentrated to give crude product. Crude product was purified through silica gel to give final product as a white semi-solid. (120 mg, 34%) $^1$H NMR (400 MHz, MeOD-d4) δ 8.29-8.34 (m, 2H), 8.05 (d, J=8.2 Hz, 2H), 7.53 (d, J=8.2 Hz, 2H), 7.36 (d, J=8.8 Hz, 1H), 4.79-4.83 (m, 1H), 4.72-4.77 (m, 1H), 4.67-4.71 (m, 1H), 4.36-4.48 (m, 2H), 3.59-3.70 (m, 2H). $^{13}$C NMR (101 MHz, MeOD-d4) δ 174.4, 168.5, 159.9, 145.8, 133.3, 126.9, 126.7 (q, $J_{C-F}$=5.25 Hz), 126.6, 125.6, 122.9 (q, $J_{C-F}$=273 Hz), 119.4 (q, $J_{C-F}$=32 Hz), 116.4, 113.8, 81.2 (d, $J_{C-F}$=171 Hz), 74.1, 68.6 (d, $J_{C-F}$=20.2 Hz), 67.1. HRMS (ESI) calcd for $C_{19}H_{16}F_4N_2O_4$ [M+H$^+$] 413.1119, found 413.1115.

Example 28: Synthesis of 4-(5-(4-(2-Fluoroethoxy)-3-(trifluoromethyl)phenyl)-1,2,4-oxadiazol-3-yl)benzaldehyde (9)

The synthesis of compound 9 is indicated by reaction "e" in FIG. 1. To an oven-dried 100 mL round-bottomed flask equipped with a stir bar was added 29 mL of CH$_2$Cl$_2$ and DMSO (1.15 mL, 16.2 mmol). The reaction mixture was cooled to −78° C. (acetone/CO$_2$(s)), and oxalyl chloride (0.93 mL, 11.0 mmol) was added carefully. The reaction mixture was stirred for 30 min at which time alcohol 8c (2.0 g, 5.23 mmol) was added. The reaction mixture was stirred for 30 min at which time Et3N (5.83 mL, 41.8 mmol) was added. The cooling bath was removed, and the reaction was allowed to warm to r.t. over 2 h. The reaction mixture was concentrated in vacuo and partitioned between EtOAc and 1 M HCl(aq). The layers were separated, and the aqueous layer was extracted with EtOAc (×2). The combined organic layers were washed with 1 M HCl(aq), sat. NaHCO3(aq), brine, dried over MgSO4, concentrated in vacuo, and triturated with MTBE to give a pale-yellow solid (1.75 g, 88% yield). 1H NMR (400 MHz, CDCl3) δ=10.11 (s, 1H), 8.47 (d, J=1.6 Hz, 1H), 8.39-8.31 (m, 3H), 8.02 (d, J=8.4 Hz, 2H), 7.19 (d, J=8.8 Hz, 1H), 4.93-4.75 (m 2H), 4.49-4.35 (m, 2H). 13C NMR (101 MHz, CDCl3) δ=191.7, 174.9, 168.3, 159.9, 138.2, 133.5, 132.2, 130.2, 128.3, 127.9 (q, JC-F=5.4 Hz), 122.9 (q, JC-F=274 Hz), 120.5 (q, JC-F=32.3 Hz), 116.9, 113.6, 81.4 (d, JC-F=173 Hz), 68.6 (d, JC-F=21.1 Hz). MP: 149-150° C. HRMS (ESI) calcd for C18H13F4N2O3 [M+H+] 381.0857. Found [M+H+] 381.0857.

Example 29: General Procedure for the Synthesis of 10a-b

The synthesis of compounds 10a-b is indicated by reaction "f" in FIG. 1. To a round-bottom flask equipped with a stir bar was added aldehyde 9 (1.0 eq), amine (1.5 eq), methanol (14 mL/mmol), and acetic acid (0.5 mL/mmol). The reaction mixture was stirred 1 h at which time sodium cyanoborohydride (1.0 eq) was added. The reaction mixture was stirred overnight and diluted with water. The precipitate was filtered off and washed with water to give an off-white solid product.

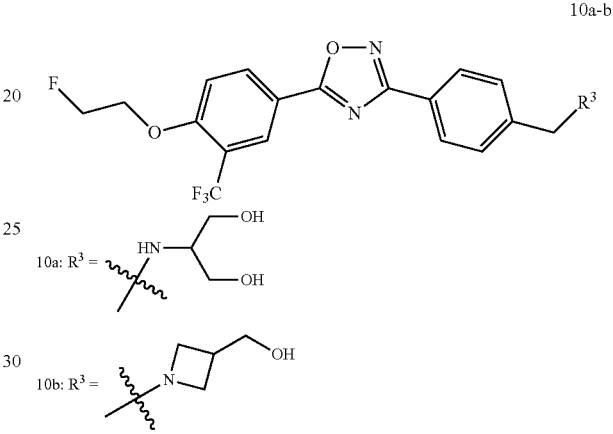

Example 30: Synthesis of 2-((4-(5-(4-(2-Fluoroethoxy)-3-(trifluoromethyl)phenyl)-1,2,4-oxadiazol-3-yl)benzyl)amino)propane-1,3-diol (10a)

The synthesis follows the general procedure described in Example 29. Yield: 50%, off-white solid, MP: 135-137° C. $^1$H NMR (400 MHz, DMSO-d6) δ=8.44 (dd, J=8.8 Hz, 2.0 Hz, 1H), 8.34 (s, 1H), 8.04 (d, J=8.0 Hz, 2H), 7.57 (d, J=8.0 Hz, 2H), 4.89-4.50 (m, 4H), 4.46 (br, 1H), 3.88 (s, 2H), 3.49-3.35 (m, 4H), 2.58 (pent, J=6.0 Hz, 1H; $^{13}$C NMR (101 MHz, DMSO-d6) δ 174.2, 168.3, 159.8, 142.1, 133.3, 129.0, 127.8 (q, $J_{C-F}$=5.25 Hz), 127.3, 126.0, 122.8 (q, $J_{C-F}$=274 Hz), 119.6 (q, $J_{C-F}$=32 Hz), 116.8, 113.4, 81.0 (d, $J_{C-F}$=170 Hz), 68.6 (d, $J_{C-F}$=20.2 Hz), 64.5, 56.8, 55.7. HRMS (ESI) calcd for $C_{21}H_{21}F_4N_3O_4$ [M+H$^+$] 456.1541, found 456.1537.

Example 31: Synthesis of (1-(4-(5-(4-(2-Fluoroethoxy)-3-(trifluoromethyl)phenyl)-1,2,4-oxadiazol-3-yl)benzyl)azetidin-3-yl)methanol (10b)

The synthesis follows the general procedure described in Example 29. Yield: 23%, white solid, MP: 114-116° C. $^1$H NMR (400 MHz, DMSO-d6) δ 8.45 (d, J=8.8 Hz, 1H), 8.36-8.32 (m, 1H), 8.12 (d, J=8.2 Hz, 2H), 7.65-7.55 (m, 3H), 5.49 (s, 1H), 4.88-4.82 (m, 1H), 4.78-4.71 (m, 1H), 4.64-4.57 (m, 1H), 4.57-4.49 (m, 1H), 3.31-3.27 (m, 6H).

Example 32: Synthesis of 3-(4-(chloromethyl)phenyl)-5-(4-(2-fluoroethoxy)-3-(trifluoromethyl)phenyl)-1,2,4-oxadiazole (11)

To a 25 mL of round bottle flask was added cyanuric chloride (253 mg, 1.37 mmol) and DMF (2.5 mL). A solution of 8c (500 mg, 1.31 mmol) in dichloromethane (3.5 mL) was added dropwise at room temperature. The reaction was stirred at room temperature overnight, then cooled and diluted with dichloromethane and water. Separating the organic layer from the aqueous layer, and dried with anhydrous sodium sulfate. After removing the solvent, crude product (400 mg, 73%) was afforded. The crude product was used directly for the next step. 1H NMR (400 MHz, CDCl3) δ=8.47 (d, J=2.0 Hz, 1H), 8.35 (dd, J=8.8 Hz, 2.0 Hz, 1H), 8.17 (d, J=8.0 Hz, 2H), 7.54 (d, J=8.4 Hz, 2H), 7.18 (d, J=8.8 Hz, 1H), 4.93-4.76 (m, 2H), 4.65 (s, 2H), 4.48-4.36 (m, 2H).

Example 33: General procedure for the synthesis of 12a-e and 12g

The synthesis of compounds 12a-e and 12g is indicated as reaction "h" in FIG. 1. To a round-bottom flask equipped with a stir bar was added alcohols (10 eq) and THF (2 mL/mmol). After cooling to 0° C., sodium hydride (1.8 eq) was added portionwise, and the reaction vessel was equipped with a reflux condenser and heated to 80° C. and stirred for 30 min. Chloride 11 (1.0 eq) was added to the flask and the mixture was stirred overnight. The reaction was cooled to room temperature and quenched with water. The crude was extracted with ethyl acetate, washed with saturated brine, and dried over MgSO$_4$. After filtering and concentrated, the residue was purified by flash chromatography on silica gel using hexane and ethyl acetate as eluent to afford product.

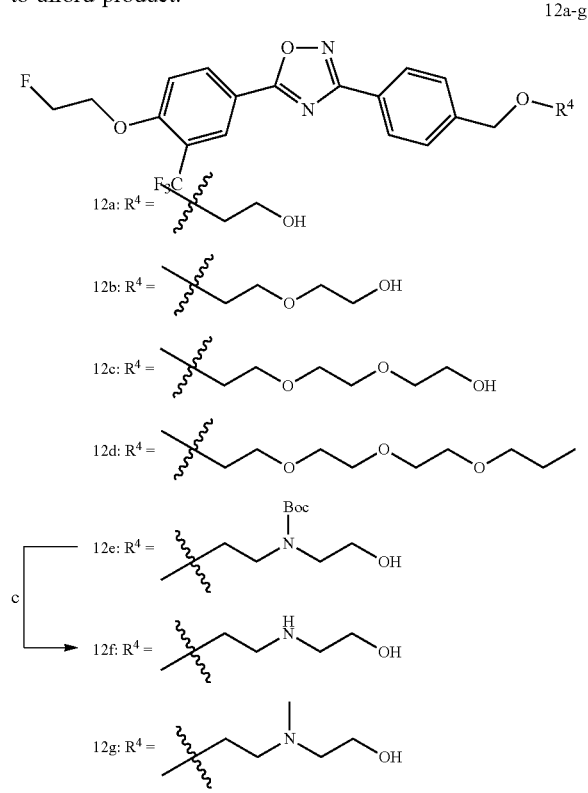

Example 34: Synthesis of 2-((4-(5-(4-(2-Fluoroethoxy)-3-(trifluoromethyl)phenyl)-1,2,4-oxadiazol-3-yl)benzypoxy)ethan-1-ol (12a)

The synthesis follows the general procedure described in Example 33. Yield: 35%, off-white solid, MP: 109-110° C. $^1$H NMR (400 MHz, CDCl$_3$) δ 8.42 (s, 1H), 8.30 (dd, J=8.6, 1.4 Hz, 1H), 8.11 (d, J=8.1 Hz, 2H), 7.46 (d, J=8.0 Hz, 2H), 7.13 (d, J=8.7 Hz, 1H), 4.71-4.89 (m, 2H), 4.62 (s, 2H), 4.33-4.45 (m, 2H), 3.78 (m, 2H), 3.63 (m, 2H). 3.78 (t, J=4.4 Hz, 2H), 3.63 (t, J=4.4 Hz, 2H). $^{13}$C NMR (101 MHz, CDCl$_3$) δ 174.2, 168.7, 159.6, 141.4, 133.3, 127.9, 127.7 (q, J$_{C-F}$=5.2 Hz), 127.6, 126.1, 122.7 (q, J$_{C-F}$=271 Hz), 120.2 (q, J$_{C-F}$=32 Hz), 117.0, 113.4, 81.3 (d, J$_{C-F}$=172 Hz), 72.7, 71.7, 68.4 (d, J$_{C-F}$=21 Hz), 61.9. HRMS (ESI) calcd for C$_{20}$H$_{18}$F$_4$N$_2$O$_4$ [M H$^+$] 427.1245, found 427.1240.

Example 35: Synthesis of 2-(2((4-(5-(4-(2-Fluoroethoxy)-3-(trifluoromethyl)phenyl)-1,2,4-oxadiazol-3-yl)benzypoxy)ethoxy)ethan-1-ol (12b)

The synthesis follows the general procedure described in Example 33. Yield: 39%, an off-white semi-solid. $^1$H NMR (400 MHz, CDCl$_3$) δ=8.47 (s, 1H), 8.34 (d, J=8.8 Hz, 1H), 8.14 (d, J=8.0 Hz, 2H), 7.49 (d, J=8.0 Hz, 2H), 7.17 (d, J=8.8 Hz, 1H), 4.83 (dt, J=47.2 Hz, 4.0 Hz, 2H), 4.65 (s, 2H), 4.42 (dt, J=26.8 Hz, 4.4 Hz, 2H), 3.78-3.60 (m, 8H). $^{13}$C NMR (101 MHz, CDCl$_3$) δ 174.4, 168.0, 159.5, 141.8, 133.3, 128.0, 127.7 (q, J$_{C-F}$=5.4 Hz), 127.2, 126.5, 122.8 (q, J$_{C-F}$=274 Hz), 119.0 (q, J$_{C-F}$=32 Hz), 116.8, 113.4, 81.2 (d, J$_{C-F}$=173 Hz), 72.5, 70.3, 70.0, 68.4 (d, J$_{C-F}$=21 Hz), 66.4, 61.8. HRMS (ESI) calcd for C$_{22}$H$_{22}$F$_4$N$_2$O$_5$ [M+H$^+$] 471.1583, found 471.1589.

Example 36: Synthesis of 2-(2-((4(4-(5-(4-(2-Fluoroethoxy)-3-(trifluoromethyl)phenyl)-1,2,4-oxadiazol-3-yl)benzypoxy)ethoxy)ethoxy)ethan-1-ol (12c)

The synthesis follows the general procedure described in Example 33. Yield: 42%, an off-white semi-solid. $^1$H NMR (400 MHz, CDCl$_3$) δ 8.38 (s, 1H), 8.27 (d, J=8.7 Hz, 1H), 8.06 (d, J=8.1 Hz, 2H), 7.41 (t, J=7.6 Hz, 2H), 7.09 (d, J=8.8 Hz, 1H), 4.69-4.83 (m, 2H), 4.57 (s, 2H), 4.29-4.40(m, 2H), 4.38 (m, 1H), 3.52-43.69 (m, 12H). $^{13}$C NMR (101 MHz, CDCl$_3$) δ 174.2, 168.8, 159.6, 141.7, 132.2, 127.9, 127.7 (q, J$_{C-F}$=5.2 Hz), 127.6, 125.9, 122.7 (q, J$_{C-F}$=271 Hz), 120.2 (q, J$_{C-F}$=32 Hz), 117.1, 113.4, 81.3 (d, J$_{C-F}$=171 Hz), 72.7, 72.5, 70.7, 70.6, 70.3, 69.7, 68.4 (d, J$_{C-F}$=21 Hz), 61.7. HRMS (ESI) calcd for C$_{24}$H$_{26}$F$_4$N$_2$O$_6$ [M+H$^+$] 515.1800, found 515.1806.

Example 37: Synthesis of 1-(4-(5-(4-(2-Fluoroethoxy)-3-(trifluoromethyl)phenyl)-1,2,4-oxadiazol-3-yl)phenyl)-2,5,8,11-tetraoxatridecan-13-ol (12d)

The synthesis follows the general procedure described in Example 33. Yield: 25%, an off-white semi-solid. $^1$H NMR (400 MHz, CDCl$_3$) δ 8.40 (s, 1H), 8.29 (d, J=8.8 Hz, 1H), 8.07 (d, J=8.0 Hz, 2H), 7.43 (d, J=8.0 Hz, 2H), 7.11 (d, J=8.8 Hz, 1H), 4.68-4.85 (m, 2H), 4.58 (s, 2H), 4.30-4.42 (m, 2H), 3.51-3.68 (m, 16H). $^{13}$C NMR (101 MHz, CDCl$_3$) δ 173.9, 168.3, 159.3, 141.8, 132.2, 127.9, 127.7 (q, J$_{C-F}$=5.2 Hz), 127.6, 125.9, 122.7 (q, J$_{C-F}$=271 Hz), 120.2 (q, J$_{C-F}$=32 Hz), 117.1, 113.4, 81.3 (d, J=172.5 Hz), 72.7, 72.5, 70.6, 70.5, 70.4, 70.3, 70.2, 69.7, 68.4 (d, J$_{C-F}$=21 Hz), 61.7. HRMS (ESI) calcd for C$_{26}$H$_{30}$F$_4$N$_2$O$_7$ [M+H$^+$] 559.2062, found 559.2066.

Example 38: Synthesis of Tert-butyl (2-((4-(5-(4-(2-fluoroethoxy)-3-(trifluoromethyl)phenyl)-1,2,4-oxadiazol-3-yl)benzypoxy)ethyl)(2-hydroxyethyl)carbamate (12e)

The synthesis follows the general procedure described in Example 33. The crude product was used directly for the next step reaction without further purification.

Example 39: Synthesis of 2-((2-((4-(5-(4-(2-fluoroethoxy)-3-(trifluoromethyl)phenyl)-1,2,4-oxadiazol-3-yl)benzy)oxy)ethyl)amino)ethan-1-ol (12f)

The synthesis of compound 12f is indicated as reaction "c" in FIG. 1. To a solution of 12e (284 mg, 0.50 mmol) in methanol (5.0 mL) was added 4 M HCl in dioxane (5.0 mL). The reaction was stirred at RT for 6 h, then the solvent was removed by and the residue was dissolved in ethyl acetate. The solution was washed with saturated $NaHCO_3$, water, and dried over $MgSO_4$. After filtering and concentration, the final white solid product was obtained. (199 mg, 85%) MP: 126-130° C. $^1$H NMR (400 MHz, $CDCl_3$) δ 8.38 (s, 1H), 8.27 (d, J=8.7 Hz, 1H), 8.07 (d, J=8 Hz, 2H), 7.34-7.43 (m, 2H), 7.10 (d, J=8.8 Hz, 1H), 4.67-4.84 (m, 2H), 4.53 (s, 2H), 4.30-4.41 (m, 2H), 4.26 (t, J=8 Hz, 2H), 3.60-3.67 (m, 4H), 3.45 (t, J=5.2 Hz, 2H). $^{13}$C NMR (101 MHz, $CDCl_3$) δ 174.3, 168.7, 158.6, 141.3, 133.3, 127.8, 127.7 (q, $J_{C-F}$=5.25 Hz), 127.6, 126.1, 122.7 (q, $J_{C-F}$=275 Hz), 120.3 (q, $J_{C-F}$=31 Hz), 117.0, 113.4, 86.3 (d, $J_{C-F}$=173 Hz), 72.6, 68.9, 68.4 (d, $J_{C-F}$=21.1 Hz), 62.0, 46.0, 44.2. HRMS (ESI) calcd for $C_{22}H_{23}F_4N_3O_4$ [M+H$^+$] 470.1697, found 470.1694.

Example 40: Synthesis of 2-((2-((4-(5-(4-(2-fluoroethoxy)-3-(trifluoromethyl)phenyl)-1,2,4-oxadiazol-3-yl)benzy)oxy)ethyl)(methypamino)ethan-1-ol (12g)

The synthesis follows the general procedure described in Example 33. Yield: 26%, pale yellow semi-solid. $^1$H NMR (400 MHz, $CDCl_3$) δ 8.40 (d, J=1.8 Hz, 1H), 8.29 (dd, J=8.7, 2.0 Hz, 1H), 8.07 (d, J=8.1 Hz, 2H), 7.42 (d, J=8.1 Hz, 2H), 7.11 (d, J=8.8 Hz, 1H), 4.88-4.79 (m, 1H), 4.75-4.65 (m, 1H), 4.54 (s, 2H), 4.44-4.25 (m, 2H), 4.12 (s, 3H), 3.55 (s, 2H), 2.73-2.60 (m, 4H), 2.29 (s, 3H). $^{13}$C NMR (101 MHz, $CDCl_3$) δ 174.8, 168.7, 160.2, 159.0, 141.3, 133.3, 128.0, 127.8 (q, $J_{C-F}$=5.25 Hz), 127.4, 125.9, 122.8 (q, $J_{C-F}$=275 Hz), 120.4 (q, $J_{C-F}$=31 Hz), 116.8, 113.4, 72.8, 60.4, 59.9, 57.7, 43.0. HRMS (ESI) calcd for $C_{17}H_{21}F_4N_3O_4$ [M+H$^+$] 408.1541, found 408.1536.

Example 41: In Vitro S1P1 Receptor Binding Assay of Compounds 8a-8k and 10a-b, and 12a-g The binding potency of the newly synthesized compounds were determined by competition against the binding of [$^{32}$P]S1P to commercial cell membranes expressing recombinant human S1P1 (1, 2, 3, 4, and 5) according to the methods reported previously (A. J. Rosenberg, H. Liu, Z. Tu, Applied radiation and isotopes: including data, instrumentation and methods for use in agriculture, industry and medicine 2015, 102, 5-9).

As shown in Table 1, the previously synthesized compound 8c showed high binding potency toward S1P1 ($IC_{50}$=6.67±0.70 nM). Replacing of trifluoromethyl with cyano group caused a 2-fold decrease of potency (8b, $IC_{50}$=15.4±3.8 nM) but removing of trifluoromethyl resulted in a significant decrease of binding potency (8a, $IC_{50}$>1000 nM). Therefore, the trifluoromethyl group was maintained and further modification focused on interposing various hydroxyl-containing groups. The p-amino alcohol derivatives 8e, 8f, 8g, and 10a showed less binding potency than 8c with $IC_{50}$ values of 59.6, 48.2, 38.0 and 87.2 nM, also another y-amino alcohol compound 10b showed an $IC_{50}$ value more than 100 nM. It suggested that the amino alcohols are unfavorable to the S1P1 in this series of compounds. The alkyl di-alcohol compound 8k, with one more hydroxyl compared to compound 8c, exhibited a 4-fold decreased binding potency with an $IC_{50}$ value of 23.8 nM. For the ether alcohol derivatives, compound 8h ($IC_{50}$=3.9 nM) showed a 10-fold increase of binding potency compared to the amino alcohol compound 8g; both phenyl ether alcohol compound 8i and benzyl ether alcohol compound 12a showed good binding potency with $IC_{50}$ values of 19.2 and 14.0 nM, respectively. Pegylation has emerged recently as an effective strategy for improving the solubility, stability, pharmacokinetics, and pharmacodynamics of pharmaceuticals (J. M. Harris, R. B. Chess, Nature Reviews Drug Discovery 2003, 2, 214; C. S. Fishburn, Journal of Pharmaceutical Sciences 2008, 97, 4167-4183). To check if the pegylation had an impact on the binding potency, compound 12a was coupled with a different number of PEG to afford compounds 12b, 12c, and 12d. The binding data showed that compounds 12a ($IC_{50}$=14.0 nM) and 12b ($IC_{50}$=15.4 nM) having one and two PEGs were approximately 2-fold less potent than 8c. Increase the chains with three (12c, $IC_{50}$=106 nM) and four (12d, $IC_{50}$=125 nM) PEGs resulted in a significant decrease of binding activity toward S1P1, which indicated increase the PEGs will decrease the binding potency. Compounds 12f and 12g, having secondary amine and tertiary amine in the PEG chain showed reduced binding potency (12f, $IC_{50}$=75.6 nM; 12g, $IC_{50}$=130 nM) compared to compound 12b, showed again that amino alcohols are less potent than the ether alcohols.

TABLE 1

Structures and binding potency (mean ± SD) of S1P and new compounds towards S1P1.

| Compound | R$^1$ | R$^2$ | S1P1 $IC_{50}$ ± SD (nM) |
|---|---|---|---|
| S1P | | — | 1.4 ± 0.3 |
| 8a | | ⤳OH | >1,000 |

TABLE 1-continued

Structures and binding potency (mean ± SD) of S1P and new compounds towards S1P1.

| Compound | R¹ | R² | S1P1 IC$_{50}$ ± SD (nM) |
|---|---|---|---|
| 8b | N | –CH(CH₃)CH₂OH | 15.4 ± 3.8 |
| 8c | F₃ | –CH(CH₃)CH₂OH | 6.7 ± 0.7[b] |
| 8e | F₃ | –CH₂NHCH₂CH₂OH | 59.6 ± 23.8 |
| 8f | F₃ | –CH₂N(CH₃)CH₂CH₂OH | 48.2 ± 9.7 |
| 8g | F₃ | –CH₂N(CH₃)CH₂CH(OH)CH₂OH | 38.0 ± 6.0 |
| 8h | F₃ | –CH₂OCH₂CH(OH)CH₂OH | 3.9 ± 0.5 |
| 8i | F₃ | –OCH₂CH₂OH | 19.2 ± 3.0 |
| 8k | F₃ | –CH(CH₂OH)OH (diol) | 23.8 ± 5.8 |
| 10a | F₃ | –CH₂NHCH(CH₂OH)CH₂OH | 87.2 ± 17.7 |
| 10b | F₃ | –CH₂-(azetidinyl)-CH₂OH | 125 ± 27 |
| 12a | F₃ | –CH₂OCH₂CH₂OH | 14.0 ± 0.4 |
| 12b | F₃ | –(OCH₂CH₂)₂OH | 15.4 ± 3.3 |

TABLE 1-continued

Structures and binding potency (mean ± SD) of S1P and new compounds towards S1P1.

[Structure: F-CH₂CH₂-O-phenyl(R¹)-oxadiazole-phenyl-R²]

| Compound | R¹ | R² | S1P1 IC$_{50}$ ± SD (nM) |
|---|---|---|---|
| 12c | F$_3$ | ⁓(OCH$_2$CH$_2$)$_3$OH | 106 ± 25 |
| 12d | F$_3$ | ⁓(OCH$_2$CH$_2$)$_4$OH | 125 ± 22 |
| 12f | F$_3$ | ⁓O⁓N(H)⁓OH | 75.6 ± 19.3 |
| 12g | F$_3$ | ⁓O⁓N(CH$_3$)⁓OH | 130 ± 19 |

$^a$IC$_{50}$ values were determined at least 3 independent experiments, each run was performed in duplicate.
$^b$ A. J. Rosenberg, H. Liu, H. Jin, X. Yue, S. Riley, S. J. Brown, Z. Tu, J. Med. Chem. 2016, 59, 6201-6220.

According to the in vitro binding results, compounds 8c, 8h, 12a, and 12b exhibited high binding potency toward S1P1 with IC$_{50}$ values less than 20 nM. The subsequent evaluation of these ligands' binding potency toward other four S1P subtypes, S1P2-S1P5 was performed to check the binding specificity for S1P1. As shown in Table 2, all tested compounds did not show significant potential binding toward S1P2-S1P5 (IC$_{50}$>1,000 nM), showing that compounds 8c, 8h, 12a, and 12b are selective for S1P1.

TABLE 2

Binding potency (mean ± SD) of 8c, 8h, 12a, and 12b toward S1P1-S1P5$^a$

| Compound | IC$_{50}$ (nM) | | | | |
|---|---|---|---|---|---|
| | S1P1 | S1P2 | S1P3 | S1P4 | S1P5 |
| S1P | 1.4 ± 0.3 | 3.6 ± 0.5 | 0.4 ± 0.2 | 151 ± 82 | 3.1 ± 1.1 |
| 8c | 6.7 ± 0.7 | >1,000 | >1,000 | >1,000 | >1,000 |
| 8h | 3.9 ± 0.5 | >1,000 | >1,000 | >1,000 | >1,000 |
| 12a | 14.0 ± 0.4 | >1,000 | >1,000 | >1,000 | >1,000 |
| 12b | 15.4 ± 3.3 | >1,000 | >1,000 | >1,000 | >1,000 |

Example 42: Synthesis of Precursors 15a-d and Radiotracers [$^{18}$F]8c, [$^{18}$F]12a, and [$^{18}$F]12b Based on the in vitro binding potency observed in Example 41, the identified potent candidates 8c, 8h, 12a, and 12b were radiolabeled with F-18 isotope. However, prior to the radiosynthesis of [$^{18}$F]8c, [$^{18}$F]12a, [$^{18}$F]12b, and [$^{18}$F]8h, the precursors 15a-d were prepared by following the scheme diagrammed in FIG. 2. The cyclization of methoxymethyl (MOM) protected hydroxybenzimidamide 13a-d and 4-hydroxy-3-(trifluoromethyl)benzoic acid afforded 14a-d, which were alkylated with ethylene ditosylate to give precursors 15a-d. The radiosyntheses of these four radiotracers were achieved by using the nucleophilic reaction between the tosylate precursors and [$^{18}$F]KF in acetonitrile with Kryptofix 222, followed by deprotection of MOM group. The product was purified using a semi-preparative high-performance liquid chromatography (HPLC). The radioactive [$^{18}$F]8c, [$^{18}$F]8h, [$^{18}$F]12a, and [$^{18}$F]12b were authenticated by co-injecting with standard references 8c, 8h, 12a, and 12b. All the four radiotracers were achieved with radiochemical yields ~40%, radiochemical purities >98%, and specific activities >74 GBq/pmol (decay corrected to EOS). Details for these steps are outlined in the following examples (41-51).

Example 43: General Procedure for the Synthesis of 14a-d

To a round-bottom flask equipped with a stir bar was added 4-hydroxy-3-(trifluoromethyl)benzoic acid (1.0 eq), HOBt (0.2 eq), TBTU (1.0 eq), DIPEA (3.0 eq), and DMF (5.0 mL/mmol). The reaction mixture was stirred for 0.5 h followed by adding methoxymethyl (MOM) protected amidoxime 13a-d (1.0 eq, FIG. 2). The reaction mixture was stirred for 1 h at room temperature, then refluxed in a pre-heated 120° C. oil-bath for 4 h and monitored by TLC. After cooling, the reaction mixture was diluted with water and extracted with ethyl acetate. The ethyl acetate layer was washed with 1 M HCl, saturated brine, and dried over anhydrous MgSO$_4$. After filtration and concentration, the residue was purified on a silica gel column.

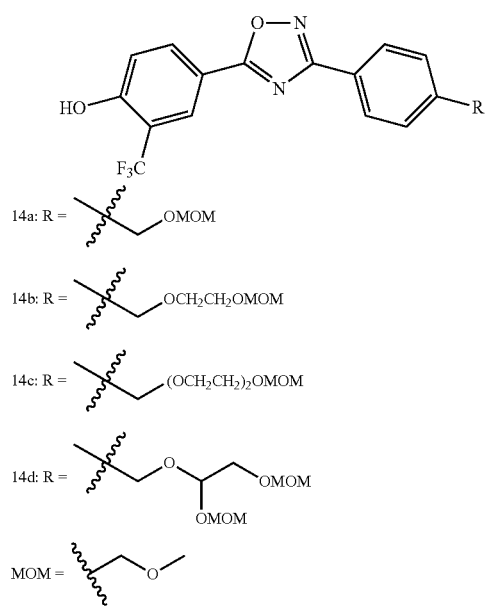

14a-d

14a: R = OMOM

14b: R = OCH₂CH₂OMOM

14c: R = (OCH₂CH₂)₂OMOM

14d: R = O-CH(OMOM)-CH₂-OMOM

MOM = CH₂OCH₃

Example 44: Synthesis of 4-(3-(4-((Methoxymethoxy)methyl)phenyl)-1,2,4-oxadiazol-5-yl)-2-(trifluoromethyl)phenol (14a)

The synthesis follows the general procedure described in Example 43. Yield: 50%, white solid, MP: 130-135° C. $^1$H NMR (400 MHz, DMSO-d6) δ=11.83 (br s, 1H), 8.29-8.24 (m, 2H), 8.07 (d, J=8.0 Hz, 2H), 7.55 (d, J=8.0 Hz, 2H), 7.27 (d, J=8.8 Hz, 1H), 4.70 (s, 2H), 4.63 (s, 2H), 3.33 (s, 3H).

Example 45: Synthesis of 4-(3-(4-((2-(Methoxymethoxy)ethoxy)methyl)phenyl)-1,2,4-oxadiazol-5-yl)-2-(trifluoromethyl)phenol (14b)

The synthesis follows the general procedure described in Example 43. Yield: 45%, white solid, MP: 120-122° C. $^1$H NMR (400 MHz, CDCl₃) δ 8.32 (s, 1H), 8.01-7.93 (m, 3H), 7.50-7.43 (m, 1H), 7.39 (d, J=8.1 Hz, 2H), 6.97 (d, J=8.6 Hz, 1H), 4.72 (s, 2H), 4.60 (s, 2H), 3.84-3.74 (m, 4H), 3.39 (s, 3H).

Example 46: Synthesis of 4-(3-(4-(2,4,7,10-Tetraoxaundecan-11-yl)phenyl)-1,2,4-oxadiazol-5-yl)-2-(trifluoromethyl)phenol (14c)

The synthesis follows the general procedure described in Example 43. Yield: 60%, white solid, MP: 103-105° C. $^1$H NMR (400 MHz, CDCl₃) δ 8.24 (s, 1H), 7.89 (d, J=7.9 Hz, 2H), 7.78 (d, J=8.6 Hz, 1H), 7.29 (d, J=7.9 Hz, 2H), 6.81 (d, J=8.6 Hz, 1H), 4.59 (s, 2H), 4.52 (s, 2H), 3.84-3.68 (m, 8H), 3.33 (s, 3H).

Example 47: Synthesis of 4-(3-(4-(((2,4,7,9-Tetraoxadecan-5-yl)oxy)methyl)phenyl)-1,2,4-oxadiazol-5-yl)-2-(trifluoromethyl)phenol (14d)

The synthesis follows the general procedure described in Example 43. Yield: 50%, semi-solid. $^1$H NMR (400 MHz, CDCl₃) δ 8.38 (s, 1H), 8.14 (d, J=8.4 Hz, 1H), 8.08 (d, J=8.1 Hz, 2H), 7.48 (d, J=8.1 Hz, 2H), 7.02 (d, J=8.6 Hz, 1H), 4.89-4.84 (m, 1H), 4.73-4.69 (m, 1H), 4.68-4.61 (m, 3H), 3.84-3.69 (m, 4H), 3.38 (s, 3H), 3.29 (s, 3H).

Example 48: General Procedure for the Synthesis of 15a-d

To a round-bottom flask equipped with a stir bar was added 14a-d (1.0 eq), ethylene ditosylate (2.0 eq), K₂CO₃ (3.0 eq), and acetonitrile (10 mL/mmol). The reaction mixture was stirred for 1 hour at RT, then refluxed in a pre-heated 90° C. oil-bath overnight and monitored by TLC. The reaction was diluted with ethyl acetate and water, the ethyl acetate layer was washed with saturated brine and dried over anhydrous MgSO₄. After filtering and concentration, the residue was purified on a silica gel column.

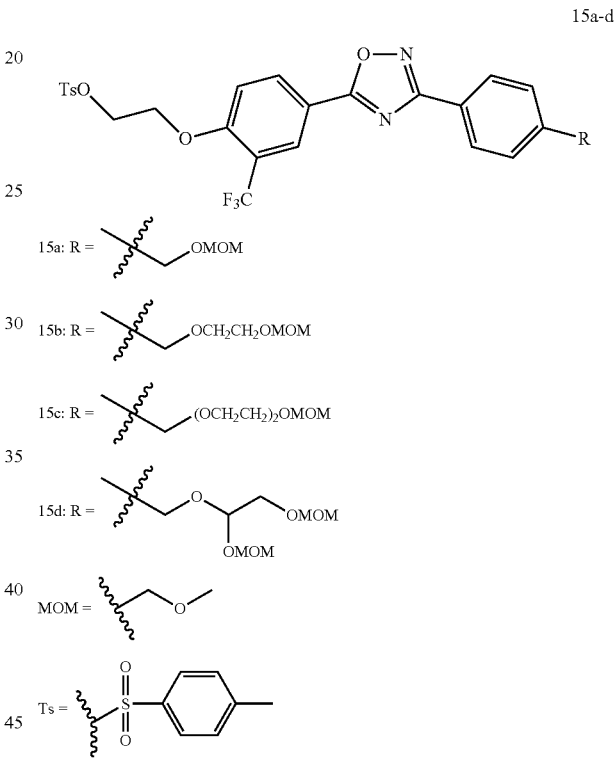

15a-d

15a: R = OMOM

15b: R = OCH₂CH₂OMOM

15c: R = (OCH₂CH₂)₂OMOM

15d: R = O-CH(OMOM)-CH₂-OMOM

MOM = CH₂OCH₃

Ts = SO₂-C₆H₄-CH₃

Example 49: Synthesis of 2-(4-(3-(4-((Methoxymethoxy)methyl)phenyl)-1,2,4-oxadiazol-5-yl)-2-(trifluoromethyl)phenoxy)ethyl 4-methylbenzenesulfonate (15a)

The synthesis follows the general procedure described in Example 48. Yield: 30%, white solid, MP: 125-127° C. $^1$H NMR (400 MHz, CDCl₃) δ 8.44 (s, 1H), 8.32 (d, J=8.8 Hz, 1H), 8.15 (d, J=8.0 Hz, 2H), 7.81 (d, J=8.0 Hz, 2H), 7.51 (d, J=8.0 Hz, 2H), 7.35 (d, J=8.0 Hz, 2H), 7.09 (d, J=8.8 Hz, 1H), 4.75 (s, 2H), 4.68 (s, 2H), 4.45-4.35 (m, 4H), 3.44 (s, 3H), 2.45 (s, 3H). $^{13}$C NMR (101 MHz, CDCl₃) δ 174.3, 169.0, 159.2, 145.3, 141.6, 133.5, 132.6, 130.1, 128.2, 128.1, 127.8 (q, $J_{C-F}$=5.5 Hz), 127.8, 126.1, 122.8 (q, $J_{C-F}$=271 Hz), 120.3 (q, $J_{C-F}$=32 Hz), 117.5, 113.5, 96.1, 68.9, 67.3, 66.8, 55.6, 21.8. HRMS (ESI) calcd for C₂₇H₂₅F₃N₂O₇S [M+H⁺] 579.1407. Found [M+H⁺] 579.1415.

Example 50: Synthesis of 2-(4-(3-(4-((2-(Methoxymethoxy)ethoxy)methyl)phenyl)-1,2,4-oxadiazol-5-yl)-2-(trifluoromethyl)phenoxy)ethyl 4-methylbenzenesulfonate (15b)

The synthesis follows the general procedure described in Example 48. Yield: 57%, white solid, MP: 115-117° C. $^1H$ NMR (400 MHz, CDCl$_3$) δ 8.41 (s, 1H), 8.30 (d, J=8.6 Hz, 1H), 8.12 (d, J=8.0 Hz, 2H), 7.79 (d, J=8.1 Hz, 2H), 7.48 (d, J=7.8 Hz, 2H), 7.33 (d, J=7.9 Hz, 2H), 7.07 (d, J=8.7 Hz, 1H), 4.66 (d, J=10.5 Hz, 4H), 4.30-4.45 (m, 4H), 3.80-3.64 (m, 4H), 3.37 (s, 3H), 2.42 (s, 3H). $^{13}$C NMR (101 MHz, CDCl$_3$): δ 174.1, 168.7, 159.0, 145.2, 141.8, 133.3, 132.3, 129.9, 127.9, 127.8, 127.7, 127.5 (q, $J_{C-F}$=5.5 Hz), 125.8, 122.6 (q, $J_{C-F}$=271 Hz), 120.0 (q, $J_{C-F}$=32 Hz), 117.1, 113.3, 96.5, 72.7, 69.7, 67.3, 66.8, 66.5, 55.2, 22.3. HRMS (ESI) calcd for C$_{29}$H$_{29}$F$_3$N$_2$O$_8$S [M+H$^+$] 623.1669, found 623.1660.

Example 51: Synthesis of 2-(4-(3-(4-(2,4,7,10-Tetraoxaundecan-11-yl)phenyl)-1,2,4-oxadiazol-5-yl)-2-(trifluoromethyl)phenoxy)ethyl 4-methylbenzenesulfonate (15c)

The synthesis follows the general procedure described in Example 48. Yield: 38%, white semi-solid. $^1$H NMR (400 MHz, CDCl$_3$) δ 8.41 (s, 1H), 8.31 (d, J=9.8 Hz, 1H), 8.12 (d, J=8.0 Hz, 2H), 7.79 (d, J=8.1 Hz, 2H), 7.48 (d, J=8.0 Hz, 2H), 7.33 (d, J=8.2 Hz, 2H), 7.08 (d, J=8.8 Hz, 1H), 4.65 (d, J=7.9 Hz, 4H), 4.43-4.33 (m, 4H), 3.73-3.65 (m, 8H), 3.37 (s, 3H), 2.43 (s, 3H). $^{13}$C NMR (101 MHz, CDCl$_3$): δ 174.1, 168.8, 159.0, 145.2, 141.9, 133.3, 132.3, 129.9, 127.9, 127.9, 127.6 (q, $J_{C-F}$=5.5 Hz), 127.5, 125.8, 122.6 (q, $J_{C-F}$=271 Hz), 120.1 (q, $J_{C-F}$=32 Hz), 117.2, 113.3, 96.5, 72.7, 70.6, 69.8, 67.2, 66.8, 66.5, 55.2, 21.6. HRMS (ESI) calcd for C$_{31}$H$_{33}$F$_3$N$_2$O$_9$S [M+H$^+$] 667.1932, found 667.1925.

Example 52: Synthesis of 2-(4-(3-(4-(((2,4,7,9-Tetraoxadecan-5-yl)oxy)methyl)phenyl)-1,2,4-oxadiazol-5-yl)-2-(trifluoromethyl)phenoxy)ethyl 4-methylbenzenesulfonate (15d)

The synthesis follows the general procedure described in Example 48. Yield: 44%, white semi-solid. $^1$H NMR (400 MHz, CDCl$_3$) δ 8.35 (s, 1H), 8.25 (d, J=8.7 Hz, 1H), 8.08 (d, J=8.1 Hz, 2H), 7.74 (d, J=7.9 Hz, 2H), 7.45 (d, J=8.2 Hz, 2H), 7.28 (d, J=8.0 Hz, 2H), 7.03 (d, J=8.7 Hz, 1H), 4.82 (dd, J=7.0, 4.2 Hz, 1H), 4.61 (q, J=6.7 Hz, 4H), 4.33 (d, J=3.7 Hz, 4H), 3.74 (dd, J=10.7, 7.1 Hz, 1H), 3.66 (dd, J=10.7, 4.3 Hz, 1H), 3.30 (d, J=10.1 Hz, 3H), 3.22 (s, 3H), 2.37 (s, 3H). $^{13}$C NMR (101 MHz, CDCl$_3$): δ 174.2, 168.7, 159.1, 145.2, 142.6, 133.3, 132.3, 129.9, 127.9, 127.7, 127.6, 127.6 (q, $J_{C-F}$=5.5 Hz), 126.3, 122.6 (q, $J_{C-F}$=271 Hz), 120.1 (q, $J_{C-F}$=32 Hz), 117.2, 113.3, 96.5, 94.8, 71.2, 67.2, 66.6, 55.5, 55.2, 46.9, 21.6. HRMS (ESI) calcd for C$_{30}$H$_{31}$F$_3$N$_2$O$_9$S [M+H$^+$] 653.1775, found 653.1770.

Example 53: General Procedure for the Radiosynthesis of [$^{18}$F]8c, [$^{18}$F]8h, [$^{18}$F]12a, and [$^{18}$F]12b

[$^{18}$F]KF (~7.4 GBq) aqueous was added to a vial containing Kryptofix 222 (~10 mg), and dried by azeotropic evaporation with acetonitrile (3×1 mL) under N$_2$ flow at 110° C. To the reaction vial was added precursor 15a-d (~2 mg) as a solution in acetonitrile (300 μL). The reaction was placed in a 110° C. oil-bath for 15 min. The reaction was removed from the oil-bath, at which time 6 M HCl (150 μL) was added. The reaction mixture was heated in a 110° C. oil-bath for another 5 min. The reaction was removed from the oil-bath and quenched with 6 M NaOH (150 μL) and diluted with 2.4 mL of the HPLC mobile phase. The mixture was passed through a SEP-PAK Alumina N Cartridge (Part No. WAT020510) and injected onto the semi-preparation HPLC column (Agilent SB-C18 250×9.6 mm, 5 μm, UV=254 nm, 4.0 mL/min). The HPLC fraction was collected into a water bottle with 60 mL of water and then trapped on a SEP-PAK C-18 Cartridge (Part No. WAT020515). The activity (~740 MBq) was washed out with 0.6 mL of ethanol and 5.4 mL of 0.9% saline. After sterile filtration into a glass vial, the radiolabeled product was ready for quality control (QC) analysis and animal studies. An aliquot of sample was injected onto an analytical HPLC to determine the concentration of tracer. Meanwhile, the tracer was authenticated by co-injected with non-radiolabeled standard sample solution.

Semi-preparation HPLC conditions were as follows: [$^{18}$F]8c, [$^{18}$F]12a, and [$^{18}$F]12b: mobile phase, 50% acetonitrile in 0.1 M ammonium formate buffer, pH=4.2; flow rate, 4.0 mL/min; UV=254 nM; $t_R$=18-21 min. [$^{18}$F]8h: mobile phase, 40% acetonitrile in 0.1 M ammonium formate buffer, pH=4.2; flow rate, 4.0 mL/min; UV=254 nM; $t_R$=25-27 min.

QC HPLC conditions were as follows: [$^{18}$F]8c: mobile phase, 75% acetonitrile in 0.1 M ammonium formate buffer, pH=4.2; flow rate, 1.5 mL/min; UV=254 nM; $t_R$=5.5 min. [$^{18}$F]12a: mobile phase, 70% acetonitrile in 0.1 M ammonium formate buffer, pH=4.2; flow rate, 1.0 mL/min; UV=254 nM; $t_R$=5.7 min. [$^{18}$F]12b: mobile phase, 70% acetonitrile in 0.1 M ammonium formate buffer, pH=4.2; flow rate, 1.0 mL/min; UV=254 nM; $t_R$=5.6 min. [$^{18}$F]8h: mobile phase, 63% acetonitrile in 0.1 M ammonium formate buffer, pH=4.2; flow rate, 1.5 mL/min; UV=254 nM; $t_R$=4.6 min.

Example 54: In Vitro Autoradiography Studies of [$^{18}$F]12a

Figure 3:
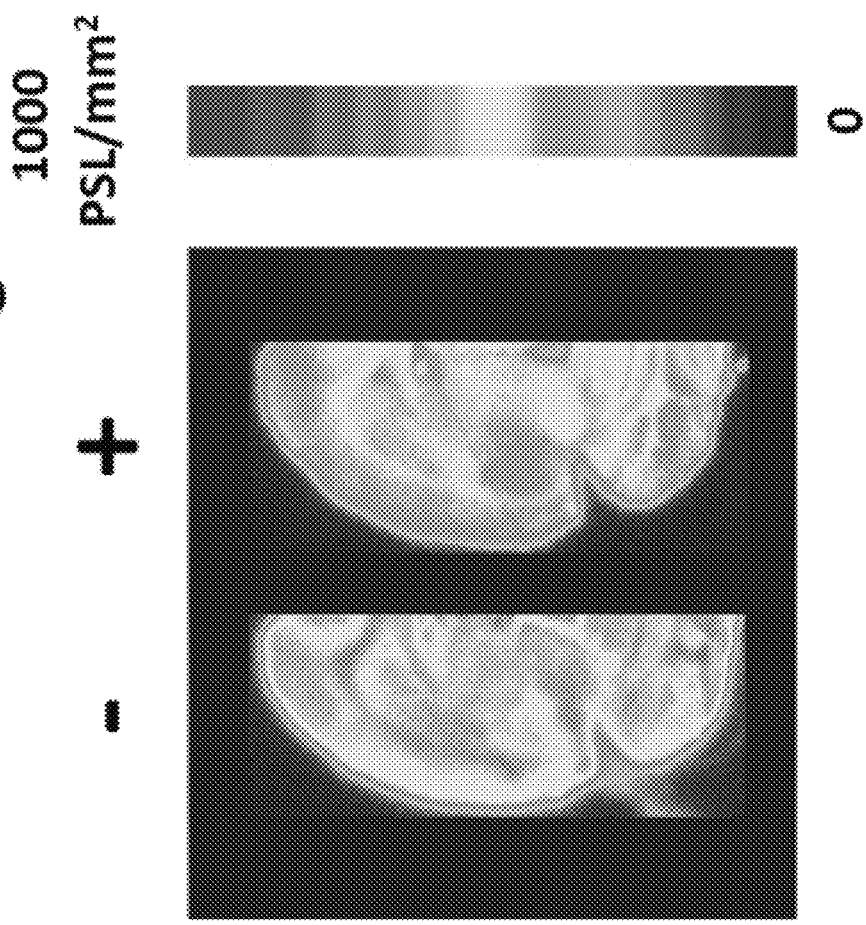

To check the binding specificity of [$^{18}$F]12a toward S1P1 in the brain, in vitro autoradiography study was performed using rat brain slices. Adult female Lewis rats (n=2, 100-125 g, Charles River) were used to perform the autoradiography study. The rats (n=2) was euthanized and the brains were collected and cut into 20 μm sequential sections using a Microm cryotome and mounted on glass slides. For the control study, the slides were incubated with ~6 nM of [$^{18}$F]12a at RT for 60 min. For the blocking studies, slides were incubated with [$^{18}$F]12a in the presence of 10 μM of SEW2871 at RT for 60 min. Following the incubation, the brain sections were washed and exposed to the Storage Phosphor Screen in an imaging cassette overnight in −20° C. at dark for 12 h. The distribution of radioactivity was visualized by a Fuji Bio-Imaging Analyzer FLA-7000 (Fuji Photo Film, Tokyo, Japan). Photo-stimulated luminescence (PSL) from the brain slices was quantified using Multi Gauge v3.0 software (Fuji Photo Film Co., Tokyo, Japan). Data were background-corrected, and expressed as photo-stimulated luminescence signals per square millimeter (PSL/mm$^2$). In vitro autoradiography study showed that SEW2871 was able to reduce ~30% of radioactivity, demonstrating that [$^{18}$F]12a has specific binding with S1P1 (FIG. 3).

Example 55: Biodistribution of [$^{18}$F]12a in Female Lewis Rats

To investigate the tissue distribution of [$^{18}$F]12a in rodent, a biodistribution study was performed in adult female Lewis rats at 5, 30, 60, and 120 min post-injection (p.i.). A solution of [$^{18}$F]12a (~2.0 MBq/100 μL) in 10% ethanol in 0.9% saline was injected via the tail vein into adult female Lewis rats (n=16, 100-125 g, Charles River) under 2-3% isoflurane/oxygen anesthesia. The rats were euthanized under anesthesia at 5, 30, 60, and 120 min post-injection (n=4 for each group). Organs of blood, heart, lung, muscle, fat, pancreas, spleen, kidney, liver, thymus, brain, and bone were dissected and collected for counting. All the samples were counted with a dilution of the injectate on an automated well counter (Beckman Gamma 8000 well counter). Tissues were weighed and the uptake was reported as background and decay-corrected percent injected dose per gram (% ID/g).

As shown in Table 3, the initial uptake (% ID/g) at 5 min p.i. in blood, heart, lung, muscle, fat, pancreas, spleen, kidney, liver, thymus, and brain was 0.36, 1.16, 1.31, 0.28, 0.24, 2.19, 1.14, 2.14, 4.87, 0.79, and 1.31, respectively. A rapid washout of radioactivity was observed in tissues pancreas, spleen, kidney, and liver, the uptake decreased from 2.19, 1.14, 2.14, and 4.87 at 5 min p.i. to 1.52, 0.79, 1.43, and 3.58 at 30 min p.i., respectively, and further decreased at 60 min and 120 min p.i.. The bone uptake was collected to check if defluorination happened in vivo. The results showed there was no significant change from 5 min to 120 min p.i., suggesting that [$^{18}$F]12a has no metabolic defluorination in vivo. For brain of interest, a 3-fold high brain uptake was observed at 5 min p.i. compared to the previous radiotracer [$^{18}$F]4 (% ID/g=0.49 at 5 min p.i.[21]). The higher brain uptake in rodent suggested that [$^{18}$F]12a may have potential to overcome the limitation of [$^{18}$F]4 and have a good uptake in the NHP brain. Example 109 below confirms this hypothesis by measuring 12a using microPET in NHP.

TABLE 3

Biodistribution of [$^{18}$F]12a in female Lewis rats[a]

| Organs | Tissue uptake (% ID/g) | | | |
|---|---|---|---|---|
| | 5 min | 30 min | 60 min | 120 min |
| Blood | 0.36 ± 0.04 | 0.51 ± 0.01 | 0.57 ± 0.03 | 0.66 ± 0.04 |
| Heart | 1.16 ± 0.01 | 1.01 ± 0.08 | 0.85 ± 0.04 | 0.74 ± 0.03 |
| Lung | 1.31 ± 0.01 | 1.20 ± 0.06 | 1.01 ± 0.04 | 0.87 ± 0.02 |
| Muscle | 0.28 ± 0.02 | 0.54 ± 0.01 | 0.49 ± 0.03 | 0.42 ± 0.01 |
| Fat | 0.24 ± 0.03 | 1.63 ± 0.36 | 1.50 ± 0.08 | 1.91 ± 0.19 |
| Pancreas | 2.19 ± 0.04 | 1.52 ± 0.04 | 1.21 ± 0.10 | 0.98 ± 0.05 |
| Spleen | 1.14 ± 0.10 | 0.79 ± 0.06 | 0.65 ± 0.02 | 0.55 ± 0.03 |
| Kidney | 2.14 ± 0.14 | 1.43 ± 0.08 | 1.18 ± 0.04 | 1.01 ± 0.04 |
| Liver | 4.87 ± 0.27 | 3.58 ± 0.28 | 3.32 ± 0.33 | 3.23 ± 0.10 |
| Thymus | 0.79 ± 0.12 | 0.68 ± 0.06 | 0.58 ± 0.04 | 0.51 ± 0.05 |
| Bone | 0.40 ± 0.04 | 0.34 ± 0.02 | 0.34 ± 0.01 | 0.42 ± 0.02 |
| Brain | 1.31 ± 0.06 | 1.34 ± 0.08 | 1.13 ± 0.05 | 0.87 ± 0.04 |

[a](% ID/g values, mean ± SD, n = 4).

Example 56: Synthesis of Oxadiazole Compounds having Hydrophilic Substitutions The following examples detail the synthesis and characterization of target compounds derived from [$^{18}$F]4. The goal of these experiments was to modify the aryl azetidine carboxylic group using other hydrophilic groups to identify new analogs having improved binding properties and physicochemical properties. In these examples, the aryl azetidine carboxyl acid group is replaced with aryl sulfonamide, amide, N-hydroxyamide, hydrazide, alcohol, carboxyl acid and amine groups. Note that while compound [$^{18}$F]4 is radiolabeled, it is understood that compound 4, as referred to in the following examples, is its non-radiolabeled counterpart.

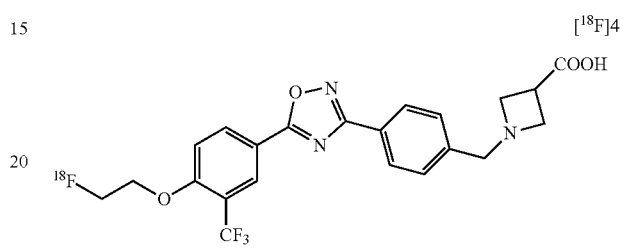

Commercially available starting materials, reagents, and solvents were used as purchased without further purification unless otherwise stated. Reactions were monitored by thin-layer chromatography (TLC) carried out on pre-coated glass plates of silica gel 60 $F_{254}$ from EMD Chemicals Inc. Visualization was accomplished with ultraviolet light (UV 254 nm). Compounds were purified by recrystallization or flash column chromatography using 230-400 mesh silica gel purchased from Silicycle. Melting points were determined on a MEL-TEMP 3.0 apparatus without corrected. $^1$H NMR and $^{13}$C NMR spectra were received from Varian 400 MHz instrument. Chemical shifts were reported in parts per million (ppm) and were calibrated using a residual undeuterated solvent as an internal reference (CDCl$_3$: δ 7.26 ppm; CD$_3$OD: δ 3.31 ppm; DMSO-d6: δ 2.50 ppm; Acetone-d6: δ 2.05 ppm). High-resolution positive ion mass was acquired by a Bruker MaXis 4G Q-TOF mass spectrometer with electrospray ionization source.

All animal experiments were conducted under Washington University's Institutional Animal Care and Use Committee (IACUC)-approved protocols in accordance with the US National Research Council's Guide for the Care and Use of Laboratory Animals.

Example 55: General Synthesis of Compounds 19a-e from Precursors 15, 16, 18a-e and 17a-e Compounds 19a-e were generated according to the scheme in FIG. 4. Alkylation of commercially available 4-fluoro-3-(trifluoromethyl)benzoic acid 15 and 2-fluoroethan-1-ol generated the intermediate 4-(2-fluoroethoxy)-3-(trifluoromethyl)benzoic acid 16 under the condition of sodium hydride in dimethyl sulfoxide (DMSO). Meanwhile, the 4-position substituted amidoximes 18a-e were prepared from corresponding benzonitriles 17a-e reacting with hydroxylamine hydrochloride and triethylamine. Coupling of 16 with 18a-e under the conventional peptide coupling conditions and subsequently thermally cyclization yielded the oxadiazoles (19a-e).

Example 56: Synthesis of Synthesis of 4-(2-Fluoroethoxy)-3-(trifluoromethyl)benzoic acid (16)

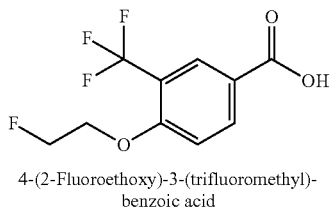

4-(2-Fluoroethoxy)-3-(trifluoromethyl)-benzoic acid

Figure 4:
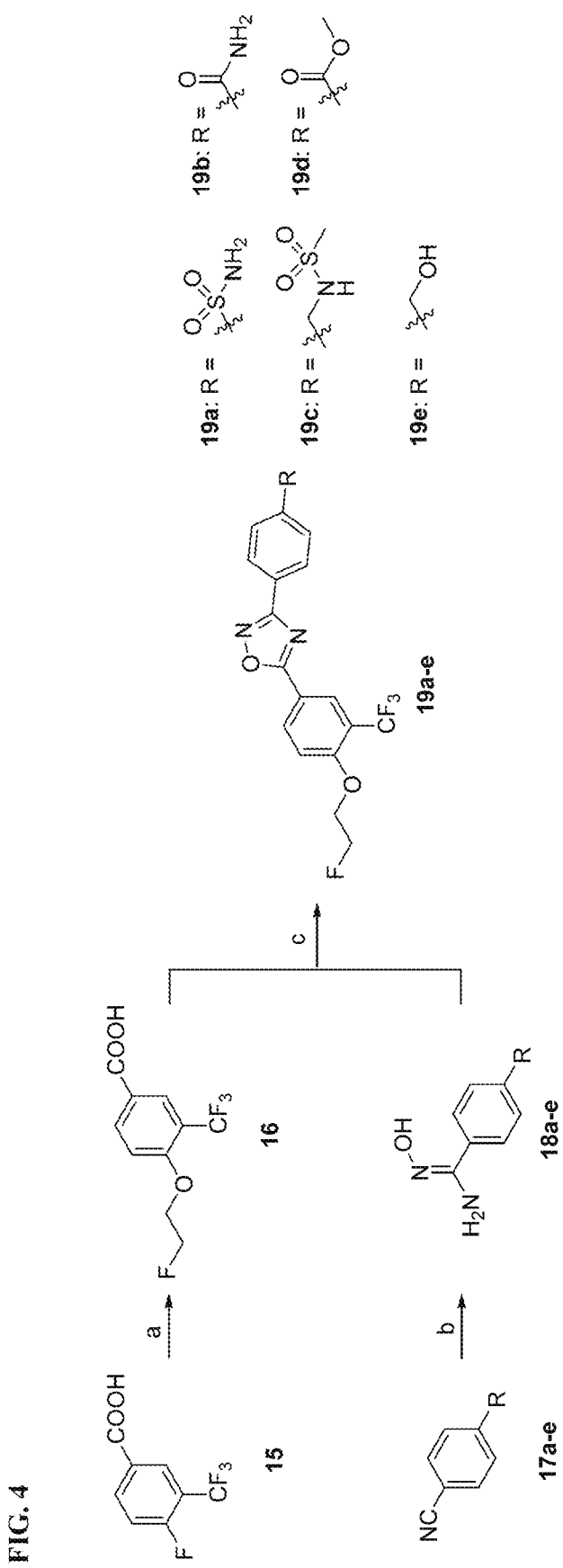
FIG. 4. Syntheses of 19a-e Reagents and conditions: (a) NaH, 2-fluoroethan-1-ol, DMSO, 1 M HCl, RT; (b) hydroxylamine hydrochloride, NaHCO$_3$, methanol, reflux; (c) TBTU, HOBt, DIPEA, DMF, RT-120° C.

Synthesis of compound (16b) is indicated as reaction "a" in FIG. 4. To a round-bottom flask equipped with a stir bar was added 4-fluoro-3-(trifluoromethyl)benzoic acid (8.32 g, 40.0 mmol), 2-fluoroethanol (3.84 g, 60 mmol), and DMSO (100 mL) under $N_2$ atmosphere. NaH (2.07 g, 90.0 mmol) was added portion wise with stirring. The reaction was stirred at room temperature overnight and monitored by TLC. The mixture was poured into ice-water (1 L) and acidified with 1 M HCl to give a precipitate. The resulting precipitate was filtered off, washed with water and hexanes to give a tan solid (9.6 g, 95%). MP: 131-133° C. $^1$H NMR (400 MHz, DMSO-d6) δ 13.18 (br, 1H, —COOH), 8.37-8.04 (m, 2H, —ArH), 7.45-7.32 (m, 1H, —ArH), 4.89-4.74 (m, 1H, —CH$_2$F), 4.72-4.58 (m, 1H, —CH$_2$F), 4.52-4.39 (m, 1H, —CH$_2$O—), 4.38-4.29 (m, 1H, —CH$_2$O—).

Example 57: General Procedure for the Synthesis of 18a-e

Note that compounds 18a to 18e are similar to compounds 6a to 6g described in examples above. Consequently they were synthesized using similar procedures to Example 7, above. Their synthesis is also indicated in FIG. 4 as reaction "b". To a round-bottom flask equipped with a stir bar was added 17a-e (1.0 eq) (prepared using similar procedures as described in Examples 2-5), hydroxylamine hydrochloride (2.0 eq), NaHCO$_3$ (4.0 eq), and methanol (5.0 mL/mmol). The reaction was refluxed and stirred in a pre-heated 75° C. oil-bath for 6 h. The reaction mixture was cooled to room temperature, and the precipitate was filtered off and washed with methanol. The filtrate was concentrated in vacuo without further purification.

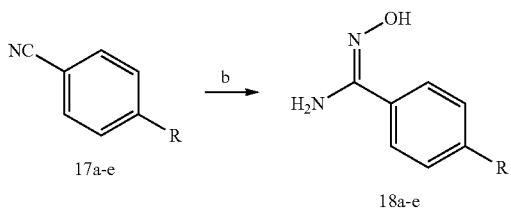

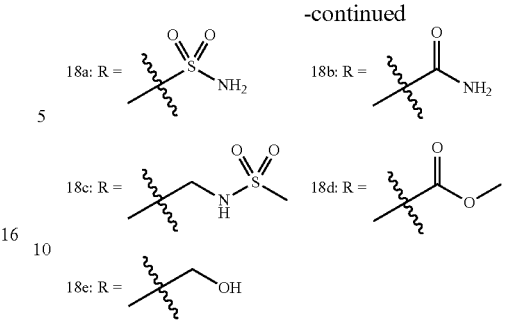

Example 58: Synthesis of (E)-N'-hydroxy-4-sulfamoylbenzimidamide (18a)

The synthesis follows the general procedure described in Example 57. Yield: 70%. MP: 217-219° C. 1H NMR (400 MHz, DMSO-d6) δ=7.88-7.78 (m, 4H, —ArH), 5.93 (s, 2H, —SO2NH2).

Example 59: Synthesis of (E)-4-(N'-hydroxycarbamimidoyl)benzamide (18b)

The synthesis follows the general procedure described in Example 57. Yield: 39%. MP: 221-224° C. 1H NMR (400 MHz, DMSO-d6) δ 9.78 (s, 1H, —OH), 7.98 (s, 1H, —NH2), 7.86 (d, J=8.4 Hz, 2H, —ArH), 7.74 (d, J=8.4 Hz, 2H, —ArH), 7.38 (s, 1H, —NH2), 5.88 (s, 2H, —CONH2).

Example 60: Synthesis of (E)-N'-hydroxy-4-(methylsulfonamidomethyl)benzimidamide (18c)

The synthesis follows the general procedure described in Example 57. Yield: 95%. MP: 178-180° C. 1H NMR (300 MHz, DMSO-d6) δ 9.62 (s, 1H, —OH), 7.63 (d, J=8.3 Hz, 2H, —ArH), 7.32 (d, J=8.4 Hz, 2H, —ArH), 5.78 (s, 2H, —NH2), 4.14 (s, 2H, —CH2-), 2.84 (s, 3H, —CH3).

Example 61: Synthesis of Methyl (E)-4-(N'-hydroxycarbamimidoyl)benzoate (18d)

The synthesis follows the general procedure described in Example 57. Yield: 86%. MP: 168-170° C. 1H NMR (400 MHz, DMSO-d6) δ=9.91 (s, 1H, —OH), 7.94 (d, J=8.0 Hz, 2H, —ArH), 7.82 (d, J=8.4 Hz, 2H, —ArH), 5.93 (s, 2H, —NH2), 3.85 (s, 3H, —OCH3)

Example 62: Synthesis of (E)-N'-hydroxy-4-(hydroxymethyl)benzimidamide (18e)

The synthesis follows the general procedure described in Example 57. Yield: 76%. MP: 152-155° C. 1H NMR (400 MHz, DMSO-d6) δ 9.57 (s, 1H, —OH), 7.71-7.57 (m, 2H, —ArH), 7.37-7.24 (m, 2H, —ArH), 5.77 (s, 2H, —NH2), 5.24 (s, 1H, —CH2OH), 4.51 (s, 2H, —CH2-).

Example 63: General Procedure for the Synthesis of 19a-e

Note that compounds 19a-e here have a similar structure to compounds 8a-j above. Therefore, they were synthesized in a similar way to Example 16, above. Their synthesis is also indicated in FIG. 4 as reaction "c". To a round-bottom flask equipped with a stir bar was added acid 16 (1.0 eq), HOBt (0.2 eq), TBTU (1.0 eq), DIPEA (3.0 eq), and DMF (5.0 mL/mmol). The reaction mixture was stirred for 0.5 h followed by adding amidoxime 18a-e (1.0 eq). The reaction mixture was stirred for 1 h at room temperature, then refluxed in a pre-heated 120° C. oil-bath for 4 h and monitored by TLC. After cooling, the reaction mixture was diluted with water and extracted with ethyl acetate. The ethyl acetate layer was washed with 1 M HCl, saturated brine, and dried over anhydrous MgSO$_4$. After filtration and concentration, the residue was purified on a silica gel column.

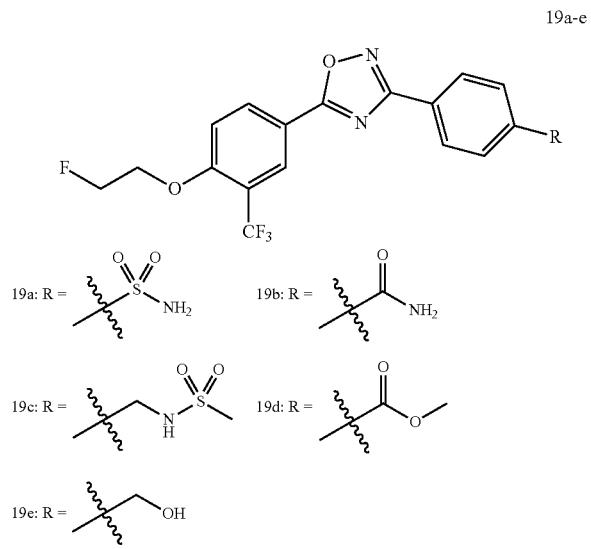

Example 64: Synthesis of 4-(5-(4-(2-Fluoroethoxy)-3-(trifluoromethyl)phenyl)-1,2,4-oxadiazol-3-Obenzenesulfonamide (19a)

The synthesis follows the general procedure described in Example 63. Yield: 51%. MP: 198-199° C. $^1$H NMR (400 MHz, DMSO-d6) δ 8.45-8.38 (m, 1H, —ArH), 8.33-8.24 (m, 3H, —ArH), 8.04 (d, J=8.4 Hz, 2H, —ArH), 7.62-7.52 (m, 3H, —ArH & —NH$_2$), 4.89-4.81 (m, 1H, —CH$_2$F), 4.76-4.70 (m, 1H, —CH$_2$F), 4.61-4.55 (m, 1H, —CH$_2$O—), 4.54-4.44 (m, 1H, —CH$_2$O—). $^{13}$C NMR (101 MHz, DMSO-d6) δ 174.92, 167.79, 160.02, 147.12, 134.58, 129.34, 128.21, 127.08 (q, J=5.1 Hz), 127.04, 123.31 (d, J=272.7 Hz), 118.61 (q, J=31.3 Hz), 116.10, 115.44, 82.10 (d, J=168.7 Hz), 69.24 (d, J=18.2 Hz). HRMS (ESI) calcd for C$_{17}$H$_{13}$F$_4$N$_3$O$_4$S [M+H$^+$] 432.0636. Found [M+H$^+$] 432.0640.

Example 65: Synthesis of 4-(5-(4-(2-Fluoroethoxy)-3-(trifluoromethyl)phenyl)-1,2,4-oxadiazol-3-yl)benzamide (19b)

The synthesis follows the general procedure described in Example 63. Yield: 29%. MP: 244-245° C. $^1$H NMR (400 MHz, DMSO-d6) δ 8.40 (d, J=8.1 Hz, 1H, —ArH), 8.30 (s, 1H, —ArH), 8.19-8.10 (m, 3H, —ArH & —NH$_2$), 8.10-8.03 (m, 2H, —ArH), 7.59-7.51 (m, 2H, —ArH), 4.89-4.82 (m, 1H, —CH$_2$F), 4.76-4.71 (m, 1H, —CH$_2$F), 4.62-4.55 (m, 1H, —CH$_2$O—), 4.53-4.47 (m, 1H, —CH$_2$O—). $^{13}$C NMR (101 MHz, DMSO-d6) δ 174.72, 168.14, 167.49, 159.96, 137.42, 134.54, 128.77, 127.42, 127.08 (q, J=5.1 Hz), 123.31 (d, J=273.7 Hz), 118.58 (q, J=31.3 Hz), 116.17, 115.41, 82.10 (d, J=168.7 Hz), 69.23 (d, J=19.2 Hz). HRMS (ESI) calcd for C$_{18}$H$_{13}$F$_4$N$_3$O$_3$ [M+H$^+$] 396. 0966. Found [M+H$^+$] 396.0959.

Example 66: Synthesis of N-(4-(5-(4-(2-Fluoroethoxy)-3-(trifluoromethyl)phenyl)-1,2,4-oxadiazol-3-yl)benzyl)methanesulfonamide (19c)

The synthesis follows the general procedure described in Example 63. Yield: 9%. MP: 208-300° C. $^1$H NMR (400 MHz, DMSO-d6) δ 8.41 (d, J=8.9 Hz, 1H, —ArH), 8.31 (s, 1H, —ArH), 8.07 (d, J=8.1 Hz, 2H, —ArH), 7.73-7.67 (m, 1H, —ArH), 7.61-7.52 (m, 3H, —ArH & —NHSO$_2$—), 4.89-4.81 (m, 1H, —CH$_2$F), 4.78-4.70 (m, 1H, —CH$_2$F), 4.63-4.56 (m, 1H, —CH$_2$O—), 4.55-4.48 (m, 1H, —CH$_2$O—), 4.26 (d, J=6.3 Hz, 2H, —ArCH$_2$—), 2.91 (s, 3H, —SO$_2$CH$_3$). $^{13}$C NMR (101 MHz, DMSO-d6) δ 174.54, 168.46, 159.91, 142.71, 134.54, 128.77, 127.64, 127.07 (q, J=5.1 Hz), 125.29, 123.34 (d, J=273.7 Hz), 118.56 (q, J=31.3 Hz), 116.31, 115.43, 82.12 (d, J=168.7 Hz), 69.23 (d, J=. 18.2 Hz), 46.13, 40.35. HRMS (ESI) calcd for C$_{19}$H$_{17}$F$_4$N$_3$O$_4$S [M+H$^+$] 460.0949. Found [M+H$^+$] 460.0936.

Example 67: Synthesis of Methyl 4-(5-(4-(2-fluoroethoxy)-3-(trifluoromethyl)phenyl)-1,2,4-oxadiazol-3-yl)benzoate (19d)

The synthesis follows the general procedure described in Example 63. Yield: 62%. MP: 166-169° C. $^1$H NMR (400 MHz, Acetone-d6) δ 8.45 (d, J=8.9 Hz, 1H, —ArH), 8.42 (s, 1H, —ArH), 8.26 (d, J=8.1 Hz, 2H, —ArH), 8.18 (d, J=8.2 Hz, 2H, —ArH), 7.57 (d, J=8.7 Hz, 1H, —ArH), 4.96-4.92 (m, 1H, —CH$_2$F), 4.85-4.80 (m, 1H, —CH$_2$F), 4.68-4.64 (m, 1H, —CH$_2$O—), 4.62-4.56 (m, 1H, —CH$_2$O—), 3.94 (s, 3H, —OCH$_3$). $^{13}$C NMR (101 MHz, Acetone-d6) δ 174.80, 168.03, 165.62, 160.06, 133.86, 132.69, 130.76, 129.94, 127.34, 126.97 (q, J=5.1 Hz), 123.12 (d, J=273.7 Hz), 119.22 (d, J=31.3 Hz), 116.41, 114.50, 81.54 (d, J=169.7 Hz), 68.95 (d, J=19.2 Hz), 51.75.

Example 68: Synthesis of (4-(5-(4-(2-Fluoroethoxy)-3-(trifluoromethyl)phenyl)-1,2,4-oxadiazol-3-Ophenyl)methanol (19e)

The synthesis follows the general procedure described in Example 63. Yield: 65%. MP: 190-192° C. $^1$H NMR (400 MHz, CDCl$_3$) δ=8.45 (d, J=2.0 Hz, 1H, —ArH), 8.33 (dd, J=8.8 Hz, 2.0 Hz, 1H, —ArH), 8.13 (d, J=8.0 Hz, 2H, —ArH), 7.50 (d, J=8.0 Hz, 2H, —ArH), 7.16 (d, J=8.4 Hz, 1H, —ArH), 4.90-4.74 (m, 4H, —CH$_2$F & —CH$_2$OH), 4.48-4.35 (m, 2H, —CH$_2$O—).

Example 69: Overview of Synthesis of 20a-c from Precursor 19d

Figure 5:
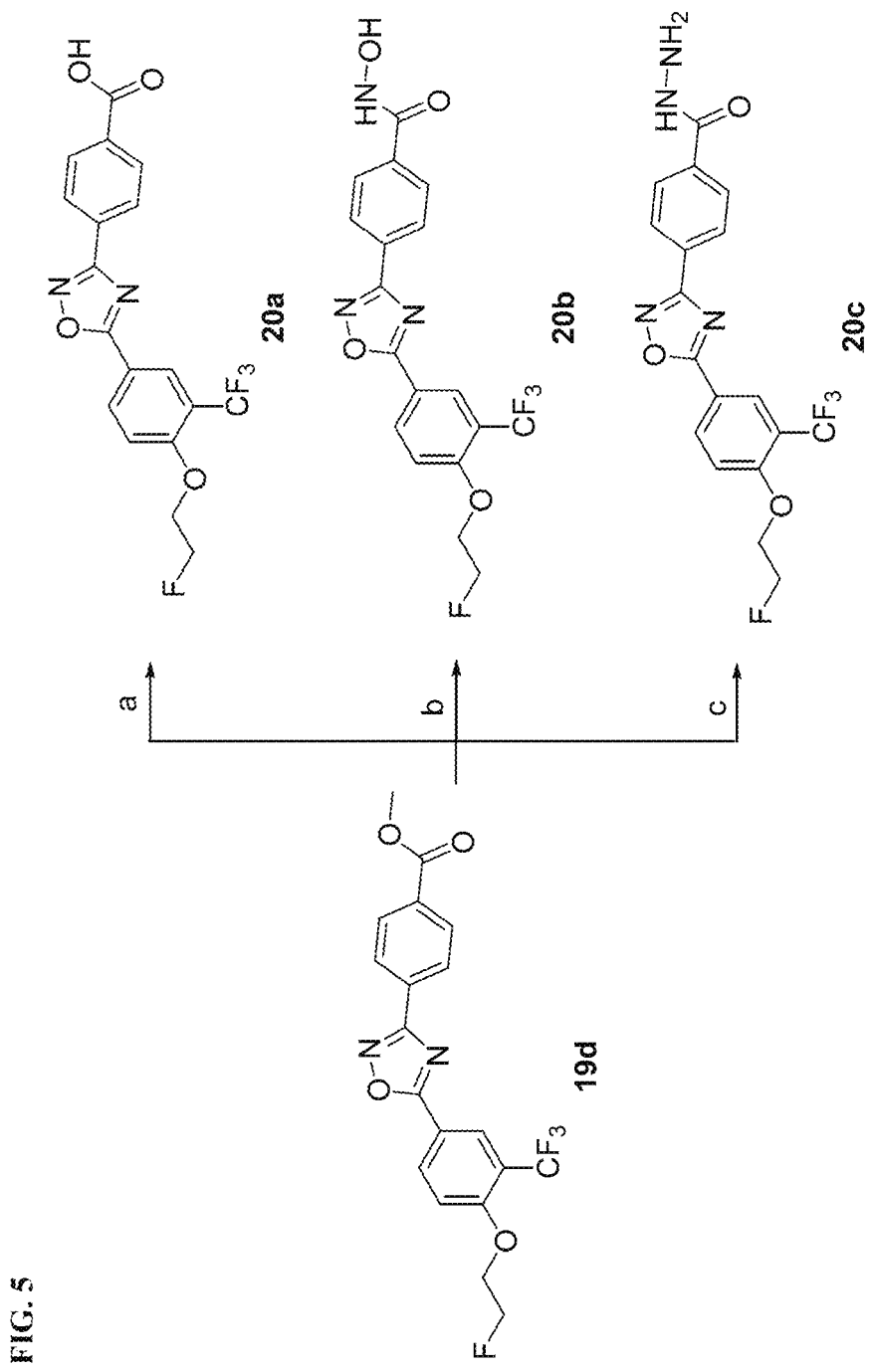
FIG. 5. Syntheses of 20a-c. Reagents and conditions: (a) LiOH, THF, H$_2$O, RT; (b) hydroxylamine, KOH, methanol, reflux; (c) hydrazine hydrate, ethanol, reflux.

The syntheses of compounds 20a-c is described in FIG. 5. Starting from compound 19d, compounds 20a-c were synthesized by the following procedures. The hydrolysis of 19d using lithium hydroxide as base gave compound 20a, and the ammonolysis of 19d with hydroxylamine or hydrazine provided 20b or 20c, respectively.

Example 70: Synthesis of 4-(5-(4-(2-Fluoroethoxy)-3-(trifluoromethyl)phenyl)-1,2,4-oxadiazol-3-yl)benzoic acid (20a)

To a round-bottom flask equipped with a stir bar was added ester 19d (2.0 g, 4.87 mmol), lithium hydroxide (230 mg, 9.75 mmol), THF (20 mL), and water (4 mL). The reaction mixture was stirred overnight and acidified with 1 M HCl to pH=1. The reaction mixture was extracted with ethyl acetate (20 mL), and the ethyl acetate layer was washed with saturated brine, and dried over anhydrous MgSO$_4$. After filtration and concentration, 20a was obtained as an off-white solid. (1.7 g, 87%). MP: 220-222° C. $^1$H NMR (400 MHz, DMSO-d6) δ 13.26 (s, 1H, —COOH), 8.39 (d, J=8.8 Hz, 1H, —ArH), 8.28 (s, 1H, —ArH), 8.19-8.08 (m, 4H, —ArH), 7.54 (d, J=8.8 Hz, 1H, —ArH), 4.91-4.81 (m, 1H, —CH$_2$F), 4.79-4.69 (m, 1H, —CH$_2$F), 4.63-4.47 (m, 2H, —CH$_2$O—). $^{13}$C NMR (101 MHz, DMSO-d6) δ 174.80, 168.02, 167.02, 159.98, 134.55, 133.84, 130.13, 129.85, 127.70, 127.07 (q, J=5.1 Hz), 123.30 (d, J=273.7 Hz), 118.57 (q, J=31.3 Hz), 116.11, 115.41, 82.09 (d, J=168.7 Hz), 69.22 (d, J=19.2 Hz).

Example 71: Synthesis of 4-(5-(4-(2-Fluoroethoxy)-3-(trifluoromethyl)phenyl)-1,2,4-oxadiazol-3-yl)-N-hydroxybenzamide (20b)

To a round-bottom flask equipped with a stir bar was added ester 19d (150 mg, 0.37 mmol), hydroxylamine hydrochloride (76 mg, 1.1 mmol) and methanol (1.9 mL), followed by adding potassium hydroxide (12.5 mg, 2.22 mmol). The reaction mixture was refluxed overnight. After cooling to room temperature, the mixture was diluted with water (20 mL) to precipitate the product. The precipitate was filtered off and washed with diethyl ether to give an off-white solid (111 mg, 73%). MP: 186-189° C. $^1$H NMR (400 MHz, DMSO-d6) δ 11.43 (s, 1H, —OH), 9.20 (s, 1H, —NH—), 8.42 (d, J=8.1 Hz, 1H, —ArH), 8.31 (s, 1H, —ArH), 8.18-8.11 (m, 2H, —ArH), 8.01-7.91 (m, 2H, —ArH), 7.61-7.51 (m, 1H, —ArH), 4.92-4.68 (m, 2H, —CH$_2$F), 4.64-4.47 (m, 2H, —CH$_2$O—). $^{13}$C NMR (101 MHz, DMSO-d6) δ 174.77, 168.12, 167.05, 159.99, 135.95, 134.59, 130.55, 128.23, 127.59, 127.12 (d, J=5.1 Hz), 123.31 (d, J=274.7 Hz), 118.57 (J=30.3 Hz), 116.19, 115.45, 82.11 (d, J=168.7 Hz), 69.24 (d, J=19.2 Hz). HRMS (ESI) calcd for C$_{18}$H$_{13}$F$_4$N$_3$O$_4$ [M+H$^+$] 412.0919. Found [M+H$^+$] 412.0915.

Example 72: Synthesis of 4-(5-(4-(2-Fluoroethoxy)-3-(trifluoromethyl)phenyl)-1,2,4-oxadiazol-3-yl) benzohydrazide (20c)

To a round-bottom flask equipped with a stir bar was added ester 19d (205 mg, 0.5 mmol), ethanol (1.3 mL), and hydrazine monohydrate (0.07 mL, 1.5 mmol). The reaction mixture was refluxed overnight. After cooling to room temperature, the precipitate was filtered off and washed with diethyl ether to give an off-white solid. (100 mg, 49%). MP: 186-188° C. $^1$H NMR (400 MHz, DMSO-d6) δ 9.98 (s, 1H, —CONH—), 8.42 (d, J=8.7 Hz, 1H, —ArH), 8.32 (s, 1H, —ArH), 8.14 (d, J=8.2 Hz, 2H, —ArH), 8.01 (d, J=8.2 Hz, 2H, —ArH), 7.56 (d, J=8.8 Hz, 1H, —ArH), 4.89-4.81 (m, 1H, —CH$_2$F), 4.77-4.70 (m, 1H, —CH$_2$F), 4.68-4.55 (m, 3H, —CH$_2$O-&-NH$_2$), 4.55-4.48 (m, 1H, —CH$_2$O—). $^{13}$C NMR (101 MHz, DMSO-d6) δ 174.75, 168.14, 165.35, 159.98, 136.46, 134.57, 128.62, 128.30, 127.52, 127.11 (q, J=5.1 Hz), 123.32 (d, J=273.7 Hz), 118.60 (q, J=31.3 Hz), 116.20, 115.46, 82.11 (d, J=167.7 Hz), 69.25 (d, J=19.2 Hz). HRMS (ESI) calcd for C$_{18}$H$_{14}$F$_4$N$_4$O$_3$ [M+H$^+$] 411. 1075. Found [M+H$^+$] 411.1067.

Example 73: Synthesis of 22a, 22b, 25, and 26a-b

Figure 6:
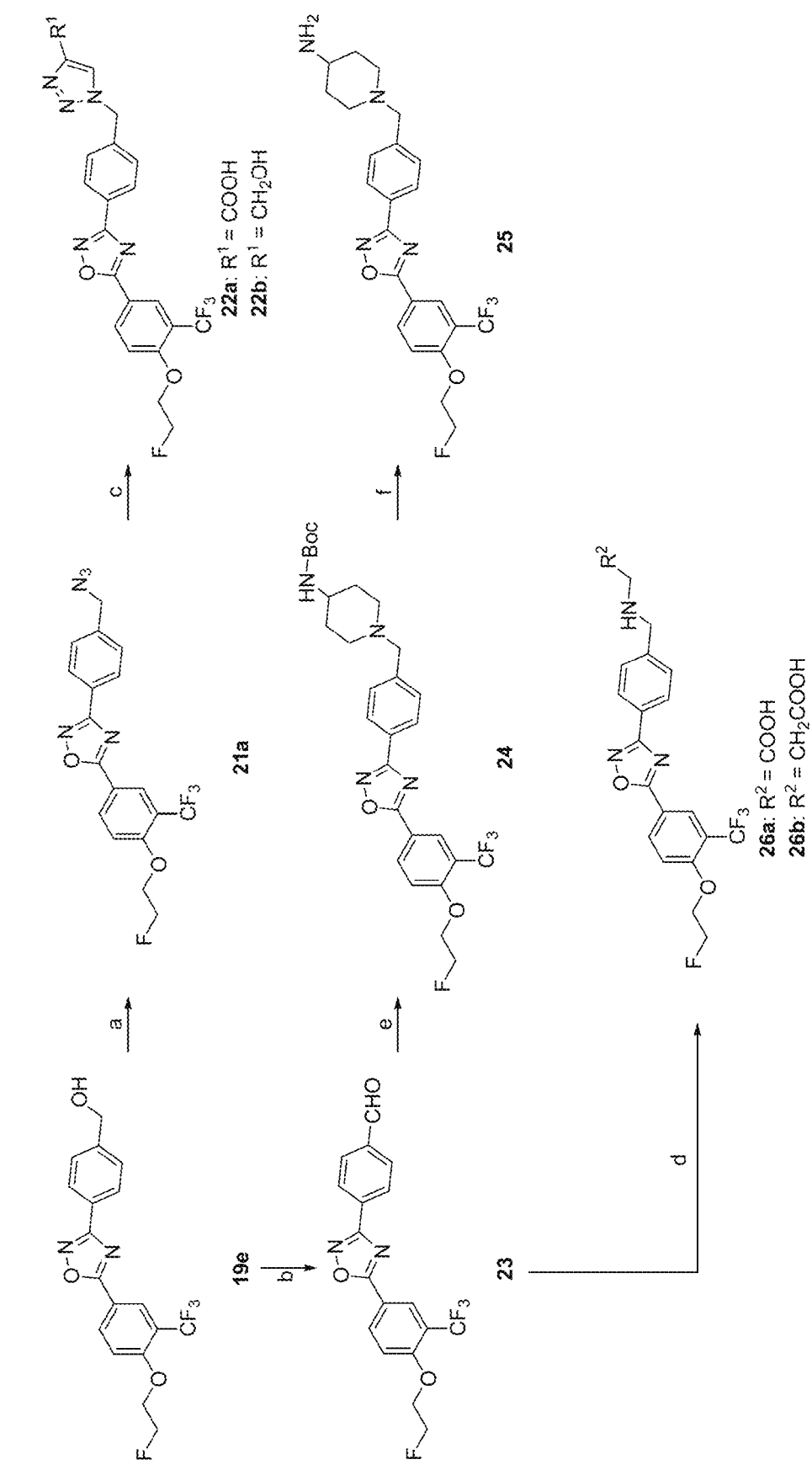
FIG. 6. Syntheses of 22a-b, 25, 26a-b. Reagents and conditions: (a) DPPA, DBU, toluene, 0° C.-RT; (b) oxalyl chloride, DMSO, CH$_2$Cl$_2$, triethylamine, −78° C.-RT; (c) propiolic acid or propargyl alcohol, CuSO$_4$.5H$_2$O, sodium ascorbate, THF, H$_2$O, RT; (d) NaBH$_3$CN, amines, acetic acid, methanol, RT; (e) 4-(N-Boc-amino)piperidine, NaBH (OAc)$_3$, acetic acid, 1,2-dichloroethane, RT; (f) 4 M HCl in dioxane, RT.

The synthesis of analogs 22a, 22b, 25, and 26a-b are illustrated in FIG. 6. The alcohol intermediate 19e was easily transformed to azide 21a under the condition of 1,8-diazabicyclo[5.4.0]undec-7-ene (DBU) and diphenyl phosphoryl azide (DPPA), which was used to proceed the copper (II)-catalyzed alkyne cycloaddition to afford compounds 22a-b. The alcohol intermediate 19e was converted to aldehyde 23 by Swern oxidation. After reductive amination from aldehyde 23 using corresponding amines afforded compounds 24 and 26a-b. Deprotection of tert-butyloxycarbonyl (Boc) group of 24 using 4 M HCl in dioxane afforded compound 25.

Example 74: Synthesis of 3-(4-(Azidomethyl)phenyl)-5-(4-(2-fluoroethoxy)-3-(trifluoromethyl)phenyl)-1,2,4-oxadiazole (21a)

To a round-bottom flask equipped with a stir bar was added 19e (1.0 g, 2.62 mmol), diphenyl phosphoryl azide (0.86 g, 3.14 mmol), and toluene (5.0 mL). The mixture was cooled to 0° C. before adding 1,8-diazabicyclo[5.4.0]undec-7-ene (0.48, 3.14 mmol) dropwise. The reaction was warmed to room temperature slowly and stirred overnight. Then, the reaction mixture was diluted with water (20 mL) and extracted with ethyl acetate (30 mL). The ethyl acetate layer was washed with 1 M HCl, saturated brine and dried over anhydrous MgSO$_4$. After filtration and concentration, the residue was purified on a silica gel column, eluted with ethyl acetate/hexanes (V/V, 3/7) to give a white solid. (330 mg, 62%). MP: 117-119° C. $^1$H NMR (400 MHz, CDCl$_3$) δ=8.47 (d, J=2.0 Hz, 1H, —ArH), 8.35 (dd, J=8.8 Hz, 2.0 Hz, 1H, —ArH), 8.19 (d, J=8.4 Hz, 2H, —ArH), 7.47 (d, J=8.0 Hz, 2H, —ArH), 7.18 (d, J=8.8 Hz, 1H, —ArH), 4.94-4.73 (m, 2H, —CH$_2$F), 4.50-4.35 (m, 4H, —CH$_2$O-&-CH$_2$N$_3$). $^{13}$C NMR (101 MHz, Acetone-d6) δ 174.54, 168.40, 159.98, 139.55, 133.81, 129.35, 128.89, 127.60, 126.92 (q, J=5.1 Hz), 123.15 (d, J=273.7 Hz), 119.21 (d, J=31.3 Hz), 116.60, 114.50, 81.55 (d, J=169.7 Hz), 68.94 (d, J=20.2 Hz), 53.69.

Example 75: General Procedure for the Synthesis of 22a-b

To a round-bottom flask equipped with a stir bar was added azide 21a (1.0 eq) and THF. Once the azide was dissolved, water (0.6 mL/mmol) was added followed by propiolic acid or propargyl alcohol (1.05 eq), sodium ascorbate (0.10 eq), and copper sulfate pentahydrate (0.06 eq). The reaction mixture was stirred for 4 h and monitored by TLC. Then, the reaction mixture was diluted with water and extracted with ethyl acetate. The ethyl acetate layer was washed with saturated brine and dried over anhydrous MgSO$_4$. After filtration and concentration, a yellow solid was obtained.

Example 76: Synthesis of 1-(4-(5-(4-(2-Fluoroethoxy)-3-(trifluoromethyl)phenyl)-1,2,4-oxadiazol-3-yl)benzyl)-1H-1,2,3-triazole-4-carbox-ylic acid (22a)

The synthesis follows the general procedure described in Example 75. MP: 157-158° C. 1H NMR (400 MHz, DMSO-d6) δ 13.09 (s, 1H, —COOH), 8.86 (s, 1H, —ArH), 8.41 (d, J=8.2 Hz, 1H, —ArH), 8.30 (s, 1H, —ArH), 8.10 (d, J=7.5 Hz, 2H, —ArH), 7.53 (d, J=7.7 Hz, 2H, —ArH), 7.17-7.11 (m, 1H, —ArH), 5.78 (s, 2H, —ArCH2-), 4.88-4.46 (m, 4H, —OCH2CH2F). 13C NMR (101 MHz, DMSO-d6) δ 174.64, 168.26, 162.01, 159.93, 140.38, 139.55, 134.57, 129.31, 129.20, 128.04, 127.08 (d, J=5.1 Hz), 123.32 (d, J=274.7 Hz), 120.33, 118.56 (q, J=31.3 Hz), 116.24, 115.43, 82.11 (d, J=167.7 Hz), 69.23 (d, J=19.2 Hz), 53.04. HRMS (ESI) calcd for C21H15F4N5O4 [M+H+] 478.1133. Found [M+H+] 478.1125.

Example 77: Synthesis of (1-(4-(5-(4-(2-Fluoroethoxy)-3-(trifluoromethyl)phenyl)-1,2,4-oxadiazol-3-yl)benzyl)-1H-1,2,3-triazol-4-yl)met-hanol (22b)

The synthesis follows the general procedure described in Example 75. MP: 175-177° C. $^1$H NMR (400 MHz, DMSO-d6) δ 8.41 (d, J=8.6 Hz, 1H, —ArH), 8.30 (s, 1H, —ArH), 8.08 (d, J=4.7 Hz, 3H, —ArH), 7.60-7.45 (m, 3H, —ArH), 5.70 (s, 2H, —ArCH$_2$—), 5.20 (s, 1H, —OH), 4.89-4.67 (m, 2H, —CH$_2$F), 4.63-4.48 (m, 4H, —CH$_2$O-&-CH$_2$OH). $^{13}$C NMR (101 MHz, DMSO-d6) δ 174.63, 168.29, 159.94, 140.24, 134.57, 129.11, 127.97, 127.08 (d, J=5.1 Hz), 126.13, 123.32 (d, J=274.7 Hz), 123.55, 120.31, 118.56 (q, J=31.3 Hz), 116.24, 115.43, 82.11 (d, J=167.7 Hz), 69.23 (d, J=19.2 Hz), 55.47, 52.71. HRMS (ESI) calcd for C$_{21}$H$_{17}$F$_4$N$_5$O$_3$ [M+H$^+$] 464.1346. Found [M+H$^+$] 464.1353.

Example 78: Synthesis of 4-(5-(4-(2-Fluoroethoxy)-3-(trifluoromethyl)phenyl)-1,2,4-oxadiazol-3-yl)benzaldehyde (23)

To an oven-dried 100 mL round-bottom flask equipped with a stir bar was added CH$_2$Cl$_2$ (32 mL) and DMSO (1.7 g, 21.7 mmol). The reaction mixture was cooled to −78° C. and oxalyl chloride (1.87 g, 14.7 mmol) was added slowly under N$_2$ atmosphere. The reaction mixture was stirred for 30 minutes at which time 19e (2.68 g, 7.0 mmol) was added. The reaction mixture was stirred for another 30 minutes at which time triethylamine (5.67 mL, 56.0 mmol) was added. The cooling bath was removed and the reaction was allowed to warm to room temperature over 2 h. The reaction mixture was concentrated in vacuo and partitioned between ethyl acetate and 1 M HCl. The layers were separated and the aqueous layer was re-extracted with ethyl acetate. The combined organic layers were washed with 1 M HCl, sat. NaHCO$_3$, brine, and dried over MgSO$_4$. After filtration and concentration in vacuo, a pale-yellow solid was obtained. (1.51 g, 76%).

Example 79: Synthesis of tert-Butyl (1-(4-(5-(4-(2-fluoroethoxy)-3-(trifluoromethyl)phenyl)-1,2,4-oxadiazol-3-yl)benzyl)piperidin-4-yl)carba-mate (24)

To a round-bottom flask equipped with a stir bar was added aldehyde 23 (380 mg, 1.0 mmol), amine (21 mg, 1.05 mmol), 1,2-dichloroethane (10 mL), sodium triacetoxyborohydride (318 mg, 1.5 mmol), and acetic acid (120 mg, 2.0 mmol). The reaction mixture was stirred overnight at room temperature. Then, the reaction was quenched with saturated NaHCO$_3$ aqueous and extracted with ethyl acetate (20 mL×3). The combined ethyl acetate layer was washed with brine and dried over anhydrous MgSO$_4$. After filtration and concentration, the crude product was purified on a silica gel column to give white solid product (250 mg, 44%). MP: 147-149° C. $^1$H NMR (400 MHz, Acetone-d6) δ 8.39-8.32 (m, 2H, —ArH), 8.02 (d, J=7.9 Hz, 2H, —ArH), 7.52-7.45 (m, 3H, —ArH), 5.83 (d, J=6.7 Hz, 1H, —ArH), 4.90-4.83 (m, 1H, —CH$_2$F), 4.79-4.72 (m, 1H, —CH$_2$F), 4.61-4.56 (m, 1H, —CH$_2$O—), 4.55-4.49 (m, 1H, —CH$_2$O—), 3.51 (s, 2H, —ArCH$_2$—), 3.41-3.27 (m, 1H, —CHNH—), 2.83-2.75 (m, 2H, —NCH$_2$—), 2.12-1.97 (m, 2H, —NCH$_2$—), 1.83-1.75 (m, 2H, —CH$_2$—), 1.55-1.43 (m, 2H, —CH$_2$—), 1.34 (s, 9H, —CH$_3$). $^{13}$C NMR (101 MHz, Acetone-d6) δ 174.29, 168.62, 159.90, 159.89, 155.00, 143.07, 133.74, 129.26, 127.11, 126.86 (q, J=5.1 Hz), 125.33, 123.15 (d, J=273.7 Hz), 119.17 (q, J=31.3 Hz), 116.65, 114.43, 81.54 (d, J=169.7 Hz), 77.51, 68.91 (d, J=20.2 Hz), 62.18, 52.44, 47.89, 32.27, 27.75.

Example 80: Synthesis of 1-(4-(5-(4-(2-Fluoroethoxy)-3-(trifluoromethyl)phenyl)-1,2,4-oxadiazol-3-yl)benzyl)piperidin-4-amine dihydro-chloride (25)

To a round-bottom flask equipped with a stir bar was added the Boc-protected amine 24 (90 mg, 0.16 mmol) and 2 mL of 4 M HCl in 1,4-dioxane. The reaction was stirred 4 h at room temperature, and the precipitate was filtered off, washed with ethyl ether to give a white solid. (51 mg, 59%). MP: 268-269° C. $^1$H NMR (400 MHz, DMSO-d6) δ 8.50 (s, 2H, —NH$_2$), 8.42 (d, J=9.0 Hz, 1H, —ArH), 8.31 (s, 1H, —ArH), 8.14 (d, J=7.9 Hz, 2H, —ArH), 7.85 (d, J=7.4 Hz, 2H, —ArH), 7.58 (d, J=8.8 Hz, 1H, —ArH), 4.90-4.81 (m, 1H, —CH$_2$F), 4.78-4.70 (m, 1H, —CH$_2$F), 4.63-4.56 (m, 1H, —CH$_2$O—), 4.55-4.49 (m, 1H, —CH$_2$O—), 4.36 (s, 2H, —ArCH$_2$—), 3.36-3.17 (m, 3H, —N—CH$_2$-&-CHNH$_2$), 3.16-3.00 (m, 2H, —N—CH$_2$—), 2.22-1.95 (m, 4H, —CH$_2$CH—). $^{13}$C NMR (101 MHz, DMSO-d6) δ 174.75, 168.26, 159.99, 134.60, 133.60, 132.92, 127.81, 127.36, 127.10 (d, J=5.1 Hz), 123.32 (d, J=273.7 Hz), 118.58 (q, J=31.3 Hz), 116.20, 115.52, 82.13 (d, J=168.7 Hz), 69.27 (d, J=18.2 Hz), 58.66, 49.97, 45.68, 27.21. HRMS (ESI) calcd for C$_{23}$H$_{24}$F$_4$N$_4$O$_2$ [M+H$^+$] 465.1908. Found [M+H$^+$] 465.1907.

Example 81: General Procedure for the Synthesis of 26a-b

To a round-bottom flask equipped with a stir bar was added aldehyde 23 (1.0 eq), amine (1.5 eq), methanol (14 mL/mmol), and acetic acid (0.5 mL/mmol). The reaction mixture was stirred 1 h at which time sodium cyanoborohydride (1.0 eq) was added. The reaction mixture was stirred overnight and diluted with water. The precipitate was filtered off and washed with water to give an off-white solid product.

Example 82: Synthesis of (4-(5-(4-(2-Fluoroethoxy)-3-(trifluoromethyl)phenyl)-1,2,4-oxadiazol-3-yl)benzyl)glycine (26a)

The synthesis follows the general procedure described in Example 81. Yield: 24%. MP: 175-176° C. $^1$H NMR (400 MHz, Acetone-d6) δ 8.49-8.35 (m, 2H, —ArH), 8.12 (d, J=7.8 Hz, 2H, —ArH), 7.67 (d, J=7.9 Hz, 2H, —ArH), 7.56 (d, J=8.7 Hz, 1H, —ArH), 4.98-4.75 (m, 2H, —CH$_2$F), 4.71-4.54 (m, 2H, —CH$_2$O—), 3.98 (s, 2H, —ArCH$_2$—), 3.42 (s, 2H, —CH$_2$COOH). $^{13}$C NMR (101 MHz, Acetone-d6) δ 174.36, 171.35, 168.62, 159.93, 143.12, 133.77, 129.47, 127.27, 126.88 (q, J=5.1 Hz), 125.65, 123.15 (d, J=273.7 Hz), 119.19 (q, J=31.3 Hz), 116.66, 114.47, 81.56 (d, J=168.7 Hz), 68.92 (d, J=20.2 Hz), 57.26, 53.12. HRMS (ESI) calcd for C$_{20}$H$_{17}$F$_4$N$_3$O$_4$ [M+H$^+$] 440.1228. Found [M+H$^+$] 440.1210.

Example 83: Synthesis of 3-((4-(5-(4-(2-Fluoroethoxy)-3-(trifluoromethyl)phenyl)-1,2,4-oxadiazol-3-yl)benzypamino)propanoic acid (26b)

The synthesis follows the general procedure described in Example 81. Yield: 17%. MP: 198-200° C. $^1$H NMR (400

MHz, DMSO-d6) δ 8.49-8.37 (m, 1H, —ArH), 8.30 (s, 1H, —ArH), 8.17-7.98 (m, 2H, —ArH), 7.67-7.44 (m, 3H, —ArH), 4.92-4.70 (m, 2H, —CH$_2$F), 4.63-4.45 (m, 2H, —CH$_2$O—), 3.87 (s, 2H, —ArCH$_2$—), 2.87-2.71 (m, 2H, —NHCH$_2$—), 2.45-2.31 (m, 2H, —CH$_2$COOH). $^{13}$C NMR (101 MHz, DMSO-d6) δ 174.48, 174.15, 168.53, 159.91, 143.50, 134.53, 129.37, 127.52, 127.05 (d, J=5.1 Hz), 125.10, 123.33 (d, J=5.1 Hz), 118.56 (d, J=273.7 Hz), 116.31, 115.43, 82.12 (d, J=168.7 Hz), 69.24 (d, J=19.2 Hz), 51.89, 44.51, 34.00. HRMS (ESI) calcd for C$_{21}$H$_{19}$F$_4$N$_3$O$_4$ [M+H$^+$] 454.1384. Found [M+H$^+$] 454.1370.

Example 84: General Overview of Synthesis of 31a-b

Figure 7:
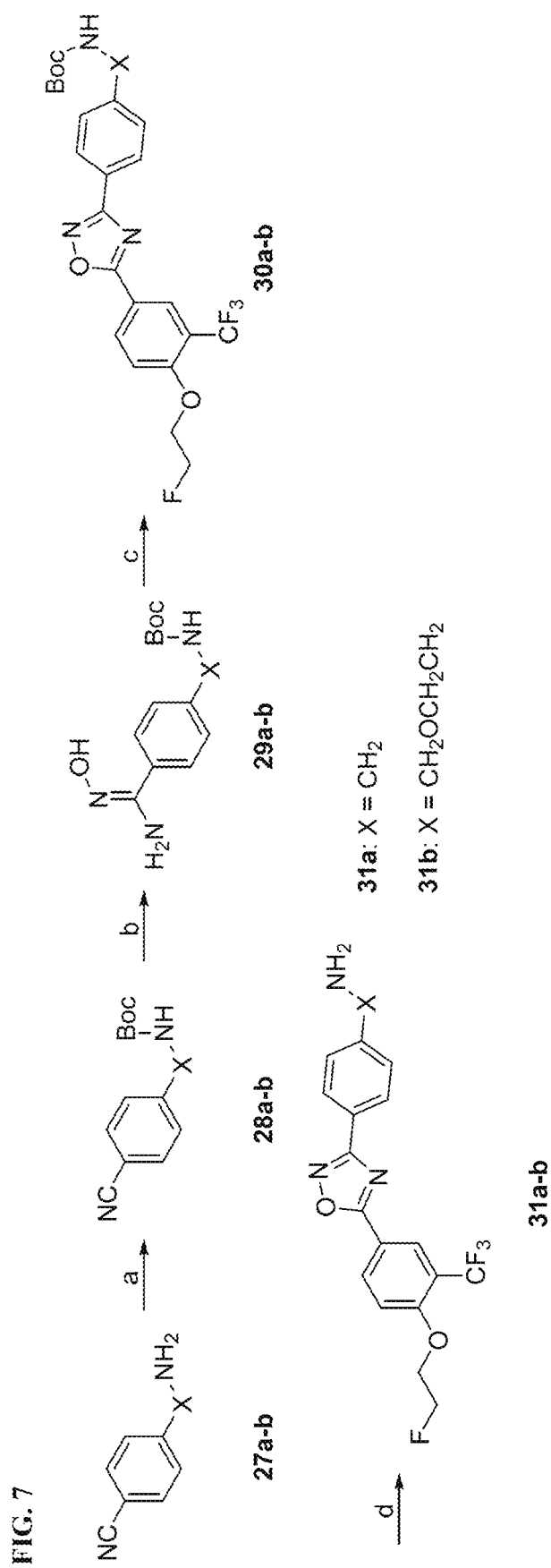
FIG. 7. Syntheses of 31a-b. Reagents and conditions: (a) di-tert-butyl dicarbonate, triethylamine, CH$_2$Cl$_2$, RT; (b) hydroxylamine hydrochloride, NaHCO$_3$, methanol, reflux; (c) TBTU, HOBt, DIPEA, 6, DMF, RT-120° C.; (d) 4 M HCl in dioxane, RT.

The syntheses of the analogs 31a-b are shown in FIG. 7. Amines 27a-b were protected using Boc group to afford 28a-b. Oxadiazoles 30a-b were prepared via a similar procedure shown in Scheme 1, followed by deprotection of Boc group yielded compounds 31a-b.

Example 85: General Procedure for the Synthesis of 28a-b

To a round-bottom flask equipped with a stir bar was added 27a-b (1.0 eq), Boc$_2$O (1.1 eq), CH$_2$Cl$_2$ (10 mL/mmol), and triethylamine (1.5 eq). The reaction mixture was stirred at room temperature overnight. The reaction was concentrated in vacuo and partitioned between ethyl ether and 1 M HCl. The organic layer were separated, washed with saturated NaHCO$_3$, brine, dried over MgSO$_4$, and concentrated in vacuo to give a white crystalline solid.

Example 86: Synthesis of tert-Butyl (4-cyanobenzyl) carbamate (28a)

The synthesis follows the general procedure described in Example 85. Yield: 93%. MP: 114-116° C. $^1$H NMR (400 MHz, CDCl$_3$) δ 7.62 (d, J=7.9 Hz, 2H, —ArH), 7.39 (d, J=8.5 Hz, 2H, —ArH), 4.96 (s, 1H, —NH—), 4.37 (d, J=5.9 Hz, 2H, —CH$_2$—), 1.46 (s, 9H, —CH$_3$).

Example 87: Synthesis of tert-Butyl (2-((4-cyanobenzyl)oxy)ethyl)carbamate (28b)

The synthesis follows the general procedure described in Example 85. Yield: 83%. MP: 100-102° C. $^1$H NMR (400 MHz, CDCl$_3$) δ 7.62 (d, J=7.9 Hz, 2H, —ArH), 7.33 (d, J=7.9 Hz, 2H, —ArH), 4.53 (s, 2H, —ArCH$_2$—), 3.80-3.65 (m, 2H, —OCH$_2$—), 3.49-3.30 (m, 2H, —CH$_2$NH—), 1.40 (s, 9H, —CH$_3$).

Example 88: General Procedure for the Synthesis of 29a-b

To a round-bottom flask equipped with a stir bar was added 28a-b (1.0 eq), hydroxylamine hydrochloride (2.0 eq), NaHCO$_3$ (4.0 eq), and methanol (10 mL/mmol). The reaction was refluxed and stirred in a pre-heated 75° C. oil-bath for 6 h. After cooling to room temperature, the precipitate was filtered off and washed with methanol. The filtrate was concentrated in vacuo and further purified on a silica gel column.

Example 89: Synthesis of tert-Butyl (E)-(4-(N'-hydroxycarbamimidoyl)benzyl) carbamate (29a)

The synthesis follows the general procedure described in Example 88. Yield: 65%. MP: 142-145° C. $^1$H NMR (400 MHz, DMSO-d6) δ 9.57 (s, 1H, —OH), 7.61 (d, J=8.1 Hz, 2H, —ArH), 7.40 (t, J=6.1 Hz, 1H, —NHCO—), 7.22 (d, J=8.1 Hz, 2H, —ArH), 5.77 (s, 2H, —NH$_2$), 4.13 (d, J=6.1 Hz, 2H, —ArCH$_2$—), 1.40 (s, 9H, —CH$_3$).

Example 90: Synthesis of tert-Butyl (E)-(2((4-(N'-hydroxycarbamimidoyl)benzyl)oxy) ethyl)carbamate (29b)

The synthesis follows the general procedure described in Example 88. Yield: 40%. MP: 138-140° C. $^1$H NMR (400 MHz, Acetone-d6) δ 8.87 (s, 1H, —OH), 7.69 (d, J=7.7 Hz, 2H, —ArH), 7.28 (d, J=8.1 Hz, 2H, —ArH), 5.45 (s, 2H, —NH$_2$), 4.54 (s, 2H, —ArCH$_2$—), 3.75 (s, 1H, —NHCO—), 3.68-3.59 (m, 2H, —OCH$_2$—), 3.40-3.24 (m, 2H, —CH$_2$NH—), 1.47 (s, 9H, —CH$_3$).

Example 91: General Procedure for the Synthesis of (30a-b)

To a round-bottom flask equipped with a stir bar was added acid 16 (1.0 eq), HOBt (0.2 eq), TBTU (1.0 eq), DMF (5 mL/mmol), and DIPEA (3.0 eq). The reaction mixture was stirred for 0.5 h before adding amidoxime 29a-b (1.0 eq). The reaction mixture was stirred for 1 h at room temperature, then heated in a pre-heated 120° C. oil-bath. The reaction mixture was stirred for 4 h and monitored by TLC. After cooling, the reaction mixture was diluted with water and extracted with ethyl acetate. The ethyl acetate layer was washed with 1 M HCl, saturated brine, and dried over anhydrous MgSO$_4$. After filtration and concentration, the residue was purified on a silica gel column.

Example 92: Synthesis of tert-Butyl (4-(5-(4-(2-fluoroethoxy)-3-(trifluoromethyl)phenyl)-1,2,4-oxadiazol-3-yl)benzyl)carbamate (30a)

The synthesis follows the general procedure described in Example 91. Yield: 56%. MP: 158-160° C. $^1$H NMR (400 MHz, DMSO-d6) δ 8.40 (d, J=9.0 Hz, 1H, —ArH), 8.30 (s, 1H, —ArH), 8.03 (d, J=8.0 Hz, 2H, —ArH), 7.58-7.47 (m, 2H, —ArH&-NHCO), 7.44 (d, J=8.0 Hz, 2H, —ArH), 4.88-4.82 (m, 1H, —CH$_2$F), 4.76-4.70 (m, 1H, —CH$_2$F), 4.61-4.55 (m, 1H, —CH$_2$O—), 4.54-4.48 (m, 1H, —CH$_2$O—), 4.22 (d, J=5.9 Hz, 2H, —ArCH$_2$—), 1.41 (s, 9H, —CH$_3$). $^{13}$C NMR (101 MHz, DMSO-d6) δ 174.45, 168.52, 159.88, 156.27, 144.53, 134.49, 128.04, 127.54, 127.04 (q, J=5.1 Hz), 123.33 (d, J=273.7 Hz), 121.97, 118.56 (d, J=30.3 Hz), 116.32, 115.40, 82.11 (d, J=168.7 Hz), 78.39, 69.22 (d, J=19.2 Hz), 43.66, 28.65.

Example 93: Synthesis of tert-Butyl (2-((4-(5-(4-(2-fluoroethoxy)-3-(trifluoromethyl)phenyl)-1,2,4-oxadiazol-3-yl)benzypoxy)ethyl)-carbamate (30b)

The synthesis follows the general procedure described in Example 91. Yield: 42%. MP: 144-147° C. $^1$H NMR (400 MHz, CDCl$_3$) δ 8.47 (s, 1H, —ArH), 8.35 (d, J=8.7 Hz, 1H, —ArH), 8.13 (d, J=8.1 Hz, 2H, —ArH), 7.38 (d, J=7.8 Hz, 2H, —ArH), 7.18 (d, J=8.8 Hz, 1H, —ArH), 4.92-4.86 (m, 1H, —CH$_2$F), 4.80-4.75 (m, 1H, —CH$_2$F), 4.56 (s, 2H, —ArCH$_2$—), 4.49-4.44 (m, 1H, —CH$_2$O—), 4.42-4.37 (m, 1H, —CH$_2$OAr—), 3.80-3.69 (m, 2H, —OCH$_2$—), 3.52-3.35 (m, 2H, —CH$_2$NH—), 1.46 (s, 9H, —CH$_3$).

Example 94: General Procedure for the Synthesis of 31a-b

To a round-bottom flask equipped with a stir bar was added Boc-protected amine 30a-b (1.0 eq), followed by 4 M HCl in 1,4-dioxane (20 eq). The reaction mixture was stirred for 2 h and concentrated in vacuo. The resulting residue was suspended in a mixture of ethanol and tert-butyl methyl ether (V/V, 3/1), and the resulting solid was filtered to give the white solid product.

Example 95: Synthesis of (4-(5-(4-(2-Fluoroethoxy)-3-(trifluoromethyl)phenyl)-1,2,4-oxadiazol-3-Ophenyl)methanamine hydrochloride (31a)

The synthesis follows the general procedure described in Example 94. Yield: 77%. MP: 276-277° C. $^1$H NMR (400 MHz, DMSO-d6) δ 8.71 (s, 2H, —NH$_2$), 8.39 (d, J=8.4 Hz, 1H, —ArH), 8.29 (s, 1H, —ArH), 8.10 (d, J=7.6 Hz, 2H, —ArH), 7.73 (d, J=7.6 Hz, 2H, —ArH), 7.56 (d, J=8.7 Hz, 1H, —ArH), 4.91-4.67 (m, 2H, —CH$_2$F), 4.62-4.46 (m, 2H, —CH$_2$O—), 4.12 (s, 2H, —CH$_2$—). $^{13}$C NMR (101 MHz, DMSO-d6) δ 174.69, 168.31, 159.97, 138.18, 134.58, 130.23, 127.69, 127.10 (d, J=5.1 Hz), 126.37, 123.34 (d, J=273.7 Hz), 118.56 (d, J=31.3 Hz), 116.24, 115.50, 82.13 (d, J=168.7 Hz), 69.27 (d, J=19.2 Hz), 42.24. HRMS (ESI) calcd for $C_{18}H_{15}F_4N_3O_2$ [M+H$^+$] 382.1173. Found [M+H$^+$] 382.1169.

Example 96: Synthesis of 2-((4-(5-(4-(2-Fluoroethoxy)-3-(trifluoromethyl)phenyl)-1,2,4-oxadiazol-3-yl)benzypoxy)ethan-1-amine (31b)

The synthesis follows the general procedure described in Example 94. Yield: 57%. MP: 266-267° C. $^1$H NMR (400 MHz, Acetone-d6) δ 8.47-8.35 (m, 2H, —ArH), 8.13-8.02 (m, 2H, —ArH), 7.65-7.49 (m, 3H, —ArH), 4.87 (d, J=47.8 Hz, 2H, —CH$_2$F), 4.61 (d, J=28.7 Hz, 2H, —CH$_2$O—), 3.89 (s, 2H, —ArCH$_2$O—), 3.71-3.57 (m, 2H, —CH$_2$O—), 2.78-2.66 (m, 2H, —CH$_2$NH$_2$). $^{13}$C NMR (101 MHz, Acetone-d6) δ 174.27, 168.67, 159.90, 145.17, 133.73, 128.82, 128.49, 127.16, 127.08, 126.86 (q, J=5.1 Hz), 123.15 (d, J=273.7 Hz), 119.18 (q, J=31.3 Hz), 114.43, 81.54 (d, J=169.7 Hz), 68.91 (d, J=31.3 Hz), 60.86, 52.94, 51.25. HRMS (ESI) calcd for $C_{20}H_{19}F_4N_3O_3$ [M+H$^+$] 426.1435. Found [M+H$^+$] 426.1432.

Example 97: In Vitro Binding Assay

Newly synthesized compounds were first evaluated for binding potency toward S1P1 by a [$^{32}$P]S1P competitive binding assay following published procedure (J. Rosenberg, H. Liu, Z. Tu, A practical process for the preparation of [$^{32}$P]S1P and binding assay for S1P receptor ligands, Appl. Radiat. Isot. 102 (2015) 5-9), and using S1P as a reference compound. [$^{32}$P]S1P was first prepared by incubating sphingosine and [γ-$^{32}$P]ATP with sphingosine kinase 1 as previously reported (J. Rosenberg, H. Liu, Z. Tu, A practical process for the preparation of [$^{32}$P]S1P and binding assay for S1P receptor ligands, Appl. Radiat. Isot. 102 (2015) 5-9). [$^{32}$P]S1P was dissolved in DMSO, and then diluted in the assay buffer (50 mM HEPES-Na with 5 mM MgCl$_2$, 1 mM CaCl$_2$, and 0.5% fatty acid-free bovine serum albumin, pH=7.5). Compounds were dissolved in DMSO and diluted to different concentrations with assay buffer, followed by adding commercial cell membranes expressing recombinant human S1P receptors (1, 2, 3, 4, and 5) in the assay buffer at room temperature in 96-well plate. [$^{32}$P]S1P solution was then added to give a final volume of 150 μL containing 0.1 nM of [$^{32}$P]S1P and 1 μg of membrane protein per well. Competitive binding was performed for 60 min at room temperature and terminated by collecting the membranes onto 96-well glass fiber (GF/B) filtration plates (Millipore, Billerica, Mass.). Each filter was washed with 200 μL of assay buffer for five times. The filter bound radionuclide was measured by a Beckman LS3801 scintillation counter using Cherenkov counting. The reported IC$_{50}$ values were calculated using the 4 parameter equation, least-square non-linear regression curve-fit, with GraphPad Prism software (GraphPad Software, Inc). Each assay was repeated at least three times with duplicate wells for each compound; the reported values (mean±SD, nM) are calculated from the average of all assays. Assays for compounds which showed no activity (IC$_{50}$>1000 nM) were only repeated twice.

Figure 8:
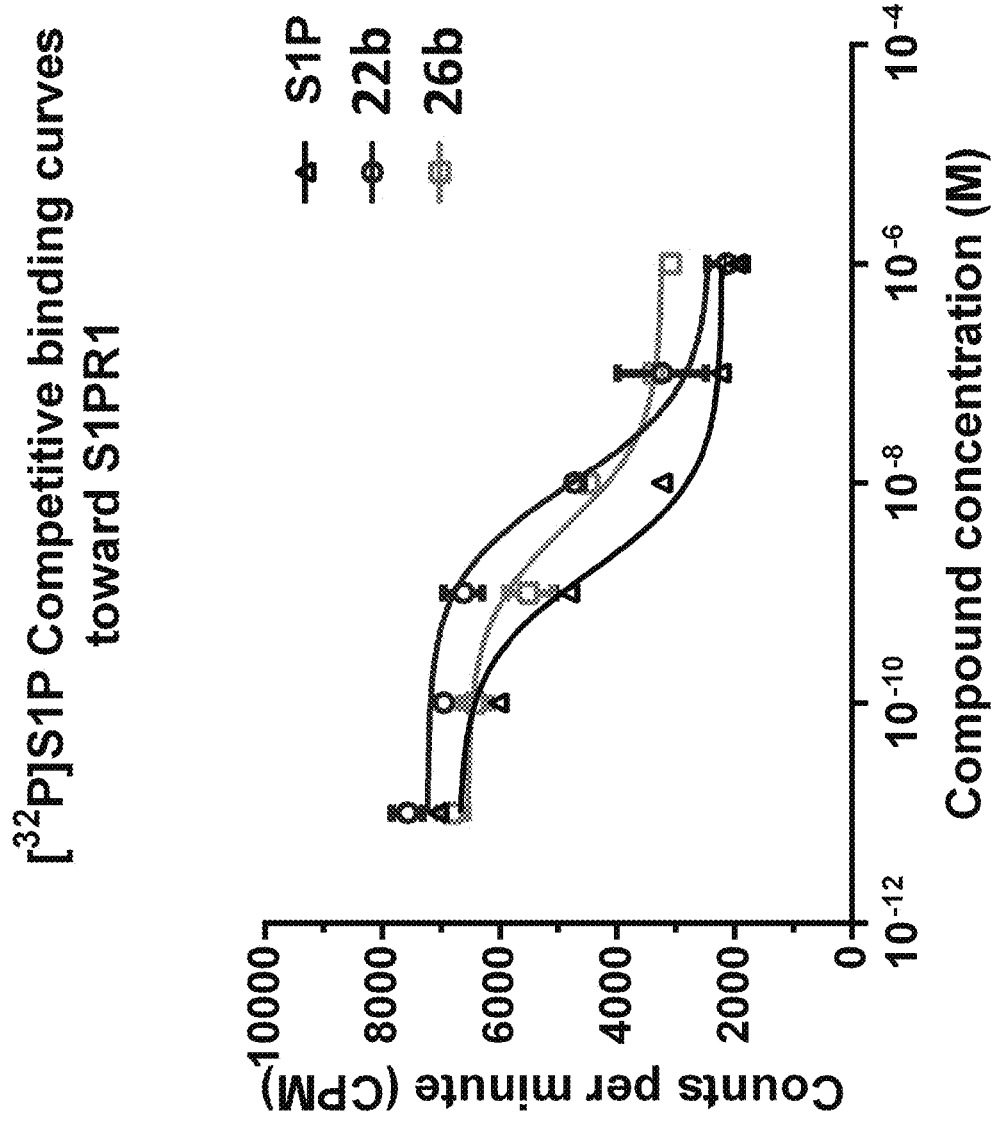
FIG. 8 Competitive binding curves of compounds 22b, 26b, and S1P for S1P1. A CHO cell membrane containing recombinant human S1P1 was used in a [32P]S1P competitive binding assay to measure the binding affinities. S1P (fitted IC50=1.4±0.3 nM) 12b (fitted IC50=9.7±1.6 nM); and 16b (fitted IC50=6.3±1.3 nM).

The binding potency was expressed as the IC$_{50}$ value. As shown in Table 4, most of the new analogs have good binding potency for S1P1 with the IC$_{50}$ values from 6.3 nM to 341 nM except compound 20a (>1000 nM) that has a carboxyl group. Compounds 19a and 19c bearing sulfonamides group exhibited good binding potency with the IC$_{50}$ values of 13.2 and 40.0 nM, respectively. Compound 19b having an amide group on the benzene ring showed a reduced potency with an IC$_{50}$ value of 67.1 nM compared to sulfonamide compounds 19a and 19c. Introducing N-hydroxy amide or hydrazide group on the benzene ring displayed a different impact on S1P1 binding potency. Compared to benzamide compound 19b, benzohydrazide compound 20c showed a 5-fold decreased IC$_{50}$ value of 14.7 nM, but N-hydroxybenzamide compound 20b exhibited a 4-fold increased IC$_{50}$ value of 272 nM. Replacing the azetidine carboxylic acid with 1,2,3-triazole-4-carboxylic acid, 2-amino acetic acid, and 3-amino propanoic acid resulted in different S1P1 binding potency. Compared to the IC$_{50}$ value of compound 4 (2.6 nM, A. J. Rosenberg, H. Liu, H. Jin, X. Yue, S. Riley, S. J. Brown, Z. Tu, Design, synthesis, and in vitro and in vivo evaluation of an $^{18}$F-labeled sphingosine 1-phosphate receptor 1 (S1P1) PET tracer, J. Med. Chem. 59 (2016) 6201-6220), 1,2,3-triazole-4-carboxylic acid containing compound 22a (341 nM) has 130-fold increased IC$_{50}$ value; the 2-amino acetic acid containing compound 26a (99.8 nM) has 38-fold increased IC$_{50}$ value; 3-amino propanoic acid containing compound 26b (6.3 nM) has comparable binding potency. Compound 22b showed a 35-fold decreased IC$_{50}$ value of 9.7 nM compared to the corresponding acid 22a (341 nM), which is also comparable to compound 4. Replacing the azetidine carboxylic acid of compound 4 with different amines were evaluated, and the piperidine-4-amine caused the most increased IC$_{50}$ value, the IC$_{50}$ value of compound 25 was 156 nM; both methylamine and O-ethylamine caused increased IC$_{50}$ values too (34.2 nM for 31a, 44.2 nM for 31b), but less increase than compound 25. The representative competitive binding curves of compounds 22b, 26b and S1P for S1P1 are displayed in FIG. 8.

TABLE 4

Structures and binding affinities (mean ± SD) of S1P and new compounds toward S1P1[a,b].

| Compd. | R | S1P1 IC$_{50}$ (nM) | MW | ClogP | TPSA | HBD |
|---|---|---|---|---|---|---|
| S1P | N/A | 1.4 ± 0.3 | 379.5 | 4.1 | 113.0 | 4 |
| 19a | -S(O)$_2$NH$_2$ | 13.2 ± 3.2 | 431.4 | 3.4 | 103.3 | 1 |
| 19b | -C(O)NH$_2$ | 67.1 ± 12.6 | 395.3 | 3.7 | 86.3 | 1 |
| 19c | -CH$_2$NHS(O)$_2$CH$_3$ | 40.0 ± 17.8 | 459.4 | 3.7 | 89.4 | 1 |
| 20a | -COOH | >1000 | 396.3 | 4.9 | 80.5 | 1 |
| 20b | -C(O)NHOH | 272 ± 65 | 411.3 | 3.3 | 92.5 | 2 |
| 20c | -C(O)NHNH$_2$ | 14.7 ± 1.7 | 410.3 | 3.3 | 98.3 | 2 |
| 22a | -CH$_2$-(triazole)-COOH | 341 ± 126 | 477.4 | 4.2 | 108.4 | 1 |
| 22b | -CH$_2$-(triazole)-CH$_2$OH | 9.7 ± 1.6 | 463.4 | 3.1 | 91.4 | 1 |
| 25 | -CH$_2$-(4-aminopiperidin-1-yl) | 156 ± 47 | 464.5 | 4.1 | 72.4 | 1 |
| 26a | -CH$_2$NHCH$_2$COOH | 99.8 ± 12.2 | 439.4 | 1.3 | 92.5 | 2 |

TABLE 4-continued

Structures and binding affinities (mean ± SD) of S1P and new compounds toward S1P1[a,b].

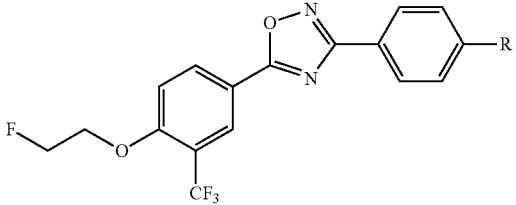

| Compd. | R | S1P1 IC$_{50}$ (nM) | MW | ClogP | TPSA | HBD |
|---|---|---|---|---|---|---|
| 26b | ⟶N(H)–CH₂CH₂–COOH | 6.3 ± 1.3 | 453.4 | 2.0 | 92.5 | 2 |
| 31a | ⟶CH₂–NH₂ | 34.2 ± 7.1 | 381.3 | 4.0 | 69.2 | 1 |
| 31b | ⟶O–CH₂CH₂–NH₂ | 44.2 ± 6.8 | 425.4 | 4.1 | 78.4 | 1 |

[a] IC$_{50}$ values were determined at least 3 independent experiments, each run was performed in duplicate; Assays for compounds which showed no activity (IC$_{50}$ >1000 nM) were only repeated twice;
[b] MW, ClogP, TPSA, and HBD were calculated by ChemDraw Professional 16.0.1.4 (77) (PerkinElmer Informatics, Inc.).

Our in vitro binding data showed that compounds 19a, 20c, 22b and 26b, were potent for S1P1 with the IC$_{50}$ values less than 20 nM. Consequentially, their IC$_{50}$ values of binding to other S1P receptor subtypes S1P2, S1P3, S1P4, and S1P5 were determined to check the binding selectivity. The IC$_{50}$ values of these four compounds binding toward S1P1-S1P5 were displayed in Table 5. Our data showed the IC$_{50}$ values of compounds binding toward S1P2-S1P5 are >1000 nM, indicating all four compounds 19a, 20c, 22b and 26b are selective for S1P1 over S1P2-S1P5.

TABLE 5

The IC$_{50}$ values (mean ± SD) of S1P, 19a, 20c, 22b, and 26b toward other S1P receptors.[a]

| Compd. | S1P1 | S1P2 | S1P3 | S1P4 | S1P5 |
|---|---|---|---|---|---|
| | | | IC$_{50}$ (nM) | | |
| S1P | 1.4 ± 0.3 | 3.6 ± 0.5 | 0.4 ± 0.2 | 151 ± 82 | 3.1 ± 1.1 |
| 19a | 13.2 ± 3.2 | >1000 | >1000 | >1000 | >1000 |
| 20c | 14.7 ± 1.7 | >1000 | >1000 | >1000 | >1000 |
| 22b | 9.7 ± 1.6 | >1000 | >1000 | >1000 | >1000 |
| 26b | 6.3 ± 1.3 | >1000 | >1000 | >1000 | >1000 |

[a] IC$_{50}$ values were determined at least 3 independent experiments, each run was performed in duplicate; Assays for compounds which showed no activity (IC$_{50}$ > 1000 nM) were only repeated twice.

The physicochemical properties of compounds play crucial role in brain penetration, and studies showed marketed CNS drugs were found to generally have smaller molecular weight (MW), higher calculated partition coefficient (ClogP), fewer hydrogen bond donors (HBDs), and lower topological polar surface area (TPSA) compared with non-CNS drugs (A. K. Ghose, T. Herbertz, R. L. Hudkins, B. D. Dorsey, J. P. Mallamo, Knowledge-based, central nervous system (CNS) lead selection and lead optimization for CNS drug discovery, ACS Chem. Neurosci. 3 (2012) 50-68.; T. T. Wager, X. Hou, P. R. Verhoest, A. Villalobos, Central nervous system multiparameter optimization desirability: application in drug discovery, ACS Chem. Neurosci. 7 (2016) 767-775; T. T. Wager, Moving beyond rules: the development of a central nervous system multiparameter optimization (CNS MPO) approach to enable alignment of druglike properties, ACS Chem. Neurosci. 1 (2010) 435-449.). A useful guideline was concluded as follows to assess the molecules for CNS drugs: MW≤470; 1<ClogP≤3; 40<TPSA 90; and HBD 2 (Z. Rankovic, CNS drug design: balancing physicochemical properties for optimal brain exposure, J Med Chem 58 (2015) 2584-2608.; Z. Rankovic, CNS physicochemical property space shaped by a diverse set of molecules with experimentally determined exposure in the mouse brain, J. Med. Chem. 60 (2017) 5943-5954.). Among these four compounds, both compounds 22b and 26b have good MW (463.4 and 453.4, respectively), ClogP (3.1 and 2.0, respectively), TPSA (91.4 and 92.5, respectively), and HBD (1 and 2, respectively) parameters for CNS drugs, showing the F-18 labeled version counterparts can have the capability of penetrating the BBB and entering the brain.

Example 98: Overview of the Radiosynthesis of [$^{18}$F] 22b

Figure 9:
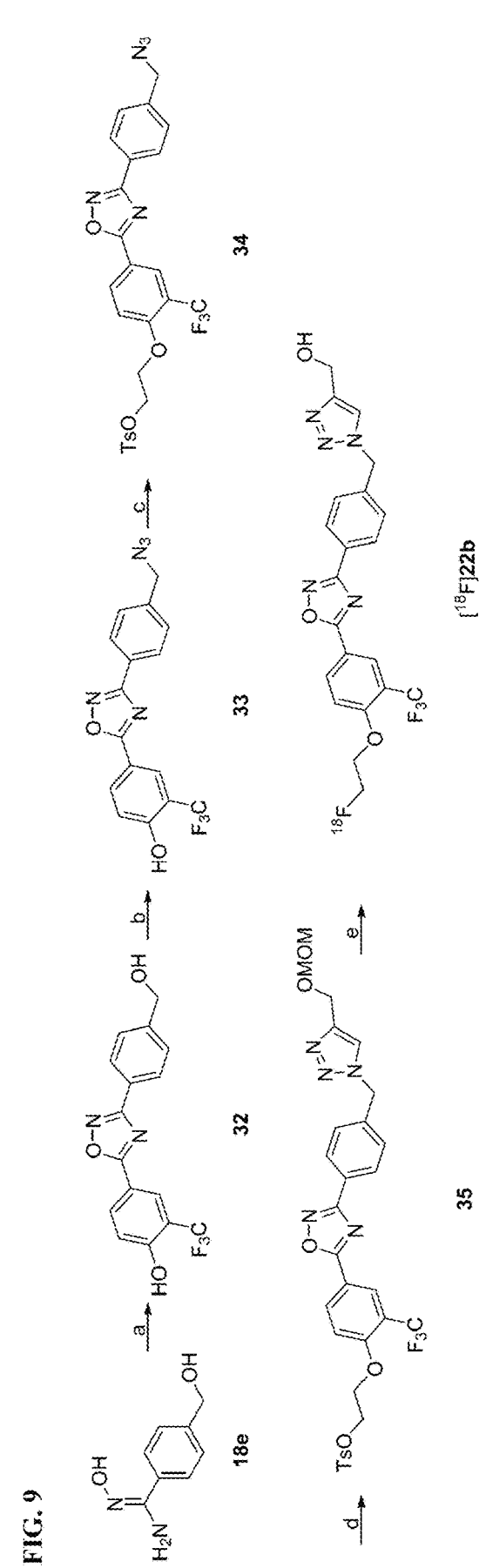
FIG. 9 Syntheses of the precursor 35 and [$^{18}$F]22b. Reagents and conditions: (a) 4-hydroxy-3-(trifluoromethyl) benzoic acid, TBTU, HOBt, DIPEA, DMF, RT-120° C.; (b) DPPA, DBU, toluene, 0° C., RT; (c) ethylene ditosylate, K$_2$CO$_3$, CH$_3$CN, 90° C.; (d) 3-(methoxymethoxy)prop-1-yne, CuSO$_4$.5H$_2$O, sodium ascorbate, THF, H$_2$O, RT; (e) [$^{18}$F]KF, Kryptofix 222, K$_2$CO$_3$, CH$_3$CN, 110° C., 15 min, 6 M HCl, 110° C., 5 min, 6 M NaOH.

Compound 35, the precursor for radiolabeling [$^{18}$F]22b was prepared by following the scheme in FIG. 9. The cyclization of compound 18e with 4-hydroxy-3-(trifluoromethyl)benzoic acid yielded compound 32, which was converted to azide 33 in the presence of DPPA and DBU. After alkylating with ethylene ditosylate, followed by azide-alkyne cycloaddition, tosylate precursor 35 was obtained. Radiosynthesis of [$^{18}$F] 22b was achieved by using the nucleophilic reaction between the tosylate precursor 35 and [$^{18}$F]KF in acetonitrile with Kryptofix 222 followed by deprotection of methoxymethyl (MOM) group. After purification using semi-preparative high-performance liquid chromatography (HPLC) combined with solid-phase extraction (SPE), [$^{18}$F]22b was formulated using 10% ethanol in 0.9% saline with high chemical and radiochemical purity (>98%), good radiochemical yields (14.1±2.9%), and high specific activity (54.1±8.3 GBq/pmol, n=6, decay corrected to EOS)

Example 99: Synthesis of 4-(3-(4-(Hydroxymethyl)phenyl)-1,2,4-oxadiazol-5-yl)-2-(trifluoromethyl) phenol (32)

The synthesis of compound 32 is indicated as reaction "a" in FIG. 9. To a round-bottom flask equipped with a stir bar was added 4-hydroxy-3-(trifluoromethyl)benzoic acid (1.96 g, 9.51 mmol), HOBt (0.26g, 1.90 mmol), TBTU (3.05 g, 9.51 mmol), DMF (20 mL), and DIPEA (3.69 g, 28.5 mmol). The reaction mixture was stirred for 0.5 h before adding 18e (1.58 g, 9.51 mmol). The reaction mixture was stirred for 1 h at room temperature and refluxed in a pre-heated 120° C. oil-bath. The reaction mixture was stirred for 4 h and monitored by TLC. After cooling, the reaction mixture was diluted with water and extracted with ethyl acetate. The ethyl acetate layer was washed with 1 M HCl, saturated brine, and dried over anhydrous MgSO$_4$. After filtration and concentration, the residue was purified on a silica gel column. (1.43 g, 45%)

Example 100: Synthesis of 4-(3-(4-(Azidomethyl)phenyl)-1,2,4-oxadiazol-5-yl)-2-(trifluoromethyl) phenol (33)

The synthesis of compound 33 is indicated as reaction "b" in FIG. 9. To a round-bottom flask equipped with a stir bar was added 32 (1.39 g, 4.13 mmol), diphenyl phosphoryl azide (1.37 g, 4.96 mmol), and toluene (10.0 mL). The mixture was cooled to 0° C. before adding 1,8-Diazabicyclo[5.4.0]undec-7-ene (0.76, 4.96 mmol) dropwise. The reaction was warmed to room temperature slowly and stirred overnight. Then, the reaction mixture was diluted with water and extracted with ethyl acetate. The ethyl acetate layer was washed with 1 M HCl, saturated brine and dried over anhydrous MgSO$_4$. After filtration and concentration, the residue was purified on a silica gel column to give yellow solid (815 mg, 55%). MP: 158-161° C. $^1$H NMR (400 MHz, CDCl$_3$) δ 8.41 (s, 1H, —ArH), 8.22 (d, J=8.5 Hz, 1H, —ArH), 8.17 (d, J=7.8 Hz, 2H, —ArH), 7.47 (d, J=7.9 Hz, 2H, —ArH), 7.09 (d, J=8.6 Hz, 1H, —ArH), 4.44 (s, 2H, —CH$_2$—).

Example 101: Synthesis of 2-(4-(3-(4-(Azidomethyl)phenyl)-1,2,4-oxadiazol-5-yl)-2-(trifluoromethyl)phenoxy)ethyl 4-methylbenzene-sulfonate (34)

The synthesis of compound 34 is indicated as reaction "c" in FIG. 9. To a round-bottom flask equipped with a stir bar was added 33 (500 mg, 1.38 mmol), ethylene ditosylate (767 mg, 2.07 mmol), K$_2$CO$_3$ (953 mg, 6.90 mmol), and CH$_3$CN (10.0 mL). The reaction mixture was refluxed in a pre-heated 90° C. oil-bath for 12 h. After cooling, the reaction mixture was diluted with water and extracted with ethyl acetate. The ethyl acetate layer was washed with saturated brine and dried over anhydrous MgSO$_4$. After filtration and concentration, the residue was purified on a silica gel column to give white solid (300 mg, 39%). MP: 169-170° C. $^1$H NMR (400 MHz, CDCl$_3$) δ 8.44 (s, 1H, —ArH), 8.33 (d, J=8.7 Hz, 1H, —ArH), 8.19 (d, J=8.2 Hz, 2H, —ArH), 7.81 (d, J=8.3 Hz, 2H, —ArH), 7.48 (d, J=8.1 Hz, 2H, —ArH), 7.38-7.32 (m, 2H, —ArH), 7.10 (d, J=8.7 Hz, 1H, —ArH), 4.45 (s, 2H, —ArCH$_2$—), 4.43-4.38 (m, 4H, —OCH$_2$CH$_2$O—), 2.45 (s, 3H, —CH$_3$).

Example 102: Synthesis of 2-(4-(3-(4-((4-(hydroxymethyl)-1H-1,2,3-triazol-1-yl)methyl)phenyl)-1,2,4-oxadiazol-5-yl)-2-(trifluoromethyl)phenoxy) ethyl 4-methylbenzenesulfonate (35)

The synthesis of compound 35 is indicated as reaction "d" in FIG. 9. To a round-bottom flask equipped with a stir bar was added azide 34 (243 mg, 0.43 mmol) and THF (2.0 mL). Once the azide was dissolved, water (1.1 mL) was added followed by 3-(methoxymethoxy)prop-1-yne (46 mg, 0.46 mmol), sodium ascorbate (8.5 mg, 0.043 mmol), and copper sulfate pentahydrate (6.4 mg, 0.026 mmol). The reaction mixture was stirred for 4 h and monitored by TLC. Then, the reaction mixture was diluted with water and extracted with ethyl acetate. The ethyl acetate layer was washed with saturated brine and dried over anhydrous MgSO$_4$. After filtration and concentration, a white solid was obtained (100 mg, 35%). MP: 168-171° C. $^1$H NMR (400 MHz, CD$_3$OD) δ 8.35-8.29 (m, 2H, —ArH), 8.11 (d, J=7.2 Hz, 2H, —ArH), 8.02 (s, 1H, —ArH), 7.74 (d, J=7.3 Hz, 2H, —ArH), 7.45 (d, J=7.5 Hz, 2H, —ArH), 7.36 (d, J=8.0 Hz, 2H, —ArH), 7.31 (d, J=8.4 Hz, 1H, —ArH), 5.67 (s, 2H, —ArCH$_2$—), 4.65-4.61 (m, 4H, —CH$_2$OCH$_2$O—), 4.43-4.34 (m, 4H, —OCH$_2$CH$_2$O—), 3.27 (s, 3H, —OCH$_3$), 2.37 (s, 3H, —ArCH$_3$).

Example 103: Radiosynthesis of [$^{18}$F]22b

The radiosynthesis of [$^{18}$F]22b is indicated as reaction "e" in FIG. 9. [$^{18}$F]KF (~7.4 GBq) aqueous was added to a vial containing Kryptofix 222 (~6 mg), and dried by azeotropic evaporation with CH$_3$CN (3×1 mL) under N$_2$ flow at 110° C. To the reaction vial was added precursor 35 (2 mg) as a solution in CH$_3$CN (300 µL). The reaction was placed in a 110° C. oil-bath for 15 min. The reaction was removed from the oil-bath, at which time 6 M HCl (150 µL) was added. The reaction mixture was heated in a 110° C. oil-bath for another 5 min. The reaction was removed from the oil-bath and quenched with 6 M NaOH (150 µL) and diluted with 2.4 mL of the HPLC mobile phase (45% CH$_3$CN in 0.1 M ammonium formate buffer, pH=4.5). The mixture was passed through a SEP-PAK Alumina N Cartridge (Part No. WAT020510) and injected onto the semi-preparation HPLC column (Agilent SB-C18 250×9.6 mm, 5 µm, UV=254 nm, 4.0 mL/min). The retention time of [$^{18}$F] 22b is around 19-22 min. The HPLC fraction was collected into a water bottle with 60 mL of water and then trapped on a SEP-PAK C-18 Cartridge (Part No. WAT020515). The activity (~740 MBq) was washed out with 0.6 mL of ethanol and 5.4 mL of 0.9% saline. After sterile filtration into a glass vial, the [$^{18}$F] 22b was ready for quality control (QC) analysis and animal studies. An aliquot of sample was injected onto an analytical HPLC to determine the concentration of tracer. Meanwhile, the tracer was authenticated by co-injected with non-radiolabeled standard 22b sample solution. The HPLC condition are as follows: Agilent Zorbax SB-C18 column (250×4.6 mm); UV absorbance at 254 nM; the mobile phase is consisted of 45% CH$_3$CN in 0.1 M ammonium formate buffer, pH=4.5; the flow rate is 1.0 mL/min; the retention time of [$^{18}$F]22b is 5.7 min.

Example 104: Ex Vivo Autoradiography Study

Figure 10:
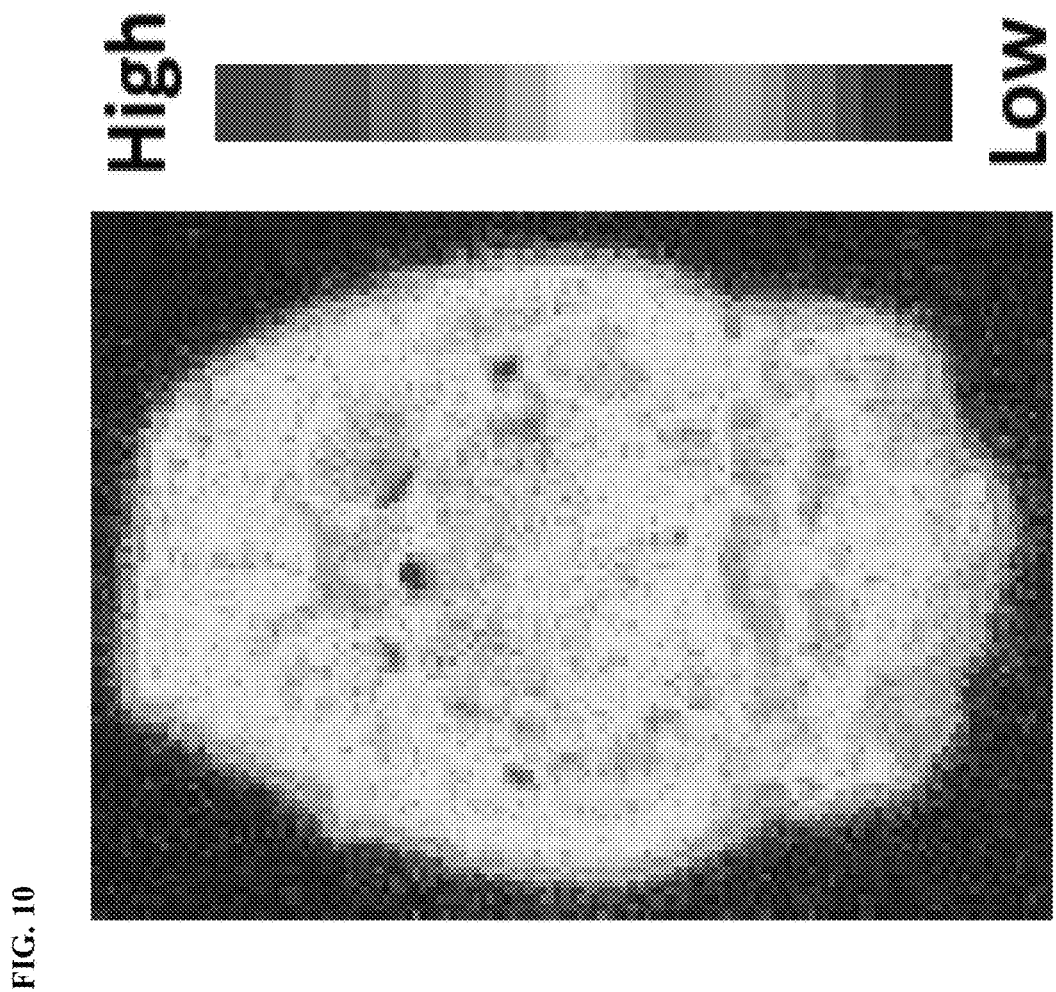
FIG. 10 Ex vivo autoradiography of [$^{18}$F]22b in rat brain.

An adult male SD rat (~450 g, Charles River) was injected with [$^{18}$F]22b (~55 MBq) via the tail vein under 2-3% isoflurane/oxygen anesthesia and euthanized at 60 min post-injection. The brain was immediately removed and snap-frozen over dry ice followed by sectioning at 100 μm and mounting on glass slides. Frozen slides were directly exposed to a BAS storage phosphor screen film (BAS-IP-MS-2025) in an imaging cassette (Fuji Photo Film Co., Tokyo, Japan) for 12 h at −80° C. under the dark. The distribution of radioactivity was visualized by a Fuji Bio-Imaging Analyzer FLA-7000 (Fuji Photo Film Co., Tokyo, Japan). As shown in FIG. 10, [$^{18}$F]22b was able to cross the BBB and showed high uptake in the rat brain, which is consistent to the expression of S1P1 in the brain of rodents and human (R. E. Toman, S. Spiegel, Lysophospholipid receptors in the nervous system, Neurochem. Res. 27 (2002) 619-627; H. Ohuchi, A. Hamada, H. Matsuda, A. Takagi, M. Tanaka, J. Aoki, H. Arai, S. Noji, Expression patterns of the lysophospholipid receptor genes during mouse early development, Dev. Dyn. 237 (2008) 3280-3294; H. Nishimura, T. Akiyama, I. Irei, S. Hamazaki, Y. Sadahira, Cellular localization of sphingosine-1-phosphate receptor 1 expression in the human central nervous system, J. Histochem. Cytochem. 58 (2010) 847-856).

Example 105: In Vitro Autoradiography Study in LPS-Treated Mice

To confirm the binding specificity of [$^{18}$F]22b toward S1P1, in vitro autoradiography studies were performed using mouse brain slices that generated from LPS-induced murine neuroinflammation model, a widely used model for neuroinflammation, and the expression of S1P1 was activated in the mouse brain following the LPS injection according to the report (M. Kono, E. G. Conlon, S. Y. Lux, K. Yanagida, T. Hla, R. L. Proia, Bioluminescence imaging of G protein-coupled receptor activation in living mice, Nat. Commun. 8 (2017) 1163). Adult male C57BL/6 mice (20-25 g, Charles River Inc., Frederick, Md.) were used to generate LPS-induced neuroinflammation murine model. The mice (n=2) received an intraperitoneal injection of LPS from *E. coli* 055:65 (Sigma-Aldrich, St. Louis, Mo., USA) in saline (3 mg/mL) at dose of 15 mg/kg (5 mL/kg) and then euthanized at 24 h post-injection. Mouse brains were collected and cut into 20 μm sequential sections using a Microm cryotome and mounted on glass slides. For the control study, the slides were incubated with ~6 nM of [$^{18}$F]22b at room temperature for 60 min. For the blocking studies, slides were incubated with [$^{18}$F]22b in the presence of 10 μM of SEW2871 at room temperature for 60 min. Following the incubation, the brain sections were washed and exposed to the Storage Phosphor Screen in an imaging cassette overnight in −20° C. at dark for 12 h. The distribution of radioactivity was visualized by a Fuji Bio-Imaging Analyzer FLA-7000 (Fuji Photo Film, Tokyo, Japan). Photo-stimulated luminescence (PSL) from the brain slices was quantified using Multi Gauge v3.0 software (Fuji Photo Film Co., Tokyo, Japan). Data were background-corrected, and expressed as photo-stimulated luminescence signals per square millimeter (PSL/mm$^2$).

Figure 11:
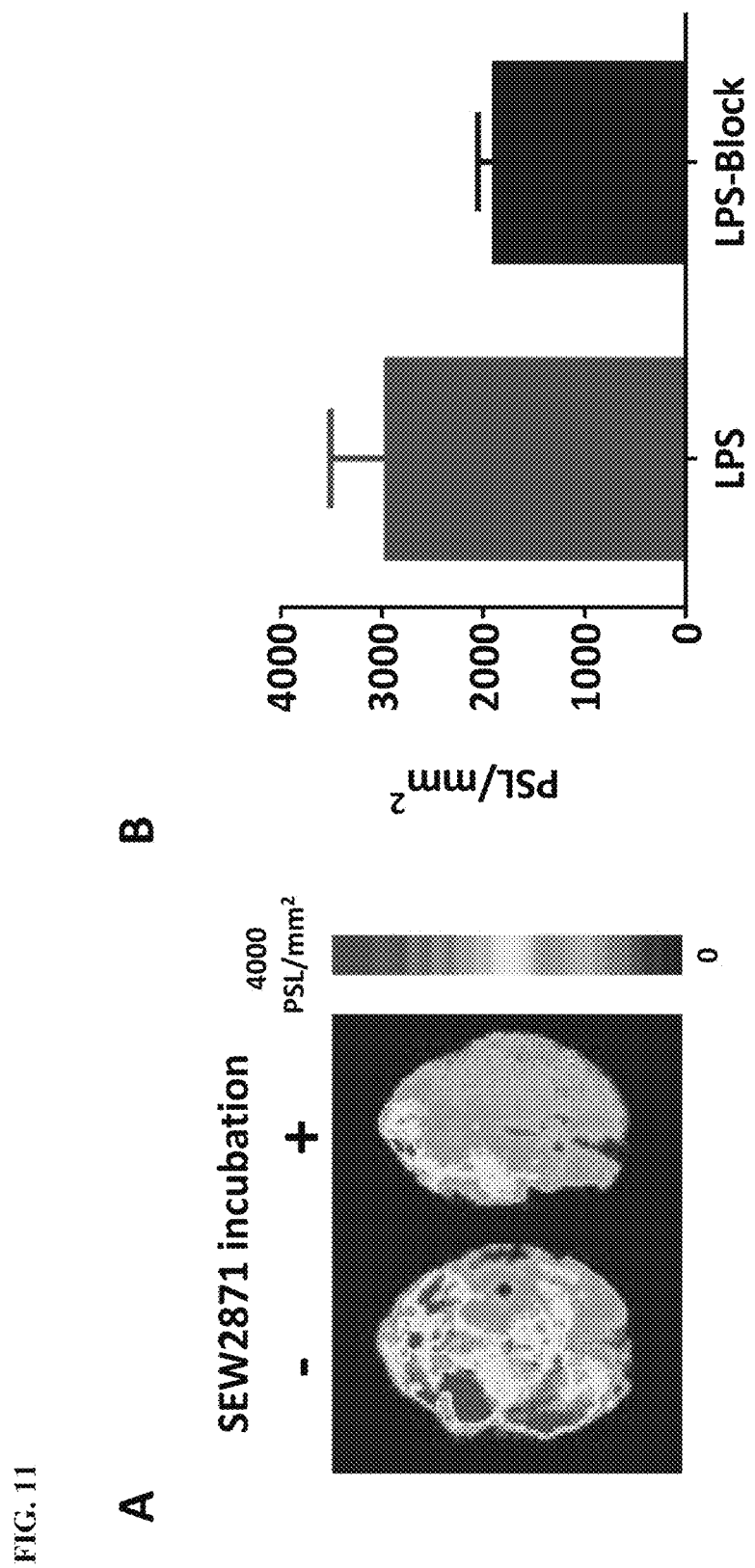
FIG. 11 Representative in vitro autoradiographic images (A) and quantification of autoradiography (B) of brain sections from LPS-induced neuroinflammation mice under control or blocking condition. SEW2871, an S1P1-specific ligand (IC$_{50}$=37 nM), was used as the blocking agent.

In vitro autoradiography study showed that SEW2871 was able to reduce the uptake of [$^{18}$F]22b by ~36%, demonstrating the binding of [$^{18}$F]22b toward S1P1 is specific (FIG. 11).

Example 106: Biodistribution Study

To further investigate the tissue distribution of [$^{18}$F]22b in rodents, an ex vivo biodistribution study was performed in adult female Lewis rats. A solution of [$^{18}$F]22b (~2.2 MBq/100 μL) in 10% ethanol in 0.9% saline was injected via the tail vein into adult female Lewis rats (n=16, 120-140 g, Charles River) under 2-3% isoflurane/oxygen anesthesia. The rats were euthanized under anesthesia at 5, 30, 60, and 120 min post-injection (n=4 for each group). The whole brains were quickly harvested and dissected into regions of cerebellum, brain stem, cortex, striatum, thalamus, and hippocampus, the remainder of the brain was also collected to determine the total brain uptake. Organs of blood, heart, lung, muscle, fat, pancreas, spleen, kidney, liver, thymus, and bone were also dissected and collected for counting. All the samples were counted with a dilution of the injectate on an automated well counter (Beckman Gamma 8000 well counter). Tissues were weighed and the uptake was reported as background and decay-corrected percent injected dose per gram (% ID/g).

Figure 12:
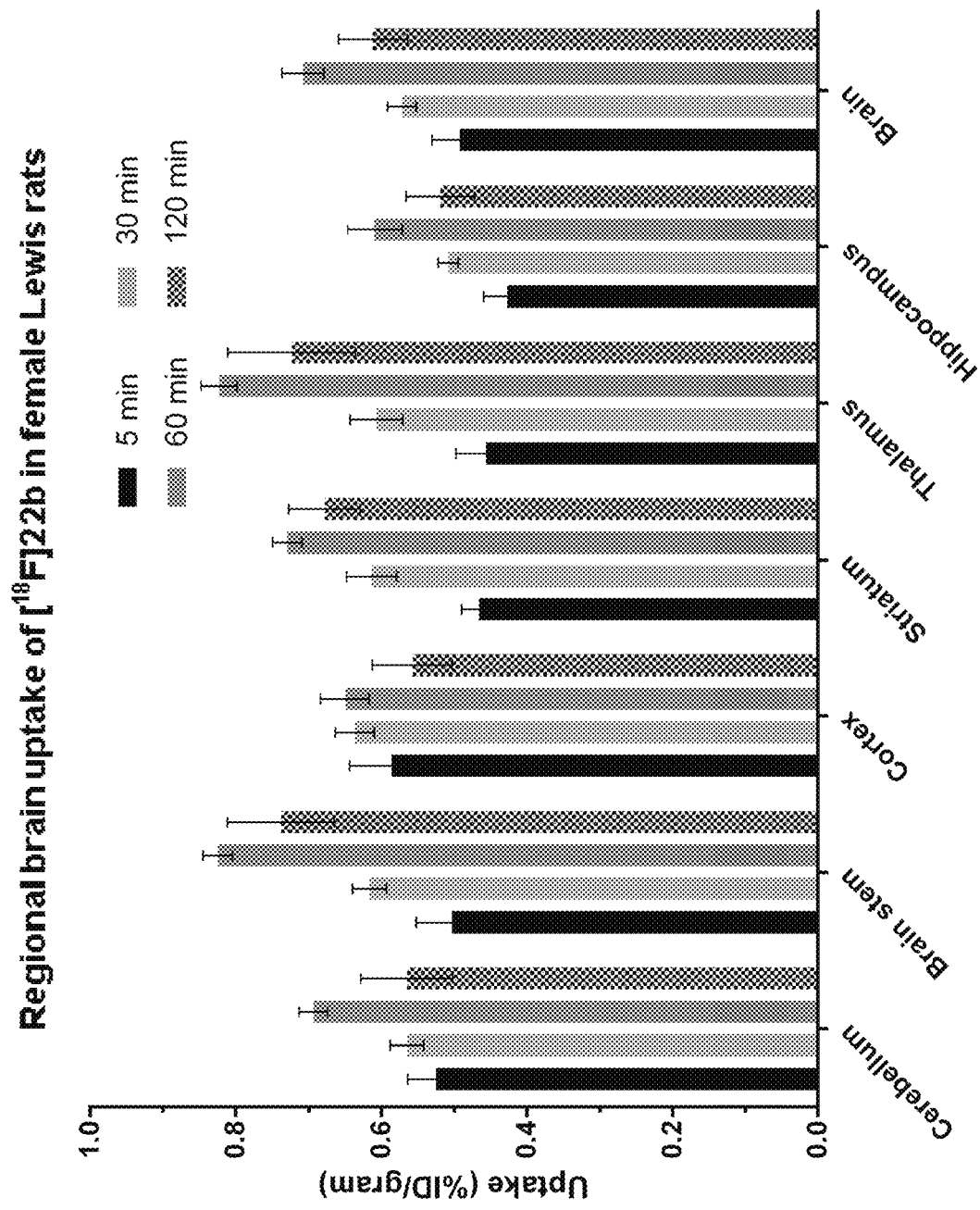
FIG. 12 Regional brain uptake of [$^{18}$F]22b in female Lewis rats. Animals were sacrificed at 5, 30, 60, and 120 min post-injection. % ID/gram values (mean±SD) with 4 rats per group.

As shown in the Table 6, the initial uptake (ID %/g) at 5 min post injection in blood, heart, lung, muscle, fat, pancreas, spleen, kidney, liver, bone, thymus, and brain was 0.49, 1.65, 2.79, 0.39, 0.51, 1.96, 2.22, 3.43, 5.69, 0.55, 0.69, and 0.49, respectively. A rapid clearance of radioactivity was observed in tissues heart, lung, spleen, kidney, and liver; uptake (ID %/g) was decreased to 1.19, 1.96, 1.36, 2.11, and 4.30 at 30 min from 1.65, 2.79, 2.22, 3.43, and 5.69 at 5 min, respectively. The radioactivity accumulation in the bone has no change from 5 min to 120 min, suggesting [$^{13}$F]22b had no defluorination in vivo. A high uptake (ID %/g) of [$^{18}$F]22b in the brain was observed compared to radiotracer [$^{18}$F]4 (A. J. Rosenberg, H. Liu, H. Jin, X. Yue, S. Riley, S. J. Brown, Z. Tu, Design, synthesis, and in vitro and in vivo evaluation of an $^{18}$F-labeled sphingosine 1-phosphate receptor 1 (S1P1) PET tracer, J. Med. Chem. 59 (2016) 6201-6220). The brain uptake (ID %/g) of [$^{18}$F]22b was 0.49, 0.57, 0.71, and 0.61 at 5, 30, 60, and 120 min, respectively. In brain regions including cerebellum, brain stem, cortex, striatum, thalamus, and hippocampus, [$^{18}$F]22b had similar distribution, the uptake (ID %/g) in each region was 0.53, 0.50, 0.59, 0.47, 0.46, and 0.43, respectively at 5 min; the brain uptake at 60 min post injection reached the maximum, then gradually washed out as shown in FIG. 12. This data show that [$^{18}$F]22b can be a PET tracer for imaging S1P1 expression in the brain in vivo.

TABLE 6

Biodistribution of [$^{18}$F]22b in female Lewis rats. (% ID/g values, mean ± SD, n = 4)

| Organs | Tissue uptake (% ID/g) | | | |
|---|---|---|---|---|
| | 5 min | 30 min | 60 min | 120 min |
| Blood | 0.49 ± 0.07 | 0.42 ± 0.05 | 0.36 ± 0.02 | 0.35 ± 0.01 |
| Heart | 1.65 ± 0.27 | 1.19 ± 0.06 | 1.05 ± 0.08 | 0.94 ± 0.06 |
| Lung | 2.79 ± 0.57 | 1.96 ± 0.07 | 1.67 ± 0.09 | 1.54 ± 0.07 |
| Muscle | 0.39 ± 0.04 | 0.59 ± 0.05 | 0.51 ± 0.02 | 0.47 ± 0.02 |
| Fat | 0.51 ± 0.22 | 0.62 ± 0.10 | 0.69 ± 0.07 | 0.57 ± 0.07 |
| Pancreas | 1.96 ± 0.56 | 1.89 ± 0.16 | 1.52 ± 0.25 | 1.45 ± 0.15 |
| Spleen | 2.22 ± 0.23 | 1.36 ± 0.04 | 1.27 ± 0.08 | 1.14 ± 0.10 |
| Kidney | 3.43 ± 0.31 | 2.11 ± 0.08 | 1.91 ± 0.10 | 1.62 ± 0.09 |
| Liver | 5.69 ± 0.60 | 4.30 ± 0.37 | 4.21 ± 0.21 | 3.66 ± 0.14 |
| Bone | 0.55 ± 0.05 | 0.45 ± 0.03 | 0.45 ± 0.01 | 0.51 ± 0.05 |
| Thymus | 0.69 ± 0.08 | 0.83 ± 0.07 | 0.82 ± 0.04 | 0.78 ± 0.05 |
| Brain | 0.49 ± 0.04 | 0.57 ± 0.02 | 0.71 ± 0.03 | 0.61 ± 0.05 |

Example 107: In Vivo Evaluation of F-18 Labeled S1P1 PET Radiotracers for Imaging Neuroinflammation A subset of compounds synthesized and described in the examples above were further examined for their use as radiotracers in models of neuroinflammation. Four potent S1P1 ligands, TZ43113 ($IC_{50}$=9.7±1.6 nM, referred to as 22b in the Examples above), TZ35104 ($IC_{50}$=6.7±0.7 nM, referred to as (8c or 19e in the Examples above), TZ4877 ($IC_{50}$=14.1±0.4 nM, referred to as 12a in the Examples above), and TZ4881 ($IC_{50}$=15.4±3.3 nM referred to as 12b in the Examples above) were radiolabeled with fluorine-18 according to the previous reported methods [add reference]. The compounds chosen are listed in Table 8 below and all were radiosynthesized using the techniques described above to form $^{18}$F-TZ35104 ([$^{18}$F]8c/[$^{18}$F]19e), $^{18}$F-TZ4877 ([$^{18}$F]12a), $^{18}$F-TZ4881 ([$^{18}$F]12b), and $^{18}$F-TZ43113 ([$^{18}$F]22b) (with a 40±5% radiochemical yield and high specific activity (>45 GBq/pmol, decay corrected to the end of synthesis).

published procedure (Liu H, Jin H, Yue X, et al. PET Imaging Study of S1P1 Expression in a Rat Model of Multiple Sclerosis. *Mol Imaging Biol.* 2016; 18(5):724-732).

MicroPET scans were performed using an Inveon PET/CT system (Siemens Inc., Knoxville, Tenn.). Rats were anesthetized in an induction chamber with 2-3% isoflurane in oxygen, and a catheter was placed in the lateral tail vein. Each rat was secured to a custom-designed acrylic bed equipped with a nosecone for gas anesthesia. PET/CT scans were conducted under 1.5-2% isoflurane anesthesia with the rat placed in transaxial position and centered with the T13 vertebral spine in the field of view. Following a CT scan for anatomical coregistration, animals received a bolus injection of one $^{18}$F labeled newly-synthesized S1P1 ligand ($^{18}$F-

TABLE 7

| Ligands | Structures | $IC_{50}$, nM S1P1 | $IC_{50}$, nM S1P2-S1P5 | logP | TPSA |
|---|---|---|---|---|---|
| TZ35104* (8c/19e) | [structure] | 6.67 ± 0.70 | >1000 | 4.0 | 63.4 |
| TZ4877* (12a) | [structure] | 14.01 ± 0.04 | >1000 | 4.0 | 72.6 |
| TZ4881* (12b) | [structure] | 15.40 ± 3.30 | >1000 | 3.8 | 81.9 |
| TZ43113** (22b) | [structure] | 9.65 ± 1.61 | >1000 | 3.1 | 91.4 |

Example 108: Induction of a Rat EAE Model and MicroPET Scan

Table 6 above showed that the brain uptake of $^{18}$F-TZ43113 ([$^{18}$F]22b) reached 0.71% ID/g at 60 min post injection, demonstrating its ability to penetrate the BBB. Therefore, the microPET study was performed to evaluate if $^{18}$F-TZ43113 ([$^{18}$F]22b) could differentiate S1P1 expression in EAE rat lumbar spinal cord with shams. The rat EAE model provided a reliable and repeatable tool for testing newly-synthesized S1P1 radioligands in quantifying the change of S1P1 expression in response to neuroinflammation. All rodent experiments were conducted in compliance with the Guidelines for the Care and Use of Research Animals under protocols approved by Washington University's Institutional Animal Care and Use Committee (IACUC). The EAE rat model was induced according to a published procedure TZ35104 ([$^{18}$F]8c/[$^{18}$F]19e), $^{18}$F-TZ43113 ([$^{18}$F]22b), $^{18}$F-TZ4877 ([$^{18}$F]12a), or $^{18}$F-TZ4881 ([$^{18}$F]12b)) (0.4-0.6 mCi) via the tail vein catheter; body temperature was maintained with heat lamps during the imaging session. A list mode protocol was used with 60-min dynamic data acquisition.

Figure 13:
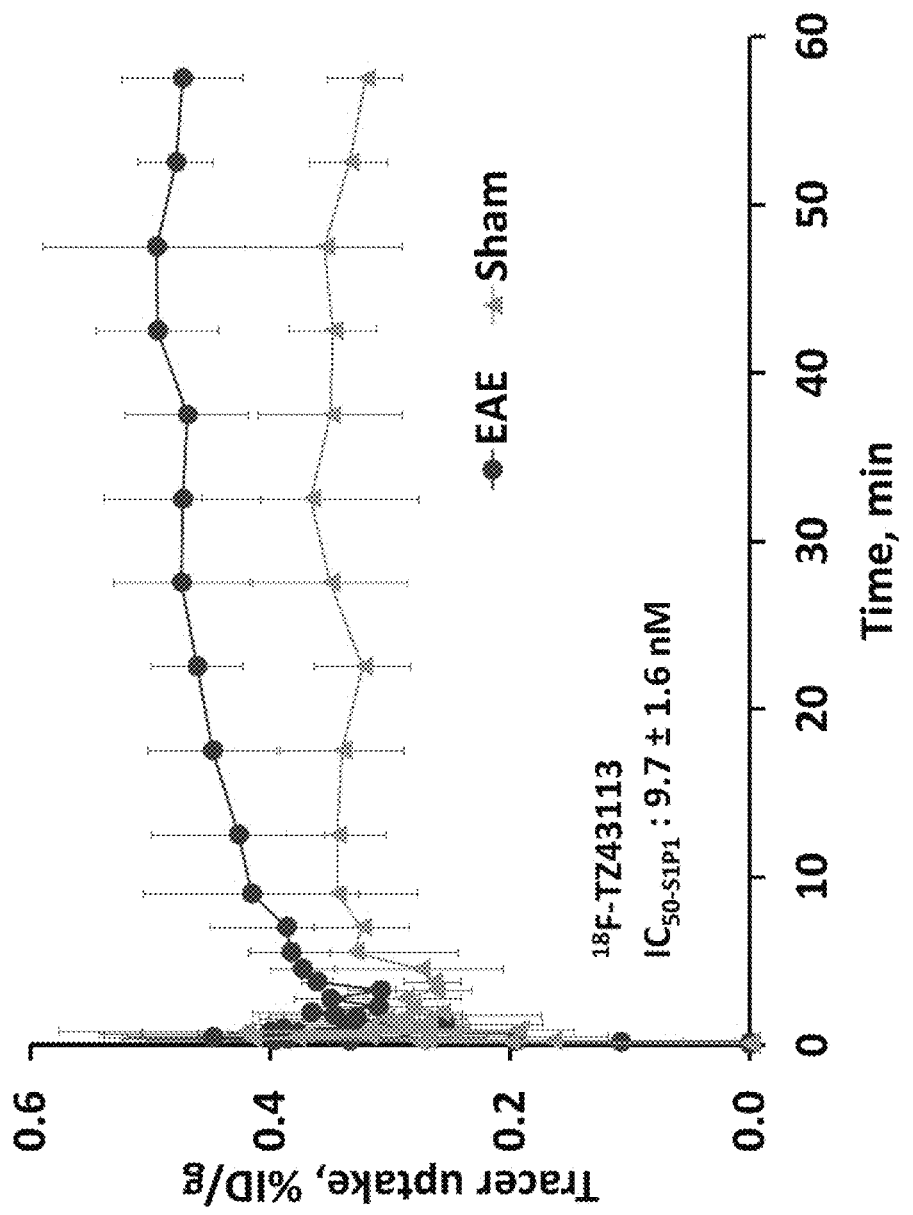
FIG. 13. Time-activity curves of $^{18}$F-TZ43113 ([$^{18}$F]22b) uptake in EAE and sham rat lumbar spinal cord, indicating EAE groups had ~37% increase of tracer uptake compared to shams (EAE 0.47±0.05 vs sham 0.34±0.05, summed % ID/g value, 10-60 min post injection, n=4, P<0.05). EAE, experimental autoimmune encephalomyelitis.

TAC curves showed the uptake increased by 36.7% in EAE groups compared to shams (EAE 0.47±0.05 vs sham 0.34±0.05, summed % ID/g value, 10-60 min post injection, n=4, P<0.05, FIG. 13). However, the uptake of $^{18}$F-TZ43113 ([$^{18}$F]22b) was not high enough for clear visualization of rat spinal cord by microPET.

Figure 14:
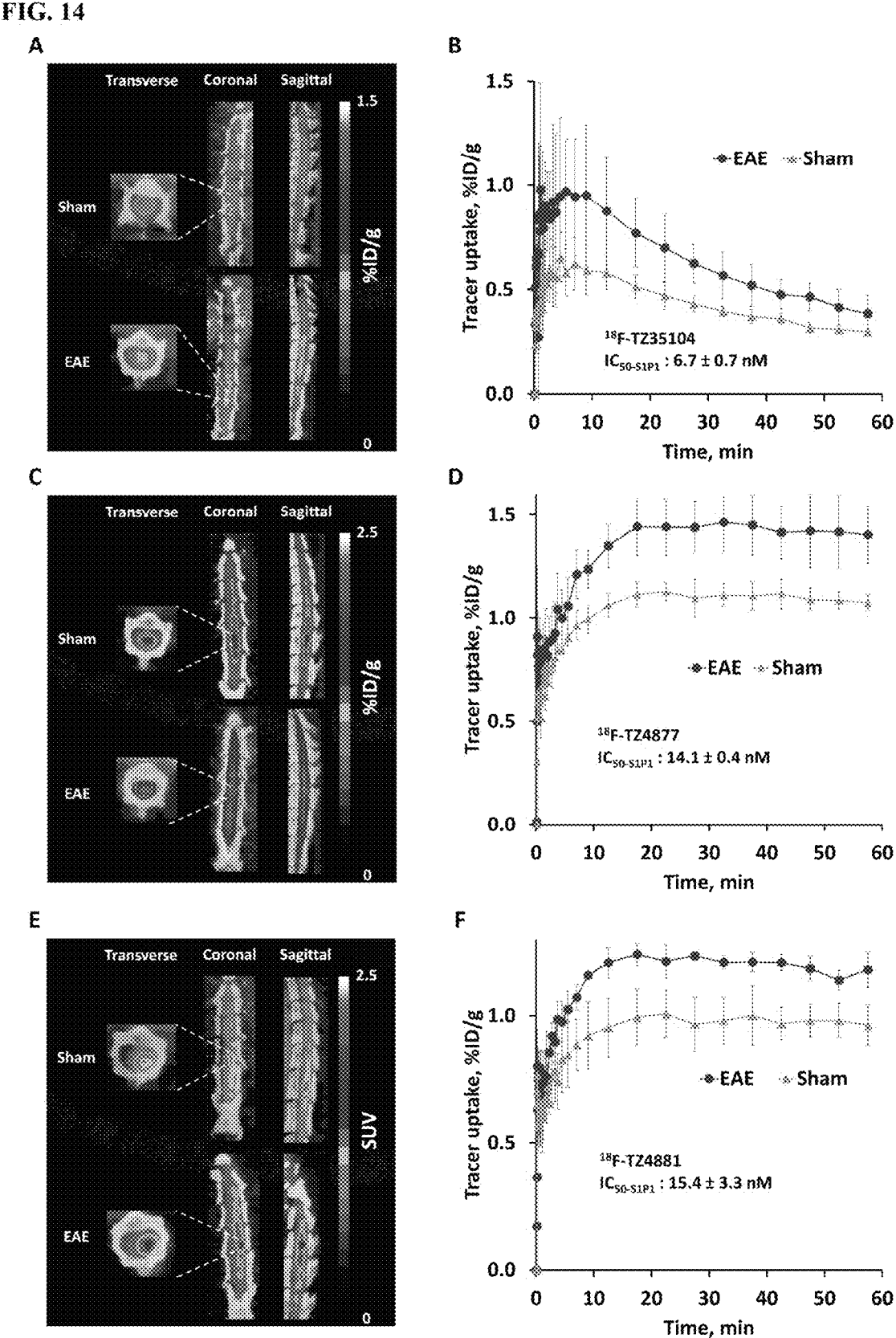
FIG. 14. MicroPET studies of $^{18}$F-TZ35104 ([$^{18}$F]8c/ [$^{18}$F]19e), $^{18}$F-TZ4877 ([$^{18}$F]12a) and $^{18}$F-TZ4881 ([$^{18}$F] 12b) in the EAE rat model. A&B, representative microPET/ CT images and time-activity curves of $^{18}$F-TZ35104 ([$^{18}$F] 8c/[$^{18}$F]19e), showing 43.5% increase of tracer uptake in EAE rat lumbar spinal cord, compared with shams (EAE 0.58±0.12 vs sham 0.40±0.04, n=3, P<0.05); C&D, representative microPET/CT images and time-activity curves of $^{18}$F-TZ4877([$^{18}$F]12a), showing 29.5% increase of tracer uptake in EAE rats (EAE 1.42±0.14 vs sham 1.10±0.06, n=3, P<0.01); E&F, representative microPET/CT images and time-activity curves of 18F-TZ4881([$^{18}$F]12b), showing 22.9% increase of tracer uptake in EAE rats (EAE 1.20±0.04 vs sham 0.98±0.09, n=3-4, P<0.01).
Figure 15:
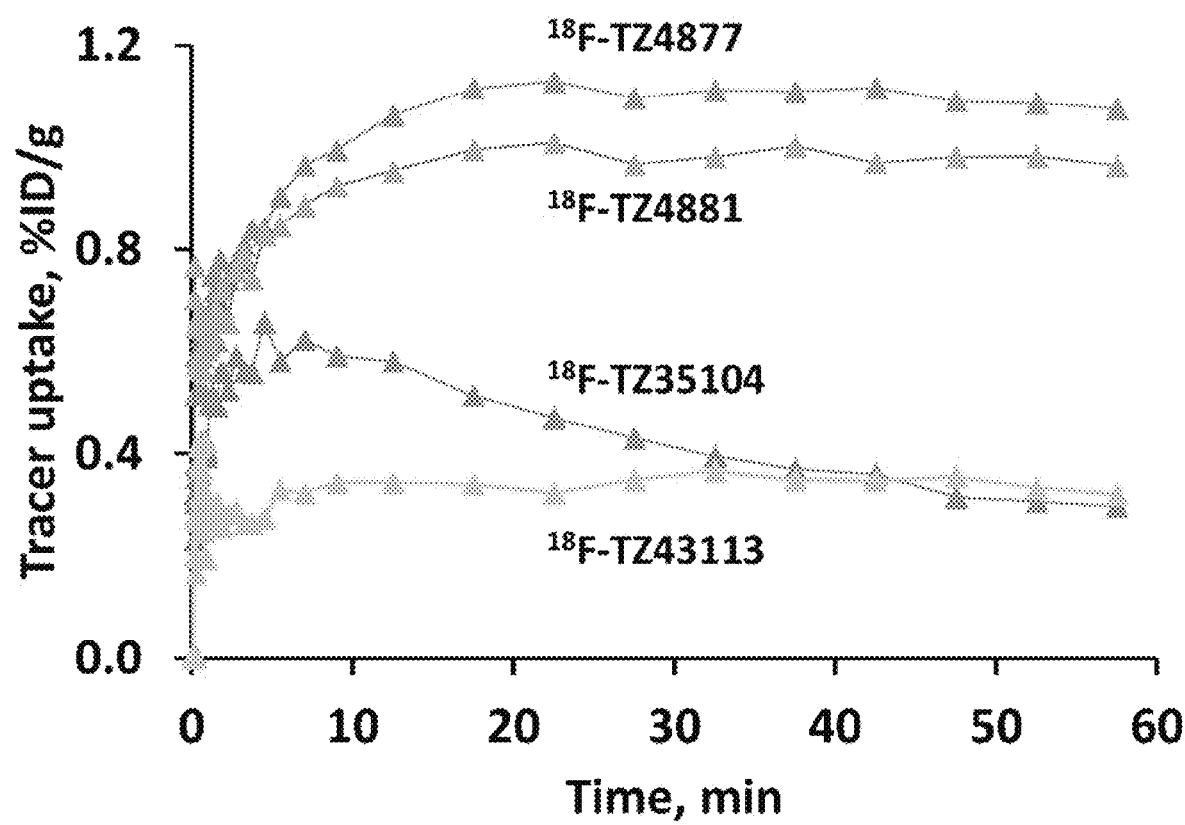
FIG. 15. Comparison of tracer uptake of four S1P1 radioligands in sham rat lumbar spinal cord. Time-activity curves demonstrate that $^{18}$F-TZ43113 ([$^{18}$F]22b) showed lowest uptake in rat spinal cord, followed by $^{18}$F-TZ35104 ($^{18}$F-8c/19e), $^{18}$F-TZ4881 ($^{1}$[$^{18}$F]12b) and $^{18}$F-TZ4877 ([$^{18}$F]12a).

Encouragingly, for $^{18}$F-TZ35104 ([$^{18}$F]8c/[$^{18}$F]19e), $^{18}$F-TZ4877 ([$^{18}$F]12a), and $^{18}$F-TZ4881 ([$^{18}$F]12b), microPET images of all three tracers demonstrated clear visualization of lumbar spinal cord in both EAE and sham rats (FIG. 14). Moreover, TAC curves of sham rat spinal cord showed 18F-TZ43113 ([$^{18}$F]22b) had lowest tracer uptake, approximately 0.35% ID/g at 10-60 min post injection. $^{18}$F-TZ35104 ([$^{18}$F]8c/[$^{18}$F]19e) had a higher initial tracer uptake (~0.65% ID/g at 5-10 min post injection) than $^{18}$F-TZ43113 ([$^{18}$F]22b), however, washed out fast from rat spinal cord and its uptake decreased to 0.32% ID/g at 60 min post injection. Both $^{18}$F-TZ4877 ([$^{18}$F]12a) and $^{18}$F-TZ4881 ([$^{18}$F]12b) showed significantly elevated initial tracer uptake and higher tracer retention (averaged tracer uptake: 1.0-1.1, 10-60 min post injection) than 18F-TZ35104 ([$^{18}$F]8c/[$^{18}$F]19e) and $^{18}$F-TZ43113 ([$^{18}$F]22b) (FIG. 15).

Regardless of tracer kinetics, rat microPET scans using $^{18}$F-TZ35104 ([$^{18}$F]8c/[$^{18}$F]19e) revealed a 43.5% increase of tracer uptake (EAE 0.58±0.12 vs sham 0.40±0.04, n=3, P<0.05, FIG. 14 panel A and 14 panel B) in EAE rat lumbar spinal cord, compared with shams. $^{18}$F-TZ4877 ([$^{18}$F]12a) was able to detect 29.5% increase of tracer uptake in EAE group (EAE 1.42±0.14 vs sham 1.10±0.06, n=3, P<0.01, FIG. 14 panel C and panel D), and $^{18}$F-TZ4881 ([$^{18}$F]12b) found 22.9% increase of tracer uptake in EAE rats (EAE 1.20±0.04 vs sham 0.98±0.09, n=3-4, P<0.01, FIG. 14 panel E and panel F). Tracer uptake was presented as summed SUV values 10-60 min post injection for each tracer.

Based on the microPET data, tracer kinetic modeling was performed to provide additional information for tracer validation and comparison. PET image data was processed using filter back projection algorithm with attenuation and scatter corrections. The data were reconstructed per time frame employing an iterative reconstructional algorithm (three-dimensional ordered subset expectation maximization (3D-OSEM), maximum a posteriori (MAP)) and corrected for decay, random coincidences, scatter, and attenuation. The list mode data of the emission scans were reframed into a dynamic sequence of 1×3, 6×2, 9×5, 6×10, 4×30, 2×60 s, 2×2, 10×5 min. Image data was analyzed using Inveon Research Workstation software IRW 4.2 (Siemens Inc., Knoxville, Tenn.). The regions of interest (ROI), the lumbar spinal cord and bilateral common carotid arteries, were drawn over the co-registered PET/CT images using the standard protocol published previously. Time-activity curves (TACs) were obtained and were expressed as % ID/g. A two-tailed t-test was used for the comparison of the tracer uptake in EAE rat lumbar spinal cord versus sham. A P value less than 0.05 was considered statistically significant. Time-activity curves were further analyzed using 2-tissue-compartment model (2TCM), as well as Logan graphical analysis, using the ROI over bilateral common carotid arteries for image-based arterial blood input function.

Figure 16:
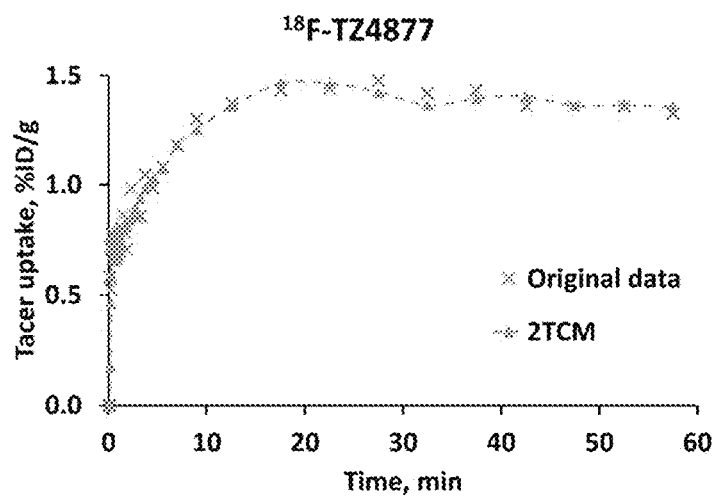
FIG. 16. Representative 2TCM fits for $^{18}$F-TZ35104 ([$^{18}$F]8c/[$^{18}$F]19e), $^{18}$F-TZ4877 ([$^{18}$F]12a), and $^{18}$F-TZ4881 ([$^{18}$F]12b) in rat spinal cord. The results indicate that 2TCM provide good fits for these three radioligands. 2TCM, 2-tissue-compartment models.
Figure 16:
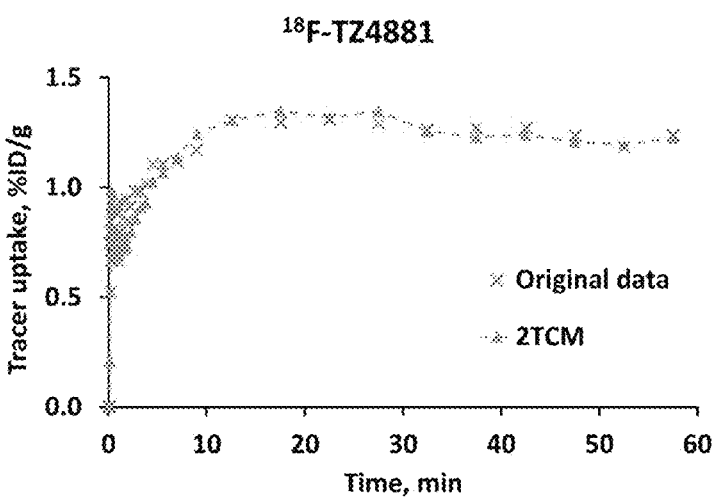
Figure 16:
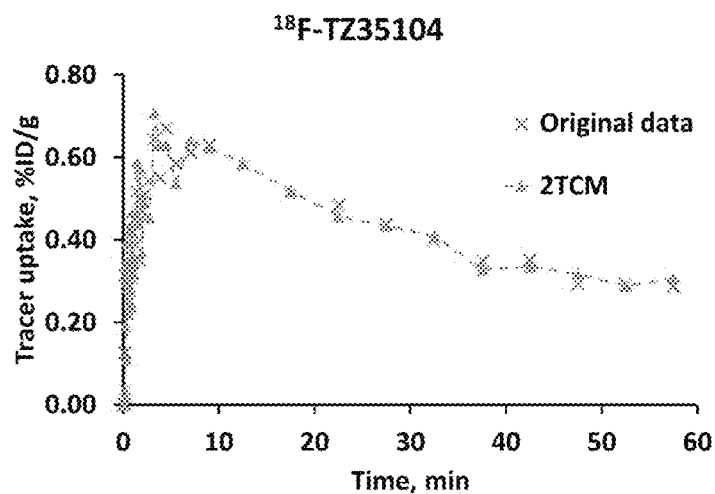
Figure 17:
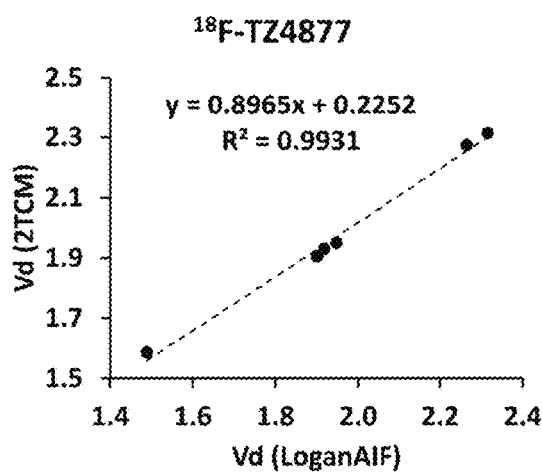
FIG. 17. Correlation of Vd values estimated by LoganAIF and 2TCM for $^{18}$F-TZ35104 ([$^{18}$F]8c/19e), $^{18}$F-TZ4877 ([$^{18}$F]12a), and $^{18}$F-TZ4881([$^{18}$F]12b). The Logan plot (t*=10-50 min) provided Vd estimates in good agreement with 2TCM for these three tracers (r$^2$=0.98-0.99).
Figure 17:
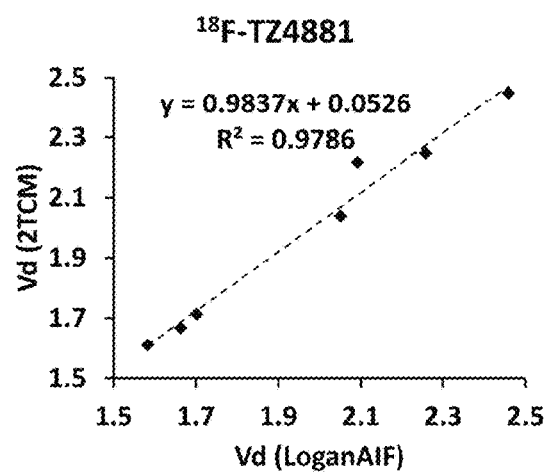
Figure 17:
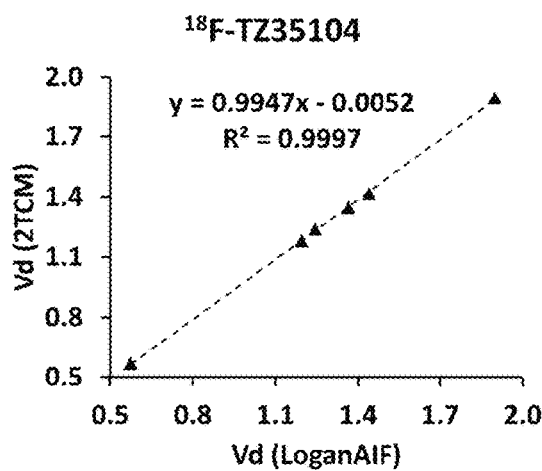

2TCM and Logan graphical analysis Vd data for three S1P1 radioligands in EAE and sham rats are presented in Table 8. Typical 2TCM fits are shown in FIG. 16. 2TCM provided good fits of all three tracers. Small variations of Vd values were observed for $^{18}$F-TZ4877 ([$^{18}$F]12a) and $^{18}$F-TZ4881 ([$^{18}$F]12b) scans, while large variation was found in shams when using $^{18}$F-TZ35104 ([$^{18}$F]22b). The Logan plot (t*=10-50 min) provided Vd estimates in good agreement with 2TCM for all three tracers (FIG. 17, $r^2$=0.98-0.99). Based on Vd estimates from 2TCM and Logan plot, EAE rats showed significantly increased Vd values than shams for $^{18}$F-TZ4877 ([$^{18}$F]12a) and $^{18}$F-TZ4881 ([$^{18}$F]12b), but not for $^{18}$F-TZ35104 ([$^{18}$F]22b).

TABLE 8

| Tracers | Groups | LoganAIF Vd, mL/g | 2TCM Vd, mL/g |
|---|---|---|---|
| $^{18}$F-TZ35104 | EAE | 1.35 ± 0.10 | 1.33 ± 0.09 |
| ([$^{18}$F]22b) | Sham | 1.22 ± 0.66 | 1.21 ± 0.66 |
| $^{18}$F-TZ4877 | EAE | 2.18 ± 0.20 | 2.18 ± 0.20 |
| ([$^{18}$F]12a) | Sham | 1.77 ± 0.24 | 1.80 ± 0.20 |
| $^{18}$F-TZ4881 | EAE | 2.27 ± 0.18 | 2.30 ± 0.13 |
| ([$^{18}$F]12b) | Sham | 1.75 ± 0.21 | 1.76 ± 0.19 | n = 3-4 in each group for each radioligand.

Example 109: Nonhuman Primate (NHP) MicroPET Scan

To examine if newly-synthesized S1P1 radioligands could cross the BBB of NHPs, two male macaques (9-10 kg) were studied with a microPET Focus 220 scanner (Concorde/CTI/Siemens Microsystems, Knoxville, Tenn.). The welfare of the animals conformed to the requirements of *National Institutes of Health* (NIH). This work was conducted at the Nonhuman Primate Facility of Washington University in St. Louis with approval from the IACUC. Animals were maintained in facilities with 12-hour dark and light cycles, given access to food and water ad libitum and provided a variety of psychologically enriching tasks to prevent inappropriate deprivation. Animals were scanned under anesthesia (induced with ketamine and glycopyrrolate and maintained with inhalation isoflurane). Core temperature was kept about 37° C. with a heated water blanket. The head was secured in a head holder with the brain in the center of the field of view. Subsequently, a 2-hr dynamic emission scan was acquired after administration of 8.08±1.89 mCi of an $^{18}$F labeled potent newly-synthesized S1P1 ligands ($^{18}$F-TZ4877 ([$^{18}$F]12a) or $^{18}$F-TZ4881 ([$^{18}$F]12b)) via the venous catheter.

PET scans were collected from O-120 min with the following time frames: 3×1 min, 4×2 min, 3×3 min and 20×5 min. Emission data were corrected for dead time, scatter and attenuation and then reconstructed to a final resolution of 2.0 mm full-width half maximum in all 3 dimensions at the center of the field of view. PET and MRI images were co-registered using automated image registration program (AIR). For quantitative analyses, three-dimensional ROI (the global brain) was identified on the MRI and transformed to the reconstructed PET images to obtain time-activity curves. Activity measures were standardized to body weight and the dose of radioactivity injected to yield standardized uptake value (SUV).

Figure 18:
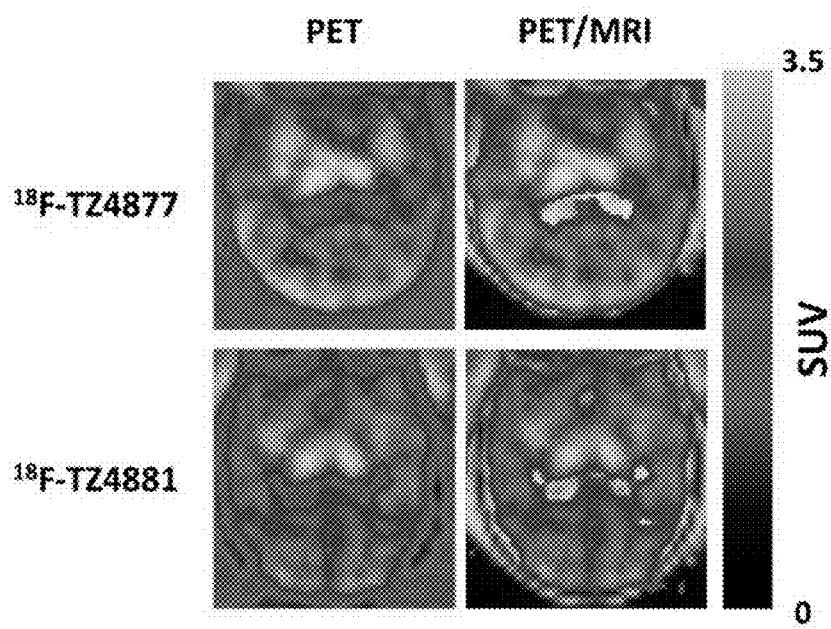
FIG. 18. MicroPET studies of $^{18}$F-TZ4877 ([$^{18}$F]12a) and $^{18}$F-TZ4881([$^{18}$F]12b) in normal nonhuman primates (NHPs). Panel A, representative microPET/CT images of $^{18}$F-TZ4877 ([$^{18}$F]12a) and $^{18}$F-TZ4881 ([$^{18}$F]12b) in NHP brains, showing both S1P1 radiotracers are able to cross the blood brain barrier and widely distributed throughout the NHP brain; Panel B, time-activity curves showing that the uptake of both S1P1 radiotracers in the total brain reached the max SUV value (~2.9 for $^{18}$F-TZ4877 ([$^{18}$F]12a), ~2.4 for $^{18}$F-TZ4881 ([$^{18}$F]12b) fast, at ~5 min post injection, and washed out gradually.
Figure 18:
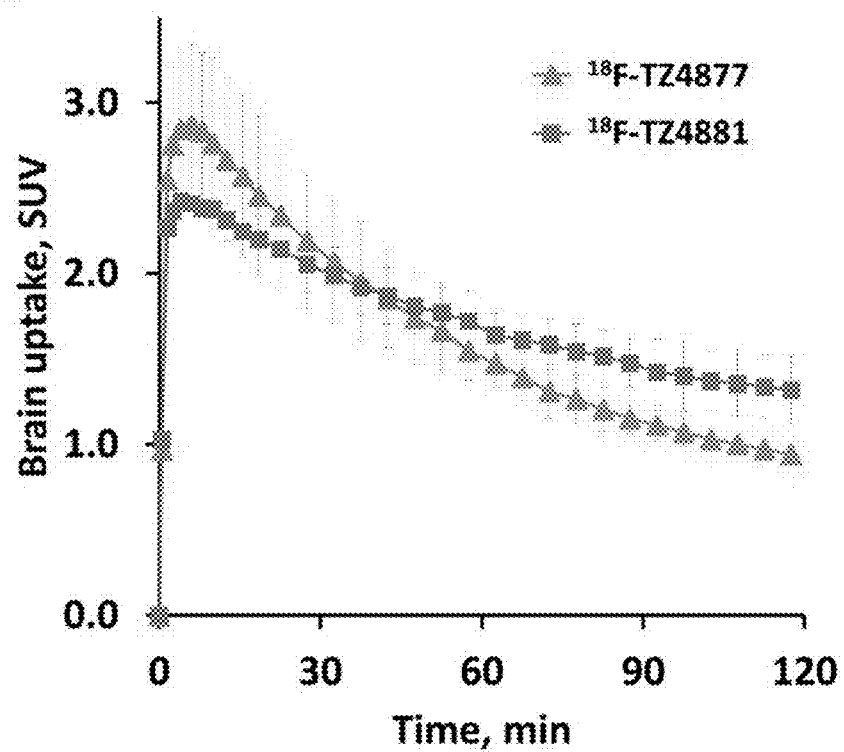

NHP microPET studies were performed to further characterize and compare tracer binding and kinetics profiles of $^{18}$F-TZ4877 ([$^{18}$F]12a) and $^{18}$F-TZ4881 ([$^{18}$F]12b). The PET images showed $^{18}$F-TZ4877 ([$^{18}$F]12a) and $^{18}$F-TZ4881 ([$^{18}$F]12b) were able to cross the BBB and widely distributed throughout the NHP brain (FIG. 18 panel A). The SUV curves revealed that the total brain uptake of both two S1P1 tracers in the total brain reached the max SUV value (~2.9 for $^{18}$F-TZ4877 ([$^{18}$F]12a), ~2.4 for $^{18}$F-TZ4881) fast at ~5 min post injection, and washed out gradually, as shown in FIG. 18 panel B. $^{18}$F-TZ4877 ([$^{18}$F]12a) had a higher initial brain uptake and faster washout speed than $^{18}$F-TZ4881 ([$^{18}$F]12b), while $^{18}$F-TZ4881 ([$^{18}$F]12b) showed higher tracer retention in late time points (>50 min) post injection.

Example 110: Binding Affinity of S1P1 Compounds

A variety of compounds having the benzoxazole or oxadiazole core were synthesized and their respective binding affinity for S1P1 was determined using a competitive binding experiment as described in Example 41. Those having high affinity for S1P1 were additionally tested for binding to S1P2-S1P5. Results are listed in Table 9, below. Note that many of the compounds below were also synthesized and described in the preceding Examples.

TABLE 9

| Compound | Structure | S1P1 IC$_{50}$ (nM) | S1P2 IC$_{50}$ (nM) | S1P3 IC$_{50}$ (nM) | S1P4 IC$_{50}$ (nM) | S1P5 IC$_{50}$ (nM) |
|---|---|---|---|---|---|---|
| TZ-31-39 | 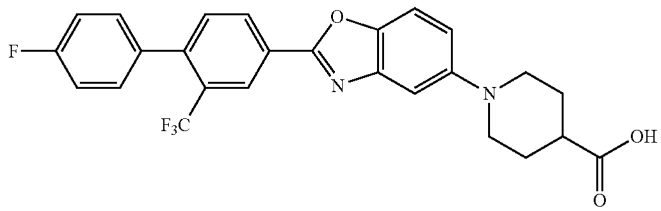 [SMILES: O=C(O)C1CCN(c2ccc3oc(-c4ccc(-c5ccc(F)cc5)c(C(F)(F)F)c4)nc3c2)CC1] | 486 ± 69 | | | | |
| TZ-31-53 | 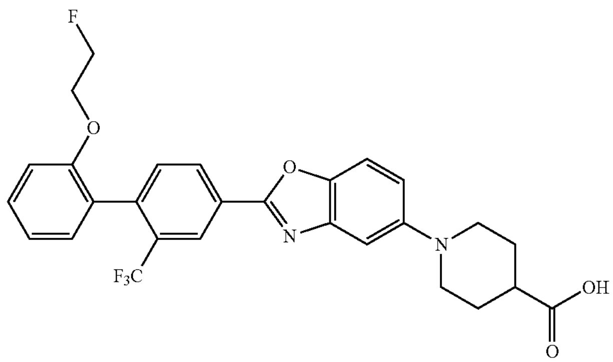 [SMILES: O=C(O)C1CCN(c2ccc3oc(-c4ccc(-c5ccccc5OCCF)c(C(F)(F)F)c4)nc3c2)CC1] | 894 ± 367 | | | | |
| TZ-31-72 | 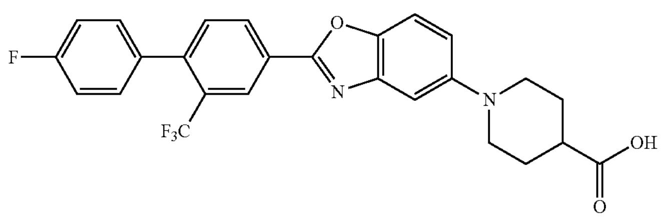 [SMILES: O=C(O)C1CCN(c2ccc3oc(-c4ccc(-c5ccc(F)cc5)c(C(F)(F)F)c4)nc3c2)CC1] | 497.7 ± 334.5 | | | | |
| TZ-31-56 | 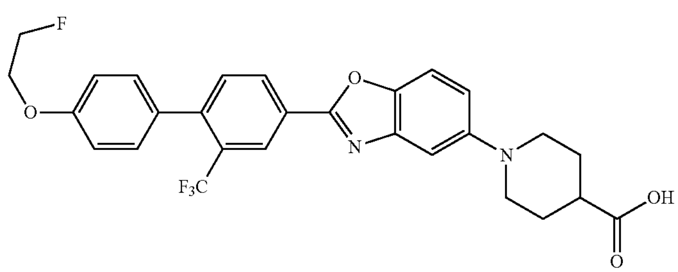 [SMILES: O=C(O)C1CCN(c2ccc3oc(-c4ccc(-c5ccc(OCCF)cc5)c(C(F)(F)F)c4)nc3c2)CC1] | 113.8 ± 72.64 | | | | |
| TZ-35-73 | 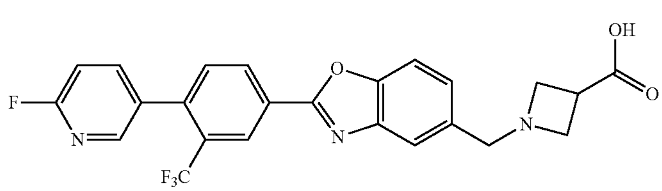 [SMILES: O=C(O)C1CN(Cc2ccc3oc(-c4ccc(-c5ccc(F)nc5)c(C(F)(F)F)c4)nc3c2)C1] | 92.68 ± 35.27 | | | | |

TABLE 9-continued
| Compound | Structure | S1P1 IC$_{50}$ (nM) | S1P2 IC$_{50}$ (nM) | S1P3 IC$_{50}$ (nM) | S1P4 IC$_{50}$ (nM) | S1P5 IC$_{50}$ (nM) |
|---|---|---|---|---|---|---|
| TZ-31-120 | 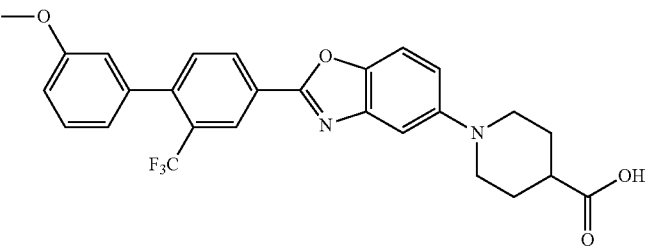 [SMILES: COc1cccc(-c2ccc(-c3nc4cc(N5CCC(C(=O)O)CC5)ccc4o3)cc2C(F)(F)F)c1] | 95.68 ± 25.10 | | | | |
| TZ-31-85 | 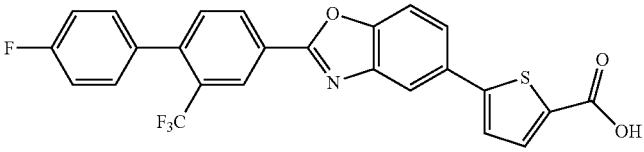 [SMILES: O=C(O)c1ccc(-c2ccc3oc(-c4ccc(-c5ccc(F)cc5)c(C(F)(F)F)c4)nc3c2)s1] | 334.0 ± 58.8 | | | | |
| TZ-35-100 | 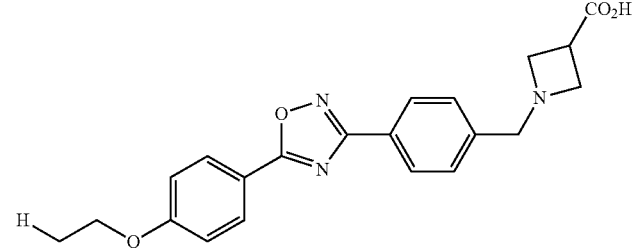 [SMILES: O=C(O)C1CN(Cc2ccc(-c3noc(-c4ccc(OCCF)cc4)n3)cc2)C1] | 8.53 ± 3.14 | >1000 | >1000 | | |
| TZ-35-115 | 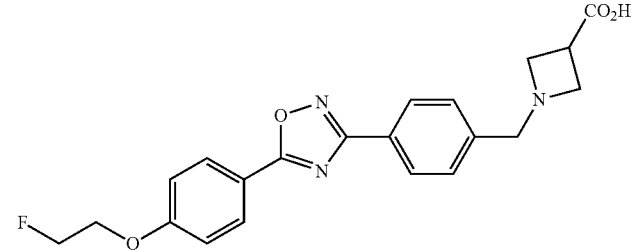 | 9.94 ± 1.03 | >1000 | >1000 | | |
| TZ-35-110 | 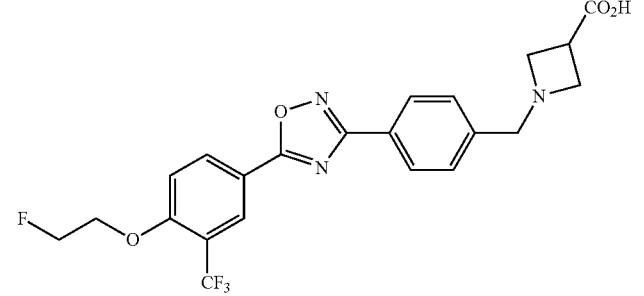 [SMILES: O=C(O)C1CN(Cc2ccc(-c3noc(-c4ccc(OCCF)c(C(F)(F)F)c4)n3)cc2)C1] | 2.63 ± 0.27 | >1000 | >1000 | | |
| TZ-35-124 | 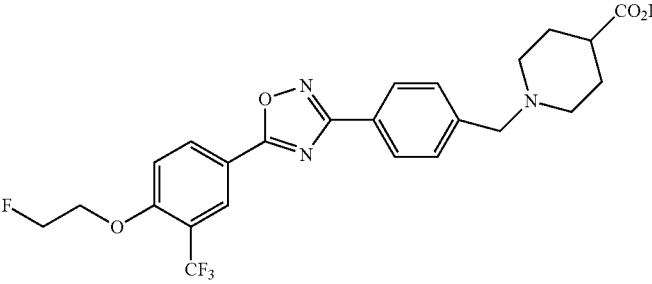 | 45.41 ± 2.70 | >1000 | >1000 | | |

TABLE 9-continued

| Compound | Structure | S1P1 IC$_{50}$ (nM) | S1P2 IC$_{50}$ (nM) | S1P3 IC$_{50}$ (nM) | S1P4 IC$_{50}$ (nM) | S1P5 IC$_{50}$ (nM) |
|---|---|---|---|---|---|---|
| TZ-35-126 | 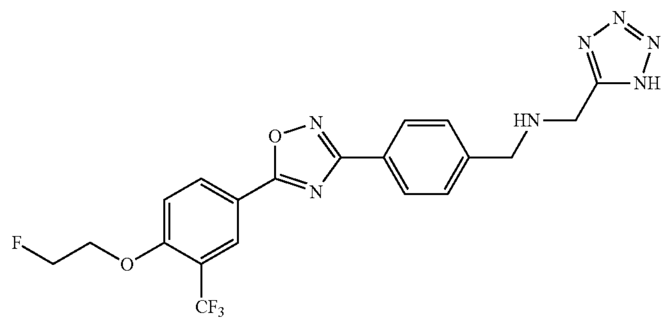 [SMILES: FCCOc1ccc(-c2nc(-c3ccc(CNCc4nnn[nH]4)cc3)no2)cc1C(F)(F)F] | 509 ± 167 | | | | |
| TZ-14-50 | 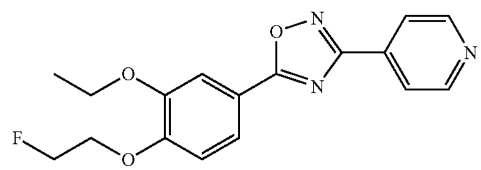 [SMILES: CCOc1cc(-c2nc(-c3ccncc3)no2)ccc1OCCF] | 182 ± 75.3 | | | | |
| TZ-33-21 | 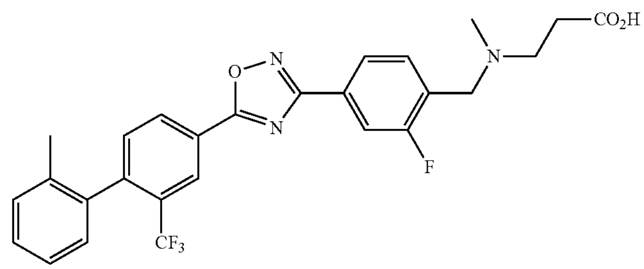 [SMILES: Cc1ccccc1-c1ccc(-c2nc(-c3ccc(CN(C)CCC(=O)O)c(F)c3)no2)cc1C(F)(F)F] | 3.80 ± 1.03 | | | >1000 | >1000 |
| TZ-33-37 | 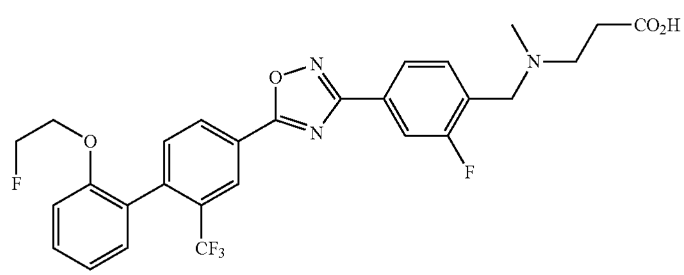 [SMILES: CN(CCC(=O)O)Cc1ccc(-c2noc(-c3ccc(-c4ccccc4OCCF)c(C(F)(F)F)c3)n2)cc1F] | 75.26 ± 20.95 | | | | |
| TZ-35-104 | 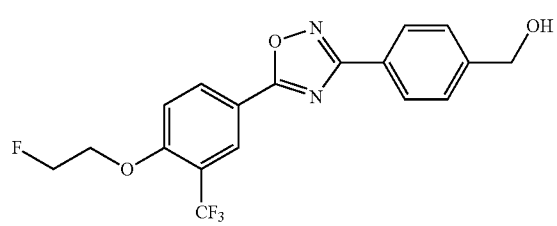 [SMILES: OCc1ccc(-c2noc(-c3ccc(OCCF)c(C(F)(F)F)c3)n2)cc1] | 6.67 ± 0.70 (10.5: avg, n = 3) | | | >1000 | >1000 |

TABLE 9-continued

| Compound | Structure | S1P1 IC$_{50}$ (nM) | S1P2 IC$_{50}$ (nM) | S1P3 IC$_{50}$ (nM) | S1P4 IC$_{50}$ (nM) | S1P5 IC$_{50}$ (nM) |
| --- | --- | --- | --- | --- | --- | --- |
| TZ-43-57 | 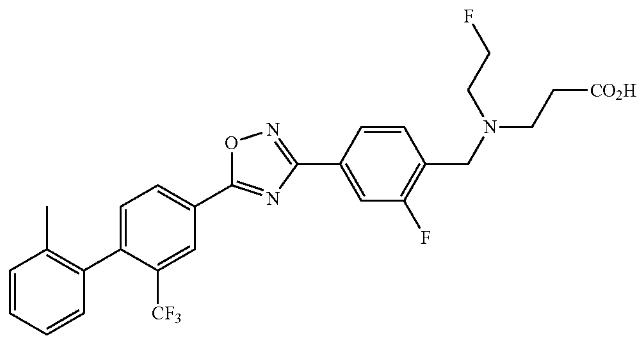 [SMILES: Cc1ccccc1-c1ccc(-c2nc(-c3ccc(CN(CCF)CCC(=O)O)c(F)c3)no2)cc1C(F)(F)F] | 41.71 ± 9.45 | | | | |
| TZ-35-139 | 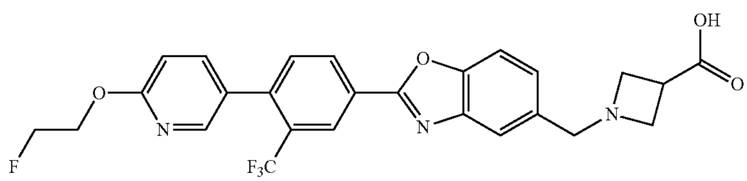 [SMILES: O=C(O)C1CN(Cc2ccc3oc(-c4ccc(-c5ccc(OCCF)nc5)c(C(F)(F)F)c4)nc3c2)C1] | 76.37 ± 21.6 | | | | |
| TZ-43-18 | 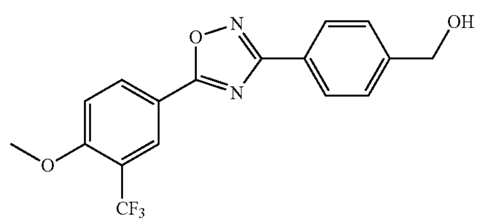 [SMILES: COc1ccc(-c2nc(-c3ccc(CO)cc3)no2)cc1C(F)(F)F] | 53.66 ± 15.79 | | | | |
| TZ-43-83 | 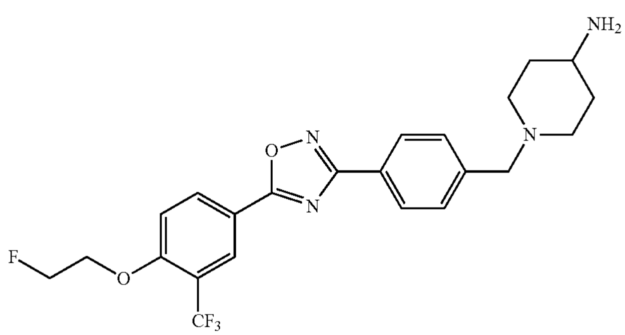 [SMILES: NC1CCN(Cc2ccc(-c3noc(-c4ccc(OCCF)c(C(F)(F)F)c4)n3)cc2)CC1] | 156.2 ± 47.1 | | | | |
| TZ-43-73 | 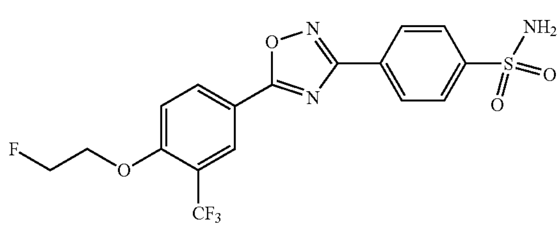 [SMILES: NS(=O)(=O)c1ccc(-c2noc(-c3ccc(OCCF)c(C(F)(F)F)c3)n2)cc1] | 13.16 ± 3.23 | >1000 | >1000 | | |
| TZ-43-77 | 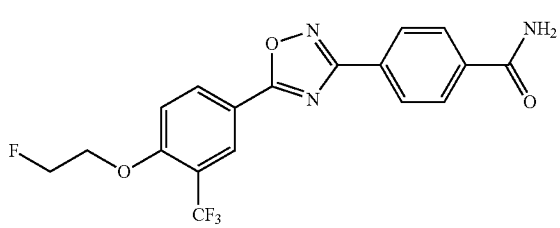 [SMILES: NC(=O)c1ccc(-c2noc(-c3ccc(OCCF)c(C(F)(F)F)c3)n2)cc1] | 67.05 ± 12.56 | | | | |

TABLE 9-continued

| Compound | Structure | S1P1 IC$_{50}$ (nM) | S1P2 IC$_{50}$ (nM) | S1P3 IC$_{50}$ (nM) | S1P4 IC$_{50}$ (nM) | S1P5 IC$_{50}$ (nM) |
|---|---|---|---|---|---|---|
| TZ-43-26 | 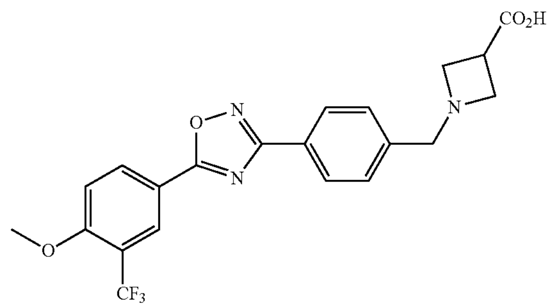 [SMILES: COc1ccc(-c2nc(-c3ccc(CN4CC(C(=O)O)C4)cc3)no2)cc1C(F)(F)F] | 103.1 ± 20.91 | | | | |
| TZ-43-102 | 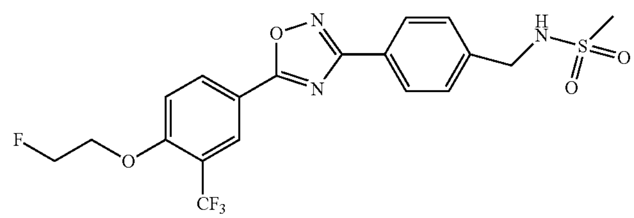 [SMILES: CS(=O)(=O)NCc1ccc(-c2noc(-c3ccc(OCCF)c(C(F)(F)F)c3)n2)cc1] | 40.01 ± 17.80 | | | | |
| TZ-43-107 | 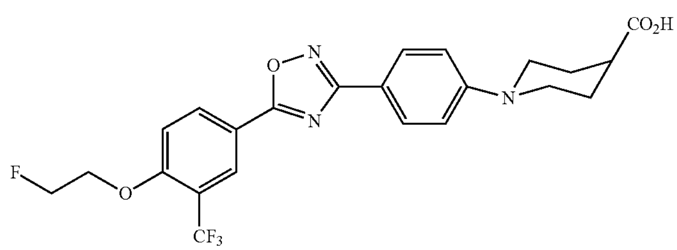 [SMILES: O=C(O)C1CCN(c2ccc(-c3noc(-c4ccc(OCCF)c(C(F)(F)F)c4)n3)cc2)CC1] | 102.3 ± 40.01 | | | | |
| TZ-43-113 | 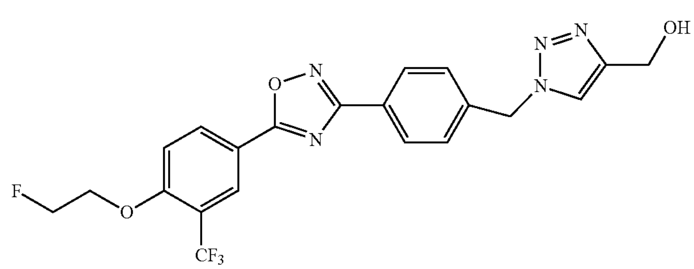 [SMILES: OCc1cn(Cc2ccc(-c3noc(-c4ccc(OCCF)c(C(F)(F)F)c4)n3)cc2)nn1] | 9.65 ± 1.61 (9.8 average, n = 2) | | >1000 | >1000 | |
| TZ-48-22 | 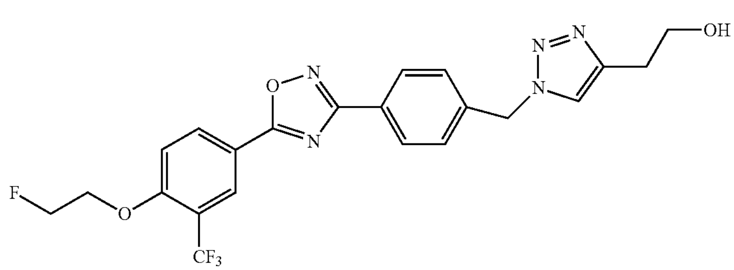 [SMILES: OCCc1cn(Cc2ccc(-c3noc(-c4ccc(OCCF)c(C(F)(F)F)c4)n3)cc2)nn1] | 5.05 ± 1.07 (5.5 average, n = 2) | | >1000 | >1000 | |

TABLE 9-continued

| Compound | Structure | S1P1 IC$_{50}$ (nM) | S1P2 IC$_{50}$ (nM) | S1P3 IC$_{50}$ (nM) | S1P4 IC$_{50}$ (nM) | S1P5 IC$_{50}$ (nM) |
|---|---|---|---|---|---|---|
| TZ-43-117 | 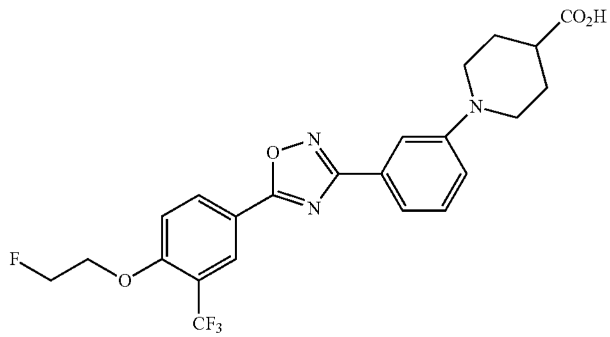 [SMILES: O=C(O)C1CCN(c2cccc(-c3noc(-c4ccc(OCCF)c(C(F)(F)F)c4)n3)c2)CC1] | 72.9 ± 11.2 | | | | |
| TZ-43-140 | 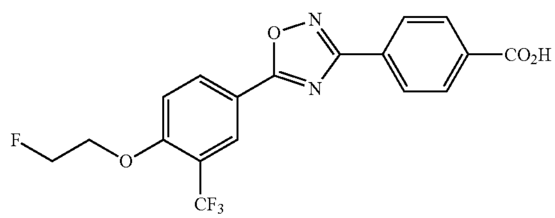 [SMILES: O=C(O)c1ccc(-c2noc(-c3ccc(OCCF)c(C(F)(F)F)c3)n2)cc1] | >1000 | | | | |
| TZ-43-143 | 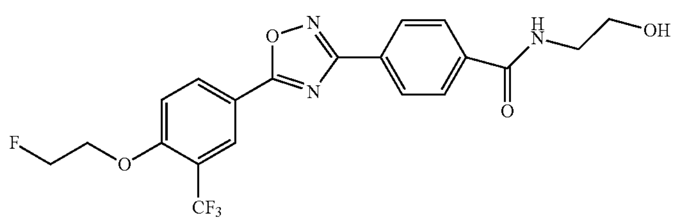 [SMILES: O=C(NCCO)c1ccc(-c2noc(-c3ccc(OCCF)c(C(F)(F)F)c3)n2)cc1] | 45.4 ± 10.2 | | | | |
| TZ-43-151-A | 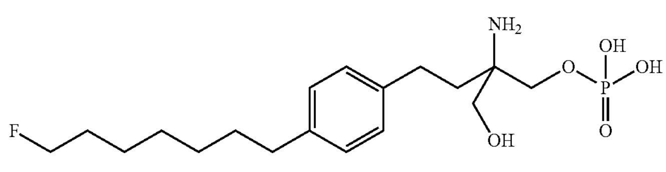 [SMILES: NC(CO)(CCc1ccc(CCCCCCCF)cc1)COP(=O)(O)O] | 30.8 ± 7.8 | >1000 | 253 ± 68 | | |
| TZ-43-153 | 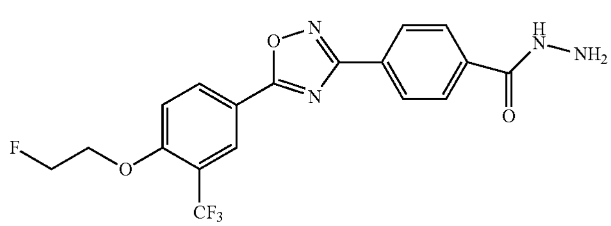 [SMILES: NNC(=O)c1ccc(-c2noc(-c3ccc(OCCF)c(C(F)(F)F)c3)n2)cc1] | 14.7 ± 1.67 | >1000 | >1000 | | |
| TZ-43-157 | 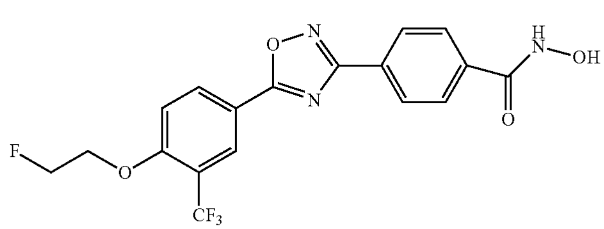 [SMILES: O=C(NO)c1ccc(-c2noc(-c3ccc(OCCF)c(C(F)(F)F)c3)n2)cc1] | 272 ± 65 | | | | |

TABLE 9-continued

| Compound | Structure | S1P1 IC$_{50}$ (nM) | S1P2 IC$_{50}$ (nM) | S1P3 IC$_{50}$ (nM) | S1P4 IC$_{50}$ (nM) | S1P5 IC$_{50}$ (nM) |
|---|---|---|---|---|---|---|
| TZ-43-158 | 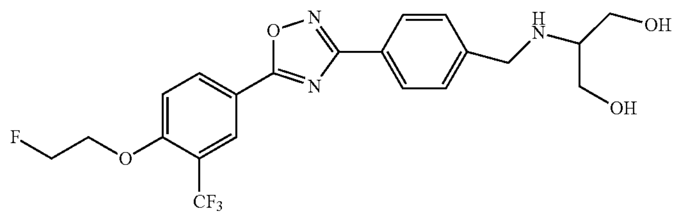 [SMILES: OCC(CO)NCc1ccc(-c2noc(-c3ccc(OCCF)c(C(F)(F)F)c3)n2)cc1] | 87.2 ± 17.7 | | | | |
| TZ-43-146 | 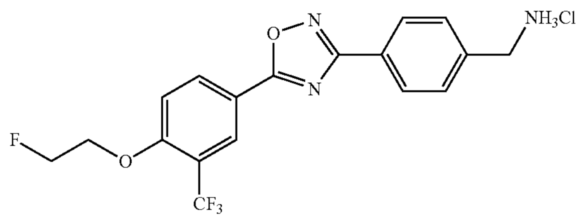 | 34.2 ± 7.1 | | | | |
| TZ-48-10 | 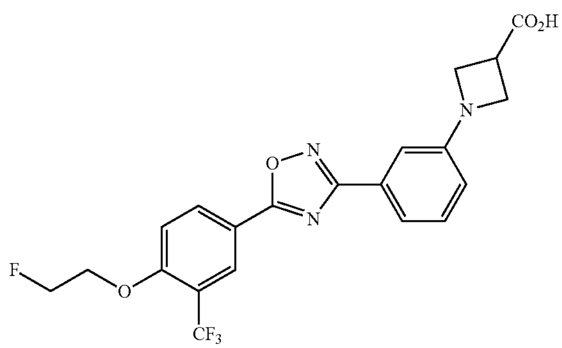 [SMILES: O=C(O)C1CN(c2cccc(-c3noc(-c4ccc(OCCF)c(C(F)(F)F)c4)n3)c2)C1] | >1000 | | | | |
| TZ-48-24 | 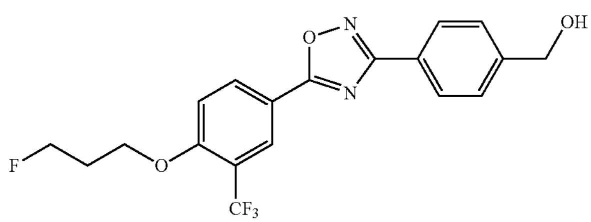 [SMILES: OCc1ccc(-c2noc(-c3ccc(OCCCF)c(C(F)(F)F)c3)n2)cc1] | 18.44 ± 3.20 | | | | |
| TZ-48-16 | 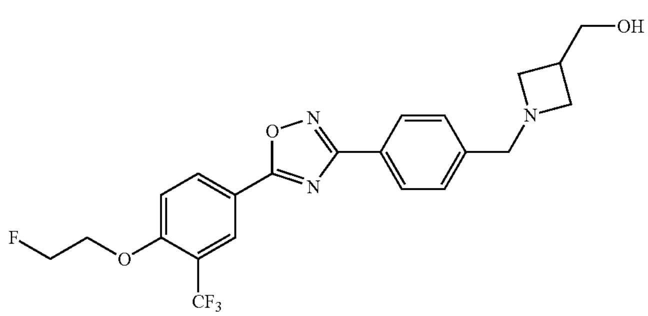 [SMILES: OCC1CN(Cc2ccc(-c3noc(-c4ccc(OCCF)c(C(F)(F)F)c4)n3)cc2)C1] | 125 ± 27 | | | | |

TABLE 9-continued

| Compound | Structure | S1P1 IC$_{50}$ (nM) | S1P2 IC$_{50}$ (nM) | S1P3 IC$_{50}$ (nM) | S1P4 IC$_{50}$ (nM) | S1P5 IC$_{50}$ (nM) |
|---|---|---|---|---|---|---|
| TZ-50-13 | 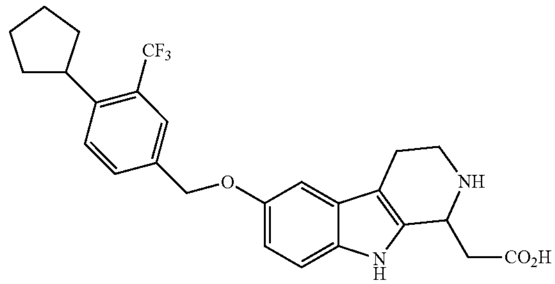 [SMILES: O=C(O)CC1NCCc2c1[nH]c1ccc(OCc3ccc(C4CCCC4)c(C(F)(F)F)c3)cc21] | 8.34 ± 1.39 | >1000 | >1000 | | |
| TZ-50-17 | 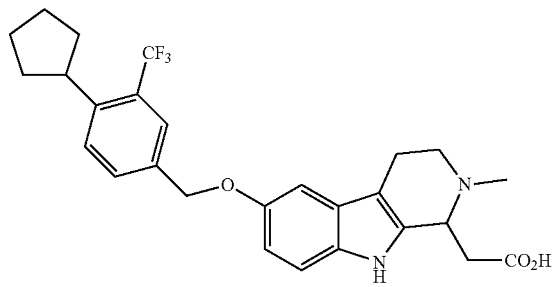 [SMILES: CN1CCc2c([nH]c3ccc(OCc4ccc(C5CCCC5)c(C(F)(F)F)c4)cc23)C1CC(=O)O] | 7.30 ± 0.62 | >1000 | >1000 | | |
| TZ-43-91 | 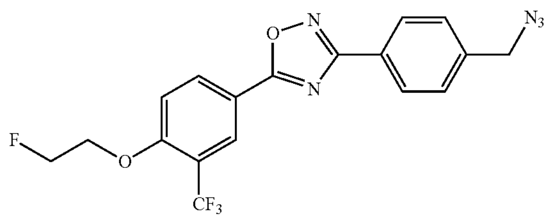 [SMILES: [N-]=[N+]=NCc1ccc(-c2noc(-c3ccc(OCCF)c(C(F)(F)F)c3)n2)cc1] | 7.4 ± 1.8 | | | | |
| TZ-48-25 | 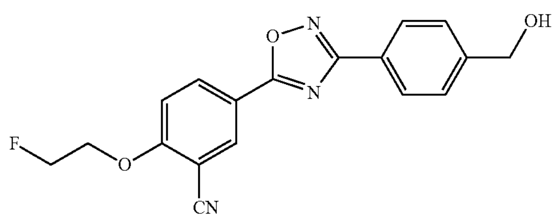 [SMILES: N#Cc1cc(-c2nc(-c3ccc(CO)cc3)no2)ccc1OCCF] | 15.4 ± 3.8 | | | | |
| TZ-48-60 | 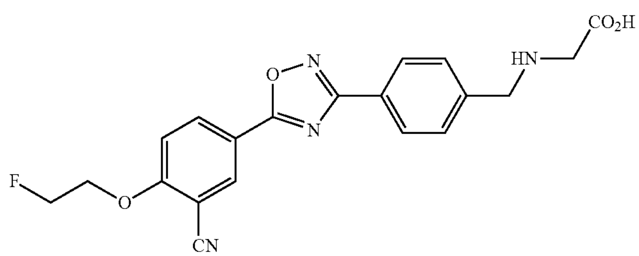 [SMILES: N#Cc1cc(-c2nc(-c3ccc(CNCC(=O)O)cc3)no2)ccc1OCCF] | 99.8 ± 12.2 | | | | |
| TZ-48-65 | 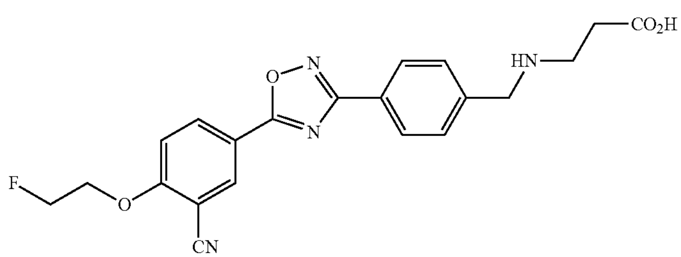 [SMILES: N#Cc1cc(-c2nc(-c3ccc(CNCCC(=O)O)cc3)no2)ccc1OCCF] | 6.3 ± 1.3 | | | | |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A compound having a structure of Formula (I) or (II), or a pharmaceutically acceptable salt thereof:

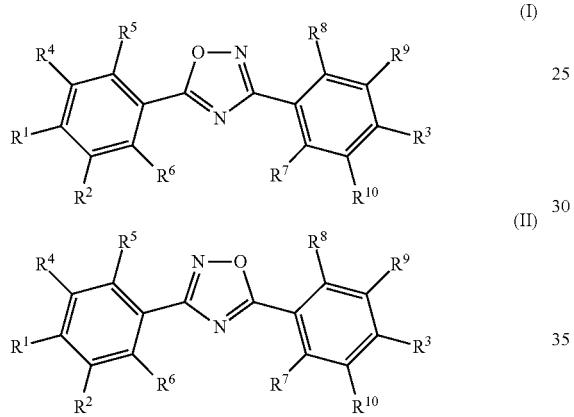

wherein
$R^1$ is halo-substituted $C_1$-$C_6$ alkoxy;
$R^2$ is $C_1$-$C_4$ haloalkyl or cyano;
$R^3$, $R^9$ and $R^{10}$ are each independently hydrogen, halo, hydroxy, amino, $C_1$-$C_6$ alkyl, $C_1$-$C_6$ alkoxy,

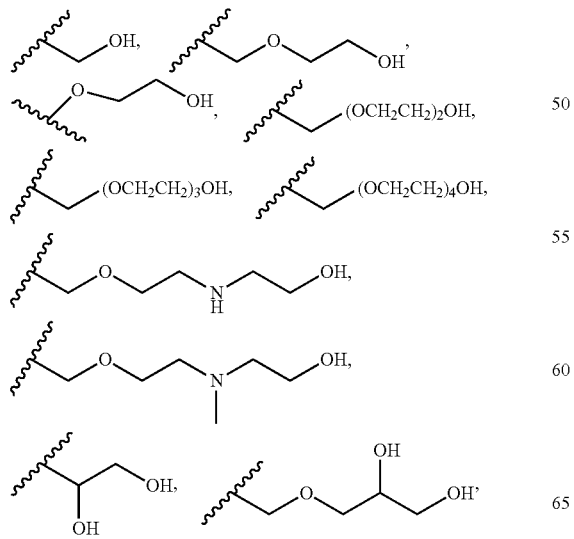

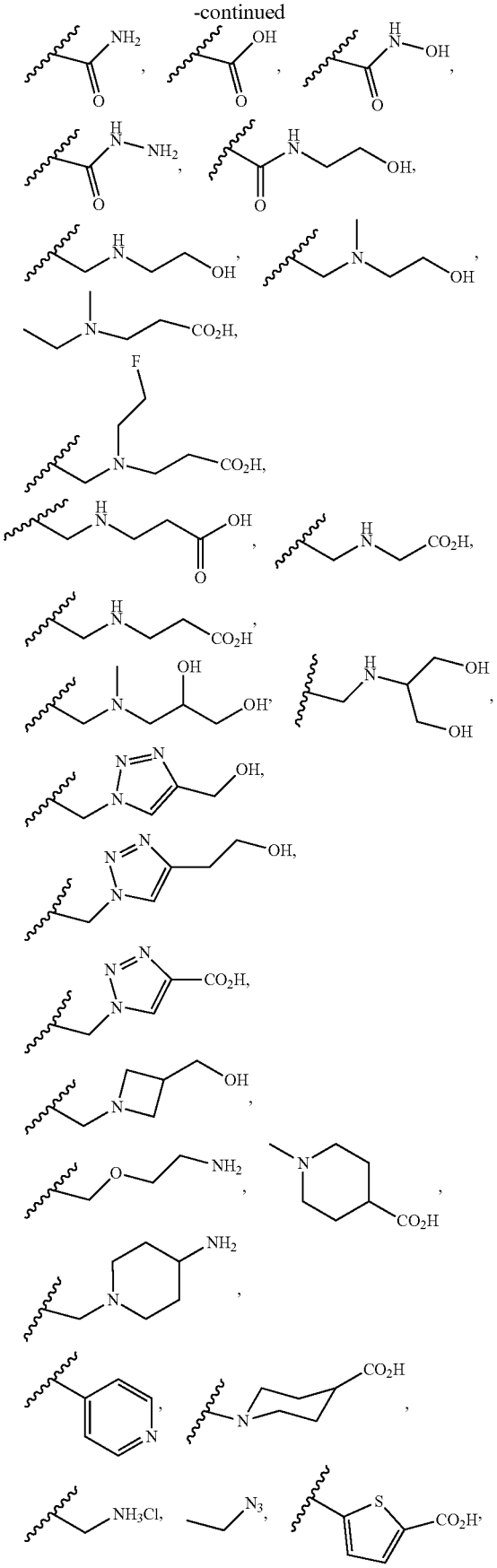

-continued

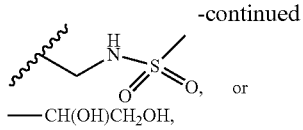

or

—CH(OH)CH₂OH, wherein at least one of $R^3$, $R^9$ and $R^{10}$ is not hydrogen;

$R^4$ is hydrogen, $C_1$-$C_6$ alkyl, $C_1$-$C_6$ alkoxy, or halo-substituted $C_1$-$C_6$ alkoxy; and $R^5$, $R^6$, $R^7$ and $R^8$ are each independently hydrogen, halo, hydroxy, $C_1$-$C_6$ alkyl, or $C_1$-$C_6$ alkoxy, and wherein $R^3$ is not —CH₂OH when $R^1$ is —OCH₂CH₂F and $R^2$ is —CF₃.

2. The compound of claim 1 wherein $R^1$ is —OCH₂CH₂F.

3. The compound of claim 1 wherein $R^4$ is hydrogen.

4. The compound of claim 1 wherein $R^2$ is —CF₃.

5. The compound of claim 1 wherein at least one of $R^3$, $R^9$ or $R^{10}$ is $C_1$-$C_6$ alkyl or $C_1$-$C_6$ alkoxy.

6. The compound of claim 1 wherein $R^9$ and $R^{10}$ are each hydrogen.

7. The compound of claim 1 wherein $R^5$, $R^6$, $R^7$, $R^8$, $R^9$, and $R^{10}$ are each hydrogen.

8. The compound of claim 1 wherein $R^3$ is

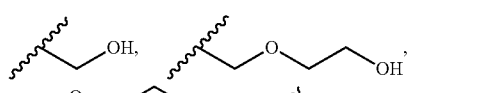

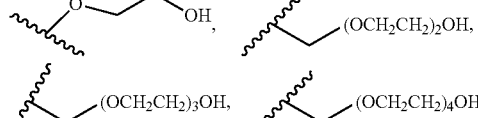

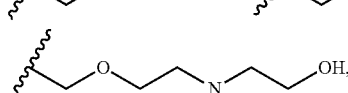

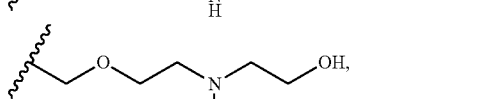

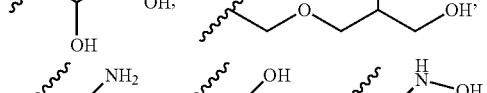

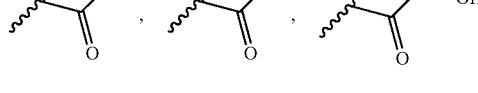

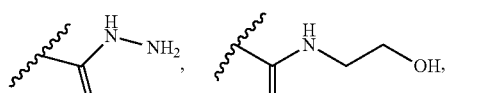

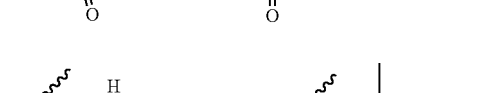

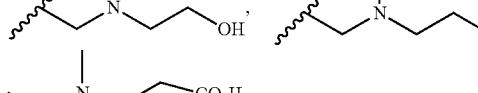

-continued

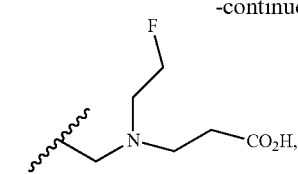

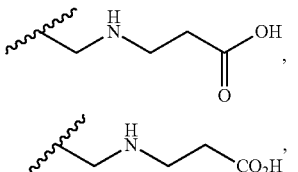

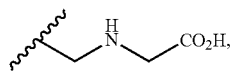

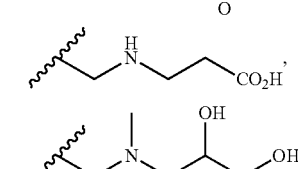

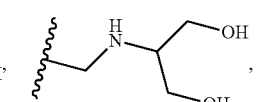

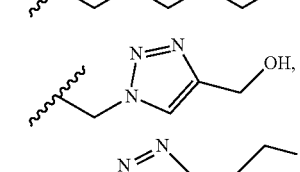

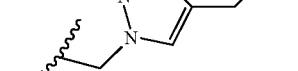

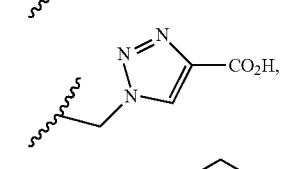

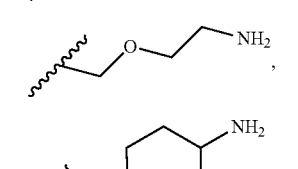

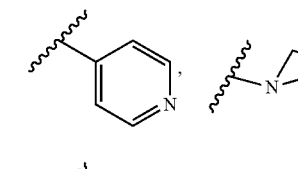

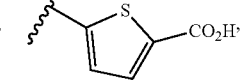

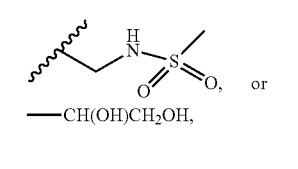

 or

—CH(OH)CH₂OH.

9. The compound of claim 1 wherein $R^9$ and $R^{10}$ are each independently hydrogen, halo, hydroxy, $C_1$-$C_6$ alkyl, or $C_1$-$C_6$ alkoxy.

10. The compound of claim 1 having a structure selected from the group consisting of:

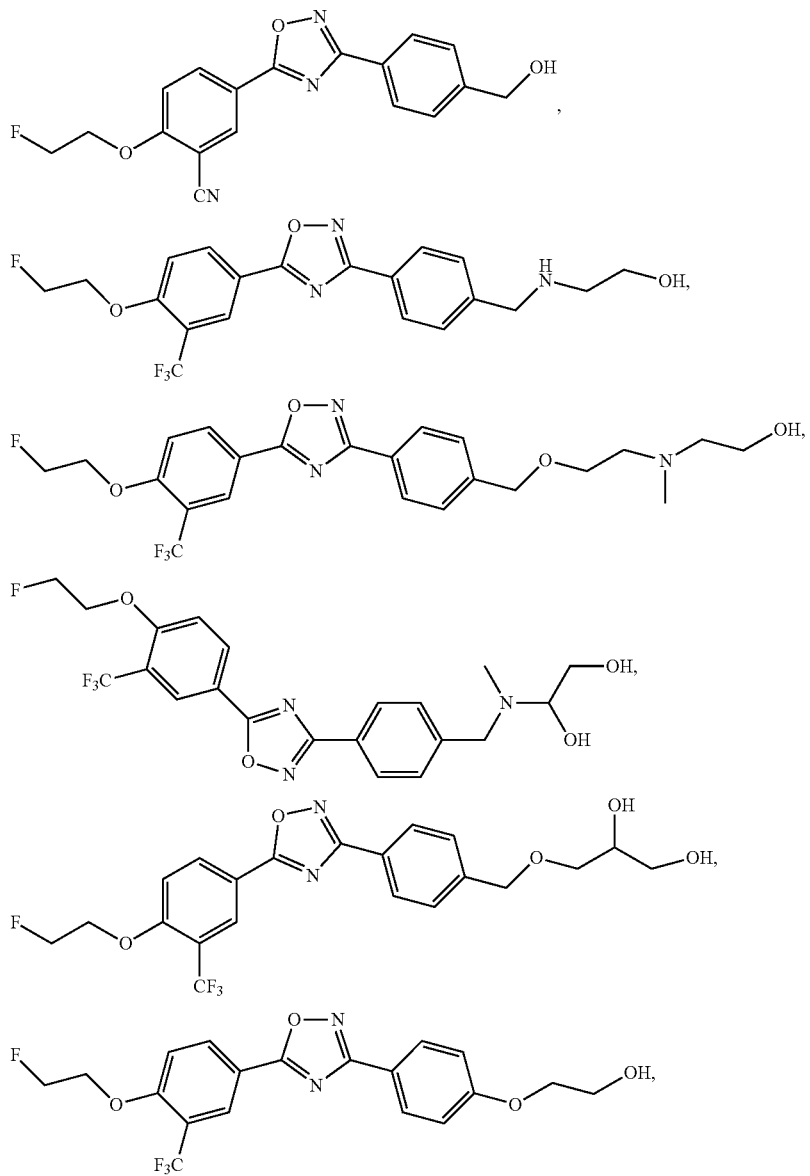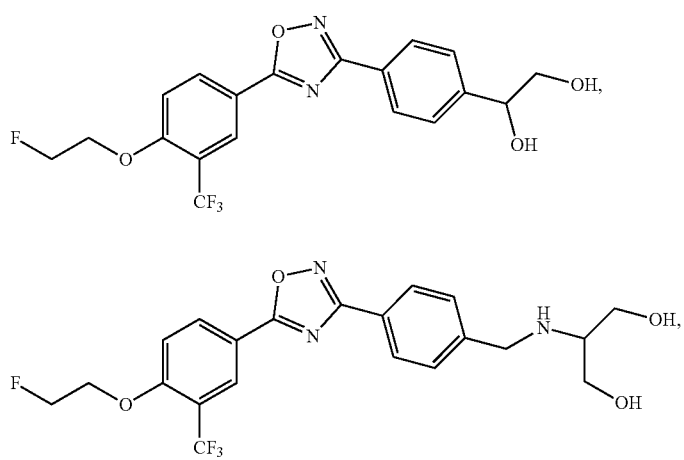

-continued
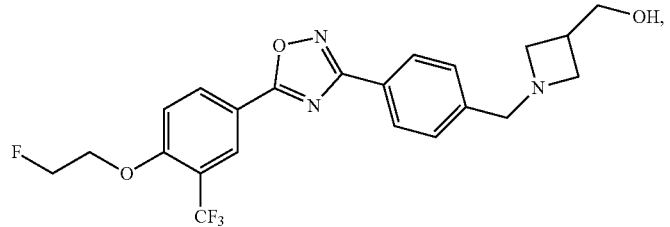
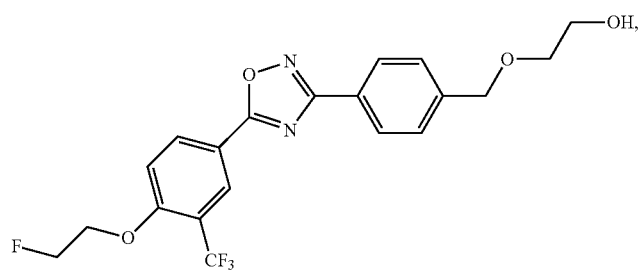
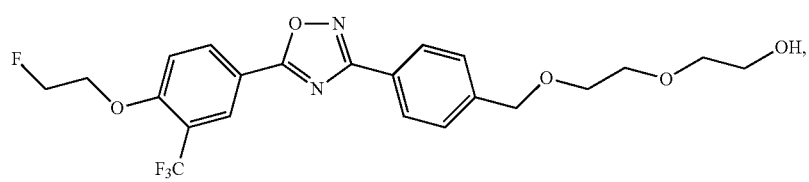
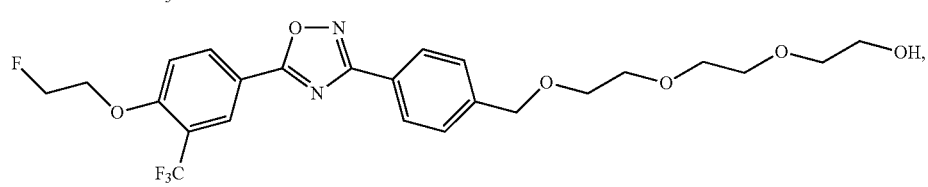
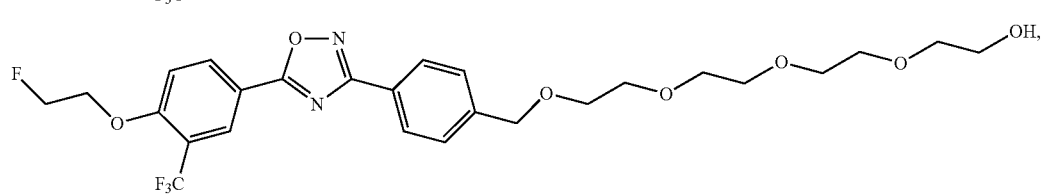
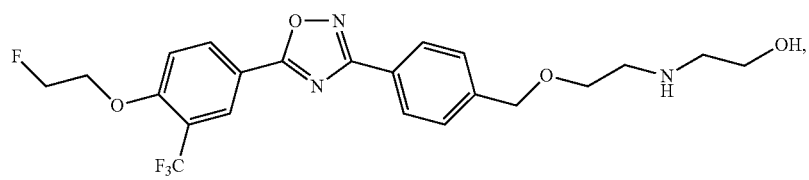
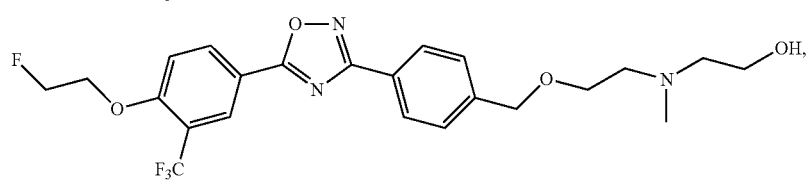
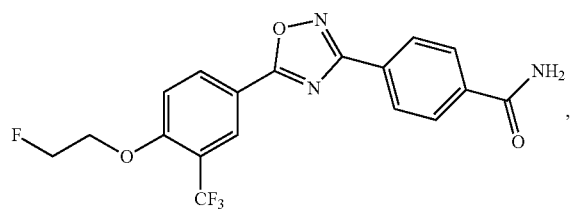

-continued
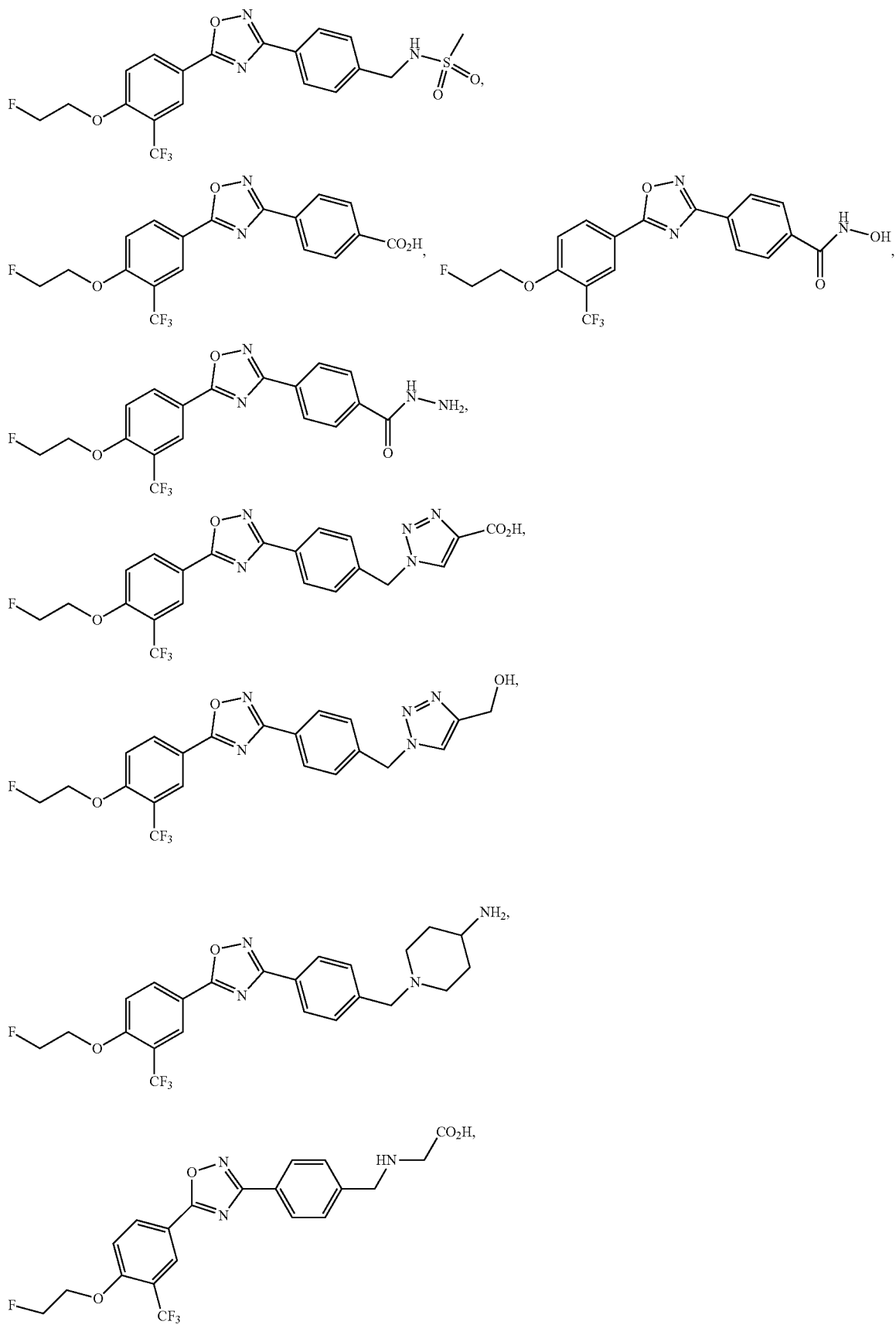

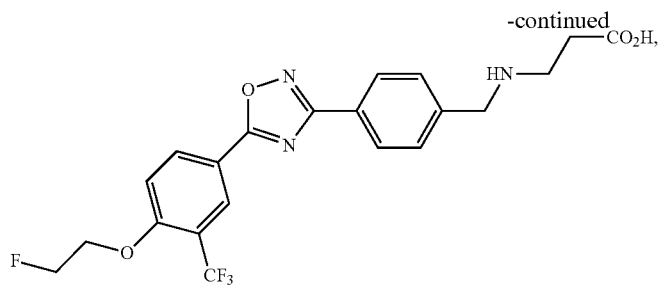
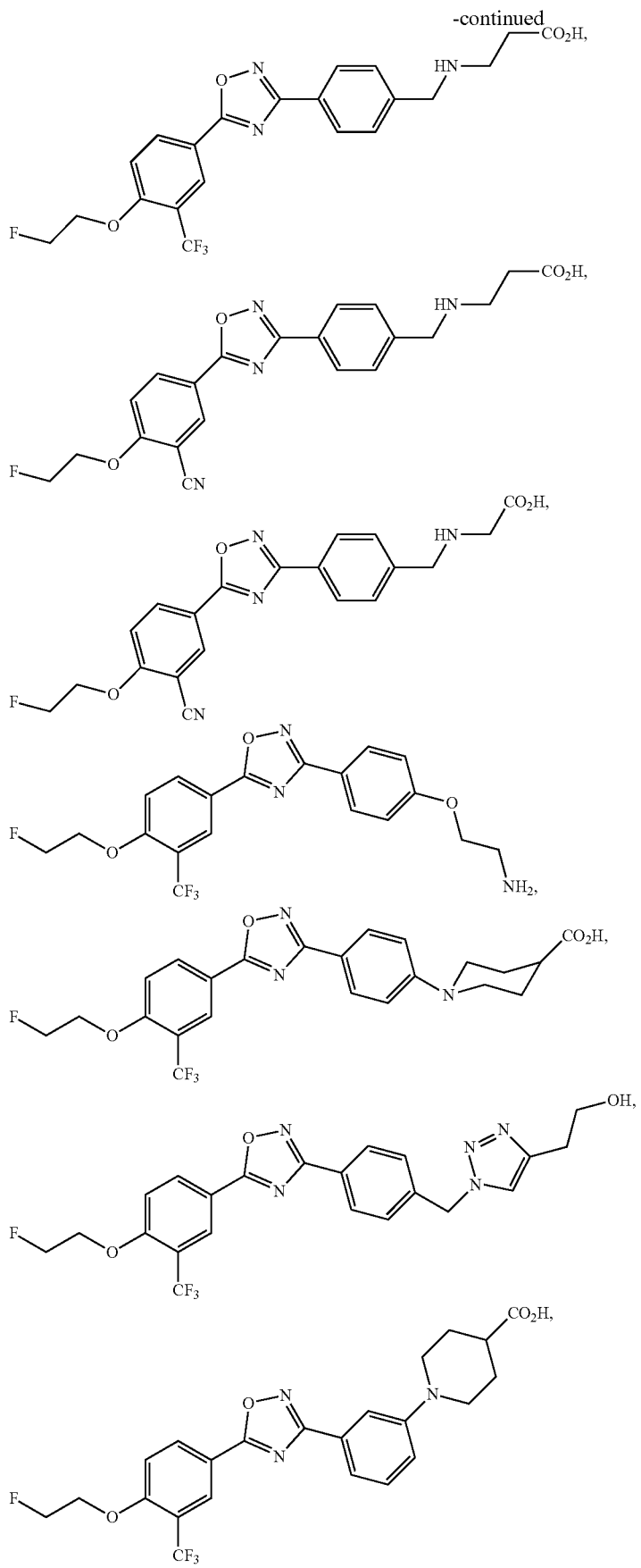

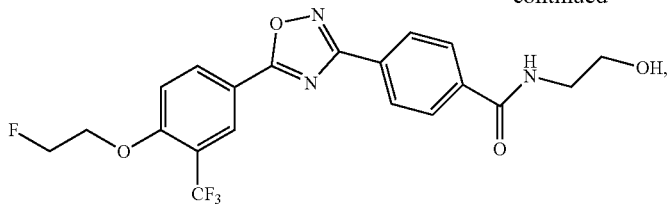

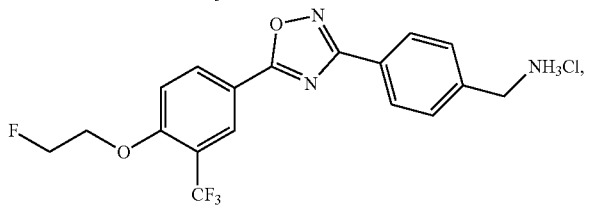

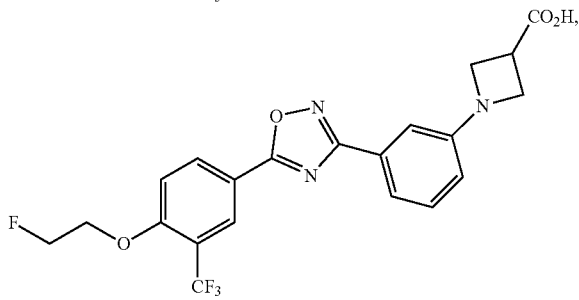

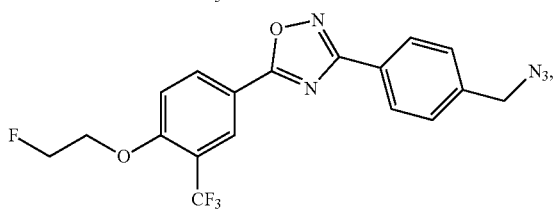

pharmaceutically acceptable salts thereof, and mixtures thereof.

11. The compound of claim 1 wherein the compound comprises an atom that is a synthetic radioactive isotope.

12. The compound of claim 11 wherein the synthetic radioactive isotope is selected from the group consisting of $^{11}C$, $^{13}N$, $^{15}O$, $^{18}F$, $^{76}Br$, $^{123}I$, and $^{125}I$.

13. The compound of claim 11 having a structure selected from the group consisting of:

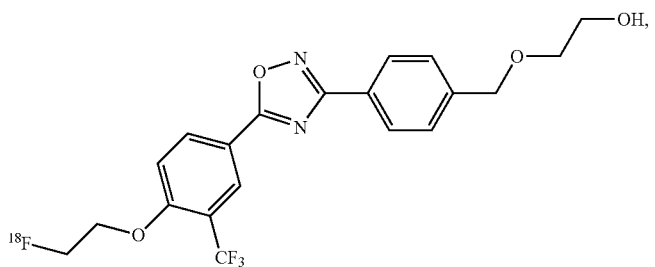

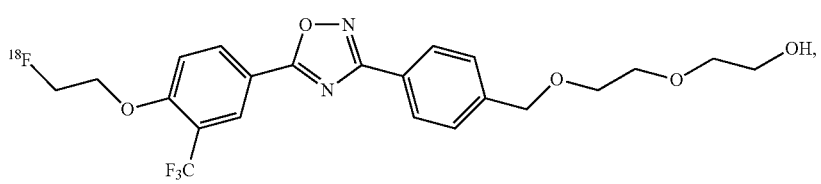

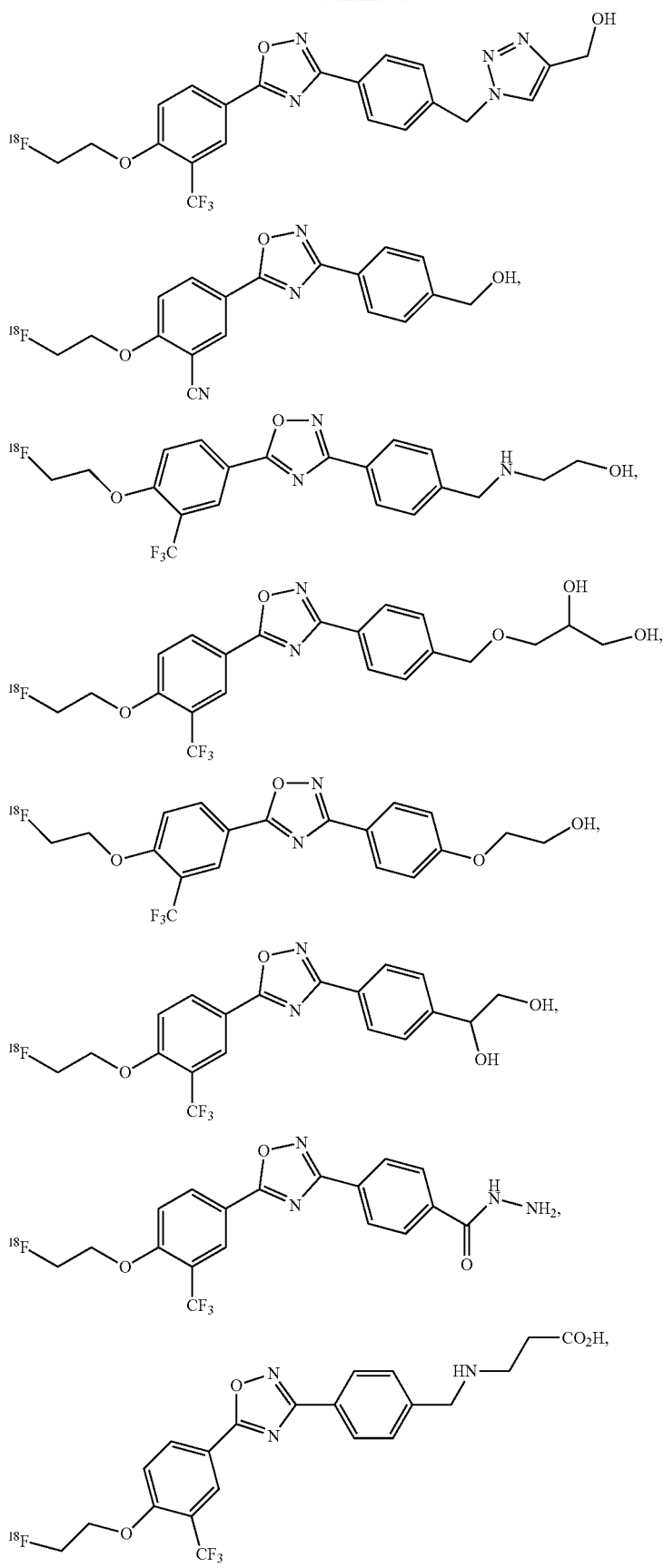

-continued

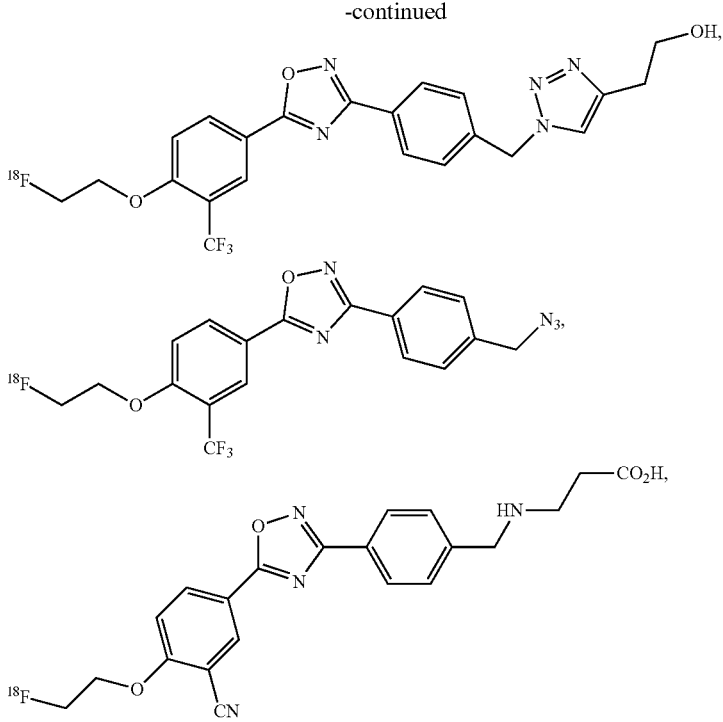

pharmaceutically acceptable salts thereof, and mixtures thereof.

14. A pharmaceutical composition comprising at least one compound of claim 13 and at least one pharmaceutically acceptable excipient.

15. A pharmaceutical composition comprising at least one compound of claim 11 and at least one pharmaceutically acceptable excipient.

16. A pharmaceutical composition comprising a pharmaceutically acceptable carrier and at least one compound of claim 11 wherein the composition comprises from about 0.001 mg to about 10 g of the compound.

17. A method of diagnosing or monitoring an S1P1 associated disease, disorder or condition in a mammal comprising administering a composition comprising a compound of claim 11 to the mammal; and detecting the compound in the mammal, wherein the S1P1 associated disease disorder or condition is selected from the group consisting of an inflammatory disease, a neuroinflammatory disease, an autoimmune disease, a pulmonary infection disease, a vascular injury disease, a neurological disease, a psychological disorder, a cardiovascular disease, atherosclerosis, multiple sclerosis, rheumatoid arthritis, and cancer.

18. The method of claim 17 wherein the S1P1 associated disease, disorder or condition is multiple sclerosis.

19. A method of quantifying S1P1 expression in a mammalian brain or central nervous system comprising administering a composition comprising a compound of claim 11 to the mammal; and detecting the compound in the mammal.

20. A method of diagnosing or monitoring an S1P1 associated disease, disorder or condition in a mammal comprising administering a composition of comprising a compound of claim 13 to the mammal; and detecting the compound in the mammal, wherein the S1P1 associated disease disorder or condition is selected from the group consisting of an inflammatory disease, a neuroinflammatory disease, an autoimmune disease, a pulmonary infection disease, a vascular injury disease, a neurological disease, a psychological disorder, a cardiovascular disease, atherosclerosis, multiple sclerosis, rheumatoid arthritis, and cancer.

* * * * *